US007067658B2

(12) United States Patent
Sielecki-Dzurdz et al.

(10) Patent No.: US 7,067,658 B2
(45) Date of Patent: Jun. 27, 2006

(54) PYRIDINO AND PYRIMIDINO PYRAZINONES

(75) Inventors: Thais Motria Sielecki-Dzurdz, Kennett Square, PA (US); Argyrios George Arvanitis, Kennett Square, PA (US); Carolyn Diane Dzierba, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 308 days.

(21) Appl. No.: 10/670,519

(22) Filed: Sep. 26, 2003

(65) Prior Publication Data

US 2004/0082784 A1      Apr. 29, 2004

Related U.S. Application Data

(60) Provisional application No. 60/414,853, filed on Sep. 30, 2002.

(51) Int. Cl.
*C07D 471/04* (2006.01)
*C07D 475/00* (2006.01)
*A61K 31/4985* (2006.01)
*A61K 31/519* (2006.01)
*A61P 25/24* (2006.01)

(52) U.S. Cl. ............... 544/257; 544/279; 514/249; 514/264.1

(58) Field of Classification Search ............... 514/249, 514/264.1; 544/257, 279
See application file for complete search history.

(56) References Cited

U.S. PATENT DOCUMENTS 5,236,901 A    8/1993   Burks et al. ............ 514/21

FOREIGN PATENT DOCUMENTS

| WO | WO 97/44038 | 11/1997 |
|---|---|---|
| WO | WO 98/08846 | 3/1998 |
| WO | WO 99/01454 | 1/1999 |
| WO | WO 01/19825 | 3/2001 |
| WO | WO 01/62758 | 8/2001 |
| WO | WO 02/19975 | 3/2002 |

OTHER PUBLICATIONS

David A. Gutman, Michael J. Owens, Kelly H. Skelton, K. V. Thrivikraman, and Charles B. Nemeroff, J. Pharmacol. Exp. Ther., Feb. 2003; 304: 874-880.*
SC Heinrichs, EB De Souza, G Schulteis, JL , Neuropsychopharmacology, 2002, 27:194-202.*
Kamal E. Habib, Katherine P. Weld, Kenner C. Rice, Judy Pushkas, Maribeth Champoux, Samuel Listwaa, Elizabeth L. Webster, Arthur J. Atkinson, Jay Schulkin, Carlo Contoregg, George P. Chrousos, PNAS, May 23, 2000, vol. 97, No. 11, 6079-6084.*

Wolff, Manfred E. "Burger's Mdeicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Taylor, Edward C.; Thompson, Malcolm J.; Perlman, Katherine; Mengel, Rudolf; Pfleiderer, Wolfgang, Journal of Organic Chemistry, 36(26), 4012-25 (English) 1971.*
E. Anthony Evans in Principles of Radiopharmacology, Colombetti, L.G. editor, CRC Press, 1979, pp. 11-13, and 24.*
Arborelius, L., et al., "The role of corticotrophin-releasing factor in depression and anxiety disorders," *J. of Endocrinology*, 1999, 160, 1-12.
Arvanitis, A.G., et al., "Imidazo[4,5-c]pyridines as corticotrophin releasing factor receptor ligands," *Bioorg. & Med. Chem. Lett.*, 2003, 13, 129-31.
Boissier, J.R., et al., "A new method for rapid screening of minor tranquillizers in mice," *Eur. J. Pharmacol.*, 1968, 4, 145-151.
Boulton, A.J. (Ed.), "The structure, reacations, synthesis, and uses of heterocyclic compounds," Comprehensive Heterocyclic Chemistry II, A review of Literature 1982-1995, vol. 6, 120-130.
Chalmers, D.T., et al., "Corticotrophin-releasing factor receptors: from molecular biology to drug design," *TiPS*, 1996, 17, 166-173.
Chrousos, G.P., "The role of stress and the hypothalamic-pituitary-adrenal axis in the pathogenesis of the metabolic syndrome: neuro-endocrine and target tissue-related causes," *Int. J. Obesity*, 2000, 24(*Suppl.* 2), S50-S55.

(Continued)

*Primary Examiner*—Thomas C. McKenzie
(74) *Attorney, Agent, or Firm*—Shah R. Makujina; Woodcock Washburn LLP

(57) ABSTRACT

The present invention provides compounds of Formula I:

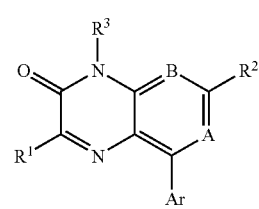

wherein the variables A, B, Ar, $R^1$, $R^2$, and $R^3$ are as defined herein. The compounds of Formula (I) can function as corticotropin releasing factor (CRF) receptor antagonists and can be useful, for example, in the treatment of disorders characterized by abnormal levels of CRF such as anxiety and depression.

60 Claims, No Drawings

OTHER PUBLICATIONS

De Souza, E.B., "CRH defects in alzheimer's and other neurologic diseases," *Hosp. Practice*, Sep. 15, 1988, 59-71.

Dunn, A.J., et al., "Physiological and behavioral responses to corticotrophin-releasing factor administration: is CRF a mediator of anxiety or stress response?," *Brain Research Reviews*, 1990, 15, 71-100.

Funk, D., et al., "Role of catecholamines in the frontal cortex in the modulation of basal and stress-induced autonomic output in rats," *Brain Res.*, 1996, 741, 220-229.

Gilligan, P.J., et al., "Corticotropin releasing factor (CRF) receptor modulators: progress and opportunities for new therapeutic agents," *J. Medicinal Chem.*, May 4, 2000, 43(9), 1641-1660.

Griebel, G., et al., "Genetic differences in the mouse defense test battery," *Aggress. Behav.*, 1997, 23, 19-31.

Grigoriadis, D.E., et al., "Corticotropin-releasing factor (CRF) receptors in intermediate lobe of the pituitary: biochemical characterization and autoradiographic localization," *Peptides*, 1989, 10, 179-188.

Heinrichs, S.C., et al., "Corticotropin-releasing factor antagonists, binding-protein and receptors: implications for central nervouse system disorders," *Ballier's Clinical Endocrinology and Metabolism*, 1999, 13(4), 541-554.

Hoffman, J.M., "Synthesis and evaluation of 2-pyridinone derivatives as HIV-1-specific reverse transcriptase inhibitors," *J. Med. Chem.*, 1993, 36, 953-966.

Huynh, C., et al., "Copper-catalysed reactions of grignard reagents with epoxides and oxetane," *Tetrahedron Letters*, 1979, 17, 1503-1506.

Koob, G.F., et al., "Neurobiology of addition toward the development of new therapies," *Ann. N.Y. Acad. Sci.*, 2000, 909, 170-185.

Maillot, C., et al., "Peripheral corticotrophin-releasing factor and stress-stimulated colonic motor activity involve type 1 receptor in rats," *Gastroenterology*, 2000, 119, 1569-1579.

Mastorakos, G., et al., "Maternal hypothalamic-pituitary-adrenal axis in pregnancy and the postpartum period," *Ann. N.Y. Acad. Sci.*, 2000, 900, 95-106.

McCarthy, J. R., et al., "Recent advances with the $CRF_1$ receptor: design of small molecule inhibitors, receptor subtypes and clinical indications," *Current Pharmaceutical Design*, 1999, 5, 289-315.

Misslin, R., et al., "Behavioural validation of a light/dark choice procedure for testing anti-anxiety agents," *Behav. Process*, 1989, 18, 119-132.

Negishi, E., et al., "Selective carbon-carbon bond formation via transition metal catalysis.3. A highly selective synthesis of unsymmetrical biaryls and diarylmethanes by the nickel- or-palladium-catalyzed reaction of aryl-and benzylzinc derivatives with aryl halides," *J. Org. Chem.*, 1977, 42(10), 1821-1823.

Newport, D.J., et al., "Neurobiology of posttraumatic stress disorder," *Curr. Opin. In Neurobiology*, 2000, 10, 211-218.

Owens, M.J., et al., "Corticotropin-releasing factor antagonists in affective disorders," *Exp. Opin. Invest. Drugs*, 1999, 8(11), 1849-1858.

Pellow, S., et al., "Validation of open: closed arm entries in an elevated plus-maze as a measure of anxiety in the rat," *J. Neurosci. Methods*, 1985, 14, 149-167.

Porsolt, D.R., et al., "Depression: a new animal model sensitive to antidepressant treatments," *Nature*, Apr. 21, 1997, 266, 730-732.

Sato, M., et al., "Cross-coupling reaction of alkyl- or arylboronic acid esters with organic halides induced by thallium(I) salts and palladium-catalyst," *Chem. Letters*, 1989, 1405-1408.

Speicher, A., et al., "Syntheses of chlorinated bisbibenzyls from bryophytes," *Synthesis*, 2002, 17, 2503-2512.

Tomczuk, B.E., et al., "2-pheyl-3H-imidazo[4,5-b]pyridine-3-acetamides as non-benzodiazepine anticonvulsants and anxiolytics," *J. med. Chem.*, 1991, 34, 2993-3006.

Vogel, J.R., et al., "A simple and reliable conflict procedure for testing anti-anxiety agents," *Psychopharmcologia (Berl.)*, 1971, 21, 1-7.

Webster, E.L., et al., "Corticotropin-releasing hormone and inflammation," *Ann. N.Y. Acad. Sci.*, 1998, 840, 21.

Willner, P., et al., "An animal model of anhedonia," *Clin. Neuropharmacol.*, 1992, 15(*Supple*. 1), 550A-551A.

Wynn, P.C., et al., "Regulation of corticotrophin-releasing factor (CRF) receptors in the rat pituitary gland: effects of adrenalectomy on CRF receptors and corticotroph responses," *The Endocrinology Soc.*, 1985, 116(4), 1653-1659.

Copy of the PCT International Search Report dated Feb. 11, 2004 (PCT/US03/30570).

\* cited by examiner

PYRIDINO AND PYRIMIDINO PYRAZINONES

CROSS-REFERENCE TO RELATED APPLICATIONS

This application claims priority of U.S. Provisional Application Ser. No. 60/414,853, filed Sep. 30, 2002, the disclosure of which is incorporated herein by reference in its entirety for all purposes.

FIELD OF THE INVENTION

The present invention provides pyridino and pyrimidino pyrazinone compounds useful as corticotropin releasing factor (CRF) receptor antagonists for the treatment of disorders characterized by physiologically abnormal levels of CRF.

BACKGROUND OF THE INVENTION

Corticotropin releasing factor (CRF), synonymous with corticotropin releasing hormone (CRH), is a 41 amino acid peptide that coordinates the overall response of the body to stress. As an agonist of CRF receptors (e.g., $CRF_1$ and $CRF_2$), CRF is well known as the primary physiological secretagogue controlling hypothalamic-pituitary-adrenal (HPA) axis activity which mediates the endocrine stress response. CRF also plays a central role in the autonomic and behavioral responses to stress. Variation in physiological levels of CRF has been correlated with various disorders including depression, anxiety, and irritable bowel syndrome.

Antagonists of CRF receptors have been shown to effectively ameliorate behavioral stress responses in animal models. It is well established that systemic administration of $CRF_1$ receptor antagonists leads to anxiolytic and antidepressant effects in rodents. Animal model evidence also shows that $CRF_1$ antagonists can help alleviate the symptoms of drug withdrawal, stress-induced seizures, and certain inflammations. A role for CRF has also been postulated in the etiology and pathophysiology of Alzheimer's disease, Parkinson's disease, Huntington's disease, progressive supranuclear palsy, and amyotrophic lateral sclerosis as they relate to the dysfunction of CRF neurons in the central nervous system. Eating disorders, such as anorexia nervosa, have also been linked to elevated levels of CRF.

Though widely dispersed throughout the central nervous system, CRF receptors are also found in peripheral systems including glandular, vascular, gastrointestinal, and immune system tissues. Accordingly, CRF antagonists are believed to have potential in treating numerous disorders of the peripheral systems. Some CRF-related disorders of peripheral systems include, for example, hypertension, tachycardia, congestive heart failure, stroke, irritable bowel syndrome, post-operative ileus, and colonic hypersensitivity. Studies have indicated that $CRF_1$ antagonists may also be useful as hair growth stimulators.

Numerous articles have reported the physiological role of CRF and the potential therapeutic activity of non-peptidic CRF receptor antagonists. Some of these articles, detailing much of the above discussion, include, for example; Gilligan, et al., *J. Medicinal Chem.*, 2000, 43, 1641, Newport, et al., *Curr. Opin. Neurobiology*, 2000, 10, 211; Mastorakos, et al., *Ann. N.Y. Acad. Sci.*, 2000, 900, 95; Koob, et al., *Ann. N.Y. Acad. Sci.*, 2000, 909, 170; Maillot, et al., *Gastroenterology*, 2000, 119, 1569; Chrousos, *Int. J. Obesity*, 2000, 24, Suppl. 2, S50; Owens, et al., *Exp. Opin. Invest. Drugs*, 1999, 8, 1849; McCarthy, et al., *Current Pharmaceutical Design*, 1999, 5, 289; Heinrichs, et al., *Baillier's Clinical Endocrinology and Metabolism*, 1999, 13, 541; Arborelius, et al., *Journal of Endocrinology*, 1999, 160, 1; Webster, et al., *Ann. N.Y. Acad. Sci.*, 1998, 840, 21; and Chalmers, et al., *TiPS*, 1996, 17, 166; De Souza, *Hosp. Practice*, 1988, 23, 59; WO 02/19975; and U.S. Pat. No. 5,236,901, each of which is incorporated herein by reference in its entirety.

Separate from the compounds reported herein, some pyrimidino pyrazinone-based compounds have been reported in WO 01/62758 as kinase inhibitors and WO 01/19825 for the treatment of chemokine mediated diseases.

As evidenced by the numerous publications directed to the study of CRF and its connection with various disorders, there is a current need for new ways in which to reduce the effects of abnormal levels of CRF or CRF receptors. For example, treatment methods for alleviating or reducing the physiological and/or neurological symptoms associated with elevated levels of CRF are desirable. The compounds described herein help fulfill these and other needs.

SUMMARY OF THE INVENTION

The present invention provides compounds of Formula (I):

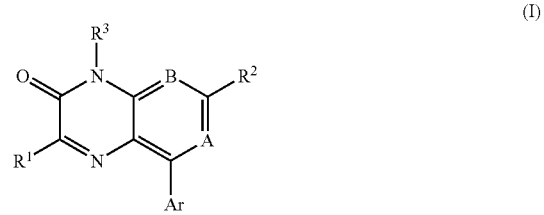

or pharmaceutically acceptable salt form thereof, or prodrug form thereof, or radiolabeled form thereof, wherein the variables A, B, Ar, $R^1$, $R^2$, and $R^3$ are as defined herein below. The compounds of Formula (I) can have $CRF_1$ receptor antagonist activity and therefore can be useful in various methods including the treatment of disorders characterized by abnormal levels of CRF.

Accordingly, the present invention provides compositions comprising a compound of Formula (I) and a pharmaceutically acceptable carrier.

The present invention further provides methods of reducing symptoms caused by elevated levels of corticotropin releasing factor in a mammal comprising administering to the mammal a therapeutically effective amount of a compound Formula (I).

The present invention further provides methods of treating stress-related symptoms in a mammal comprising administering to the mammal a therapeutically effective amount of a compound of Formula (I).

Further provided by the present invention are methods of treating disorders characterized by abnormal levels of corticotropin releasing factor in a mammal comprising administering to the mammal a therapeutically effective amount of a compound of Formula (I).

In yet further embodiments, methods are provided for the treatment of anxiety, depression, or irritable bowel syndrome in a mammal comprising administering to the mammal a therapeutically effective amount of a compound of Formula (I).

DETAILED DESCRIPTION OF PREFERRED EMBODIMENTS

In a first aspect, the present invention provides, inter alia, compounds of Formula (I):

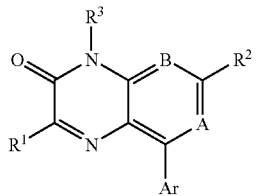

or a pharmaceutically acceptable salt forms thereof, or prodrug form thereof, or radiolabeled form thereof, wherein:

A and B are independently $CR^4$ or N, with the proviso that at least one of A and B is N;

Ar is aryl or heteroaryl, wherein the aryl or heteroaryl is optionally substituted by one or more substituents independently selected from $C_1–C_6$ alkyl, $C_3–C_6$ cycloalkyl, $C_4–C_7$ cycloalkylalkyl, $C_2–C_6$ alkenyl, $C_2–C_6$ alkynyl, $C_1–C_4$ haloalkyl, $C_1–C_4$ haloalkoxy, halogen, CN, $NO_2$, $OR^5$, and $SR^5$;

$R^1$ is H, CN, $C_1–C_4$ haloalkyl, $NR^{1c}R^{1d}$, $NR^{1c}COR^{1b}$, $COR^{1b}$, $CONR^{1c}R^{1d}$, $OR^{1c}$, $SR^{1c}$, $C_1–C_4$ alkyl substituted with 0 to 3 $R^{1a}$, $C_2–C_4$ alkenyl substituted with 0 to 3 $R^{1a}$, $C_2–C_4$ alkynyl substituted with 0 to 3 $R^{1a}$, $C_3–C_6$ cycloalkyl substituted with 0 to 3 $R^{1a}$, or $C_4–C_8$ cycloalkylalkyl substituted with 0 to 3 $R^{1a}$, with the proviso that $R^1$ is not $CH_2X$, wherein X is halogen;

each $R^{1a}$ is, independently at each occurrence, halogen, CN, $N_3$, $NO_2$, $C_1–C_2$ haloalkyl, $NR^{1c}R^{1d}$, $NR^{1c}COR^{1b}$, $COR^{1b}$, $OR^{1c}$, $SR^{1c}$, $S(O)R^8$, or $S(O)_2R^8$;

each $R^{1b}$ is, independently at each occurrence, $C_1–C_4$ alkyl, $C_1–C_4$ haloalkyl, $C_3–C_6$ cycloalkyl, $C_2–C_4$ alkenyl, or $C_2–C_4$ alkynyl;

each $R^{1c}$ is, independently at each occurrence, selected from H, $C_1–C_4$ alkyl, $C_1–C_4$ haloalkyl, $C_3–C_6$ cycloalkyl, $C_2–C_4$ alkenyl, or $C_2–C_4$ alkynyl;

each $R^{1d}$ is, independently at each occurrence, selected from H, $C_1–C_4$ alkyl, $C_1–C_4$ haloalkyl, $C_3–C_6$ cycloalkyl, $C_2–C_4$ alkenyl, or $C_2–C_4$ alkynyl;

$R^2$ is H, $C_1–C_3$ haloalkyl, CN, OH, $COR^{2b}$, SH, $SR^{2b}$, $SO_2NHR^{2c}$, $SO_2NR^{2c}R^{2d}$, $CONHR^{2c}$, $CONR^{2c}R^{2d}$, $OCOR^{2b}$, $OR^{2b}$, $NR^{2c}R^{2d}$, $CO_2R^{2b}$, $C_1–C_4$ alkyl substituted with 0 to 3 $R^{2a}$, $C_2–C_4$ alkenyl substituted with 0 to 3 $R^{2a}$, $C_2–C_4$ alkynyl substituted with 0 to 3 $R^{2a}$, or $C_3–C_6$ cycloalkyl substituted with 0 to 3 $R^{2a}$; with the proviso that $R^2$ is not $CH_2X$, wherein X is halogen;

each $R^{2a}$ is, independently at each occurrence, halogen, CN, $N_3$, $NO_2$, $CF_3$, $OR^{2c}$, $NR^{2c}$, $NR^{2c}R^{2d}$, $NR^{2c}CO_2R^{2b}$, $SR^{2b}$, $SOR^8$, $SO_2R^8$, $CO_2R^{2b}$, $CONR^{2c}R^{2d}$, $COR^{2b}$, $OCOR^{2b}$, $NR^{2c}CONR^{2c}R^{2d}$, $NR^{2c}CO_2R^{2b}$, $OCONR^{2c}R^{2d}$, piperidinyl, pyrrolidinyl, piperazinyl, N-methylpiperazinyl, morpholinyl, or thiomorpholinyl;

each $R^{2b}$ is, independently at each occurrence, $C_1–C_4$ alkyl, $C_1–C_4$ haloalkyl, $C_3–C_6$ cycloalkyl, $C_4–C_{12}$ cycloalkylalkyl, aryl, heteroaryl, aryl-$C_1–C_4$ alkyl, or heteroaryl-$C_1–C_4$ alkyl;

each $R^{2c}$ is, independently at each occurrence, H, $C_1–C_4$ alkyl, $C_1–C_4$ haloalkyl, $C_3–C_6$ cycloalkyl, $C_4–C_{12}$ cycloalkylalkyl aryl, heteroaryl, aryl-$C_1–C_4$ alkyl, or heteroaryl-$C_1–C_4$ alkyl;

each $R^{2d}$ is, independently at each occurrence, H, $C_1–C_4$ alkyl, $C_1–C_4$ haloalkyl, $C_3–C_6$ cycloalkyl, $C_4–C_{12}$ cycloalkylalkyl aryl, heteroaryl, aryl-$C_1–C_4$ alkyl, or heteroaryl-$C_1–C_4$ alkyl;

$R^3$ is $OR^{3c}$, $NR^{3c}R^{3d}$, $NHR^{3c}$, $SR^{3c}$, $S(O)R^8$, $S(O)_2R^8$, $SO_2NHR^{3c}$, $SO_2NR^{3c}R^{3d}$, $COR^{3c}$, $CONHR^{3c}$, $CONR^{3c}R^{3d}$, aryl substituted with 0 to 3 $R^{3a}$, heteroaryl substituted with 0 to 3 $R^{3a}$, heterocyclyl substituted with 0 to 3 $R^{3f}$, $C_1–C_{10}$ alkyl substituted with 0 to 3 $R^{3a}$, $C_3–C_{10}$ alkenyl substituted with 0 to 3 $R^{3a}$, $C_3–C_{10}$ alkynyl substituted with 0 to 3 $R^{3a}$, $C_3–C_8$ cycloalkyl substituted with 0 to 3 $R^{3a}$, $C_4–C_{12}$ cycloalkylalkyl substituted with 0 to 3 $R^{3a}$, $C_2–C_{10}$ alkoxyalkyl substituted with 0 to 3 $R^{3a}$, $C_2–C_{10}$ thioalkoxyalkyl substituted with 0 to 3 $R^{3a}$, $C_5–C_{10}$ cycloalkenyl substituted with 0 to 3 $R^{3a}$, or $C_6–C_{10}$ cycloalkenylalkyl substituted with 0 to 3 $R^{3a}$, wherein one carbon in any cycloalkyl moiety is optionally replaced with O, S or $NR^5$;

each $R^{3a}$ is, independently at each occurrence, $C_1–C_{10}$ alkyl, $C_2–C_{10}$ alkenyl, $C_2–C_{10}$ alkynyl, $C_3–C_6$ cycloalkyl, halogen, $C_1–C_4$ haloalkyl, CN, $OR^{3c}$, $SR^{3c}$, $S(O)_nR^8$, $COR^{3b}$, $NHR^{3c}SO_2R^{3b}$, $OC(O)NR^{3c}R^{3d}$, $N_3$, $OC(O)OR^{3b}$, $CO_2R^{3c}$, $OC(O)R^{3b}$, $NR^{3c}COR^{3b}$, $N(COR^{3b})_2$, $NR^{3c}CONR^{3c}R^{3d}$, $NR^{3c}CO_2R^{3b}$, $NR^{3c}R^{3d}$, $CONR^{3c}R^{3d}$, aryl, heteroaryl, or heterocyclyl;

each $R^{3b}$ is, independently at each occurrence, $C_1–C_{10}$ alkyl substituted with 0 to 3 $R^{3e}$, $C_2–C_{10}$ alkenyl substituted with 0 to 3 $R^{3e}$, $C_2–C_{10}$ alkynyl substituted with 0 to 3 $R^{3e}$, $C_3–C_8$ cycloalkyl substituted with 0 to 3 $R^{3e}$, $C_4–C_{12}$ cycloalkylalkyl substituted with 0 to 3 $R^{3e}$, $C_2–C_{10}$ alkoxyalkyl substituted with 0 to 3 $R^{3e}$, $C_5–C_{10}$ cycloalkenyl substituted with 0 to 3 $R^{3e}$, or $C_6–C_{10}$ cycloalkenylalkyl substituted with 0 to 3 $R^{3e}$, wherein one carbon in any cycloalkyl moiety is optionally replaced with O, S or $NR^5$;

each $R^{3c}$ is, independently at each occurrence, H, $C_1–C_{10}$ alkyl substituted with 0 to 3 $R^{3e}$, $C_2–C_{10}$ alkenyl substituted with 0 to 3 $R^{3e}$, $C_2–C_{10}$ alkynyl substituted with 0 to 3 $R^{3e}$, $C_3–C_8$ cycloalkyl substituted with 0 to 3 $R^{3e}$, $C_4–C_{12}$ cycloalkylalkyl substituted with 0 to 3 $R^{3e}$, $C_2–C_{10}$ alkoxyalkyl substituted with 0 to 3 $R^{3e}$, $C_5–C_{10}$ cycloalkenyl substituted with 0 to 3 $R^{3e}$, or $C_6–C_{10}$ cycloalkenylalkyl substituted with 0 to 3 $R^{3e}$, wherein one carbon in any cycloalkyl moiety is optionally replaced with O, S or $NR^5$;

each $R^{3d}$ is, independently at each occurrence, H, $C_1–C_{10}$ alkyl substituted with 0 to 3 $R^{3e}$, $C_2–C_{10}$ alkenyl substituted with 0 to 3 $R^{3e}$, $C_2–C_{10}$ alkynyl substituted with 0 to 3 $R^{3e}$, $C_3–C_8$ cycloalkyl substituted with 0 to 3 $R^{3e}$, $C_4–C_{12}$ cycloalkylalkyl substituted with 0 to 3 $R^{3e}$, $C_2–C_{10}$ alkoxyalkyl substituted with 0 to 3 $R^{3e}$, $C_5–C_{10}$ cycloalkenyl substituted with 0 to 3 $R^{3e}$, or $C_6–C_{10}$ cycloalkenylalkyl substituted with 0 to 3 $R^{3e}$, wherein one carbon in any cycloalkyl moiety is optionally replaced with O, S or $NR^5$;

each $R^{3e}$ is, independently at each occurrence, $C_1–C_6$ alkyl, $C_2–C_6$ alkenyl, $C_2–C_{10}$ alkynyl, $C_3–C_6$ cycloalkyl, halogen, $C_1–C_4$ haloalkyl, CN, $OR^{7a}$, $SR^{7a}$, $S(O)_nR^8$, $COR^6$, $CO_2R^{7a}$, $OC(O)R^6$, $NR^{7a}COR^6$, $N(COR^6)_2$, $NR^{7a}CONR^{7a}R^{7b}$, $NR^{7a}CO_2R^6$, $NR^{7a}R^{7b}$, NHR$^{7a}$SO$_2$R$^6$, OC(O)NR$^{7a}$R$^{7b}$, N$_3$, OC(O)OR$^6$, CONR$^{7a}$R$^{7b}$, aryl, heteroaryl, or heterocyclyl;

each R$^{3f}$ is, independently at each occurrence, oxo, sulfido, or R$^{3a}$;

R$^4$ is H, halogen, CN, C$_1$–C$_3$ haloalkyl, COR$^{4b}$, OR$^{4c}$, SR$^{4c}$, SO$_2$NHR$^{4c}$, SO$_2$NR$^{4c}$R$^{4d}$, CONHR$^{4c}$, CONR$^{4c}$R$^{4d}$, OCOR$^{4b}$, NR$^{4c}$CONHR$^{4c}$, NR$^{4c}$CONR$^{4c}$R$^{4d}$, NR$^{4c}$CO$_2$R$^{4b}$, OCONR$^{4c}$R$^{4d}$, NR$^{4c}$R$^{4d}$, CO$_2$R$^{4b}$, C$_1$–C$_4$ alkyl substituted with 0 to 1 R$^{4a}$, C$_2$–C$_4$ alkenyl substituted with 0 to 1 R$^{4a}$, C$_2$–C$_4$ alkynyl substituted with 0 to 1 R$^{4a}$, C$_3$–C$_6$ cycloalkyl substituted with 0 to 1 R$^{4a}$, piperidinyl, pyrrolidinyl, piperazinyl, N-methylpiperazinyl, morpholinyl, or thiomorpholinyl;

each R$^{4a}$ is, independently at each occurrence, halogen, CN, CF$_3$, OR$^{4c}$, NHR$^{4c}$, NR$^{4c}$R$^{4d}$, NR$^{4c}$CO$_2$R$^{4b}$, SR$^{4c}$, SOR$^8$, SO$_2$R$^8$, CO$_2$R$^{4b}$, CONHR$^{4c}$, CONR$^{4c}$R$^{4d}$, COR$^{4b}$, OCOR$^{4b}$, NR$^{4c}$CONR$^{4c}$R$^{4d}$, NR$^{4c}$CO$_2$R$^{4b}$, OCONR$^{4c}$R$^{4d}$, piperidinyl, pyrrolidinyl, piperazinyl, N-methylpiperazinyl, morpholinyl, or thiomorpholinyl;

each R$^{4b}$ is, independently at each occurrence, C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl;

each R$^{4c}$ is, independently at each occurrence, H, C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl;

each R$^{4d}$ is, independently at each occurrence, H, C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl;

R$^5$ is H, C$_1$–C$_4$ alkyl, C$_1$–C$_4$ haloalkyl, C$_2$–C$_6$ alkenyl, C$_2$–C$_6$ alkynyl, C$_3$–C$_6$ cycloalkyl, C$_4$–C$_7$ cycloalkylalkyl, or C$_2$–C$_6$ alkoxyalkyl;

R$^6$ is, independently at each occurrence, C$_1$–C$_6$ alkyl, C$_1$–C$_6$ haloalkyl C$_2$–C$_6$ alkenyl, C$_2$–C$_6$ alkynyl, C$_3$–C$_6$ cycloalkyl, C$_4$–C$_{12}$ cycloalkylalkyl, C$_2$–C$_8$ alkoxyalkyl, C$_5$–C$_{12}$ bis(alkoxy)alkyl, aryl, aryl-C$_1$–C$_4$ alkyl, heteroaryl, or heteroaryl-C$_1$–C$_4$ alkyl;

each R$^{7a}$ is, independently at each occurrence, H, C$_1$–C$_6$ alkyl, C$_1$–C$_6$ haloalkyl C$_2$–C$_6$ alkenyl, C$_2$–C$_6$ alkynyl, C$_3$–C$_6$ cycloalkyl, C$_4$–C$_{12}$ cycloalkylalkyl, C$_2$–C$_8$ alkoxyalkyl, C$_5$–C$_{12}$ bis(alkoxy)alkyl, aryl, aryl-C$_1$–C$_4$ alkyl, heteroaryl, or heteroaryl-C$_1$–C$_4$ alkyl;

each R$^{7b}$ is, independently at each occurrence, H, C$_1$–C$_6$ alkyl, C$_1$–C$_6$ haloalkyl C$_2$–C$_6$ alkenyl, C$_2$–C$_6$ alkynyl, C$_3$–C$_6$ cycloalkyl, C$_4$–C$_{12}$ cycloalkylalkyl, C$_2$–C$_8$ alkoxyalkyl, C$_5$–C$_{12}$ bis(alkoxy)alkyl, aryl, aryl-C$_1$–C$_4$ alkyl, heteroaryl, or heteroaryl-C$_1$–C$_4$ alkyl; and R$^8$ is C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl, or NR$^{7a}$R$^{7b}$.

According to some embodiments according to the first aspect, the present invention includes compounds of Formula (I) where A and B are both N. In other embodiments, the present invention includes compounds of Formula (I) wherein one of A and B is CR$^4$. For example, the present invention includes compounds of Formula (Ia) and (Ib):

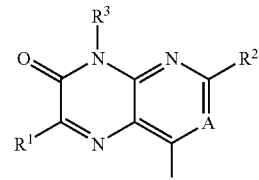

(Ia)

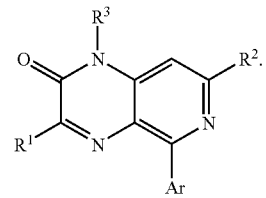

(Ib)

In some embodiments according to the first aspect, compounds of Formula (I) include those where Ar is aryl. Aryl can be, for example, phenyl substituted with 0 to 5 substituents or naphthyl substituted with 0 to 7 substituents. Example substituents include C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, C$_1$–C$_4$ haloalkyl, C$_1$–C$_4$ haloalkoxy, halogen, CN, NO$_2$, OR$^5$, and SR$^5$.

In other embodiments according to the first aspect, the present invention includes compounds wherein Ar is heteroaryl, including for example, heteroaryl groups having six-membered or five-membered rings. Example heteroaryl groups include pyridyl or pyrimidinyl. In some embodiments, the heteroaryl group is substituted with 0 to 4 substituents such as, for example, C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, C$_1$–C$_4$ haloalkyl, C$_1$–C$_4$ haloalkoxy, halogen, CN, NO$_2$, OR$^5$, and SR$^5$. Other example heteroaryl groups include oxazolyl, isoxazolyl, or thienyl. According to such embodiments, the heteroaryl group can be substituted with 0 to 4 substituents such as, for example, C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, C$_1$–C$_4$ haloalkyl, C$_1$–C$_4$ haloalkoxy, halogen, CN, NO$_2$, OR$^5$, and SR$^5$.

In some embodiments according to the first aspect, the present invention includes compounds of Formula (I) where R$^1$ is H, CN, OH, C$_1$–C$_4$ alkyl, or C$_1$–C$_2$ haloalkyl. In other embodiments, R$^1$ can be C$_1$–C$_4$ alkyl.

In further embodiments according to the first aspect, the present invention includes compounds of Formula (I) where R$^2$ is H, CN, OH, SH, OR$^{2b}$, SR$^{2b}$, C$_1$–C$_3$ haloalkyl, or C$_1$–C$_4$ alkyl substituted with 0 to 3 R$^{2a}$. In other embodiments, R$^2$ can be H.

In yet further embodiments according to the first aspect, the present invention includes compounds of Formula (I) where R$^3$ is S(O)R$^8$, S(O)$_2$R$^8$, COR$^{3c}$, CONHR$^{3c}$, CONR$^{3c}$R$^{3d}$, C$_1$–C$_8$ alkyl substituted with 0 to 3 R$^{3a}$, C$_3$–C$_8$ alkenyl substituted with 0 to 3 R$^{3a}$, C$_3$–C$_8$ alkynyl substituted with 0 to 3 R$^{3a}$, C$_3$–C$_6$ cycloalkyl substituted with 0 to 3 R$^{3a}$, or C$_4$–C$_{10}$ cycloalkylalkyl substituted with 0 to 3 R$^{3a}$. In some embodiments, one carbon in any cycloalkyl moiety can be optionally replaced with O, S or NR$^5$.

According to some embodiments according to the first aspect, compounds of Formula (I) can include those where R$^3$ is C$_1$–C$_6$ alkyl substituted with 0 to 2 R$^{3a}$. In yet further embodiments, R$^{3a}$ can be, for example, methyl, ethyl, propyl, cyclopropyl, cyclobutyl, F, Cl, Br, CF$_3$, CN, C$_1$–C$_{10}$ alkyl, $C_2$–$C_{10}$ alkenyl, $OR^{3c}$, $SR^{3c}$, $COR^{3b}$, $NHR^{3c}SO_2R^{3b}$, $OC(O)NR^{3c}R^{3d}$, $N_3$, $OC(O)OR^{3b}$, $CO_2R^{3c}$, $OC(O)R^{3b}$, $NR^{3c}COR^{3b}$, $N(COR^{3b})_2$, $NR^{3c}CONR^{3c}R^{3d}$, $NR^{3c}CO_2R^{3b}$, $NR^{3c}R^{3d}$, or $CONR^{3c}R^{3d}$.

According to further embodiments, the present invention includes compounds of Formula (I) where $R^4$ is H, CN, OH, $C_1$–$C_4$ alkyl, $C_1$–$C_3$ haloalkyl, $SR^{4c}$, or $OR^{4c}$. According to some embodiments, $R^4$ can be H.

In a second aspect, the present invention includes compounds of Formula (I) wherein:

A is $CR^4$ or N;

Ar is aryl or heteroaryl, wherein the aryl or heteroaryl is optionally substituted by one or more substituents independently selected from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $SR^5$;

$R^1$ is H, CN, OH, SH, $C_1$–$C_4$ haloalkyl, methoxy, ethoxy, cyclopropyl, cyclobutyl, cyclopropylmethyl, cyclopropylethyl, cyclobutylmethyl, cyclobutylethyl, $C_1$–$C_4$ alkyl substituted with 0 to 3 $R^{1a}$, $C_2$–$C_4$ alkenyl substituted with 0 to 3 $R^{1a}$, or $C_2$–$C_4$ alkynyl substituted with 0 to 3 $R^{1a}$;

$R^{1a}$ is F, Cl, Br, CN, $NO_2$, OH, methyl, ethyl, $OCH_3$, $CF_3$, $CHF_2$, or $OCF_3$;

$R^2$ is H, CN, OH, $NR^{2c}R^{2d}$, $C_1$–$C_3$ alkyl substituted with 0 to 3 $R^{2a}$, $C_1$–$C_3$ alkoxy, $C_1$–$C_2$ haloalkyl, or $C_1$–$C_2$ haloalkoxy;

$R^3$ is $SOR^8$, $SO_2R^8$, $SO_2NR^{3c}R^{3d}$, $COR^{3c}$, $CONHR^{3c}$, $CONR^{3c}R^{3d}$, aryl substituted with 0 to 3 $R^{3a}$, heteroaryl substituted with 0 to 3 $R^{3a}$, heterocyclyl substituted with 0 to 3 $R^{3f}$, $C_1$–$C_{10}$ alkyl substituted with 0 to 3 $R^{3a}$, $C_3$–$C_{10}$ alkenyl substituted with 0 to 3 $R^{3a}$, $C_3$–$C_{10}$ alkynyl substituted with 0 to 3 $R^{3a}$, $C_3$–$C_8$ cycloalkyl substituted with 0 to 3 $R^{3a}$, $C_4$–$C_{12}$ cycloalkylalkyl substituted with 0 to 3 $R^{3a}$, $C_2$–$C_{10}$ alkoxyalkyl substituted with 0 to 3 $R^{3a}$, $C_2$–$C_{10}$ thioalkoxyalkyl substituted with 0 to 3 $R^{3a}$, $C_5$–$C_{10}$ cycloalkenyl substituted with 0 to 3 $R^{3a}$, or $C_6$–$C_{10}$ cycloalkenylalkyl substituted with 0 to 3 $R^{3a}$, wherein one carbon in any cycloalkyl moiety is optionally replaced with O, S or $NR^5$;

$R^4$ is H, halogen, CN, $C_1$–$C_3$ haloalkyl, $OR^{4c}$, $SR^{4c}$, $NR^{4c}R^{4d}$, $CO_2R^{4b}$, $C_1$–$C_4$ alkyl substituted with 0 to 1 $R^{4a}$, or $C_3$–$C_6$ cycloalkyl substituted with 0 to 1 $R^{4a}$;

each $R^{4a}$ is, independently at each occurrence, halogen, CN, $CF_3$, $OR^{4c}$, $NHR^{4c}$, $NR^{4c}R^{4d}$, $NR^{4c}CO_2R^{4b}$, $SR^{4c}$, $SOR^8$, $SO_2R^8$, $CO_2R^{4b}$, $CONHR^{4c}$, $CONR^{4c}R^{4d}$, $COR^{4b}$, $OCOR^{4b}$, $NR^{4c}CONR^{4c}R^{4d}$, $NR^{4c}CO_2R^{4b}$, $OCONR^{4c}R^{4d}$;

each $R^{4b}$ is, independently at each occurrence, $C_1$–$C_4$ alkyl, $C_1$–$C_4$ haloalkyl, $C_3$–$C_6$ cycloalkyl, $C_4$–$C_{12}$ cycloalkylalkyl, aryl, heteroaryl, aryl-$C_1$–$C_4$ alkyl, or heteroaryl-$C_1$–$C_4$ alkyl;

each $R^{4c}$ is, independently at each occurrence, H, $C_1$–$C_4$ alkyl, $C_1$–$C_4$ haloalkyl, $C_3$–$C_6$ cycloalkyl, $C_4$–$C_{12}$ cycloalkylalkyl, aryl, heteroaryl, aryl-$C_1$–$C_4$ alkyl, or heteroaryl-$C_1$–$C_4$ alkyl;

each $R^{4d}$ is, independently at each occurrence, H, $C_1$–$C_4$ alkyl, $C_1$–$C_4$ haloalkyl, $C_3$–$C_6$ cycloalkyl, $C_4$–$C_{12}$ cycloalkylalkyl, aryl, heteroaryl, aryl-$C_1$–$C_4$ alkyl, or heteroaryl-$C_1$–$C_4$ alkyl;

$R^5$ is H, $C_1$–$C_4$ alkyl, $C_1$–$C_4$ haloalkyl, $C_3$–$C_6$ cycloalkyl, $C_4$–$C_7$ cycloalkylalkyl, or $C_2$–$C_6$ alkoxyalkyl;

each $R^{7a}$ is, independently at each occurrence, H, $C_1$–$C_6$ alkyl, $C_1$–$C_6$ haloalkyl, $C_3$–$C_6$ cycloalkyl, $C_4$–$C_{12}$ cycloalkylalkyl, or $C_2$–$C_8$ alkoxyalkyl;

each $R^{7b}$ is, independently at each occurrence, H, $C_1$–$C_6$ alkyl, $C_1$–$C_6$ haloalkyl, $C_3$–$C_6$ cycloalkyl, $C_4$–$C_{12}$ cycloalkylalkyl, or $C_2$–$C_8$ alkoxyalkyl; and $R^8$ is $C_1$–$C_4$ alkyl, $C_1$–$C_4$ haloalkyl, $C_3$–$C_6$ cycloalkyl, $C_4$–$C_{12}$ cycloalkylalkyl, aryl, heteroaryl, aryl-$C_1$–$C_4$ alkyl, or heteroaryl-$C_1$–$C_4$ alkyl, or $NR^{7a}R^{7b}$. Remaining variables can be defined as described above in the first aspect of the invention.

In some embodiments according to the second and first aspects of the invention, A can be N or A can be $CR^4$.

In further embodiments according to the second and first aspects of the invention, $R^1$ can be H, CN, OH, $C_1$–$C_4$ alkyl, or $C_1$–$C_2$ haloalkyl.

In yet further embodiments according to the second and first aspects of the invention, $R^2$ can be H, CN, OH, methyl, ethyl, methoxy, $OCF_3$, $CF_3$, $CHF_2$, $CH_2CF_3$, or $CF_2CH_3$. In other embodiments, $R^2$ can be H.

In yet further embodiments according to the second and first aspects of the invention, $R^{3e}$ can be $C_1$–$C_6$ alkyl substituted with 0 to 2 $R^{3a}$.

In even further embodiments according to the second and first aspects of the invention, $R^4$ can be H, CN, OH, $C_1$–$C_4$ alkyl, $C_1$–$C_3$ haloalkyl, $SR^{4c}$, or $OR^4$. In other embodiments, $R^4$ can be H.

In still further embodiments according to the second and first aspects of the invention, Ar can be aryl. Aryl, can be, for example, phenyl substituted with 0 to 5 substituents or naphthyl substituted with 0 to 7 substituents. Example substituents can be independently selected from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $S^5$.

In other embodiments according to the second and first aspects of the invention, Ar can be heteroaryl, such as for example a six-membered heteroaryl ring or a five-membered heteroaryl ring. Some example heteroaryl groups include pyridyl or pyrimidinyl. These groups can be substituted with 0 to 4 substituents such as, for example, $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $SR^5$. Other example heteroaryl groups include oxazolyl, isoxazolyl, or thienyl. These groups can be substituted with 0 to 4 substituents such as, for example, $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $SR^5$.

In a third aspect, the present invention includes compounds of Formula (I) wherein:

A is N or $CR^4$;

Ar is phenyl, pyridyl, pyrimidinyl, oxazolyl, isoxazolyl, or thienyl, wherein the phenyl is substituted with 0 to 5 $R^{9a}$ and the pyridyl, pyrimidinyl, oxazolyl, isoxazolyl, or thienyl is substituted with 0 to 4 $R^{9b}$;

$R^1$ is H, CN, methyl, ethyl, methoxy, OH, or $C_1$–$C_2$ haloalkyl;

$R^2$ is H, CN, OH, $CH_3$, $OCH_3$, $CF_3$, $CHF_2$, or $OCF_3$;

$R^3$, is $S(O)R^8$, $S(O)_2R^8$, $COR^{3c}$, $CONHR^{3c}$, $CONR^{3c}R^{3d}$, $C_1$–$C_8$ alkyl substituted with 0 to 3 $R^{3a}$, $C_3$–$C_8$ alkenyl substituted with 0 to 3 $R^{3a}$, $C_3$–$C_8$ alkynyl substituted with 0 to 3 $R^{3a}$, $C_3$–$C_6$ cycloalkyl substituted with 0 to 3 $R^{3a}$, or $C_4$–$C_{10}$ cycloalkylalkyl substituted with 0 to 3 $R^{3a}$, wherein one carbon in any cycloalkyl moiety is optionally replaced with O, S or $NR^5$;

each $R^{3a}$ is, independently at each occurrence, methyl, ethyl, methoxy, ethoxy, thiomethoxy, thioethoxy, cyclopropyl, cyclobutyl, F, Cl, $CF_3$ $CHF_2$, $CH_3$, or $OCF_3$;

R⁴ is H, CHF₂, CF₃, methyl, ethyl, Cl, F, OH, SH, methoxy, thiomethoxy, CH₂CF₃, or CF₂CH₃; and each R⁹ᵃ and R⁹ᵇ is, independently at each occurrence, F, Cl, Br, CN, methyl, ethyl, propyl, methoxy, ethoxy, propoxy, isopropoxy, C₁–C₂ haloalkyl, or C₁–C₂ haloalkoxy. Remaining variables can be defined as recited above according to the second aspect of the invention.

In embodiments according to the first, second, and third aspects, compounds of Formula (I) include those where A is N or A is CR⁴.

In further embodiments according to the first, second, and third aspects, compounds of Formula (I) include those where R² is H.

In yet further embodiments according to the first, second, and third aspects, compounds of Formula (I) include those where R³ is butyl, pentyl, hexyl, heptyl, methoxyethyl, methoxypropyl, methoxybutyl, methoxypentyl, methoxyhexyl, thiomethoxyethyl, thiomethoxypropyl, thiomethoxybutyl, thiomethoxypentyl, thiomethoxyhexyl, 1-cyclopropylpropyl, 1-cyclopropylbutyl, 1-cyclopropylpentyl, 1-cyclobutylpropyl, 1-cyclobutylbutyl, 1-cyclobutylpentyl, 1-cyclopropyl-1-(CF₃)-methyl, 1-cyclopropyl-1-(CF₃)-ethyl, 1-cyclopropyl-1-(CF₃)-propyl, 1-cyclobutyl-1-(CF₃)-methyl, 1-cyclobutyl-2-(CF₃)-ethyl, 1-cyclobutyl-3-(CF₃)-propyl, or (cyclopropyl)₂CH.

In yet further embodiments according to the first, second, and third aspects, compounds of Formula (I) include those wherein R⁴ is H.

In even further embodiments according to the first, second, and third aspects, compounds of Formula (I) include those wherein Ar is phenyl substituted with 0 to 5 R⁹ᵃ. Alternatively, Ar can be pyridyl substituted with 0 to 4 R⁹ᵇ or pyrimidinyl substituted with 0 to 4 R⁹ᵇ.

In a fourth aspect, the present invention includes compounds of Formula (I) wherein:

A is N or CR⁴;

Ar is phenyl substituted with 0 to 3 substituents each independently selected from F, Cl, Br, CN, methyl, ethyl, propyl, methoxy, ethoxy, propoxy, isopropoxy, CF₃, CHF₂, and OCF₃; or Ar is pyridyl or pyrimidinyl substituted with 0 to 2 substituents each independently selected from F, Cl, Br, CN, methyl, ethyl, propyl, methoxy, ethoxy, propoxy, isopropoxy, CF₃, CHF₂, and OCF₃;

R¹ is H, CN, OH, methyl, ethyl, methoxy, or C₁–C₂ haloalkyl;

R² is H;

R³ᵉ is C₁–C₆ alkyl substituted with 0 to 2 R³ᵃ; and

R⁴ is H. Remaining variables can be defined as described above in the third aspect of the invention.

In embodiments according to the above first, second, third, and fourth aspects, Ar can be phenyl substituted with 0 to 3 substituents each independently selected from F, Cl, Br, CN, methyl, ethyl, propyl, methoxy, ethoxy, propoxy, isopropoxy, CF₃, CHF₂, and OCF₃.

In further embodiments according to the above first, second, third, and fourth aspects, Ar can be pyridyl or pyrimidinyl substituted with 0 to 2 substituents each independently selected from F, Cl, Br, CN, methyl, ethyl, propyl, methoxy, ethoxy, propoxy, isopropoxy, CF₃, CHF₂, and OCF₃. In some embodiments, pyridyl can be pyrid-3-yl.

In yet further embodiments according to the above first, second, third, and fourth aspects, A can be N or A can be CR⁴.

In even further embodiments according to the above first, second, and fourth aspects, R³ can be butyl, pentyl, hexyl, heptyl, methoxyethyl, methoxypropyl, methoxybutyl, methoxypentyl, methoxyhexyl, thiomethoxyethyl, thiomethoxypropyl, thiomethoxybutyl, thiomethoxypentyl, thiomethoxyhexyl, 1-cyclopropylpropyl, 1-cyclopropylbutyl, 1-cyclopropylpentyl, 1-cyclobutylpropyl, 1-cyclobutylbutyl, 1-cyclobutylpentyl, 1-cyclopropyl-1-(CF₃)-methyl, 1-cyclopropyl-1-(CF₃)-ethyl, 1-cyclopropyl-1-(CF₃)-propyl, 1-cyclobutyl-1-(CF₃)-methyl, 1-cyclobutyl-2-(CF₃)-ethyl, 1-cyclobutyl-3-(CF₃)-propyl, or (cyclopropyl)₂CH.

In a fifth aspect, the present invention includes the compounds of Formula (Ia):

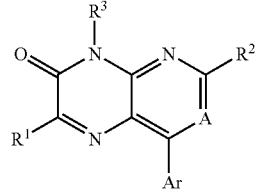

selected from the group consisting of:

(R)-8-(2,4-dichloro-phenyl)-4-isobutyl-2-methyl-4H-pyrido[2,3-b]pyrazin-3-one;
(S)-8-(2,4-dichloro-phenyl)-4-isobutyl-2-methyl-4H-pyrido[2,3-b]pyrazin-3-one;
(R)-8-(2,4-dichloro-phenyl)-2-methyl-4-(1-methyl-butyl)-4H-pyrido[2,3-b]pyrazin-3-one;
(S)-8-(2,4-dichloro-phenyl)-2-methyl-4-(1-methyl-butyl)-4H-pyrido[2,3-b]pyrazin-3-one;
(S)-4-(1-cyclopropyl-propyl)-8-(2,4-dichloro-phenyl)-2-methyl-4H-pyrido[2,3-b]pyrazin-3-one;
(R)-4-(1-cyclopropyl-propyl)-8-(2,4-dichloro-phenyl)-2-methyl-4H-pyrido[2,3-b]pyrazin-3-one;
(R)-8-(2,4-dichloro-phenyl)-4-(1,2-dimethyl-propyl)-2-methyl-4H-pyrido[2,3-b]pyrazin-3-one;
(S)-8-(2,4-dichloro-phenyl)-4-(1,2-dimethyl-propyl)-2-methyl-4H-pyrido[2,3-b]pyrazin-3-one;
(R)-4-(1-cyclopropyl-butyl)-8-(2,4-dichloro-phenyl)-2-methyl-4H-pyrido[2,3-]pyrazin-3-one;
(S)-4-(1-cyclopropyl-butyl)-8-(2,4-dichloro-phenyl)-2-methyl-4H-pyrido[2,3-b]pyrazin-3-one;
(R)-8-(2,4-dichloro-phenyl)-4-(2-methoxy-1-methyl-ethyl)-2-methyl-4H-pyrido[2,3-b]pyrazin-3-one;
(S)-8-(2,4-dichloro-phenyl)-4-(2-methoxy-1-methyl-ethyl)-2-methyl-4H-pyrido[2,3-b]pyrazin-3-one;
(S)-8-(2,4-dichloro-phenyl)-4-(1-methoxymethyl-propyl)-2-methyl-4H-pyrido[2,3-b]pyrazin-3-one;
(R)-8-(2,4-dichloro-phenyl)-4-(1-methoxymethyl-propyl)-2-methyl-4H-pyrido[2,3-b]pyrazin-3-one;
(R,S)-8-(2-chloro-4-methoxy-phenyl)-2-methyl-4-(1-propyl-butyl)-4H-pyrido[2,3-b]pyrazin-3-one;
(S)-8-(2-chloro-4-methoxy-phenyl)-4-(1-cyclopropyl-propyl)-2-methyl-4H-pyrido[2,3-b]pyrazin-3-one;
(R)-8-(2-chloro-4-methoxy-phenyl)-4-(1-cyclopropyl-propyl)-2-methyl-4H-pyrido[2,3-b]pyrazin-3-one;
(R)-8-(2-chloro-4-methoxy-phenyl)-4-(1-cyclobutyl-propyl)-2-methyl-4H-pyrido[2,3-b]pyrazin-3-one;
(S)-8-(2-chloro-4-methoxy-phenyl)-4-(1-cyclobutyl-propyl)-2-methyl-4H-pyrido[2,3-b]pyrazin-3-one;
(S)-8-(2-chloro-4-methoxy-phenyl)-4-(2-methoxy-1-methyl-ethyl)-2-methyl-4H-pyrido[2,3-b]pyrazin-3-one;
(R)-8-(2-chloro-4-methoxy-phenyl)-4-(2-methoxy-1-methyl-ethyl)-2-methyl-4H-pyrido[2,3-b]pyrazin-3-one;
(S)-8-(2-chloro-4-methoxy-phenyl)-4-(1-methoxymethyl-propyl)-2-methyl-4H-pyrido[2,3-b]pyrazin-3-one;

(R)-4-(1-cylcopropropyl-propyl)-8-(4-methoxy-2-methyl-phenyl)-2-methyl-4H-pyrido[2,3-b]pyrazin-3-one;
(R)-4-(1-cyclopropyl-butyl)-8-(4-methoxy-2-methyl-phenyl)-2-methyl-4H-pyrido[2,3-b]pyrazin-3-one;
(S)-4-(1-cyclopropyl-butyl)-8-(4-methoxy-2-methyl-phenyl)-2-methyl-4H-pyrido[2,3-b]pyrazin-3-one;
(R)-4-(2-methoxy-1-methyl-ethyl)-8-(4-methoxy-2-methyl-phenyl)-2-methyl-4H-pyrido[2,3-b]pyrazin-3-one;
(R)-4-(1-ethyl-pentyl)-8-(6-methoxy-2-methyl-pyridin-3-yl)-2-methyl-4H-pyrido[2,3-b]pyrazin-3-one;
(S)-4-(1-ethyl-pentyl)-8-(6-methoxy-2-methyl-pyridin-3-yl)-2-methyl-4H-pyrido[2,3-b]pyrazin-3-one;
(R)-4-(1-cyclopropyl-propyl)-8-(6-methoxy-2-methyl-pyridin-3-yl)-2-methyl-4H-pyrido[2,3-b]pyrazin-3-one;
(R)-4-(1-cyclopropyl-butyl)-8-(6-methoxy-2-methyl-pyridin-3-yl)-2-methyl-4H-pyrido[2,3-b]pyrazin-3-one;
(S)-4-(1-cyclopropyl-butyl)-8-(6-methoxy-2-methyl-pyridin-3-yl)-2-methyl-4H-pyrido[2,3-b]pyrazin-3-one;
(R)-4-(2-methoxy-1-methyl-ethyl)-8-(6-methoxy-2-methyl-pyridyl)-2-methyl-4H-pyrido[2,3-b]pyrazin-3-one;
(R)-4-sec-butyl-8-(2-chloro-4-difluoromethoxy-phenyl)-2-methyl-4H-pyrido[2,3-b]pyrazin-3-one;
(S)-4-(1-cyclopropyl-butyl)-8-(6-methoxy-2-methyl-pyridin-3-yl)-2-methyl-4H-pyrido[2,3-b]pyrazin-3-one;
(S)-8-(2-chloro-4-difluoromethoxy-phenyl)-4-(1-cyclopropyl-propyl)2-methyl-4H-pyrido[2,3-b]pyrazin-3-one;
(R)-8-(2-chloro-4-difluoromethoxy-phenyl)-4-(1-cyclopropyl-propyl)2-methyl-4H-pyrido[2,3-b]pyrazin-3-one;
(R)-8-(2-chloro-4-difluoromethoxy-phenyl)-4-(1-cyclopropyl-butyl)-2-methyl-4H-pyrido[2,3-b]pyrazin-3-one;
(S)-8-(2-chloro-4-difluoromethoxy-phenyl)-4-(1-cyclopropyl-butyl)-2-methyl-4H-pyrido[2,3-b]pyrazin-3-one;
(R)-8-(2-chloro-4-difluoromethoxy-phenyl)-4-(2-methoxy-1-methyl-ethyl)-2-methyl-4H-pyrido[2,3-b]pyrazin-3-one;
(R)-8-(2-chloro-4-difluoromethoxy-phenyl)-4-(1-methoxymethyl-propyl)-2-methyl-4H-pyrido[2,3-b]pyrazin-3-one;
(S)-8-(2-chloro-4-difluoromethoxy-phenyl)-4-(1-methoxymethyl-propyl)-2-methyl-4H-pyrido[2,3-b]pyrazin-3-one;
(S)-8-(2-chloro-4-trifluoromethyl-phenyl)-4-(1-cyclopropyl-propyl)-2-methyl-4H-pyrido[2,3-b]pyrazin-3-one;
(R)-8-(2-chloro-4-trifluoromethyl-phenyl)-4-(2-methoxy-1-methyl-ethyl)-2-methyl-4H-pyrido[2,3-b]pyrazin-3-one;
(R)-8-(2-chloro-4-trifluoromethyl-phenyl)-4-(1-methoxymethyl-propyl)-2-methyl-4H-pyrido[2,3-b]pyrazin-3-one;
(R)-3-chloro-4-(4-(1-methoxymethylpropyl)-2-methyl-3-oxo-3,4-dihydro-pyrido[2,3-b]pyrazin-8-yl]-benzonitrile;
(R)-8-sec-butyl-4-(2,4-dichloro-phenyl)-6-methyl-8H-pteridin-7-one; and
(S)-8-sec-butyl-4-(2,4-dichloro-phenyl)-6-methyl-8H-pteridin-7-one.

In a sixth aspect of the invention, there are provided compounds of Formula (Ib):

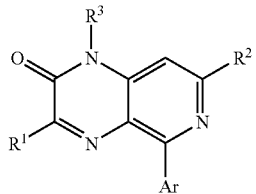

(Ib)

selected from the group consisting of:
(R)-5-(2,4-Dichloro-phenyl)-1-isobutyl-3-methyl-1H-pyrido[3,4-b]pyrazin-2-one;
(S)-5-(2,4-Dichloro-phenyl)-1-isobutyl-3-methyl-1H-pyrido[3,4-b]pyrazin-2-one;
(R)-1-(1-Cyclopropyl-propyl)-5-(2,4-dichloro-phenyl)-3-methyl-1H-pyrido[3,4-b]pyrazin-2-one;
(S)-1-(1-Cyclopropyl-propyl)-5-(2,4-dichloro-phenyl)-3-methyl-1H-pyrido[3,4-b]pyrazin-2-one;
(R)-5-(2,4-Dichloro-phenyl)-1-(1-methoxymethyl-propyl)-3-methyl-1H-pyrido[3,4-b]pyrazin-2-one;
(S)-5-(2,4-Dichloro-phenyl)-1-(1-methoxymethyl-propyl)-3-methyl-1H-pyrido[3,4-b]pyrazin-2-one;
(R)-5-(2,4-Dichloro-phenyl)-1-(2-methoxy-1-methyl-ethyl)-3-methyl-1H-pyrido[3,4-b]pyrazin-2-one;
(S)-5-(2,4-Dichloro-phenyl)-1-(2-methoxy-1-methyl-ethyl)-3-methyl-1H-pyrido[3,4-b]pyrazin-2-one;
(R)-1-(1-Cyclopropyl-2-methoxy-ethyl)-5-(2,4-dichloro-phenyl)-3-methyl-1H-pyrido[3,4-b]pyrazin-2-one;
(S)-1-(1-Cyclopropyl-2-methoxy-ethyl)-5-(2,4-dichloro-phenyl)-3-methyl-1H-pyrido[3,4-b]pyrazin-2-one;
(R)-1-(1-Cyclobutyl-ethyl)-5-(2,4-dichloro-phenyl)-3-methyl-1H-pyrido[3,4-b]pyrazin-2-one;
(S)-1-(1-Cyclobutyl-ethyl)-5-(2,4-dichloro-phenyl)-3-methyl-1H-pyrido[3,4-b]pyrazin-2-one;
(R)-1-(1-Cyclobutyl-propyl)-5-(2,4-dichloro-phenyl)-3-methyl-1H-pyrido[3,4-b]pyrazin-2-one;
(S)-1-(1-Cyclobutyl-propyl)-5-(2,4-dichloro-phenyl)-3-methyl-1H-pyrido[3,4-b]pyrazin-2-one;
(R)-5-(2-Chloro-5-fluoro-4-methoxy-phenyl)-1-(1-cyclopropyl-ethyl)-3-methyl-1H-pyrido[3,4-b]pyrazin-2-one;
(S)-5-(2-Chloro-5-fluoro-4-methoxy-phenyl)-1-(1-cyclopropyl-ethyl)-3-methyl-1H-pyrido[3,4-b]pyrazin-2-one;
(R)-5-(2-Chloro-5-fluoro-4-methoxy-phenyl)-1-(1-cyclopropyl-propyl)-3-methyl-1H-pyrido[3,4-b]pyrazin-2-one;
(S)-5-(2-Chloro-5-fluoro-4-methoxy-phenyl)-1-(1-cyclopropyl-propyl)-3-methyl-1H-pyrido[3,4-b]pyrazin-2-one;
(R)-5-(2-Chloro-5-fluoro-4-methoxy-phenyl)-1-(2-methoxy-1-methyl-ethyl)-3-methyl-1H-pyrido[3,4-b]pyrazin-2-one;
(S)-5-(2-Chloro-5-fluoro-4-methoxy-phenyl)-1-(2-methoxy-1-methyl-ethyl)-3-methyl-1H-pyrido[3,4-b]pyrazin-2-one;
(R)-5-(2-Chloro-5-fluoro-4-methoxy-phenyl)-1-(1-methoxymethyl-propyl)-3-methyl-1H-pyrido[3,4-b]pyrazin-2-one;
(S)-5-(2-Chloro-5-fluoro-4-methoxy-phenyl)-1-(1-methoxymethyl-propyl)-3-methyl-1H-pyrido[3,4-b]pyrazin-2-one;
(R)-5-(2-Chloro-5-fluoro-4-methoxy-phenyl)-1-(1-cyclopropyl-2-methoxy-ethyl)-3-methyl-1H-pyrido[3,4-b]pyrazin-2-one;
(S)-5-(2-Chloro-5-fluoro-4-methoxy-phenyl)-1-(1-cyclopropyl-2-methoxy-ethyl)-3-methyl-1H-pyrido[3,4-b]pyrazin-2-one;
(R)-5-(2-Chloro-5-fluoro-4-methoxy-phenyl)-1-(1-cyclobutyl-ethyl)-3-methyl-1H-pyrido[3,4-b]pyrazin-2-one;
(S)-5-(2-Chloro-5-fluoro-4-methoxy-phenyl)-1-(1-cyclobutyl-ethyl)-3-methyl-1H-pyrido[3,4-b]pyrazin-2-one;
(R)-5-(2-Chloro-5-fluoro-4-methoxy-phenyl)-1-(1-cyclobutyl-propyl)-3-methyl-1H-pyrido[3,4-b]pyrazin-2-one;
(S)-5-(2-Chloro-5-fluoro-4-methoxy-phenyl)-1-(1-cyclobutyl-propyl)-3-methyl-1H-pyrido[3,4-b]pyrazin-2-one;
(R)-1-(1-Cyclopropyl-ethyl)-5-(6-methoxy-2-methyl-pyridin-3-yl)-3-methyl-1H-pyrido[3,4-b]pyrazin-2-one;
(S)-1-(1-Cyclopropyl-ethyl)-5-(6-methoxy-2-methyl-pyridin-3-yl)-3-methyl-1H-pyrido[3,4-b]pyrazin-2-one;

(R)-1-(1-Cyclopropyl-propyl)-5-(6-methoxy-2-methyl-pyridin-3-yl)-3-methyl-1H-pyrido[3,4-b]pyrazin-2-one;
(S)-1-(1-Cyclopropyl-propyl)-5-(6-methoxy-2-methyl-pyridin-3-yl)-3-methyl-1H-pyrido[3,4-b]pyrazin-2-one;
(R)-1-(2-Methoxy-1-methyl-ethyl)-5-(6-methoxy-2-methyl-pyridin-3-yl)-3-methyl-1H-pyrido[3,4-b]pyrazin-2-one;
(S)-1-(2-Methoxy-1-methyl-ethyl)-5-(6-methoxy-2-methyl-pyridin-3-yl)-3-methyl-1H-pyrido[3,4-b]pyrazin-2-one;
(R)-1-(1-Methoxymethyl-propyl)-5-(6-methoxy-2-methyl-pyridin-3-yl)-3-methyl-1H-pyrido[3,4-b]pyrazin-2-one;
(S)-1-(1-Methoxymethyl-propyl)-5-(6-methoxy-2-methyl-pyridin-3-yl)-3-methyl-1H-pyrido[3,4-b]pyrazin-2-one;
(R)-1-(1-Cyclopropyl-2-methoxy-ethyl)-5-(6-methoxy-2-methyl-pyridin-3-yl)-3-methyl-1H-pyrido[3,4-b]pyrazin-2-one;
(S)-1-(1-Cyclopropyl-2-methoxy-ethyl)-5-(6-methoxy-2-methyl-pyridin-3-yl)-3-methyl-1H-pyrido[3,4-b]pyrazin-2-one;
(R)-1-(1-Cyclobutyl-ethyl)-5-(6-methoxy-2-methyl-pyridin-3-yl)-3-methyl-1H-pyrido[3,4-b]pyrazin-2-one;
(S)-1-(1-Cyclobutyl-ethyl)-5-(6-methoxy-2-methyl-pyridin-3-yl)-3-methyl-1H-pyrido[3,4-b]pyrazin-2-one;
(R)-1-(1-Cyclobutyl-propyl)-5-(6-methoxy-2-methyl-pyridin-3-yl)-3-methyl-1H-pyrido[3,4-b]pyrazin-2-one;
(S)-1-(1-Cyclobutyl-propyl)-5-(6-methoxy-2-methyl-pyridin-3-yl)-3-methyl-1H-pyrido[3,4-b]pyrazin-2-one;
(R)-1-(1-Cyclopropyl-ethyl)-5-(6-methoxy-2,5-dimethyl-pyridin-3-yl)-3-methyl-1H-pyrido[3,4-b]pyrazin-2-one;
(S)-1-(1-Cyclopropyl-ethyl)-5-(6-methoxy-2,5-dimethyl-pyridin-3-yl)-3-methyl-1H-pyrido[3,4-b]pyrazin-2-one;
(R)-1-(1-Cyclopropyl-propyl)-5-(6-methoxy-2,5-dimethyl-pyridin-3-yl)-3-methyl-1H-pyrido[3,4-b]pyrazin-2-one;
(S)-1-(1-Cyclopropyl-propyl)-5-(6-methoxy-2,5-dimethyl-pyridin-3-yl)-3-methyl-1H-pyrido[3,4-b]pyrazin-2-one;
(R)-5-(6-Methoxy-2,5-dimethyl-pyridin-3-yl)-1-(2-methoxy-1-methyl-ethyl)-3-methyl-1H-pyrido[3,4-b]pyrazin-2-one;
(S)-5-(6-Methoxy-2,5-dimethyl-pyridin-3-yl)-1-(2-methoxy-1-methyl-ethyl)-3-methyl-1H-pyrido[3,4-b]pyrazin-2-one;
(R)-5-(6-Methoxy-2,5-dimethyl-pyridin-3-yl)-1-(1-methoxymethyl-propyl)-3-methyl-1H-pyrido[3,4-b]pyrazin-2-one;
(S)-5-(6-Methoxy-2,5-dimethyl-pyridin-3-yl)-1-(1-methoxymethyl-propyl)-3-methyl-1H-pyrido[3,4-b]pyrazin-2-one;
(R)-1-(-Cyclopropyl-2-methoxy-ethyl)-5-(6-methoxy-2,5-dimethyl-pyridin-3-yl)-3-methyl-1H-pyrido[3,4-b]pyrazin-2-one;
(S)-1-(1-Cyclopropyl-2-methoxy-ethyl)-5-(6-methoxy-2,5-dimethyl-pyridin-3-yl)-3-methyl-1H-pyrido[3,4-b]pyrazin-2-one;
(R)-1-(1-Cyclobutyl-ethyl)-5-(6-methoxy-2,5-dimethyl-pyridin-3-yl)-3-methyl-1H-pyrido[3,4-b]pyrazin-2-one;
(S)-1-(1-Cyclobutyl-ethyl)-5-(6-methoxy-2,5-dimethyl-pyridin-3-yl)-3-methyl-1H-pyrido[3,4-b]pyrazin-2-one;
(R)-1-(1-Cyclobutyl-propyl)-5-(6-methoxy-2,5-dimethyl-pyridin-3-yl)-3-methyl-1H-pyrido[3,4-b]pyrazin-2-one;
(S)-1-(1-Cyclobutyl-propyl)-5-(6-methoxy-2,5-dimethyl-pyridin-3-yl)-3-methyl-1H-pyrido[3,4-b]pyrazin-2-one;
(R)-1-(1-Cyclopropyl-ethyl)-5-(4-methoxy-2,5-dimethyl-phenyl)-3-methyl-1H-pyrido[3,4-b]pyrazin-2-one;
(S)-1-(1-Cyclopropyl-ethyl)-5-(4-methoxy-2,5-dimethyl-phenyl)-3-methyl-1H-pyrido[3,4-b]pyrazin-2-one;
(R)-1-(1-Cyclopropyl-propyl)-5-(4-methoxy-2,5-dimethyl-phenyl)-3-methyl-1H-pyrido[3,4-b]pyrazin-2-one;
(S)-1-(1-Cyclopropyl-propyl)-5-(4-methoxy-2,5-dimethyl-phenyl)-3-methyl-1H-pyrido[3,4-b]pyrazin-2-one;
(R)-5-(4-Methoxy-2,5-dimethyl-phenyl)-1-(2-methoxy-1-methyl-ethyl)-3-methyl-1H-pyrido[3,4-b]pyrazin-2-one;
(S)-5-(4-Methoxy-2,5-dimethyl-phenyl)-1-(2-methoxy-1-methyl-ethyl)-3-methyl-1H-pyrido[3,4-b]pyrazin-2-one;
(R)-5-(4-Methoxy-2,5-dimethyl-phenyl)-1-(1-methoxymethyl-propyl)-3-methyl-1H-pyrido[3,4-b]pyrazin-2-one;
(S)-5-(4-Methoxy-2,5-dimethyl-phenyl)-1-(1-methoxymethyl-propyl)-3-methyl-1H-pyrido[3,4-b]pyrazin-2-one;
(R)-1-(1-Cyclopropyl-2-methoxy-ethyl)-5-(4-methoxy-2,5-dimethyl-phenyl)-3-methyl-1H-pyrido[3,4-b]pyrazin-2-one;
(S)-1-(1-Cyclopropyl-2-methoxy-ethyl)-5-(4-methoxy-2,5-dimethyl-phenyl)-3-methyl-1H-pyrido[3,4-b]pyrazin-2-one;
(R)-1-(1-Cyclobutyl-ethyl)-5-(4-methoxy-2,5-dimethyl-phenyl)-3-methyl-1H-pyrido[3,4-b]pyrazin-2-one;
(S)-1-(1-Cyclobutyl-ethyl)-5-(4-methoxy-2,5-dimethyl-phenyl)-3-methyl-1H-pyrido[3,4-b]pyrazin-2-one;
(R)-1-(1-Cyclobutyl-propyl)-5-(4-methoxy-2,5-dimethyl-phenyl)-3-methyl-1H-pyrido[3,4-b]pyrazin-2-one;
(S)-1-(1-Cyclobutyl-propyl)-5-(4-methoxy-2,5-dimethyl-phenyl)-3-methyl-1H-pyrido[3,4-b]pyrazin-2-one;
(R)-1-(1-Cyclopropyl-ethyl)-5-(2,4-dimethoxy-pyrimidin-5-yl)-3-methyl-1H-pyrido[3,4-b]pyrazin-2-one;
(S)-1-(1-Cyclopropyl-ethyl)-5-(2,4-dimethoxy-pyrimidin-5-yl)-3-methyl-1H-pyrido[3,4-b]pyrazin-2-one;
(R)-1-(1-Cyclopropyl-propyl)-5-(2,4-dimethoxy-pyrimidin-5-yl)-3-methyl-1H-pyrido[3,4-b]pyrazin-2-one;
(S)-1-(1-Cyclopropyl-propyl)-5-(2,4-dimethoxy-pyrimidin-5-yl)-3-methyl-1H-pyrido[3,4-b]pyrazin-2-one;
(R)-5-(2,4-Dimethoxy-pyrimidin-5-yl)-1-(2-methoxy-1-methyl-ethyl)-3-methyl-1H-pyrido[3,4-b]pyrazin-2-one;
(S)-5-(2,4-Dimethoxy-pyrimidin-5-yl)-1-(2-methoxy-1-methyl-ethyl)-3-methyl-1H-pyrido[3,4-b]pyrazin-2-one;
(R)-5-(2,4-Dimethoxy-pyrimidin-5-yl)-1-(1-methoxymethyl-propyl)-3-methyl-1H-pyrido[3,4-b]pyrazin-2-one;
(S)-5-(2,4-Dimethoxy-pyrimidin-5-yl)-1-(1-methoxymethyl-propyl)-3-methyl-1H-pyrido[3,4-b]pyrazin-2-one;
(R)-1-(1-Cyclopropyl-2-methoxy-ethyl)-5-(2,4-dimethoxy-pyrimidin-5-yl)-3-methyl-1H-pyrido[3,4-b]pyrazin-2-one;
(S)-1-(1-Cyclopropyl-2-methoxy-ethyl)-5-(2,4-dimethoxy-pyrimidin-5-yl)-3-methyl-1H-pyrido[3,4-b]pyrazin-2-one;
(R)-1-(1-Cyclobutyl-ethyl)-5-(2,4-dimethoxy-pyrimidin-5-yl)-3-methyl-1H-pyrido[3,4-b]pyrazin-2-one;
(S)-1-(1-Cyclobutyl-ethyl)-5-(2,4-dimethoxy-pyrimidin-5-yl)-3-methyl-1H-pyrido[3,4-b]pyrazin-2-one;
(R)-1-(1-Cyclobutyl-propyl)-5-(2,4-dimethoxy-pyrimidin-5-yl)-3-methyl-1H-pyrido[3,4-b]pyrazin-2-one;
(S)-1-(1-Cyclobutyl-propyl)-5-(2,4-dimethoxy-pyrimidin-5-yl)-3-methyl-1H-pyrido[3,4-b]pyrazin-2-one.

Compounds of this invention can have one or more asymmetric centers. Unless otherwise indicated, all chiral (enantiomeric and diastereomeric) and racemic forms of compounds of Formula (I) are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" as used herein is meant to refer to a saturated hydrocarbon group which is straight-chained, branched or cyclized ("cycloalkyl"). Alkyl groups can be unsubstituted or substituted so that one or more of its hydrogens are replaced by another chemical group. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), cyclopentyl, cyclohexyl, norbornyl, and the like. "Alkenyl" refers to alkyl groups having one or more double carbon-carbon bonds. Example alkenyl groups include ethenyl, propenyl, cyclohexenyl, and the like. "Alkynyl" refers to alkyl groups having one or more triple carbon-carbon bonds. Example alkynyl groups include ethynyl, propynyl, and the like. "Haloalkyl" refers to branched, straight-chained, and cyclyl alkyl groups having one or more halogen substituents. Example haloalkyl groups include $CF_3$, $C_2F_5$, $CHF_2$, $CCl_3$, $CHCl_2$, $C_2Cl_5$, and the like. The term "alkoxy" refers to an —O-alkyl group. Example alkoxy groups include, methoxy, ethoxy, propoxy (e.g., n-propoxy and isopropoxy), t-butoxy, and the like. The term "cycloalkyl" refers to cyclized alkyl groups, including mono-, bi- or poly-cyclic ring systems. Example cycloalkyl groups include cyclopropyl, cyclobutyl, cyclopentyl, cyclohexyl, and so forth. "Halo" or "halogen" includes fluoro, chloro, bromo, and iodo.

"Aryl" groups refer to monocyclic or polycyclic aromatic hydrocarbons, including, for example, phenyl, naphthyl, anthracenyl, phenanthrenyl, indanyl, indenyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

"Heteroaryl" groups are monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like. Heteroaryl groups can be substituted or unsubstituted.

"Heterocyclyl" groups can be saturated (i.e., containing no double or triple bonds) or unsaturated (i.e., containing one or more double or triple bonds) carbocyclyl groups wherein one or more of the ring-forming carbon atoms of the carbocyclyl group is replaced by a heteroatom such as O, S, or N. Heterocyclyl groups can be substituted or unsubstituted. Examples of heterocyclyl groups include morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, and the like. Some example heterocyclyl substituents can include $C_1$–$C_6$ alkyl, $C_3$–$C_6$ cycloalkyl, $C_2$–$C_6$ alkenyl, $C_2$–$C_6$ alkynyl, halogen, $C_1$–$C_4$ haloalkyl, CN, $OR^7$, SH, $NO_2$, $OCF_3$, $S(O)_nR^7$, $COR^7$, $CO_2R^7$, $OC(O)R^7$, $NR^7COR^8$, $N(COR^7)_2$, $NR^7CONR^7R^8$, $NR^7CO_2R^8$, $NR^7R^8$, or $CONR^7R^8$, wherein $R^7$ and $R^8$ are as defined above according to the first aspect of the invention. Heterocyclyl groups can be substituted with any number of substituents such as, for example, 0 to 7, 0 to 6, 0 to 5, 0 to 4, 0 to 3, 0 to 2, or 0 to 1 substituents.

As referred to herein, the term "substituted" means that one or more hydrogen atoms is replaced with a non-hydrogen group, provided that normal valencies are maintained and that the substitution results in a stable compound.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Prodrugs" refer to inactive compounds that can be converted upon absorption by a mammalian subject to an active compound of Formula (I). Prodrugs of the compounds of Formula (I) can be prepared by modifying functional groups present in the compounds of Formula (I) in such a way that the modifications are cleaved in vivo to produce the parent compounds. Examples of prodrugs include, but are not limited to, acetate, formate and benzoate derivatives of alcohol and amine functional groups in the compounds of Formula (I). Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of Formula I, i.e., wherein one or more of the atoms described are replaced by a radioactive isotope of that atom (e.g., C replaced by $^{14}C$ or by $^{11}C$, and H replaced by $^3H$ or $^{18}F$), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

The present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

The present invention further includes methods of reducing symptoms caused by elevated levels of corticotropin releasing factor in a mammal comprising administering to the mammal a therapeutically effective amount of a compound of Formula (I).

The present invention further includes methods of treating stress-related symptoms in a mammal comprising administering to the mammal a therapeutically effective amount of a compound of Formula (I).

The present invention also includes methods of treating a disorder characterized by abnormal levels of corticotropin releasing factor in a mammal comprising administering to the mammal a therapeutically effective amount of a compound of Formula (I). According to some embodiments, the disorder can be characterized by elevated levels of corticotropin releasing factor. In some embodiments, the disorder affects the central nervous system. Some example disorders that can be treated according to the methods described herein include anxiety or depression. In some embodiments, the treatable disorder is irritable bowel syndrome.

Some disorders characterized by abnormal levels of corticotropin releasing factor include the following disorders: mood disorders such as depression, including major depression, single episode depression, recurrent depression, child abuse induced depression, seasonal affective disorder, postpartum depression, dysthemia, bipolar disorders, and cyclothymia; anxiety disorders including panic, phobias, obsessive-compulsive disorder; post-traumatic stress disorder; and sleep disorders induced by stress; inflammation; pain; chronic fatigue syndrome; stress-induced headache; cancer; human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ileus, and colonic hypersensitivity associated by psychopathological disturbances or stress; eating disorders such as anorexia and bulimia nervosa; supranuclear palsy; amyotrophic lateral sclerosis; immune suppression; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular disorders including hypertension, tachycardia and congestive heart failure; stroke; immune dysfunctions including stress-induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism; hypoglycemia; hair loss; abnormal circadian rhythm; and disorders related to abnormal circadian rhythm such as time zone change syndrome, seasonal affective disorder, irregular sleep-wake pattern, delayed sleep phase syndrome, advanced sleep phase syndrome, non-24 hour sleep wake disorder, light-induced clock resetting, REM sleep disorder, hypersomnia, parasomnia, narcolepsy, nocturnal enuresis, restless legs syndrome, sleep apnea, dysthymia, and abnormal circadian rhythm associated with chronic administration and withdrawal of antidepressant agents. Thus, the compounds provided herein, because of their antagonism of CRF receptors, are expected to be useful in treating these and other disorders.

The term "therapeutically effective amount" refers to an amount of compound effective to reduce or eliminate at least one symptom of a disorder that the compound was used to treat.

Compounds of this invention can be administered to treat the above disorders by any suitable means that allows the compound to contact the compound's site of action, such as a CRF receptor, in the body of a mammal. The compounds can be administered by any conventional means available for use in conjunction with pharmaceuticals either as an individual therapeutic agent or in combination with other therapeutic agents. Compounds of the present invention can be administered alone, or in combination with a pharmaceutical carrier selected on the basis of the chosen route of administration and standard pharmaceutical practice.

The dosage of compound administered varies depending on several factors such as the pharmacodynamic character of the particular compound, and its mode and route of administration; the recipient's age, weight, and health; nature and extent of symptoms; kind of concurrent treatment; frequency of treatment; and desired effect. For use in the treatment of the above diseases or conditions, the compounds of this invention can be orally administered daily at a dosage of the active ingredient (e.g., a compound of Formula I) of about 0.002 to about 200 mg/kg of body weight. For example, a dose of about 0.01 to about 10 mg/kg can be divided into smaller doses and administered one to four times a day. Alternatively, sustained release formulations can be effective in obtaining the desired pharmacological effect.

Dosage forms (compositions) suitable for administration can contain from about 1 mg to about 100 mg of active ingredient per dosage unit. In these pharmaceutical compositions, the active ingredient (e.g., a compound of Formula I) can be present in an amount of about 0.5 to 95% by weight based on the total weight of the composition.

The active ingredient (e.g., a compound of Formula I) can be administered orally in solid dosage forms such as capsules, tablets and powders, or in liquid forms such as elixirs, syrups, and/or suspensions. The compounds of this invention can also be administered parenterally in sterile liquid dose formulations.

Gelatin capsules can be used to contain the active ingredient and a suitable carrier such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can also contain coloring or flavoring agents to increase patient acceptance.

Typically, water, pharmaceutically acceptable oils, saline, aqueous dextrose, and related sugar solutions and glycols, such as propylene glycol or polyethylene glycol, are suitable carriers for parenteral solutions. Solutions for parenteral administration can contain, for example, a water soluble salt of the active ingredient and suitable stabilizing agents. Antioxidizing agents, such as sodium bisulfite, sodium sulfite, or ascorbic acid, either alone or in combination, can act as suitable stabilizing agents. Also suitable as stabilizing agents are citric acid and its salts, and EDTA. In addition, parenteral solutions can contain preservatives such as, for example, benzalkonium chloride, methyl- or propyl-paraben, and chlorobutanol.

The compounds of this invention may also be used as reagents or standards in the biochemical study of neurological function, dysfunction, and disease.

Compounds of Formula (I) can be prepared by the following synthetic routes and schemes. Where a detailed description is not provided, it is assumed that those skilled in the art of organic synthesis will readily understand the meaning.

Compounds of Formula (I) can be prepared according to the route shown in Scheme 1.

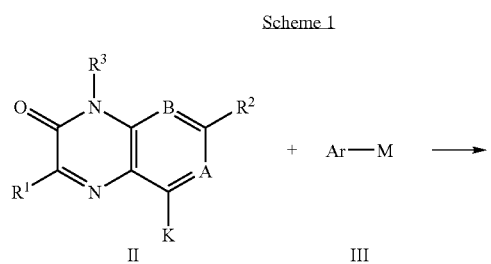

-continued

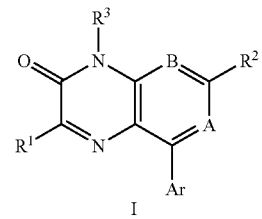

According to scheme 1, a compound of Formula II can be coupled to an aromatic compound of Formula III, with elimination of M-K. For compounds of Formula II, K can represent a halide, pseudohalide (such as, for example, mesylate, tosylate or triflate), or thiomethyl. For compounds of Formula III, M can represent groups such as lithium, bromomagnesium, chlorozinc, (dihydroxy)boron, (dialkoxy)boron, trialkylstannyl, and the like. The coupling reaction of scheme 1 can be performed in the presence of an appropriate catalyst, such as tetrakis(triphenylphosphine)palladium, bis(triphenylphosphine)palladium dichloride, [1,3-bis(diphenylphosphino)propane]nickel dichloride, etc. Example methods involve the coupling of chloroheterocycles with in-situ-prepared arylzinc reagents according to the method described in Negishi et al., *J. Org. Chem.* 1977, 42, 1821, which is incorporated herein by reference in its entirety, and the coupling with arylboronic esters according to the method described in Suzuki et al., *Chem. Letters* 1989, 1405, which is incorporated herein by reference in its entirety. Appropriate solvents for reactions of this type usually include, for example, tetrahydrofuran, diethyl ether, dimethylformamide, or dimethylsulfoxide. Typical temperatures can range, for example, from ambient up to the boiling point of the solvent.

Preparation of compounds of Formula VI wherein A is a nitrogen atom can proceed according to the route of Scheme 2.

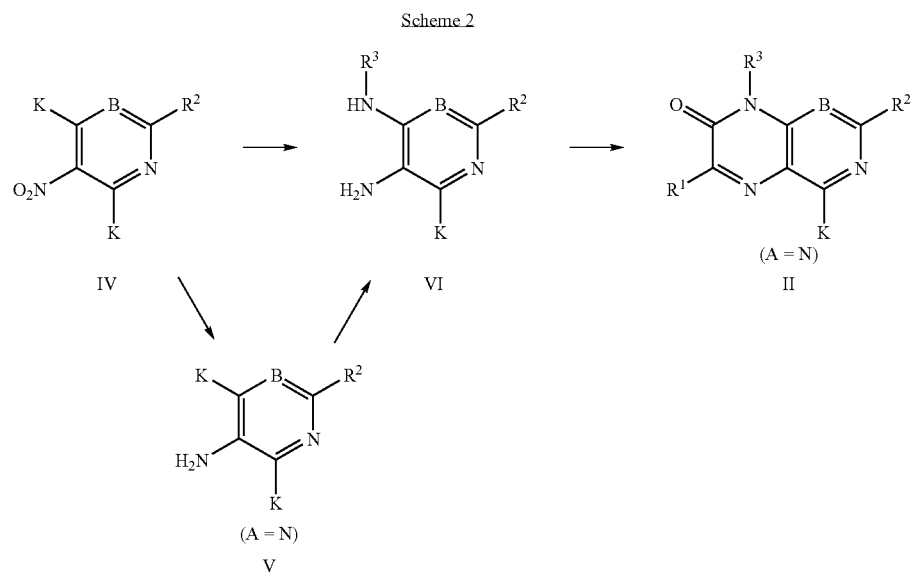

A compound of Formula IV, such as, for example, when K is chloride, can be obtained from commercial sources. Compounds bearing pseudohalide K groups can be made from the corresponding dihydroxy compounds by treatment with an appropriate activating reagent, such as an organosulfonic anhydride or sulfonyl chloride. Compounds of Formula IV can be converted to compounds of Formula VI by, for example, (i) monoalkylation with a compound P—NH$_2$, followed by reduction of the nitro group, or (ii) reduction of the nitro group, to give an amine compound of Formula V, followed by monoalkylation with a compound R$^3$—NH$_2$. Pyrimidine chemistry of this type is well represented in the literature, and is reviewed in *Comprehensive Heterocyclic Chemistry*, vol. 6, which is incorporated herein by reference in its entirety. Alkylation of chloropyrimidines with amine compounds can be accomplished under either acidic (e.g., HCl or acetic) or basic (e.g., trialkylamines, potassium tert-butoxide, etc.) conditions. Nitro groups in compounds of this type can be reduced to amino groups using one of any number of conditions, including catalytic hydrogenation, tin dichloride, sodium dithionite, zinc metal, iron powder, etc.

Compounds of Formula VI can be cyclized with an appropriate ketoester by condensation followed by intramolecular cyclization in toluene, ethanol, methanol, butanol, or other appropriate solvent either alone or in the presence of acid such as a toluenesulfonic acid, acetic acid, hydrochloric acid, Lewis acid, etc. The reaction can be run at any suitable temperature such as, for example, ambient temperature to the boiling point of any given solvent to give the compounds of Formula (I).

An example preparation of compounds of Formula V, wherein A is carbon and B is nitrogen, is shown in Scheme 3.

An hydroxypyridone compound of Formula VII can be nitrated to give compounds of Formula VIII employing conditions such as, for example, concentrated or fuming nitric acid, optionally in the presence of concentrated sulfuric or acetic acid. Both the hydroxy and pyridone groups in compounds of Formula VIII can be activated at the same time, using stronger conditions such as phosphorus oxychloride and heat, or excess toluenesulfonic anhydride, to give compounds of Formula IX. Selective monoalkylation of compounds of Formula IX is also possible, but can give mixtures of regioisomeric products. The nitro group of compounds of Formula X can then be reduced as discussed above, to give compounds of Formula V wherein A is CR$^4$. Cyclization as described above can yield compounds of Formula (I).

Another route (scheme 4) can convert compounds of Formula II to the metallated compounds of Formula XI for coupling to appropriate aryl halides as described above.

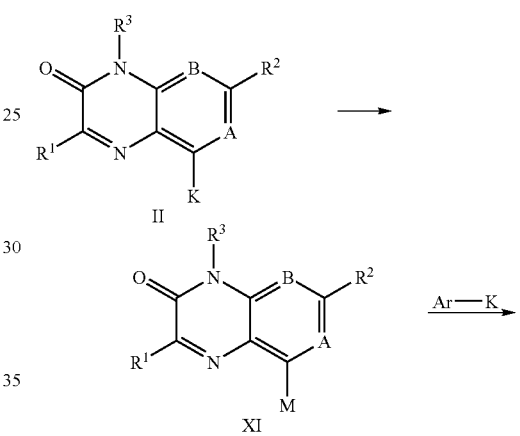

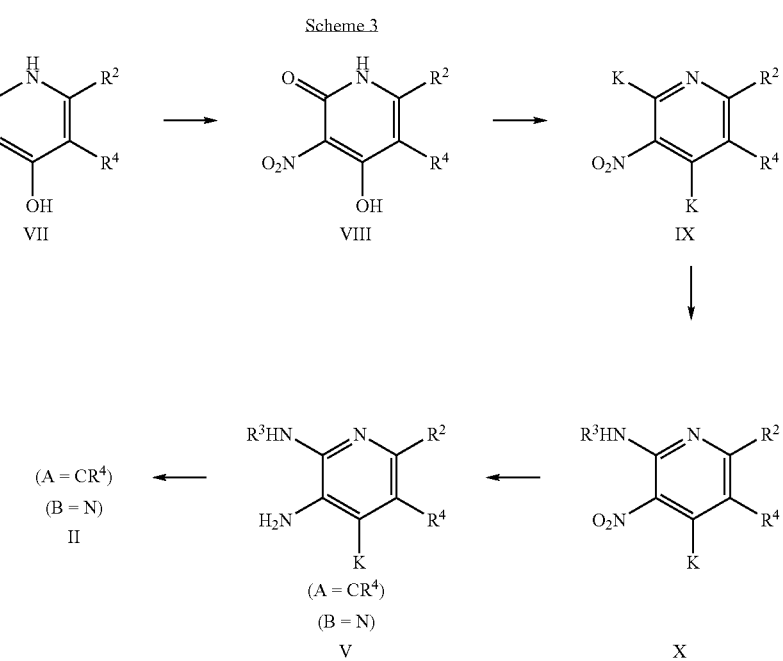

-continued

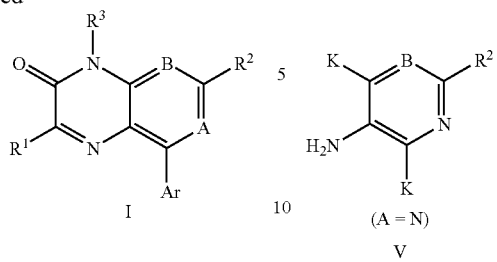

I

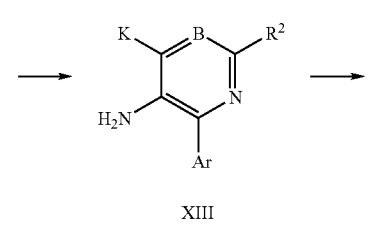

Scheme 6

V (A=N)

XIII

The compound of Formula II (A=N) can also be synthesized by direct halogenation of compounds of Formula XII (scheme 5). This can be achieved selectively by forming the N-oxide with meta-chloroperbenzoic acid, or other appropriate oxidizing agents followed by treatment with a halogenating agent such as phosphorous oxychloride as described in Tomczuk et al., *J. Med. Chem.*, 1991, 34, 2993, which is incorporated herein by reference in its entirety.

Scheme 5

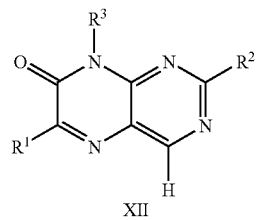

XII

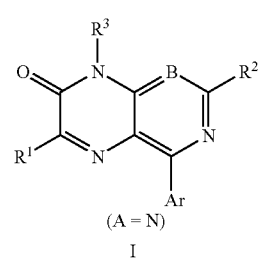

XIV

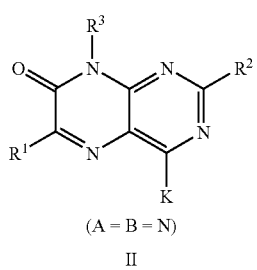

(A = B = N)

II

Compounds of Formula V, which are typically commercially available, can be exposed to aryl coupling conditions (scheme 6) as described above to give compounds of Formula XIII, which can be elaborated to give compounds of Formula XIV, which upon treatment with an appropriate keto-ester under conditions described can give rise to compounds of Formula (I) where A=N.

(A = N)

I

Compounds of Formula XV (scheme 7), which are typically commercially available, can be reacted with an appropriate amine to give compounds of Formula XVI. The nitro group can then be reduced as described above and compounds of Formula XVIII cyclized with the desired ketoester in a manner analogous to the cyclizations previously described. This cyclized material can then be halogenated to give the desired halide derivative which, in turn, can be subjected to aryl coupling conditions as previously described to give the desired analogs. Alternatively, compounds of Formula XVIII can be directly metallated and the organolithium subjected to aryl coupling conditions as described above. Compounds of Formula XVIII can also be used as a precursor to XIX following reaction conditions described earlier.

Scheme 7

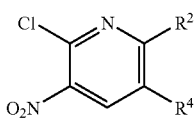

XV

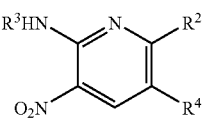

XVI

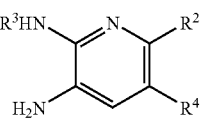

XVII

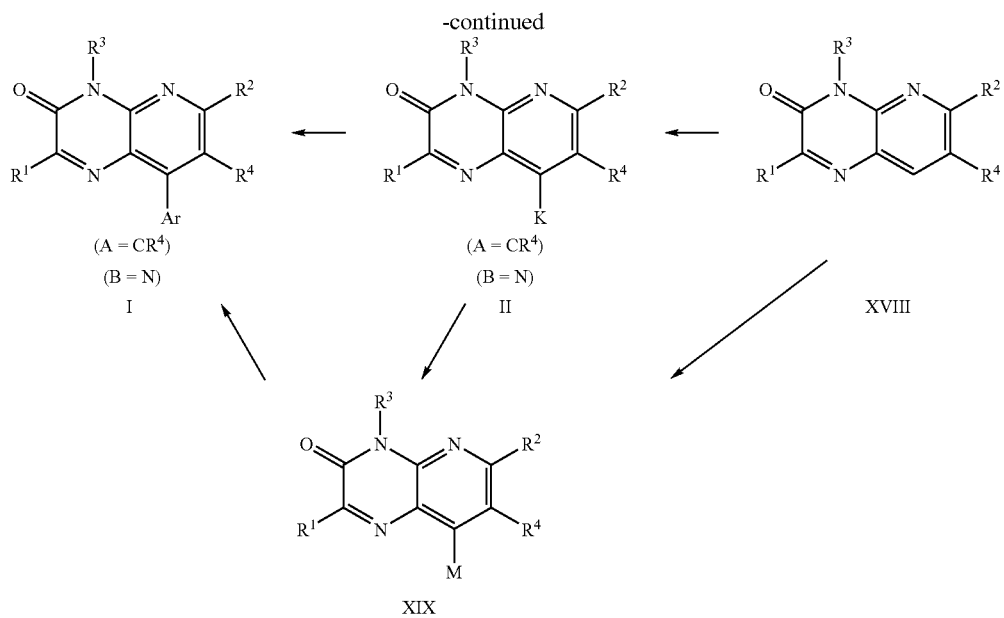

Commercially available compounds of Formula VII can be nitrated employing conditions such as fuming nitric acid, optionally in the presence of concentrated sulfuric or acetic acid (scheme 8). The hydroxypyridone compounds of Formula VIII can be selectively protected. One method of protection, for example, involves the treatment of dicyclohexylamine salts of compounds of Formula VIII. Conversion of compounds of Formula XXI, where K=Cl, can be achieved by treatment with sulfonyl chloride, or if K is a pseudohalide, treatment with organicsulfonic anhydride. The coupling reaction can be run as described above to give compounds of Formula XXII and the nitro group reduced using catalytic hydrogenation, tin dichloride, sodiumithionite, etc. Cyclization as described above can give compounds of Formula I, where A=CR$^4$.

Methods of synthesis of compounds R$^3$—OH, R$^3$—J and R$^3$—NH$_2$ are related, in that the alcohol can be used in the synthesis of the other two compounds, as is shown in Scheme 9.

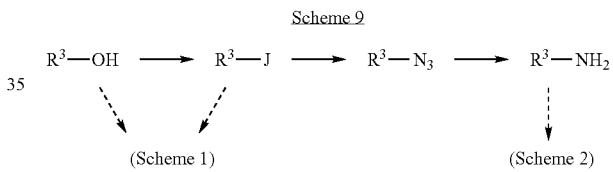

For example, the hydroxy group can be converted to the following J groups, using the indicated reagents (this route

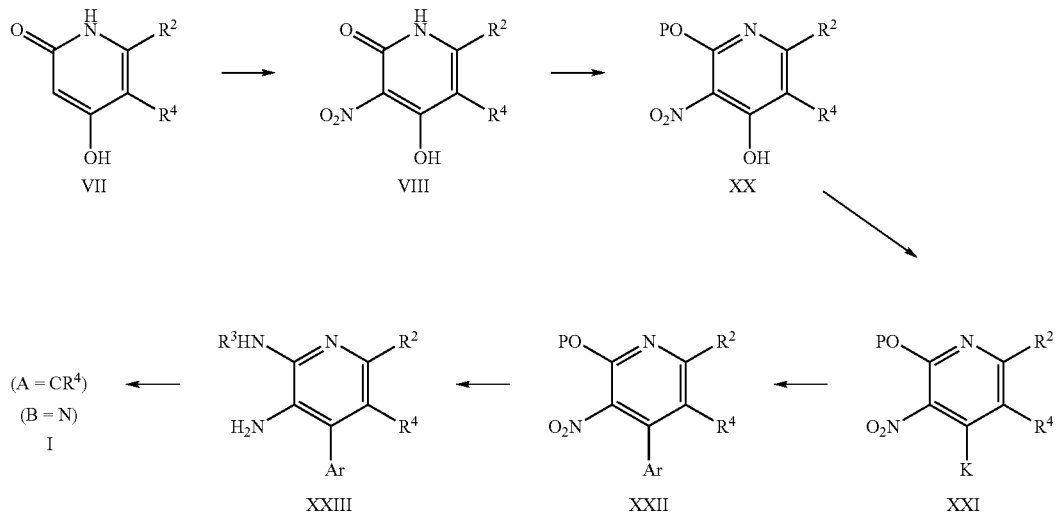

is not limited to these J groups): methanesulfonate, using methanesulfonyl chloride or anhydride and an appropriate base; toluenesulfonate, using toluenesulfonyl chloride or anhydride and an appropriate base; iodide; using iodine/triphenylphosphine; bromide, using phosphorus tribromide or carbon tetrabromide/triphenylphosphine; or trifluoromethanesulfonate, using trifluoromethane-sulfonic anhydride and an appropriate base. Both compounds $R^3$—OH and $R^3$—J are used in the methods portrayed in Scheme 1. Conversion of $R^3$—J to $R^3$—$N_3$ typically uses an azide source, such as sodium azide, and a solvent such as dimethylsulfoxide or dimethylformamide, or water and a phase-transfer catalyst (such as tetrabutylammonium hydrogen sulfate). Reduction of the azide compound $R^3$—$N_3$ to $R_3$—$NH_2$ can be accomplished using reagents such as, for example, sodium borohydride or triphenylphosphine, or hydrogen gas and a catalyst (such as palladium on carbon). The amine $R^3$—$NH_2$ can then be employed in the methods portrayed in Scheme 2.

In the cases where the compound $R^3$—OH could be represented by Formula XXIV (Scheme 10), wherein $R^a$ and $R^b$ represent substructures which, taken together with the carbinol methine group, comprise the entire group $R^3$, this compound can be prepared by addition to a carbonyl compound.

Scheme 10

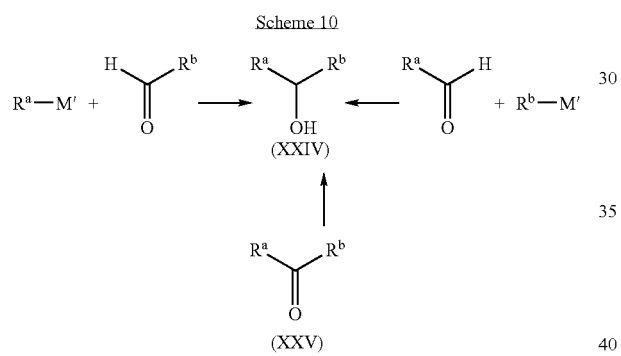

This route can be useful in the case where $R^a$ or $R^b$ represent a cycloalkyl group, such as cyclopropyl. An organometallic reagent (where M' represents a metallic group, such as Li, CuCN, CuI, MgCl, MgBr, MgI, ZnCl, CrCl, etc.) can be allowed to react with an aldehyde reagent to prepare the alcohol compound of Formula XXIV. Alternatively, a ketone of Formula XXV can be treated with a reducing agent, such as, for example, sodium borohydride, lithium aluminum hydride, etc., which can also generate the alcohol of Formula XXIV. Standard methods of ketone synthesis can be used where appropriate in the preparation of compounds of Formula XXV, which are familiar to those skilled in the art of organic synthesis.

An homologous approach can also be employed in the synthesis of alcohols $R^3$—OH, involving the ring-opening reaction of cyclic ether compounds with organometallic reagents (Scheme 11).

Scheme 11

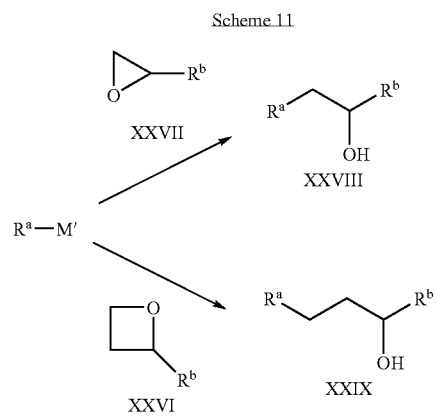

Here, an organometallic reagent $R^a$-M" is used, where M" represents metals such as Mg, Zn or Cu. An example method is described in Huynh, et al., *Tetrahedron Letters* 1979, 17, 1503–1506, which is incorporated herein by reference in its entirety, where organomagnesium reagents are reacted with cyclic ethers with catalysis provided by copper (I) iodide. Use of an epoxide compound of Formula XXVII in this manner can result in synthesis of an alcohol compound of Formula XXVIII, and use of an oxetane compound of Formula XXVI can generate an alcohol of Formula XXIX. Both compounds XXVIII and XXIX are variants of $R^3$—OH.

Synthesis of compound $R^3$—$NH_2$ with Formula XXX is portrayed in Scheme 12.

Scheme 12

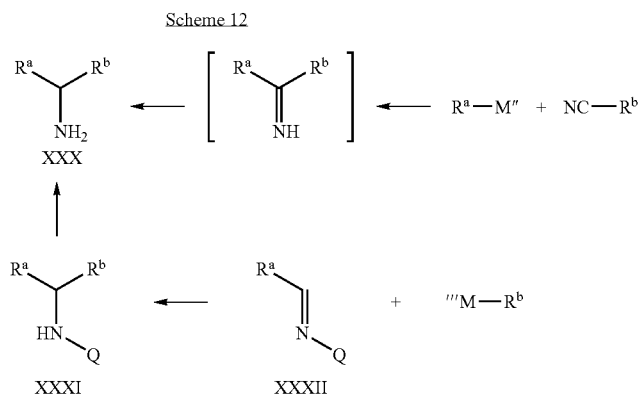

A simple reductive amination of ketones of Formula XXV can produce amines of Formula XXX. This reaction can be performed using anhydrous ammonia in the presence of hydrogen and a catalyst. Alternatively, addition of an organometallic reagent to a nitrile compound gives an imine, which can be treated in situ with a reducing agent (such as, for example, sodium cyanoborohydride) to give amines of Formula XXX. Further, a compound of Formula XXXII, wherein Q is an optionally-substituted oxygen atom (i.e., an oxime) or nitrogen atom (i.e., a hydrazone), can be allowed to react with an organometallic reagent $R^b$-M'''. Here, metallic groups M''' such as MgBr, CuCl or $CeCl_2$ can be used in additions to oximes or hydrazones. The intermediate addition products of Formula XXXI can be subjected to reductive cleavage (using conditions such as sodium/liquid ammonia or catalytic hydrogenation), which can afford amines of Formula XXX.

Amino acids, either naturally-occurring or synthetic, are potential sources of useful starting materials for the synthesis of the compounds of this invention. Scheme 13 shows some possible applications of this approach.

Scheme 13

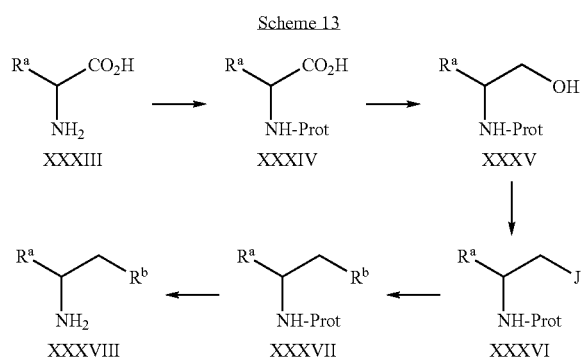

Protected amino acids of Formula XXXIV can be prepared from the parent compounds of Formula XXXIII. Some example protecting groups ("Prot") include tert-butoxycarbonyl, benzyloxycarbonyl, and triphenylmethyl. Standard texts in peptide chemistry describe amino protecting groups. The carboxylic acid group can be reduced using reagents such as lithium borohydride, giving, for example, alcohols of Formula XXV. The hydroxy group can be converted to a leaving group "J" as described before. The compounds of Formula XXXVI can be treated with appropriate reagents to produce a wide variety of functional groups (e.g., compounds of Formula XXXVII). For example, displacement of J with cyanide (e.g., sodium cyanide in warm dimethylformamide) can give a nitrile. Displacement of J with a mercaptan (in the presence of a base, such as potassium carbonate) can give a disulfide. Further, displacement of J with a secondary amine can give a tertiary amine, etc.

The compounds of Formula (I) with unsaturated $R^1$ groups can be a further source of compounds. Unsaturated (double and triple) bonds can take part in cycloaddition chemistry using appropriate reagents (Scheme 14). Cycloaddition of an alkyne compound of Formula XXXIX with 1,3-dienes to give six-membered ring compounds like that of Formula XL (commonly known as the Diels-Alder reaction), and cycloaddition with 3-atom dipolar reagents to give heterocyclic compounds of Formula XLI, are familiar to those skilled in the art of organic synthesis. An example of this approach is the synthesis of an isoxazole compound of Formula XLII from the alkyne XXXIX and a nitrile oxide reagent.

Scheme 14

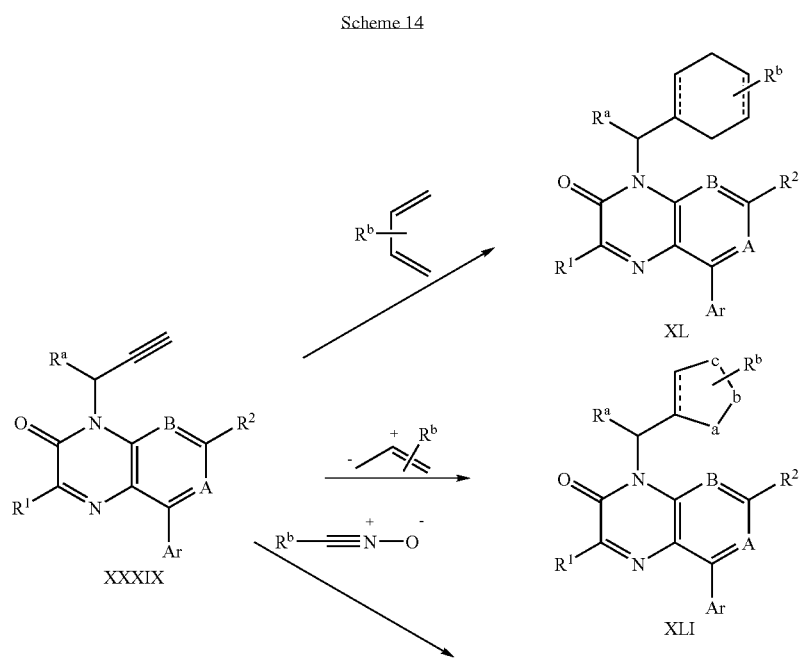

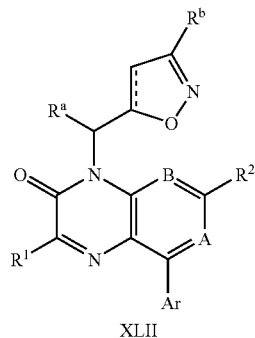

XLII

The synthetic procedure in Scheme 15 shown below can be used to prepare compounds of Formula (Ia).

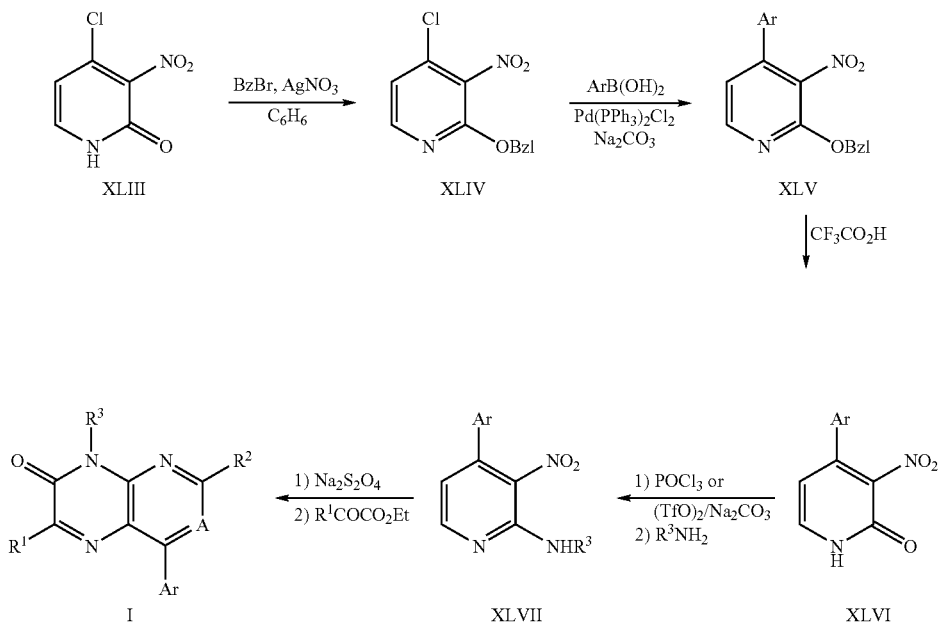

Reaction of 4-chloropyridone of Formula XLIII with an aryl halide, such as benzyl bromide in benzene and in the presence of $Ag_2CO_3$ as described in Scheme 15 (Smith A. M. et al., *J. Med. Chem.*, 1993, 36, 8, which is incorporated herein by reference) and at temperature ranges of, for example, about 30 to about 80° C. can afford the corresponding 2-benzyloxypyridine of Formula XLIV. This compound can be coupled, for example, with an arylboronic acid, $ArB(OH)_2$, under palladium-catalyzed conditions to give compounds of Formula XLV. The benzyloxy group can be removed by treatment with a strong acid, such as trifluoroacetic acid, triflic acid, sulfuric acid, HCl, etc. to give pyridones of Formula XLVI. This compound can be converted to the 2-halopyridine derivative with the action of $POX_3$, $PX_5$, (X is halo) or the corresponding triflate, tosylate or mesylate, which can be displaced with a primary amine $R^3NH_2$ to give XLVII. The nitro group can be reduced under conditions decribed in scheme 15, and the aminopyridine can be cyclized to XLVIII under the conditions described in scheme 15.

The following examples are provided to describe the invention in further detail and are intended to illustrate and not to limit the invention. Potency of binding to $CFR_1$ recetor for select compounds are listed as $IC_{50}$ ranges where a=<1 nM; b=1–10 nM; c=10–100 nM; d=100 nM–1 μM; e=>1 μM.

EXAMPLES

TABLE 1

[Structure: pyrido-pyrazinone core with R³ on N, R¹ on C adjacent to C=O, and a phenyl substituent bearing R^A, R^B, R^C with Y and Z ring atoms]

| Ex. | R¹ | R³ | R^A | R^B | R^C | Y | Z | MS (m/z) | $IC_{50}$ Range* |
|---|---|---|---|---|---|---|---|---|---|
| 1 | Me | CH₂iPr | Cl | Cl | H | CH | CH | 362.3 | e |
| 2 | Me | CH(Me)Pr | Cl | Cl | H | CH | CH | 376.3 | c |
| 3 | Me | CH(cPr)Et | Cl | Cl | H | CH | CH | 388.3 | b |
| 4 | Me | CH(cPr)Me | Cl | Cl | H | CH | CH | 376.3 | |
| 5 | Me | CH(cPr)Pr | Cl | Cl | H | CH | CH | 402.3 | b |
| 6 | Me | CH(cBu)Me | Cl | Cl | H | CH | CH | | |
| 7 | Me | CH(cBu)Et | Cl | Cl | H | CH | CH | | |
| 8 | Me | CH(cBu)Pr | Cl | Cl | H | CH | CH | | |
| 9 | Me | CH(Me)CH₂OMe | Cl | Cl | H | CH | CH | 378.3 | c |
| 10 | Me | CH(Et)CH₂OMe | Cl | Cl | H | CH | CH | 392.3 | b |
| 11 | Me | CH(CPr)CH₂OMe | Cl | Cl | H | CH | CH | | |
| 12 | Me | CH(cBu)CH₂OMe | Cl | Cl | H | CH | CH | | |
| 13 | Me | CH(nPr)CH₂OMe | Cl | Cl | H | CH | CH | | |
| 14 | Me | CH(cPr)C₂H₄OMe | Cl | Cl | H | CH | CH | | |
| 15 | Me | CH(cBu)C₂H₄OMe | Cl | Cl | H | CH | CH | | |
| 16 | Me | CH(Et)Chd 2H₄OMe | Cl | Cl | H | CH | CH | | |
| 17 | Me | CHEt₂ | Cl | OMe | H | CH | CH | | |
| 18 | Me | CHPr2 | Cl | OMe | H | CH | CH | 399.9 | b |
| 19 | Me | CH(cPr)Et | Cl | OMe | H | CH | CH | 383.9 | a |
| 20 | Me | CH(cPr)Me | Cl | OMe | H | CH | CH | | |
| 21 | Me | CH(cPr)Pr | Cl | OMe | H | CH | CH | | |
| 22 | Me | CH(cBu)Me | Cl | OMe | H | CH | CH | | |
| 23 | Me | CH(cBu)Et | Cl | OMe | H | CH | CH | 397.9 | b |
| 24 | Me | CH(cBu)Pr | Cl | OMe | H | CH | CH | | |
| 25 | Me | CH(Me)CH₂OMe | Cl | OMe | H | CH | CH | 373.8 | c |
| 26 | Me | CH(Et)CH₂OMe | Cl | OMe | H | CH | CH | 387.9 | c |
| 27 | Me | CH(cPr)CH₂OMe | Cl | OMe | H | CH | CH | | |
| 28 | Me | CH(cBu)CH₂OMe | Cl | OMe | H | CH | CH | | |
| 29 | Me | CH(nPr)CH₂OMe | Cl | OMe | H | CH | CH | | |
| 30 | Me | CH(CPr)C₂H₄OMe | Cl | OMe | H | CH | CH | | |
| 31 | Me | CH(cBu)C₂H₄OMe | Cl | OMe | H | CH | CH | | |
| 32 | Me | CH(Et)C₂H₄OMe | Cl | OMe | H | CH | CH | | |
| 33 | Me | CHEt2 | Cl | OMe | H | CF | CH | | |
| 34 | Me | CHPr2 | Cl | OMe | H | CF | CH | | |
| 35 | Me | CH(cPr)Et | Cl | OMe | H | CF | CH | | |
| 36 | Me | CH(cPr)Me | Cl | OMe | H | CF | CH | | |
| 37 | Me | CH(cPr)Pr | Cl | OMe | H | CF | CH | | |
| 38 | Me | CH(cBu)Me | Cl | OMe | H | CF | CH | | |
| 39 | Me | CH(cBu)Et | Cl | OMe | H | CF | CH | | |
| 40 | Me | CH(cBu)Pr | Cl | OMe | H | CF | CH | | |
| 41 | Me | CH(Me)CH₂OMe | Cl | OMe | H | CF | CH | | |
| 42 | Me | CH(Et)CH₂OMe | Cl | OMe | H | CF | CH | | |
| 43 | Me | CH(cPr)CH₂OMe | Cl | OMe | H | CF | CH | | |
| 44 | Me | CH(cBu)CH₂OMe | Cl | OMe | H | CF | CH | | |
| 45 | Me | CH(nPr)CH₂OMe | Cl | OMe | H | CF | CH | | |
| 46 | Me | CH(cPr)C₂H₄OMe | Cl | OMe | H | CF | CH | | |
| 47 | Me | CH(cBu)C₂H₄OMe | Cl | OMe | H | CF | CH | | |
| 48 | Me | CH(Et)C₂H₄OMe | Cl | OMe | H | CF | CH | | |
| 49 | Me | CHEt2 | Cl | Me | H | CH | CH | | |
| 50 | Me | CHPr2 | Cl | Me | H | CH | CH | | |
| 51 | Me | CH(cPr)Et | Cl | Me | H | CH | CH | | |
| 52 | Me | CH(cPr)Me | Cl | Me | H | CH | CH | | |
| 53 | Me | CH(cPr)Pr | Cl | Me | H | CH | CH | | |
| 54 | Me | CH(cBu)Me | Cl | Me | H | CH | CH | | |
| 55 | Me | CH(cBu)Et | Cl | Me | H | CH | CH | | |
| 56 | Me | CH(cBu)Pr | Cl | Me | H | CH | CH | | |

TABLE 1-continued

| Ex. | R¹ | R³ | R^A | R^B | R^C | Y | Z | MS (m/z) | IC$_{50}$ Range* |
|---|---|---|---|---|---|---|---|---|---|
| 57 | Me | CH(Me)CH$_2$OMe | Cl | Me | H | CH | CH | | |
| 58 | Me | CH(Et)CH$_2$OMe | Cl | Me | H | CH | CH | | |
| 59 | Me | CH(CPr)CH$_2$OMe | Cl | Me | H | CH | CH | | |
| 60 | Me | CH(cBu)CH$_2$OMe | Cl | Me | H | CH | CH | | |
| 61 | Me | CH(nPr)CH$_2$OMe | Cl | Me | H | CH | CH | | |
| 62 | Me | CH(cPr)C$_2$H$_4$OMe | Cl | Me | H | CH | CH | | |
| 63 | Me | CH(cBu)C$_2$H$_4$OMe | Cl | Me | H | CH | CH | | |
| 64 | Me | CH(Et)C$_2$H$_4$OMe | Cl | Me | H | CH | CH | | |
| 65 | Me | CHEt2 | Me | OMe | H | CH | CH | | |
| 66 | Me | CH(cPr)2 | Me | OMe | H | CH | CH | 376.2 | b |
| 67 | Me | CH(cPr)Et | Me | OMe | H | CH | CH | 364.1 | c |
| 68 | Me | CH(cPr)Me | Me | OMe | H | CH | CH | | |
| 69 | Me | CH(cPr)Pr | Me | OMe | H | CH | CH | 378.1 | b |
| 70 | Me | CH(cBu)Me | Me | OMe | H | CH | CH | | |
| 71 | Me | CH(cBu)Et | Me | OMe | H | CH | CH | 378.2 | c |
| 72 | Me | CH(cBu)Pr | Me | OMe | H | CH | CH | | |
| 73 | Me | CH(Me)CH$_2$OMe | Me | OMe | H | CH | CH | 354.2 | d |
| 74 | Me | CH(Et)CH$_2$OMe | Me | OMe | H | CH | CH | 368.3 | c |
| 75 | Me | CH(cPr)CH$_2$OMe | Me | OMe | H | CH | CH | | |
| 76 | Me | CH(cBu)CH$_2$OMe | Me | OMe | H | CH | CH | | |
| 77 | Me | CH(nPr)CH$_2$OMe | Me | OMe | H | CH | CH | | |
| 78 | Me | CH(cPr)C$_2$H$_4$OMe | Me | OMe | H | CH | CH | | |
| 79 | Me | CH(cBu)C$_2$H$_4$OMe | Me | OMe | H | CH | CH | | |
| 80 | Me | CH(Et)C$_2$H$_4$OMe | Me | OMe | H | CH | CH | | |
| 81 | Me | CHEt2 | Me | OMe | H | CF | CH | | |
| 82 | Me | CHPr2 | Me | OMe | H | CF | CH | | |
| 83 | Me | CH(cPr)Et | Me | OMe | H | CF | CH | 382.3 | b |
| 84 | Me | CH(cPr)Me | Me | OMe | H | CF | CH | | |
| 85 | Me | CH(cPr)Pr | Me | OMe | H | CF | CH | | |
| 86 | Me | CH(cBu)Me | Me | OMe | H | CF | CH | | |
| 87 | Me | CH(cBu)Et | Me | OMe | H | CF | CH | | |
| 88 | Me | CH(cBu)Pr | Me | OMe | H | CF | CH | | |
| 89 | Me | CH(Me)CH$_2$OMe | Me | OMe | H | CF | CH | 386.3 | c |
| 90 | Me | CH(Et)CH$_2$OMe | Me | OMe | H | CF | CH | 386.3 | b |
| 91 | Me | CH(cPr)CH$_2$OMe | Me | OMe | H | CF | CH | | |
| 92 | Me | CH(cBu)CH$_2$OMe | Me | OMe | H | CF | CH | | |
| 93 | Me | CH(nPr)CH$_2$OMe | Me | OMe | H | CF | CH | | |
| 94 | Me | CH(cPr)C$_2$H$_4$OMe | Me | OMe | H | CF | CH | | |
| 95 | Me | CH(cBu)C$_2$H$_4$OMe | Me | OMe | H | CF | CH | | |
| 96 | Me | CH(Et)C$_2$H$_4$OMe | Me | OMe | H | CF | CH | | |
| 97 | Me | CH(Et)Bu | Me | OMe | H | CH | N | 381.1 | d |
| 98 | Me | CHPr2 | Me | OMe | H | CH | N | 381.2 | c |
| 99 | Me | CH(cPr)Et | Me | OMe | H | CH | N | 365.4 | c |
| 100 | Me | CH(cPr)Me | Me | OMe | H | CH | N | | |
| 101 | Me | CH(cPr)Pr | Me | OMe | H | CH | N | 379.1 | c |
| 102 | Me | CH(cBu)Me | Me | OMe | H | CH | N | | |
| 103 | Me | CH(cBu)Et | Me | OMe | H | CH | N | | |
| 104 | Me | CH(cBu)Pr | Me | OMe | H | CH | N | | |
| 105 | Me | CH(Me)CH$_2$OMe | Me | OMe | H | CH | N | 355.6 | d |
| 106 | Me | CH(Et)CH$_2$OMe | Me | OMe | H | CH | N | | |
| 107 | Me | CH(cPr)CH$_2$OMe | Me | OMe | H | CH | N | | |
| 108 | Me | CH(cBu)CH$_2$OMe | Me | OMe | H | CH | N | | |
| 109 | Me | CH(nPr)CH$_2$OMe | Me | OMe | H | CH | N | | |
| 110 | Me | CH(cPr)C$_2$H$_4$OMe | Me | OMe | H | CH | N | | |
| 111 | Me | CH(cBu)C$_2$H$_4$OMe | Me | OMe | H | CH | N | | |
| 112 | Me | CH(Et)C$_2$H$_4$OMe | Me | OMe | H | CH | N | | |
| 113 | Me | CH(Me)Et | Cl | OCHF$_2$ | H | CH | CH | 394.2 | c |
| 114 | Me | CHPr2 | Cl | OCHF$_2$ | H | CH | CH | | |
| 115 | Me | CH(cPr)Et | Cl | OCHF$_2$ | H | CH | CH | 420.2 | b |

TABLE 1-continued

| Ex. | R¹ | R³ | R^A | R^B | R^C | Y | Z | MS (m/z) | IC₅₀ Range* |
|---|---|---|---|---|---|---|---|---|---|
| 116 | Me | CH(cPr)Me | Cl | OCHF₂ | H | CH | CH | | |
| 117 | Me | CH(cPr)Pr | Cl | OCHF₂ | H | CH | CH | 434.1 | b |
| 118 | Me | CH(cBu)Me | Cl | OCHF₂ | H | CH | CH | | |
| 119 | Me | CH(cBu)Et | Cl | OCHF₂ | H | CH | CH | | |
| 120 | Me | CH(cBu)Pr | Cl | OCHF₂ | H | CH | CH | | |
| 121 | Me | CH(Me)CH₂OMe | Cl | OCHF₂ | H | CH | CH | 410.0 | c |
| 122 | Me | CH(Et)CH₂OMe | Cl | OCHF₂ | H | CH | CH | 424.1 | b |
| 123 | Me | CH(cPr)CH₂OMe | Cl | OCHF₂ | H | CH | CH | | |
| 124 | Me | CH(cBu)CH₂OMe | Cl | OCHF₂ | H | CH | CH | | |
| 125 | Me | CH(nPr)CH₂OMe | Cl | OCHF₂ | H | CH | CH | | |
| 126 | Me | CH(cPr)C₂H₄OMe | Cl | OCHF₂ | H | CH | CH | | |
| 127 | Me | CH(cBu)C₂H₄OMe | Cl | OCHF₂ | H | CH | CH | | |
| 128 | Me | CH(Et)C₂H₄OMe | Cl | OCHF₂ | H | CH | CH | | |
| 129 | Me | CHEt2 | Cl | CF₃ | H | CH | CH | | |
| 130 | Me | CHPr2 | Cl | CF₃ | H | CH | CH | | |
| 131 | Me | CH(cPr)Et | Cl | CF₃ | H | CH | CH | 421.8 | c |
| 132 | Me | CH(cPr)Me | Cl | CF₃ | H | CH | CH | | |
| 133 | Me | CH(cPr)Pr | Cl | CF₃ | H | CH | CH | | |
| 134 | Me | CH(cBu)Me | Cl | CF₃ | H | CH | CH | | |
| 135 | Me | CH(cBu)Et | Cl | CF₃ | H | CH | CH | | |
| 136 | Me | CH(cBu)Pr | Cl | CF₃ | H | CH | CH | | |
| 137 | Me | CH(Me)CH₂OMe | Cl | CF₃ | H | CH | CH | 411.8 | c |
| 138 | Me | CH(Et)CH₂OMe | Cl | CF₃ | H | CH | CH | 425.8 | c |
| 139 | Me | CH(cPr)CH₂OMe | Cl | CF₃ | H | CH | CH | | |
| 140 | Me | CH(cBu)CH₂OMe | Cl | CF₃ | H | CH | CH | | |
| 141 | Me | CH(nPr)CH₂OMe | Cl | CF₃ | H | CH | CH | | |
| 142 | Me | CH(cPr)C₂H₄OMe | Cl | CF₃ | H | CH | CH | | |
| 143 | Me | CH(cBu)C₂H₄OMe | Cl | CF₃ | H | CH | CH | | |
| 144 | Me | CH(Et)C₂H₄OMe | Cl | CF₃ | H | CH | CH | | |
| 145 | Me | CHEt2 | Cl | OEt | H | CH | CH | | |
| 146 | Me | CHPr2 | Cl | OEt | H | CH | CH | | |
| 147 | Me | CH(cPr)Et | Cl | OEt | H | CH | CH | | |
| 148 | Me | CH(cPr)Me | Cl | OEt | H | CH | CH | | |
| 149 | Me | CH(cPr)Pr | Cl | OEt | H | CH | CH | | |
| 150 | Me | CH(cBu)Me | Cl | OEt | H | CH | CH | | |
| 151 | Me | CH(cBu)Et | Cl | OEt | H | CH | CH | | |
| 152 | Me | CH(cBu)Pr | Cl | OEt | H | CH | CH | | |
| 153 | Me | CH(Me)CH₂OMe | Cl | OEt | H | CH | CH | | |
| 154 | Me | CH(Et)CH₂OMe | Cl | OEt | H | CH | CH | | |
| 155 | Me | CH(cPr)CH₂OMe | Cl | OEt | H | CH | CH | | |
| 156 | Me | CHCcBu)CH₂OMe | Cl | OEt | H | CH | CH | | |
| 157 | Me | CH(nPr)CH₂OMe | Cl | OEt | H | CH | CH | | |
| 158 | Me | CH(cPr)C₂H₄OMe | Cl | OEt | H | CH | CH | | |
| 159 | Me | CH(cBu)C₂H₄OMe | Cl | OEt | H | CH | CH | | |
| 160 | Me | CH(Et)C₂H₄OMe | Cl | OEt | H | CH | CH | | |
| 161 | Me | CHEt2 | Cl | OiPr | H | CH | CH | | |
| 162 | Me | CHPr2 | Cl | OiPr | H | CH | CH | | |
| 163 | Me | CH(cPr)Et | Cl | OiPr | H | CH | CH | | |
| 164 | Me | CH(cPr)Me | Cl | OiPr | H | CH | CH | | |
| 165 | Me | CH(cPr)Pr | Cl | OiPr | H | CH | CH | | |
| 166 | Me | CH(cBu)Me | Cl | OiPr | H | CH | CH | | |
| 167 | Me | CH(cBu)Et | Cl | OiPr | H | CH | CH | | |
| 168 | Me | CH(cBu)Pr | Cl | OiPr | H | CH | CH | | |
| 169 | Me | CH(Me)CH₂OMe | Cl | OiPr | H | CH | CH | | |
| 170 | Me | CH(Et)CH₂OMe | Cl | OiPr | H | CH | CH | | |
| 171 | Me | CH(cPr)CH₂OMe | Cl | OiPr | H | CH | CH | | |
| 172 | Me | CH(cBu)CH₂OMe | Cl | OiPr | H | CH | CH | | |
| 173 | Me | CH(nPr)CH₂OMe | Cl | OiPr | H | CH | CH | | |
| 174 | Me | CH(CPr)C₂H₄OMe | Cl | OiPr | H | CH | CH | | |

TABLE 1-continued

| Ex. | R¹ | R³ | R^A | R^B | R^C | Y | Z | MS (m/z) | IC$_{50}$ Range* |
|---|---|---|---|---|---|---|---|---|---|
| 175 | Me | CH(cBu)C$_2$H$_4$OMe | Cl | OiPr | H | CH | CH | | |
| 176 | Me | CH(Et)C$_2$H$_4$OMe | Cl | OiPr | H | CH | CH | | |
| 177 | Me | CHEt2 | CF$_3$ | OMe | H | CH | CH | | |
| 178 | Me | CHPr2 | CF$_3$ | OMe | H | CH | CH | | |
| 179 | Me | CH(cPr)Et | CF$_3$ | OMe | H | CH | CH | | |
| 180 | Me | CH(cPr)Me | CF$_3$ | OMe | H | CH | CH | | |
| 181 | Me | CH(cPr)Pr | CF$_3$ | OMe | H | CH | CH | | |
| 182 | Me | CH(cBu)Me | CF$_3$ | OMe | H | CH | CH | | |
| 183 | Me | CH(cBu)Et | CF$_3$ | OMe | H | CH | CH | | |
| 184 | Me | CH(cBu)Pr | CF$_3$ | OMe | H | CH | CH | | |
| 185 | Me | CH(Me)CH$_2$OMe | CF$_3$ | OMe | H | CH | CH | | |
| 186 | Me | CH(Et)CH$_2$OMe | CF$_3$ | OMe | H | CH | CH | | |
| 187 | Me | CH(cPr)CH$_2$OMe | CF$_3$ | OMe | H | CH | CH | | |
| 188 | Me | CH(cBu)CH$_2$OMe | CF$_3$ | OMe | H | CH | CH | | |
| 189 | Me | CH(nPr)CH$_2$OMe | CF$_3$ | OMe | H | CH | CH | | |
| 190 | Me | CH(cPr)C$_2$H$_4$OMe | CF$_3$ | OMe | H | CH | CH | | |
| 191 | Me | CH(cBu)C$_2$H$_4$OMe | CF$_3$ | OMe | H | CH | CH | | |
| 192 | Me | CH(Et)C$_2$H$_4$OMe | CF$_3$ | OMe | H | CH | CH | | |
| 193 | Me | CHEt2 | Me | OMe | H | N | CH | | |
| 194 | Me | CHPr2 | Me | OMe | H | N | CH | | |
| 195 | Me | CH(cPr)Et | Me | OMe | H | N | CH | | |
| 196 | Me | CH(cPr)Me | Me | OMe | H | N | CH | | |
| 197 | Me | CH(cPr)Pr | Me | OMe | H | N | CH | | |
| 198 | Me | CH(cBu)Me | Me | OMe | H | N | CH | | |
| 199 | Me | CH(cBu)Et | Me | OMe | H | N | CH | | |
| 200 | Me | CH(cBu)Pr | Me | OMe | H | N | CH | | |
| 201 | Me | CH(Me)CH$_2$OMe | Me | OMe | H | N | CH | | |
| 202 | Me | CH(Et)CH$_2$OMe | Me | OMe | H | N | CH | | |
| 203 | Me | CH(cPr)CH$_2$OMe | Me | OMe | H | N | CH | | |
| 204 | Me | CH(cBu)CH$_2$OMe | Me | OMe | H | N | CH | | |
| 205 | Me | CH(nPr)CH$_2$OMe | Me | OMe | H | N | CH | | |
| 206 | Me | CH(cPr)C$_2$H$_4$OMe | Me | OMe | H | N | CH | | |
| 207 | Me | CH(cBu)C$_2$H$_4$OMe | Me | OMe | H | N | CH | | |
| 208 | Me | CH(Et)C$_2$H$_4$OMe | Me | OMe | H | N | CH | | |
| 209 | Et | CHEt2 | Cl | Cl | H | CH | CH | | |
| 210 | Et | CHPr2 | Cl | Cl | H | CH | CH | | |
| 211 | Et | CH(cPr)Et | Cl | Cl | H | CH | CH | | |
| 212 | Et | CH(cPr)Me | Cl | Cl | H | CH | CH | | |
| 213 | Et | CH(cPr)Pr | Cl | Cl | H | CH | CH | | |
| 214 | Et | CH(cBu)Me | Cl | Cl | H | CH | CH | | |
| 215 | Et | CH(cBu)Et | Cl | Cl | H | CH | CH | | |
| 216 | Et | CH(cBu)Pr | Cl | Cl | H | CH | CH | | |
| 217 | Et | CH(Me)CH$_2$OMe | Cl | Cl | H | CH | CH | | |
| 218 | Et | CH(Et)CH$_2$OMe | Cl | Cl | H | CH | CH | | |
| 219 | Et | CH(cPr)CH$_2$OMe | Cl | Cl | H | CH | CH | | |
| 220 | Et | CH(cBu)CH$_2$OMe | Cl | Cl | H | CH | CH | | |
| 221 | Et | CH(nPr)CH$_2$OMe | Cl | Cl | H | CH | CH | | |
| 222 | Et | CH(cPr)C$_2$H$_4$OMe | Cl | Cl | H | CH | CH | | |
| 223 | Et | CH(cBu)C$_2$H$_4$OMe | Cl | Cl | H | CH | CH | | |
| 224 | Et | CH(Et)C$_2$H$_4$OMe | Cl | Cl | H | CH | CH | | |
| 225 | Et | CHEt2 | Cl | OMe | H | CH | CH | | |
| 226 | Et | CHPr2 | Cl | OMe | H | CH | CH | | |
| 227 | Et | CH(cPr)Et | Cl | OMe | H | CH | CH | | |
| 228 | Et | CH(cPr)Me | Cl | OMe | H | CH | CH | | |
| 229 | Et | CH(cPr)Pr | Cl | OMe | H | CH | CH | | |
| 230 | Et | CH(cBu)Me | Cl | OMe | H | CH | CH | | |
| 231 | Et | CH(cBu)Et | Cl | OMe | H | CH | CH | | |
| 232 | Et | CH(cBu)Pr | Cl | OMe | H | CH | CH | | |
| 233 | Et | CH(Me)CH$_2$OMe | Cl | OMe | H | CH | CH | | |

TABLE 1-continued

| Ex. | R¹ | R³ | Rᴬ | Rᴮ | Rᶜ | Y | Z | MS (m/z) | IC$_{50}$ Range* |
|---|---|---|---|---|---|---|---|---|---|
| 234 | Et | CH(Et)CH$_2$OMe | Cl | OMe | H | CH | CH | | |
| 235 | Et | CH(cPr)CH$_2$OMe | Cl | OMe | H | CH | CH | | |
| 236 | Et | CH(cBu)CH$_2$OMe | Cl | OMe | H | CH | CH | | |
| 237 | Et | CH(nPr)CH$_2$OMe | Cl | OMe | H | CH | CH | | |
| 238 | Et | CH(cPr)C$_2$H$_4$OMe | Cl | OMe | H | CH | CH | | |
| 239 | Et | CH(cBu)C$_2$H$_4$OMe | Cl | OMe | H | CH | CH | | |
| 240 | Et | CH(Et)C$_2$H$_4$OMe | Cl | OMe | H | CH | CH | | |
| 241 | Et | CHEt2 | Cl | OMe | H | CF | CH | | |
| 242 | Et | CHPr2 | Cl | OMe | H | CF | CH | | |
| 243 | Et | CH(cPr)Et | Cl | OMe | H | CF | CH | 402.2 | a |
| 244 | Et | CH(cPr)Me | Cl | OMe | H | CF | CH | | |
| 245 | Et | CH(cPr)Pr | Cl | OMe | H | CF | CH | | |
| 246 | Et | CH(cBu)Me | Cl | OMe | H | CF | CH | | |
| 247 | Et | CH(cBu)Et | Cl | OMe | H | CF | CH | | |
| 248 | Et | CH(cBu)Pr | Cl | OMe | H | CF | CH | | |
| 249 | Et | CH(Me)CH$_2$OMe | Cl | OMe | H | CF | CH | | |
| 250 | Et | CH(Et)CH$_2$OMe | Cl | OMe | H | CF | CH | 406.3 | b |
| 251 | Et | CH(cPr)CH$_2$OMe | Cl | OMe | H | CF | CH | | |
| 252 | Et | CH(cBu)CH$_2$OMe | Cl | OMe | H | CF | CH | | |
| 253 | Et | CH(cPr)CH$_2$OMe | Cl | OMe | H | CF | CH | | |
| 254 | Et | CH(cPr)C$_2$H$_4$OMe | Cl | OMe | H | CF | CH | | |
| 255 | Et | CH(cBu)C$_2$H$_4$OMe | Cl | OMe | H | CF | CH | | |
| 256 | Et | CH(Et)C$_2$H$_4$OMe | Cl | OMe | H | CF | CH | | |
| 257 | Et | CHEt2 | Cl | Me | H | CH | CH | | |
| 258 | Et | CHPr2 | Cl | Me | H | CH | CH | | |
| 259 | Et | CH(cPr)Et | Cl | Me | H | CH | CH | | |
| 260 | Et | CH(cPr)Me | Cl | Me | H | CH | CH | | |
| 261 | Et | CH(cPr)Pr | Cl | Me | H | CH | CH | | |
| 262 | Et | CH(cBu)Me | Cl | Me | H | CH | CH | | |
| 263 | Et | CH(cBu)Et | Cl | Me | H | CH | CH | | |
| 264 | Et | CH(cBu)Pr | Cl | Me | H | CH | CH | | |
| 265 | Et | CH(Me)CH$_2$OMe | Cl | Me | H | CH | CH | | |
| 266 | Et | CH(Et)CH$_2$OMe | Cl | Me | H | CH | CH | | |
| 267 | Et | CH(cPr)CH$_2$OMe | Cl | Me | H | CH | CH | | |
| 268 | Et | CH(cBu)CH$_2$OMe | Cl | Me | H | CH | CH | | |
| 269 | Et | CH(nPr)CH$_2$OMe | Cl | Me | H | CH | CH | | |
| 270 | Et | CH(cPr)C$_2$H$_4$OMe | Cl | Me | H | CH | CH | | |
| 271 | Et | CH(cBu)C$_2$H$_4$OMe | Cl | Me | H | CH | CH | | |
| 272 | Et | CH(Et)C$_2$H$_4$OMe | Cl | Me | H | CH | CH | | |
| 273 | Et | CHEt2 | Me | OMe | H | CH | CH | | |
| 274 | Et | CHPr2 | Me | OMe | H | CH | CH | | |
| 275 | Et | CH(cPr)Et | Me | OMe | H | CH | CH | | |
| 276 | Et | CH(cPr)Me | Me | OMe | H | CH | CH | | |
| 277 | Et | CH(cPr)Pr | Me | OMe | H | CH | CH | | |
| 278 | Et | CH(cBu)Me | Me | OMe | H | CH | CH | | |
| 279 | Et | CH(cBu)Et | Me | OMe | H | CH | CH | | |
| 280 | Et | CH(cBu)Pr | Me | OMe | H | CH | CH | | |
| 281 | Et | CH(Me)CH$_2$OMe | Me | OMe | H | CH | CH | | |
| 282 | Et | CH(Et)CH$_2$OMe | Me | OMe | H | CH | CH | | |
| 283 | Et | CH(cPr)CH$_2$OMe | Me | OMe | H | CH | CH | | |
| 284 | Et | CH(cBu)CH$_2$OMe | Me | OMe | H | CH | CH | | |
| 285 | Et | CH(nPr)CH$_2$OMe | Me | OMe | H | CH | CH | | |
| 286 | Et | CH(cPr)C$_2$H$_4$OMe | Me | OMe | H | CH | CH | | |
| 287 | Et | CH(cBu)C$_2$H$_4$OMe | Me | OMe | H | CH | CH | | |
| 288 | Et | CH(Et)C$_2$H$_4$OMe | Me | OMe | H | CH | CH | | |
| 289 | Et | CHEt2 | Me | OMe | H | CF | CH | | |
| 290 | Et | CHPr2 | Me | OMe | H | CF | CH | | |
| 291 | Et | CH(cPr)Et | Me | OMe | H | CF | CH | | |
| 292 | Et | CH(cPr)Me | Me | OMe | H | CF | CH | | |

TABLE 1-continued

| Ex. | R¹ | R³ | R^A | R^B | R^C | Y | Z | MS (m/z) | IC$_{50}$ Range* |
|---|---|---|---|---|---|---|---|---|---|
| 293 | Et | CH(cPr)Pr | Me | OMe | H | CF | CH | | |
| 294 | Et | CH(cBu)Me | Me | OMe | H | CF | CH | | |
| 295 | Et | CH(cBu)Et | Me | OMe | H | CF | CH | | |
| 296 | Et | CH(cBu)Pr | Me | OMe | H | CF | CH | | |
| 297 | Et | CH(Me)CH$_2$OMe | Me | OMe | H | CF | CH | | |
| 298 | Et | CH(Et)CH$_2$OMe | Me | OMe | H | CF | CH | | |
| 299 | Et | CH(cPr)CH$_2$OMe | Me | OMe | H | CF | CH | | |
| 300 | Et | CH(cBu)CH$_2$OMe | Me | OMe | H | CF | CH | | |
| 301 | Et | CH(nPr)CH$_2$OMe | Me | OMe | H | CF | CH | | |
| 302 | Et | CH(cPr)C$_2$H$_4$OMe | Me | OMe | H | CF | CH | | |
| 303 | Et | CH(cBu)C$_2$H$_4$OMe | Me | OMe | H | CF | CH | | |
| 304 | Et | CH(Et)C$_2$H$_4$OMe | Me | OMe | H | CF | CH | | |
| 305 | Et | CHEt2 | Me | OMe | H | CH | N | | |
| 306 | Et | CHPr2 | Me | OMe | H | CH | N | | |
| 307 | Et | CH(cPr)Et | Me | OMe | H | CH | N | | |
| 308 | Et | CH(cPr)Me | Me | OMe | H | CH | N | | |
| 309 | Et | CH(cPr)Pr | Me | OMe | H | CH | N | | |
| 310 | Et | CH(cBu)Me | Me | OMe | H | CH | N | | |
| 311 | Et | CH(cBu)Et | Me | OMe | H | CH | N | | |
| 312 | Et | CH(cBu)Pr | Me | OMe | H | CH | N | | |
| 313 | Et | CH(Me)CH$_2$OMe | Me | OMe | H | CH | N | | |
| 314 | Et | CH(Et)CH$_2$OMe | Me | OMe | H | CH | N | | |
| 315 | Et | CH(cPr)CH$_2$OMe | Me | OMe | H | CH | N | | |
| 316 | Et | CH(cBu)CH$_2$OMe | Me | OMe | H | CH | N | | |
| 317 | Et | CH(nPr)CH$_2$OMe | Me | OMe | H | CH | N | | |
| 318 | Et | CH(cPr)C$_2$H$_4$OMe | Me | OMe | H | CH | N | | |
| 319 | Et | CH(cBu)C$_2$H$_4$OMe | Me | OMe | H | CH | N | | |
| 320 | Et | CH(Et)C$_2$OMe | Me | OMe | H | CH | N | | |
| 321 | Et | CHEt$_2$ | Cl | OCHF$_2$ | H | CH | CH | | |
| 322 | Et | CHPr2 | Cl | OCHF$_2$ | H | CH | CH | | |
| 323 | Et | CH(cPr)Et | Cl | OCHF$_2$ | H | CH | CH | | |
| 324 | Et | CH(cPr)Me | Cl | OCHF$_2$ | H | CH | CH | | |
| 325 | Et | CH(cPr)Pr | Cl | OCHF$_2$ | H | CH | CH | | |
| 326 | Et | CH(cBu)Me | Cl | OCHF$_2$ | H | CH | CH | | |
| 327 | Et | CH(cBu)Et | Cl | OCHF$_2$ | H | CH | CH | | |
| 328 | Et | CH(cBu)Pr | Cl | OCHF$_2$ | H | CH | CH | | |
| 329 | Et | CH(Me)CH$_2$OMe | Cl | OCHF$_2$ | H | CH | CH | | |
| 330 | Et | CH(Et)CH$_2$OMe | Cl | OCHF$_2$ | H | CH | CH | | |
| 331 | Et | CH(cPr)CH$_2$OMe | Cl | OCHF$_2$ | H | CH | CH | | |
| 332 | Et | CH(cBu)CH$_2$OMe | Cl | OCHF$_2$ | H | CH | CH | | |
| 333 | Et | CH(nPr)CH$_2$OMe | Cl | OCHF$_2$ | H | CH | CH | | |
| 334 | Et | CH(cPr)C$_2$H$_4$OMe | Cl | OCHF$_2$ | H | CH | CH | | |
| 335 | Et | CH(cBu)C$_2$H$_4$OMe | Cl | OCHF$_2$ | H | CH | CH | | |
| 336 | Et | CH(Et)C$_2$H$_4$OMe | Cl | OCHF$_2$ | H | CH | CH | | |
| 337 | Et | CHEt2 | Cl | CF$_3$ | H | CH | CH | | |
| 338 | Et | CHPr2 | Cl | CF$_3$ | H | CH | CH | | |
| 339 | Et | CH(cPr)Et | Cl | CF$_3$ | H | CH | CH | | |
| 340 | Et | CH(cPr)Me | Cl | CF$_3$ | H | CH | CH | | |
| 341 | Et | CH(cPr)Pr | Cl | CF$_3$ | H | CH | CH | | |
| 342 | Et | CH(cBu)Me | Cl | CF$_3$ | H | CH | CH | | |
| 343 | Et | CH(cBu)Et | Cl | CF$_3$ | H | CH | CH | | |
| 344 | Et | CH(cBu)Pr | Cl | CF$_3$ | H | CH | CH | | |
| 345 | Et | CH(Me)CH$_2$OMe | Cl | CF$_3$ | H | CH | CH | | |
| 346 | Et | CH(Et)CH$_2$OMe | Cl | CF$_3$ | H | CH | CH | | |
| 347 | Et | CH(cPr)CH$_2$OMe | Cl | CF$_3$ | H | CH | CH | | |
| 348 | Et | CH(cBu)CH$_2$OMe | Cl | CF$_3$ | H | CH | CH | | |
| 349 | Et | CH(nPr)CH$_2$OMe | Cl | CF$_3$ | H | CH | CH | | |
| 350 | Et | CH(cPr)C$_2$H$_4$OMe | Cl | CF$_3$ | H | CH | CH | | |
| 351 | Et | CH(cBu)C$_2$H$_4$OMe | Cl | CF$_3$ | H | CH | CH | | |

TABLE 1-continued

| Ex. | R¹ | R³ | R^A | R^B | R^C | Y | Z | MS (m/z) | IC$_{50}$ Range* |
|---|---|---|---|---|---|---|---|---|---|
| 352 | Et | CH(Et)C$_2$H$_4$OMe | Cl | CF$_3$ | H | CH | CH | | |
| 353 | Et | CHEt$_2$ | Cl | OEt | H | CH | CH | | |
| 354 | Et | CHPr2 | Cl | OEt | H | CH | CH | | |
| 355 | Et | CH(cPr)Et | Cl | OEt | H | CH | CH | | |
| 356 | Et | CH(cPr)Me | Cl | OEt | H | CH | CH | | |
| 357 | Et | CH(cPr)Pr | Cl | OEt | H | CH | CH | | |
| 358 | Et | CH(cBu)Me | Cl | OEt | H | CH | CH | | |
| 359 | Et | CH(cBu)Et | Cl | OEt | H | CH | CH | | |
| 360 | Et | CH(cBu)Pr | Cl | OEt | H | CH | CH | | |
| 361 | Et | CH(Me)CH$_2$OMe | Cl | OEt | H | CH | CH | | |
| 362 | Et | CH(Et)CH$_2$OMe | Cl | OEt | H | CH | CH | | |
| 363 | Et | CH(cPr)CH$_2$OMe | Cl | QEt | H | CH | CH | | |
| 364 | Et | CH(cBu)CH$_2$OMe | Cl | OEt | H | CH | CH | | |
| 365 | Et | CH(nPr)CH$_2$OMe | Cl | OEt | H | CH | CH | | |
| 366 | Et | CH(cPr)C$_2$H$_4$OMe | Cl | OEt | H | CH | CH | | |
| 367 | Et | CH(cBu)C$_2$H$_4$OMe | Cl | OEt | H | CH | CH | | |
| 368 | Et | CH(Et)C$_2$H$_4$OMe | Cl | OEt | H | CH | CH | | |
| 369 | Et | CHEt$_2$ | Cl | OiPr | H | CH | CH | | |
| 370 | Et | CHPr2 | Cl | OiPr | H | CH | CH | | |
| 371 | Et | CH(cPr)Et | Cl | OiPr | H | CH | CH | | |
| 372 | Et | CH(cPr)Me | Cl | OiPr | H | CH | CH | | |
| 373 | Et | CH(cPr)Pr | Cl | OiPr | H | CH | CH | | |
| 374 | Et | CH(cBu)Me | Cl | OiPr | H | CH | CH | | |
| 375 | Et | CH(cBu)Et | Cl | OiPr | H | CH | CH | | |
| 376 | Et | CH(cBu)Pr | Cl | OiPr | H | CH | CH | | |
| 377 | Et | CH(Me)CH$_2$OMe | Cl | OiPr | H | CH | CH | | |
| 378 | Et | CH(Et)CH$_2$OMe | Cl | OiPr | H | CH | CH | | |
| 379 | Et | CH(cPr)CH$_2$OMe | Cl | OiPr | H | CH | CH | | |
| 380 | Et | CH(cBu)CH$_2$OMe | Cl | OiPr | H | CH | CH | | |
| 381 | Et | CH(nPr)CH$_2$OMe | ci | OiPr | H | CH | CH | | |
| 382 | Et | CH(cPr)C$_2$H$_4$OMe | Cl | OiPr | H | CH | CH | | |
| 383 | Et | CH(cBu)C$_2$H$_4$OMe | Cl | OiPr | H | CH | CH | | |
| 384 | Et | CH(Et)C$_2$H$_4$OMe | Cl | OiPr | H | CH | CH | | |
| 385 | Et | CHEt$_2$ | CF$_3$ | OMe | H | CH | CH | | |
| 386 | Et | CHPr2 | CF$_3$ | OMe | H | CH | CH | | |
| 387 | Et | CH(cPr)Et | CF$_3$ | OMe | H | CH | CH | | |
| 388 | Et | CH(cPr)Me | CF$_3$ | OMe | H | CH | CH | | |
| 389 | Et | CH(cPr)Pr | CF$_3$ | OMe | H | CH | CH | | |
| 390 | Et | CH(cBu)Me | CF$_3$ | OMe | H | CH | CH | | |
| 391 | Et | CH(cBu)Et | CF$_3$ | OMe | H | CH | CH | | |
| 392 | Et | CH(cBu)Pr | CF$_3$ | OMe | H | CH | CH | | |
| 393 | Et | CH(Me)CH$_2$OMe | CF$_3$ | OMe | H | CH | CH | | |
| 394 | Et | CH(Et)CH$_2$OMe | CF$_3$ | OMe | H | CH | CH | | |
| 395 | Et | CH(cPr)CH$_2$OMe | CF$_3$ | OMe | H | CH | CH | | |
| 396 | Et | CH(cBu)CH$_2$OMe | CF$_3$ | OMe | H | CH | CH | | |
| 397 | Et | CH(nPr)CH$_2$OMe | CF$_3$ | OMe | H | CH | CH | | |
| 398 | Et | CH(cPr)C$_2$H$_4$OMe | CF$_3$ | OMe | H | CH | CH | | |
| 399 | Et | CH(cBu)C$_2$H$_4$OMe | CF$_3$ | OMe | H | CH | CH | | |
| 400 | Et | CH(Et)C$_2$H$_4$OMe | CF$_3$ | OMe | H | CH | CH | | |
| 401 | Et | CHEt$_2$ | Me | OMe | H | N | CH | | |
| 402 | Et | CHPr2 | Me | OMe | H | N | CH | | |
| 403 | Et | CH(cPr)Et | Me | OMe | H | N | CH | | |
| 404 | Et | CH(cPr)Me | Me | OMe | H | N | CH | | |
| 405 | Et | CH(cPr)Pr | Me | OMe | H | N | CH | | |
| 406 | Et | CH(cBu)Me | Me | OMe | H | N | CH | | |
| 407 | Et | CH(cBu)Et | Me | OMe | H | N | CH | | |
| 408 | Et | CH(cBu)Pr | Me | OMe | H | N | CH | | |
| 409 | Et | CH(Me)CH$_2$OMe | Me | OMe | H | N | CH | | |
| 410 | Et | CH(Et)CH$_2$OMe | Me | OMe | H | N | CH | | |

TABLE 1-continued

| Ex. | R¹ | R³ | R^A | R^B | R^C | Y | Z | MS (m/z) | IC$_{50}$ Range* |
|---|---|---|---|---|---|---|---|---|---|
| 411 | Et | CH(cPr)CH$_2$OMe | Me | OMe | H | N | CH | | |
| 412 | Et | CH(cBu)CH$_2$OMe | Me | OMe | H | N | CH | | |
| 413 | Et | CH(nPr)CH$_2$OMe | Me | OMe | H | N | CH | | |
| 414 | Et | CH(cPr)C$_2$H$_4$OMe | Me | OMe | H | N | CH | | |
| 415 | Et | CH(cBu)C$_2$H$_4$OMe | Me | OMe | H | N | CH | | |
| 416 | Et | CH(Et)C$_2$H$_4$OMe | Me | OMe | H | N | CH | | |
| 417 | Et | CHEt$_2$ | Cl | CN | H | CH | CH | | |
| 418 | Et | CHPr2 | Cl | CN | H | CH | CH | | |
| 419 | Et | CH(cPr)Et | Cl | CN | H | CH | CH | | |
| 420 | Et | CH(cPr)Me | Cl | CN | H | CH | CH | | |
| 421 | Et | CH(cPr)Pr | Cl | CN | H | CH | CH | | |
| 422 | Et | CH(cBu)Me | Cl | CN | H | CH | CH | | |
| 423 | Et | CH(cBu)Et | Cl | CN | H | CH | CH | | |
| 424 | Et | CH(cBu)Pr | Cl | CN | H | CH | CH | | |
| 425 | Et | CH(Me)CH$_2$OMe | Cl | CN | H | CH | CH | | |
| 426 | Et | CH(Et)CH$_2$OMe | Cl | CN | H | CH | CH | 382.8 | e |
| 427 | Et | CH(cPr)CH$_2$OMe | Cl | CN | H | CH | CH | | |
| 428 | Et | CH(cBu)CH$_2$OMe | Cl | CN | H | CH | CH | | |
| 429 | Et | CH(nPr)CH$_2$OMe | Cl | CN | H | CH | CH | | |
| 430 | Et | CH(cPr)C$_2$H$_4$OMe | Cl | CN | H | CH | CH | | |
| 431 | Et | CH(cBu)C$_2$H$_4$OMe | Cl | CN | H | CH | CH | | |
| 432 | Et | CH(Et)C$_2$H$_4$OMe | Cl | CN | H | CH | CH | | |
| 433 | Et | CHEt$_2$ | Cl | CN | H | CH | N | | |
| 434 | Et | CHPr2 | Cl | CN | H | CH | N | | |
| 435 | Et | CH(cPr)Et | Cl | CN | H | CH | N | | |
| 436 | Et | CH(cPr)Me | Cl | CN | H | CH | N | | |
| 437 | Et | CH(cPr)Pr | Cl | CN | H | CH | N | | |
| 438 | Et | CH(cBu)Me | Cl | CN | H | CH | N | | |
| 439 | Et | CH(cBu)Et | Cl | CN | H | CH | N | | |
| 440 | Et | CH(cBu)Pr | Cl | CN | H | CH | N | | |
| 441 | Et | CH(Me)CH$_2$OMe | Cl | CN | H | CH | N | | |
| 442 | Et | CH(Et)CH$_2$OMe | Cl | CN | H | CH | N | | |
| 443 | Et | CH(cPr)CH$_2$OMe | Cl | CN | H | CH | N | | |
| 444 | Et | CH(cBu)CH$_2$OMe | Cl | CN | H | CH | N | | |
| 445 | Et | CH(nPr)CH$_2$OMe | Cl | CN | H | CH | N | | |
| 446 | Et | CH(cPr)C$_2$H$_4$OMe | Cl | CN | H | CH | N | | |
| 447 | Et | CH(cBu)C$_2$H$_4$OMe | Cl | CN | H | CH | N | | |
| 448 | Et | CH(Et)C$_2$H$_4$OMe | Cl | CN | H | CH | N | | |
| 449 | Me | CH(Et)CH$_2$OMe | Cl | CN | H | CH | CH | 382.9 | e |
| 450 | Me | CH$_2$iPr | Me | OMe | H | CCl | CH | | |
| 451 | Me | CH(Me)Pr | Me | OMe | H | CCl | CH | | |
| 452 | Me | CH(cPr)Et | Me | OMe | H | CCl | CH | 400.2 | a |
| 453 | Me | CH(cPr)Me | Me | OMe | H | CCl | CH | | |
| 454 | Me | CH(cPr)Pr | Me | OMe | H | CCl | CH | | |
| 455 | Me | CH(cBu)Me | Me | OMe | H | CCl | CH | | |
| 456 | Me | CH(cBu)Et | Me | OMe | H | CCl | CH | | |
| 457 | Me | CH(cBu)Pr | Me | OMe | H | CCl | CH | | |
| 458 | Me | CH(Me)CH$_2$OMe | Me | OMe | H | CCl | CH | | |
| 459 | Me | CH(Et)CH$_2$OMe | Me | OMe | H | CCl | CH | 402.2 | b |
| 460 | Me | CH(cPr)CH$_2$OMe | Me | OMe | H | CCl | CH | | |
| 461 | Me | CH(cBu)CH$_2$OMe | Me | OMe | H | CCl | CH | | |
| 462 | Me | CH(nPr)CH$_2$OMe | Me | OMe | H | CCl | CH | | |
| 463 | Me | CH(cPr)C$_2$H$_4$OMe | Me | OMe | H | CCl | CH | | |
| 464 | Me | CH(cBu)C$_2$H$_4$OMe | Me | OMe | H | CCl | CH | | |
| 465 | Me | CH(Et)C$_2$H$_4$OMe | Me | OMe | H | CCl | CH | | |
| 466 | Me | CH$_2$iPr | Me | OMe | H | CMe | CH | | |
| 467 | Me | CH(Me)Pr | Me | OMe | H | CMe | CH | | c |
| 468 | Me | CH(cPr)Et | Me | OMe | H | CMe | CH | | |
| 469 | Me | CH(cPr)Me | Me | OMe | H | CMe | CH | | |

TABLE 1-continued

| Ex. | R¹ | R³ | R^A | R^B | R^C | Y | Z | MS (m/z) | IC$_{50}$ Range* |
|---|---|---|---|---|---|---|---|---|---|
| 470 | Me | CH(cPr)Pr | Me | OMe | H | CMe | CH | | |
| 471 | Me | CH(cBu)Me | Me | OMe | H | CMe | CH | | |
| 472 | Me | CH(cBu)Et | Me | OMe | H | CMe | CH | | |
| 473 | Me | CH(cBu)Pr | Me | OMe | H | CMe | CH | | |
| 474 | Me | CH(Me)CH$_2$OMe | Me | OMe | H | CMe | CH | | |
| 475 | Me | CH(Et)CH$_2$OMe | Me | OMe | H | CMe | CH | | |
| 476 | Me | CH(cPr)CH$_2$OMe | Me | OMe | H | CMe | CH | | |
| 477 | Me | CH(cBu)CH$_2$OMe | Me | OMe | H | CMe | CH | | |
| 478 | Me | CH(nPr)CH$_2$OMe | Me | OMe | H | CMe | CH | | |
| 479 | Me | CH(cPr)C$_2$H$_4$OMe | Me | OMe | H | CMe | CH | | |
| 480 | Me | CH(cBu)C$_2$H$_4$OMe | Me | OMe | H | CMe | CH | | |
| 481 | Me | CH(Et)C$_2$H$_4$OMe | Me | OMe | H | CMe | CH | | |
| 482 | Me | CH$_2$iPr | Cl | OMe | H | OMe | CH | | |
| 483 | Me | CH(Me)Pr | Cl | OMe | H | CMe | CH | | |
| 484 | Me | CH(cPr)Et | Cl | OMe | H | CMe | CH | 398.2 | a |
| 485 | Me | CH(cPr)Me | Cl | OMe | H | CMe | CH | | |
| 486 | Me | CH(cPr)Pr | Cl | OMe | H | CMe | CH | | |
| 487 | Me | CH(cBu)Me | Cl | OMe | H | CMe | CH | | |
| 488 | Me | CH(cBu)Et | Cl | OMe | H | CMe | CH | | |
| 489 | Me | CH(cBu)Pr | Cl | OMe | H | CMe | CH | | |
| 490 | Me | CH(Me)CH$_2$OMe | Cl | OMe | H | CMe | CH | | |
| 491 | Me | CH(Et)CH$_2$OMe | Cl | OMe | H | CMe | CH | 402.2 | a |
| 492 | Me | CH(CPr)CH$_2$OMe | Cl | OMe | H | CMe | CH | | |
| 493 | Me | CH(cBu)CH$_2$OMe | Cl | OMe | H | CMe | CH | | |
| 494 | Me | CH(nPr)CH$_2$OMe | Cl | OMe | H | CMe | CH | | |
| 495 | Me | CH(cPr)C$_2$H$_4$OMe | Cl | OMe | H | CMe | CH | | |
| 496 | Me | CH(cBu)C$_2$H$_4$OMe | Cl | OMe | H | CMe | CH | | |
| 497 | Me | CH(Et)C$_2$H$_4$OMe | Cl | OMe | H | CMe | CH | | |
| 498 | Me | CH$_2$iPr | Cl | NMe$_2$ | H | CF | CH | | |
| 499 | Me | CH(Me)Pr | Cl | NMe$_2$ | H | CF | CH | | |
| 500 | Me | CH(cPr)Et | Cl | NMe$_2$ | H | CF | CH | 415.3 | a |
| 501 | Me | CH(cPr)Me | Cl | NMe$_2$ | H | CF | CH | 401.2 | b |
| 502 | Me | CH(cPr)Pr | Cl | NMe$_2$ | H | CF | CH | | |
| 503 | Me | CH(cBu)Me | Cl | NMe$_2$ | H | CF | CH | 415.2 | b |
| 504 | Me | CH(cBu)Et | Cl | NMe$_2$ | H | CF | CH | | |
| 505 | Me | CH(cBu)Pr | Cl | NMe$_2$ | H | CF | CH | | |
| 506 | Me | CH(Me)CH$_2$OMe | Cl | NMe$_2$ | H | CF | CH | 405.2 | b |
| 507 | Me | CH(Et)CH$_2$OMe | Cl | NMe$_2$ | H | CF | CH | 419.3 | a |
| 508 | Me | CH(cPr)CH$_2$OMe | Cl | NMe$_2$ | H | CF | CH | | |
| 509 | Me | CH(cBu)CH$_2$OMe | Cl | NMe$_2$ | H | CF | CH | | |
| 510 | Me | CH(cPr)CH$_2$OMe | Cl | NMe$_2$ | H | CF | CH | | |
| 511 | Me | CH(cPr)C$_2$H$_4$OMe | Cl | NMe$_2$ | H | CF | CH | | |
| 512 | Me | CH(cBu)C$_2$H$_4$OMe | Cl | NMe$_2$ | H | CF | CH | | |
| 513 | Me | CH(Et)C$_2$H$_4$OMe | Cl | NMe$_2$ | H | CF | CH | | |
| 514 | Me | CH$_2$iPr | Cl | OCF$_3$ | H | CH | CH | | |
| 515 | Me | CH(Me)Pr | Cl | OCF$_3$ | H | CH | CH | 425.2 | d |
| 516 | Me | CH(cPr)Et | Cl | OCF$_3$ | H | CH | CH | 439.2 | c |
| 517 | Me | CH(cPr)Me | Cl | OCF$_3$ | H | CH | CH | | |
| 518 | Me | CH(cPr)Pr | Cl | OCF$_3$ | H | CH | CH | | |
| 519 | Me | CH(cBu)Me | Cl | OCF$_3$ | H | CH | CH | | |
| 520 | Me | CH(cBu)Et | Cl | OCF$_3$ | H | CH | CH | | |
| 521 | Me | CH(cBu)Pr | Cl | OCF$_3$ | H | CH | CH | | |
| 522 | Me | CH(Me)CH$_2$OMe | Cl | OCF$_3$ | H | CH | CH | 429.2 | d |
| 523 | Me | CH(Et)CH$_2$OMe | Cl | OCF$_3$ | H | CH | CH | | |
| 524 | Me | CH(cPr)CH$_2$OMe | Cl | OCF$_3$ | H | CH | CH | | |
| 525 | Me | CH(cBu)CH$_2$OMe | Cl | OCF$_3$ | H | CH | CH | | |
| 526 | Me | CH(nPr)CH$_2$OMe | Cl | OCF$_3$ | H | CH | CH | | |
| 527 | Me | CH(cPr)C$_2$H$_4$OMe | Cl | OCF$_3$ | H | CH | CH | | |
| 528 | Me | CH(CBu)C$_2$H$_4$OMe | Cl | OCF$_3$ | H | CH | CH | | |

TABLE 1-continued

| Ex. | R¹ | R³ | R^A | R^B | R^C | Y | Z | MS (m/z) | IC$_{50}$ Range* |
|---|---|---|---|---|---|---|---|---|---|
| 529 | Me | CH(Et)C$_2$H$_4$OMe | Cl | OCF$_3$ | H | CH | CH | | |
| 530 | Me | CH$_2$iPr | OMe | OMe | H | N | N | | |
| 531 | Me | CH(Me)Pr | OMe | OMe | H | N | N | | |
| 532 | Me | CH(cPr)Et | OMe | OMe | H | N | N | 382.4 | e |
| 533 | Me | CH(cPr)Me | OMe | OMe | H | N | N | | |
| 534 | Me | CH(cPr)Pr | OMe | OMe | H | N | N | | |
| 535 | Me | CH(cBu)Me | OMe | OMe | H | N | N | | |
| 536 | Me | CH(cBu)Et | OMe | OMe | H | N | N | | |
| 537 | Me | CH(cBu)Pr | OMe | OMe | H | N | N | | |
| 538 | Me | CH(Me)CH$_2$OMe | OMe | OMe | H | N | N | 372.4 | e |
| 539 | Me | CH(Et)CH$_2$OMe | OMe | OMe | H | N | N | | |
| 540 | Me | CH(cPr)CH$_2$OMe | OMe | OMe | H | N | N | | |
| 541 | Me | CH(cBu)CH$_2$OMe | OMe | OMe | H | N | N | | |
| 542 | Me | CH(nPr)CH$_2$OMe | OMe | OMe | H | N | N | | |
| 543 | Me | CH(cPr)C$_2$H$_4$OMe | OMe | OMe | H | N | N | | |
| 544 | Me | CH(cBu)C$_2$H$_4$OMe | OMe | OMe | H | N | N | | |
| 545 | Me | CH(Et)C$_2$H$_4$OMe | OMe | OMe | H | N | N | | |

TABLE 2

| Ex. # | R¹ | R³ | R^A | R^B | R^C | Y | Z | MS (m/z) | IC$_{50}$ Range* |
|---|---|---|---|---|---|---|---|---|---|
| 546 | Me | CHMeEt | Cl | Cl | H | CH | CH | 363.1 | d |
| 547 | Me | CHPr2 | Cl | Cl | H | CH | CH | 405.1 | d |
| 548 | Me | CH(cPr)Et | Cl | Cl | H | CH | CH | 389.1 | c |
| 549 | Me | CH(cPr)Me | Cl | Cl | H | CH | CH | | |
| 550 | Me | CH(cPr)Pr | Cl | Cl | H | CH | CH | | |
| 551 | Me | CH(cBu)Me | Cl | Cl | H | CH | CH | | |
| 552 | Me | CH(cBu)Et | Cl | Cl | H | CH | CH | 403.1 | c |
| 553 | Me | CH(cBu)Pr | Cl | Cl | H | CH | CH | | |
| 554 | Me | CH(Me)CH$_2$OMe | Cl | Cl | H | CH | CH | 379.1 | d |
| 555 | Me | CH(Et)CH$_2$OMe | Cl | Cl | H | CH | CH | 393.0 | |
| 556 | Me | CH(cPr)CH$_2$OMe | Cl | Cl | H | CH | CH | | |
| 557 | Me | CH(cBu)CH$_2$OMe | Cl | Cl | H | CH | CH | | |
| 558 | Me | CH(nPr)CH$_2$OMe | Cl | Cl | H | CH | CH | | |
| 559 | Me | CH(cPr)C$_2$H$_4$OMe | Cl | Cl | H | CH | CH | | |
| 560 | Me | CH(cBu)C$_2$H$_4$OMe | Cl | Cl | H | CH | CH | | |
| 561 | Me | CH(Et)C$_2$H$_4$OMe | Cl | Cl | H | CH | CH | | |
| 562 | Me | CHEt$_2$ | Cl | OMe | H | CH | CH | | |
| 563 | Me | CHPr2 | Cl | OMe | H | CH | CH | 401.3 | b |

TABLE 2-continued

| Ex. # | R¹ | R³ | R^A | R^B | R^C | Y | Z | MS (m/z) | IC$_{50}$ Range* |
|---|---|---|---|---|---|---|---|---|---|
| 564 | Me | CH(cPr)Et | Cl | OMe | H | CH | CH | 385.1 | c |
| 565 | Me | CH(cPr)Me | Cl | OMe | H | CH | CH | 371.3 | c |
| 566 | Me | CH(cPr)Pr | Cl | OMe | H | CH | CH | | |
| 567 | Me | CH(cBu)Me | Cl | OMe | H | CH | CH | 385.3 | b |
| 568 | Me | CH(cBu)Et | Cl | OMe | H | CH | CH | | |
| 569 | Me | CH(cBu)Pr | Cl | OMe | H | CH | CH | | |
| 570 | Me | CH(Me)CH$_2$OMe | Cl | OMe | H | CH | CH | 375.2 | d |
| 571 | Me | CH(Et)CH$_2$OMe | Cl | OMe | H | CH | CH | 389.3 | c |
| 572 | Me | CH(cPr)CH$_2$OMe | Cl | OMe | H | CH | CH | | |
| 573 | Me | CH(cBu)CH$_2$OMe | Cl | OMe | H | CH | CH | | |
| 574 | Me | CH(cPr)CH$_2$OMe | Cl | OMe | H | CH | CH | 403.4 | d |
| 575 | Me | CH(cPr)C$_2$H$_4$OMe | Cl | OMe | H | CH | CH | | |
| 576 | Me | CH(cBu)C$_2$H$_4$OMe | Cl | OMe | H | CH | CH | | |
| 577 | Me | CH(Et)C$_2$H$_4$OMe | Cl | OMe | H | CH | CH | | |
| 578 | Me | CHEt$_2$ | Cl | OMe | H | CF | CH | | |
| 579 | Me | CHPr2 | Cl | OMe | H | CF | CH | | |
| 580 | Me | CH(cPr)Et | Cl | OMe | H | CF | CH | | |
| 581 | Me | CH(cPr)Me | Cl | OMe | H | CF | CH | | |
| 582 | Me | CH(cPr)Pr | Cl | OMe | H | CF | CH | | |
| 583 | Me | CH(cBu)Me | Cl | OMe | H | CF | CH | | |
| 584 | Me | CH(cBu)Et | Cl | OMe | H | CF | CH | | |
| 585 | Me | CH(cBu)Pr | Cl | OMe | H | CF | CH | | |
| 586 | Me | CH(Me)CH$_2$OMe | Cl | OMe | H | CF | CH | | |
| 587 | Me | CH(Et)CH$_2$OMe | Cl | OMe | H | CF | CH | | |
| 588 | Me | CH(cPr)CH$_2$OMe | Cl | OMe | H | CF | CH | | |
| 589 | Me | CH(cBu)CH$_2$OMe | Cl | OMe | H | CF | CH | | |
| 590 | Me | CH(nPr)CH$_2$OMe | Cl | OMe | H | CF | CH | | |
| 591 | Me | CH(cPr)C$_2$H$_4$OMe | Cl | OMe | H | CF | CH | | |
| 592 | Me | CH(cBu)C$_2$H$_4$OMe | Cl | OMe | H | CF | CH | | |
| 593 | Me | CH(Et)C$_2$H$_4$OMe | Cl | OMe | H | CF | CH | | |
| 594 | Me | CHEt$_2$ | Cl | Me | H | CH | CH | | |
| 595 | Me | CHPr2 | Cl | Me | H | CH | CH | | |
| 596 | Me | CH(cPr)Et | Cl | Me | H | CH | CH | | |
| 597 | Me | CH(cPr)Me | Cl | Me | H | CH | CH | | |
| 598 | Me | CH(cPr)Pr | Cl | Me | H | CH | CH | | |
| 599 | Me | CH(cBu)Me | Cl | Me | H | CH | CH | | |
| 600 | Me | CH(cBu)Et | Cl | Me | H | CH | CH | | |
| 601 | Me | CH(cBu)Pr | Cl | Me | H | CH | CH | | |
| 602 | Me | CH(Me)CH$_2$OMe | Cl | Me | H | CH | CH | | |
| 603 | Me | CH(Et)CH$_2$OMe | Cl | Me | H | CH | CH | | |
| 604 | Me | CH(cPr)CH$_2$OMe | Cl | Me | H | CH | CH | | |
| 605 | Me | CH(cBu)CH$_2$OMe | Cl | Me | H | CH | CH | | |
| 606 | Me | CH(nPr)CH$_2$OMe | Cl | Me | H | CH | CH | | |
| 607 | Me | CH(cPr)C$_2$H$_4$OMe | Cl | Me | H | CH | CH | | |
| 608 | Me | CH(CBu)C$_2$H$_4$OMe | Cl | Me | H | CH | CH | | |
| 609 | Me | CH(Et)C$_2$H$_4$OMe | Cl | Me | H | CH | CH | | |
| 610 | Me | CHEt$_2$ | Me | OMe | H | CH | CH | | |
| 611 | Me | CHPr2 | Me | OMe | H | CH | CH | | |
| 612 | Me | CH(cPr)Et | Me | OMe | H | CH | CH | 377.3 | d |
| 613 | Me | CH(cPr)Me | Me | OMe | H | CH | CH | | |
| 614 | Me | CH(cPr)Pr | Me | OMe | H | CH | CH | | |
| 615 | Me | CH(cBu)Me | Me | OMe | H | CH | CH | | |
| 616 | Me | CH(cBu)Et | Me | OMe | H | CH | CH | | |
| 617 | Me | CH(cBu)Pr | Me | OMe | H | CH | CH | | |
| 618 | Me | CH(Me)CH$_2$OMe | Me | OMe | H | CH | CH | | |
| 619 | Me | CH(Et)CH$_2$OMe | Me | OMe | H | CH | CH | | |
| 620 | Me | CH(cPr)CH$_2$OMe | Me | OMe | H | CH | CH | | |
| 621 | Me | CH(cBu)CH$_2$OMe | Me | OMe | H | CH | CH | | |
| 622 | Me | CH(nPr)CH$_2$OMe | Me | OMe | H | CH | CH | | |

TABLE 2-continued

| Ex. # | R¹ | R³ | Rᴬ | Rᴮ | Rᶜ | Y | Z | MS (m/z) | IC₅₀ Range* |
|---|---|---|---|---|---|---|---|---|---|
| 623 | Me | CH(cPr)C₂H₄OMe | Me | OMe | H | CH | CH | | |
| 624 | Me | CH(cBu)C₂H₄OMe | Me | OMe | H | CH | CH | | |
| 625 | Me | CH(Et)C₂H₄OMe | Me | OMe | H | CH | CH | | |
| 626 | Me | CHEt₂ | Me | OMe | H | CF | CH | | |
| 627 | Me | CHPr2 | Me | OMe | H | CF | CH | | |
| 628 | Me | CH(cPr)Et | Me | OMe | H | CF | CH | | |
| 629 | Me | CH(cPr)Me | Me | OMe | H | CF | CH | | |
| 630 | Me | CH(cPr)Pr | Me | OMe | H | CF | CH | | |
| 631 | Me | CH(cBu)Me | Me | OMe | H | CF | CH | | |
| 632 | Me | CH(cBu)Et | Me | OMe | H | CF | CH | | |
| 633 | Me | CH(cBu)Pr | Me | OMe | H | CF | CH | | |
| 634 | Me | CH(Me)CH₂OMe | Me | OMe | H | CF | CH | | |
| 635 | Me | CH(Et)CH₂OMe | Me | OMe | H | CF | CH | | |
| 636 | Me | CH(cPr)CH₂OMe | Me | OMe | H | CF | CH | | |
| 637 | Me | CH(cBu)CH₂OMe | Me | OMe | H | CF | CH | | |
| 638 | Me | CH(nPr)CH₂OMe | Me | OMe | H | CF | CH | | |
| 639 | Me | CH(cPr)C₂H₄OMe | Me | OMe | H | CF | CH | | |
| 640 | Me | CH(cBu)C₂H₄OMe | Me | OMe | H | CF | CH | | |
| 641 | Me | CH(Et)C₂H₄OMe | Me | OMe | H | CF | CH | | |
| 642 | Me | CHEt2 | Me | OMe | H | CH | N | | |
| 643 | Me | CHPr2 | Me | OMe | H | CH | N | | |
| 644 | Me | CH(cPr)Et | Me | OMe | H | CH | N | 366.3 | d |
| 645 | Me | CH(cPr)Me | Me | OMe | H | CH | N | | |
| 646 | Me | CH(cPr)Pr | Me | OMe | H | CH | N | | |
| 647 | Me | CH(cBu)Me | Me | OMe | H | CH | N | | |
| 648 | Me | CH(cBu)Et | Me | OMe | H | CH | N | | |
| 649 | Me | CH(cBu)Pr | Me | OMe | H | CH | N | | |
| 650 | Me | CH(Me)CH₂OMe | Me | OMe | H | CH | N | 356.3 | e |
| 651 | Me | CH(Et)CH₂OMe | Me | OMe | H | CH | N | 370.3 | e |
| 652 | Me | CH(cPr)CH₂OMe | Me | OMe | H | CH | N | | |
| 653 | Me | CH(cBu)CH₂OMe | Me | OMe | H | CH | N | | |
| 654 | Me | CH(nPr)CH₂OMe | Me | OMe | H | CH | N | | |
| 655 | Me | CH(cPr)C₂H₄OMe | Me | OMe | H | CH | N | | |
| 656 | Me | CH(cBu)C₂H₄OMe | Me | OMe | H | CH | N | | |
| 657 | Me | CH(Et)C₂H₄OMe | Me | OMe | H | CH | N | | |
| 658 | Me | CHEt₂ | Cl | OCHF₂ | H | CH | CH | | |
| 659 | Me | CHPr2 | Cl | OCHF₂ | H | CH | CH | | |
| 660 | Me | CH(cPr)Et | Cl | OCHF₂ | H | CH | CH | | |
| 661 | Me | CH(cPr)Me | Cl | OCHF₂ | H | CH | CH | | |
| 662 | Me | CH(cPr)Pr | Cl | OCHF₂ | H | CH | CH | | |
| 663 | Me | CH(cBu)Me | Cl | OCHF₂ | H | CH | CH | | |
| 664 | Me | CH(cBu)Et | Cl | OCHF₂ | H | CH | CH | | |
| 665 | Me | CH(cBu)Pr | Cl | OCHF₂ | H | CH | CH | | |
| 666 | Me | CH(Me)CH₂OMe | Cl | OCHF₂ | H | CH | CH | | |
| 667 | Me | CH(Et)CH₂OMe | Cl | OCHF₂ | H | CH | CH | | |
| 668 | Me | CH(cPr)CH₂OMe | Cl | OCHF₂ | H | CH | CH | | |
| 669 | Me | CH(cBu)CH₂OMe | Cl | OCHF₂ | H | CH | CH | | |
| 670 | Me | CH(nPr)CH₂OMe | Cl | OCHF₂ | H | CH | CH | | |
| 671 | Me | CH(cPr)C₂H₄OMe | Cl | OCHF₂ | H | CH | CH | | |
| 672 | Me | CH(cBu)C₂H₄OMe | Cl | OCHF₂ | H | CH | CH | | |
| 673 | Me | CH(Et)C₂H₄OMe | Cl | OCHF₂ | H | CH | CH | | |
| 674 | Me | CHEt₂ | Cl | CF₃ | H | CH | CH | | |
| 675 | Me | CHPr2 | Cl | CF₃ | H | CH | CH | | |
| 676 | Me | CH(cPr)Et | Cl | CF₃ | H | CH | CH | | |
| 677 | Me | CH(cPr)Me | Cl | CF₃ | H | CH | CH | | |
| 678 | Me | CH(cPr)Pr | Cl | CF₃ | H | CH | CH | | |
| 679 | Me | CH(cBu)Me | Cl | CF₃ | H | CH | CH | | |
| 680 | Me | CH(cBu)Et | Cl | CF₃ | H | CH | CH | | |
| 681 | Me | CH(cBu)Pr | Cl | CF₃ | H | CH | CH | | |

TABLE 2-continued

| Ex. # | R¹ | R³ | R^A | R^B | R^C | Y | Z | MS (m/z) | IC$_{50}$ Range* |
|---|---|---|---|---|---|---|---|---|---|
| 682 | Me | CH(Me)CH$_2$OMe | Cl | CF$_3$ | H | CH | CH | | |
| 683 | Me | CH(Et)CH$_2$OMe | Cl | CF$_3$ | H | CH | CH | | |
| 684 | Me | CH(cPr)CH$_2$OMe | Cl | CF$_3$ | H | CH | CH | | |
| 685 | Me | CH(cBu)CH$_2$OMe | Cl | CF$_3$ | H | CH | CH | | |
| 686 | Me | CH(nPr)CH$_2$OMe | Cl | CF$_3$ | H | CH | CH | | |
| 687 | Me | CH(cPr)C$_2$H$_4$OMe | Cl | CF$_3$ | H | CH | CH | | |
| 688 | Me | CH(cBu)C$_2$H$_4$OMe | Cl | CF$_3$ | H | CH | CH | | |
| 689 | Me | CH(Et)C$_2$H$_4$OMe | Cl | CF$_3$ | H | CH | CH | | |
| 690 | Me | CHEt$_2$ | Cl | OEt | H | CH | CH | | |
| 691 | Me | CHPr2 | Cl | OEt | H | CH | CH | | |
| 692 | Me | CH(cPr)Et | Cl | OEt | H | CH | CH | | |
| 693 | Me | CH(cPr)Me | Cl | OEt | H | CH | CH | | |
| 694 | Me | CH(cPr)Pr | Cl | OEt | H | CH | CH | | |
| 695 | Me | CH(cBu)Me | Cl | OEt | H | CH | CH | | |
| 696 | Me | CH(cBu)Et | Cl | OEt | H | CH | CH | | |
| 697 | Me | CH(cBu)Pr | Cl | OEt | H | CH | CH | | |
| 698 | Me | CH(Me)CH$_2$OMe | Cl | OEt | H | CH | CH | | |
| 699 | Me | CH(Et)CH$_2$OMe | Cl | OEt | H | CH | CH | | |
| 700 | Me | CH(cPr)CH$_2$OMe | Cl | OEt | H | CH | CH | | |
| 701 | Me | CH(cBu)CH$_2$OMe | Cl | OEt | H | CH | CH | | |
| 702 | Me | CH(nPr)CH$_2$OMe | Cl | OEt | H | CH | CH | | |
| 703 | Me | CH(cPr)C$_2$H$_4$OMe | Cl | OEt | H | CH | CH | | |
| 704 | Me | CH(cBu)C$_2$H$_4$OMe | Cl | OEt | H | CH | CH | | |
| 705 | Me | CH(Et)C$_2$H$_4$OMe | Cl | OEt | H | CH | CH | | |
| 706 | Me | CHEt$_2$ | Cl | OiPr | H | CH | CH | | |
| 707 | Me | CHPr2 | Cl | OiPr | H | CH | CH | | |
| 708 | Me | CH(cPr)Et | Cl | OiPr | H | CH | CH | | |
| 709 | Me | CH(cPr)Me | Cl | OiPr | H | CH | CH | | |
| 710 | Me | CH(cPr)Pr | Cl | OiPr | H | CH | CH | | |
| 711 | Me | CH(cBu)Me | Cl | OiPr | H | CH | CH | | |
| 712 | Mc | CH(cBu)Et | Cl | OiPr | H | CH | CH | | |
| 713 | Me | CH(cBu)Pr | Cl | OiPr | H | CH | CH | | |
| 714 | Me | CH(Me)CH$_2$OMe | Cl | OiPr | H | CH | CH | | |
| 715 | Me | CH(Et)CH$_2$OMe | Cl | OiPr | H | CH | CH | | |
| 716 | Me | CH(cPr)CH$_2$OMe | Cl | OiPr | H | CH | CH | | |
| 717 | Me | CH(cBu)CH$_2$OMe | Cl | OiPr | H | CH | CH | | |
| 718 | Me | CH(npr)CH$_2$OMe | Cl | OiPr | H | CH | CH | | |
| 719 | Me | CH(cPr)C$_2$H$_4$OMe | Cl | OiPr | H | CH | CH | | |
| 720 | Me | CH(cBu)C$_2$H$_4$OMe | Cl | OiPr | H | CH | CH | | |
| 721 | Me | CH(Et)C$_2$H$_4$OMe | Cl | OiPr | H | CH | CH | | |
| 722 | Me | CHEt$_2$ | CF$_3$ | OMe | H | CH | CH | | |
| 723 | Me | CHPr2 | CF$_3$ | OMe | H | CH | CH | | |
| 724 | Me | CH(cPr)Et | CF$_3$ | OMe | H | CH | CH | | |
| 725 | Me | CH(cPr)Me | CF$_3$ | OMe | H | CH | CH | | |
| 726 | Me | CH(cPr)Pr | CF$_3$ | OMe | H | CH | CH | | |
| 727 | Me | CH(cBu)Me | CF$_3$ | OMe | H | CH | CH | | |
| 728 | Me | CH(cBu)Et | CF$_3$ | OMe | H | CH | CH | | |
| 729 | Me | CH(cBu)Pr | CF$_3$ | OMe | H | CH | CH | | |
| 730 | Me | CH(Me)CH$_2$OMe | CF$_3$ | OMe | H | CH | CH | | |
| 731 | Me | CH(Et)CH$_2$OMe | CF$_3$ | OMe | H | CH | CH | | |
| 732 | Me | CH(cPr)CH$_2$OMe | CF$_3$ | OMe | H | CH | CH | | |
| 733 | Me | CH(cBu)CH$_2$OMe | CF$_3$ | OMe | H | CH | CH | | |
| 734 | Me | CH(nPr)CH$_2$OMe | CF$_3$ | OMe | H | CH | CH | | |
| 735 | Me | CH(cPr)C$_2$H$_4$OMe | CF$_3$ | OMe | H | CH | CH | | |
| 736 | Me | CH(cBu)C$_2$H$_4$OMe | CF$_3$ | OMe | H | CH | CH | | |
| 737 | Me | CH(Et)C$_2$H$_4$OMe | CF$_3$ | OMe | H | CH | CH | | |
| 738 | Me | CHEt$_2$ | Me | OMe | H | N | CH | | |
| 739 | Me | CHPr2 | Me | OMe | H | N | CH | | |
| 740 | Me | CH(cPr)Et | Me | OMe | H | N | CH | | |

TABLE 2-continued

| Ex. # | R¹ | R³ | Rᴬ | Rᴮ | Rᶜ | Y | Z | MS (m/z) | IC₅₀ Range* |
|---|---|---|---|---|---|---|---|---|---|
| 741 | Me | CH(cPr)Me | Me | OMe | H | N | CH | | |
| 742 | Me | CH(cPr)Pr | Me | OMe | H | N | CH | | |
| 743 | Me | CH(cBu)Me | Me | OMe | H | N | CH | | |
| 744 | Me | CH(cBu)Et | Me | OMe | H | N | CH | | |
| 745 | Me | CH(cBu)Pr | Me | OMe | H | N | CH | | |
| 746 | Me | CH(Me)CH₂OMe | Me | OMe | H | N | CH | | |
| 747 | Me | CH(Et)CH₂OMe | Me | OMe | H | N | CH | | |
| 748 | Me | CH(cPr)CH₂OMe | Me | OMe | H | N | CH | | |
| 749 | Me | CH(cBu)CH₂OMe | Me | OMe | H | N | CH | | |
| 750 | Me | CH(nPr)CH₂OMe | Me | OMe | H | N | CH | | |
| 751 | Me | CH(cPr)C₂H₄OMe | Me | OMe | H | N | CH | | |
| 752 | Me | CH(cBu)C₂H₄OMe | Me | OMe | H | N | CH | | |
| 753 | Me | CH(Et)C₂H₄OMe | Me | OMe | H | N | CH | | |
| 754 | Et | CHEt₂ | Cl | Cl | H | CH | CH | | |
| 755 | Et | CHPr2 | Cl | Cl | H | CH | CH | | |
| 756 | Et | CH(cPr)Et | Cl | Cl | H | CH | CH | | |
| 757 | Et | CH(cPr)Me | Cl | Cl | H | CH | CH | | |
| 758 | Et | CH(cPr)Pr | Cl | Cl | H | CH | CH | | |
| 759 | Et | CH(cBu)Me | Cl | Cl | H | CH | CH | | |
| 760 | Et | CH(cBu)Et | Cl | Cl | H | CH | CH | | |
| 761 | Et | CH(cBu)Pr | Cl | Cl | H | CH | CH | | |
| 762 | Et | CH(Me)CH₂OMe | Cl | Cl | H | CH | CH | | |
| 763 | Et | CH(Et)CH₂OMe | Cl | Cl | H | CH | CH | | |
| 764 | Et | CH(cPr)CH₂OMe | Cl | Cl | H | CH | CH | | |
| 765 | Et | CH(cBu)CH₂OMe | Cl | Cl | H | CH | CH | | |
| 766 | Et | CH(nPr)CH₂OMe | Cl | Cl | H | CH | CH | | |
| 767 | Et | CH(cPr)C₂H₄OMe | Cl | Cl | H | CH | CH | | |
| 768 | Et | CH(cBu)C₂H₄OMe | Cl | Cl | H | CH | CH | | |
| 769 | Et | CH(Et)C₂H₄OMe | Cl | Cl | H | CH | CH | | |
| 770 | Et | CHEt₂ | Cl | OMe | H | CH | CH | | |
| 771 | Et | CHPr2 | Cl | OMe | H | CH | CH | | |
| 772 | Et | CH(cPr)Et | Cl | OMe | H | CH | CH | | |
| 773 | Et | CH(cPr)Me | Cl | OMe | H | CH | CH | | |
| 774 | Et | CH(cPr)Pr | Cl | OMe | H | CH | CH | | |
| 775 | Et | CH(cBu)Me | Cl | OMe | H | CH | CH | | |
| 776 | Et | CH(cBu)Et | Cl | OMe | H | CH | CH | | |
| 777 | Et | CH(cBu)Pr | Cl | OMe | H | CH | CH | | |
| 778 | Et | CH(Me)CH₂OMe | Cl | OMe | H | CH | CH | | |
| 779 | Et | CH(Et)CH₂OMe | Cl | OMe | H | CH | CH | | |
| 780 | Et | CH(cPr)CH₂OMe | Cl | OMe | H | CH | CH | | |
| 781 | Et | CH(cBu)CH₂OMe | Cl | OMe | H | CH | CH | | |
| 782 | Et | CH(nPr)CH₂OMe | Cl | OMe | H | CH | CH | | |
| 783 | Et | CH(cPr)C₂H₄OMe | Cl | OMe | H | CH | CH | | |
| 784 | Et | CH(cBu)C₂H₄OMe | Cl | OMe | H | CH | CH | | |
| 785 | Et | CH(Et)C₂H₄OMe | Cl | OMe | H | CH | CH | | |
| 786 | Et | CHEt₂ | Cl | OMe | H | CF | CH | | |
| 787 | Et | CHPr2 | Cl | OMe | H | CF | CH | | |
| 788 | Et | CH(cPr)Et | Cl | OMe | H | CF | CH | | |
| 789 | Et | CH(cPr)Me | Cl | OMe | H | CF | CH | | |
| 790 | Et | CH(cPr)Pr | Cl | OMe | H | CF | CH | | |
| 791 | Et | CH(cBu)Me | Cl | OMe | H | CF | CH | | |
| 792 | Et | CH(cBu)Et | Cl | OMe | H | CF | CH | | |
| 793 | Et | CH(cBu)Pr | Cl | OMe | H | CF | CH | | |
| 794 | Et | CH(Me)CH₂OMe | Cl | OMe | H | CF | CH | | |
| 795 | Et | CH(Et)CH₂OMe | Cl | OMe | H | CF | CH | | |
| 796 | Et | CH(cPr)CH₂OMe | Cl | OMe | H | CF | CH | | |
| 797 | Et | CH(cBu)CH₂OMe | Cl | OMe | H | CF | CH | | |
| 798 | Et | CH(nPr)CH₂OMe | Cl | OMe | H | CF | CH | | |
| 799 | Et | CH(cPr)C₂H₄OMe | Cl | OMe | H | CF | CH | | |

TABLE 2-continued

| Ex. # | R¹ | R³ | R^A | R^B | R^C | Y | Z | MS (m/z) | IC$_{50}$ Range* |
|---|---|---|---|---|---|---|---|---|---|
| 800 | Et | CH(cBu)C$_2$H$_4$OMe | Cl | OMe | H | CF | CH | | |
| 801 | Et | CH(Et)C$_2$H$_4$OMe | Cl | OMe | H | CF | CH | | |
| 802 | Et | CHEt$_2$ | Cl | Me | H | CH | CH | | |
| 803 | Et | CHPr2 | Cl | Me | H | CH | CH | | |
| 804 | Et | CH(cPr)Et | Cl | Me | H | CH | CH | | |
| 805 | Et | CH(cPr)Me | Cl | Me | H | CH | CH | | |
| 806 | Et | CH(cPr)Pr | Cl | Me | H | CH | CH | | |
| 807 | Et | CH(cBu)Me | Cl | Me | H | CH | CH | | |
| 808 | Et | CH(cBu)Et | Cl | Me | H | CH | CH | | |
| 809 | Et | CH(cBu)Pr | Cl | Me | H | CH | CH | | |
| 810 | Et | CH(Me)CH$_2$OMe | Cl | Me | H | CH | CH | | |
| 811 | Et | CH(Et)CH$_2$OMe | Cl | Me | H | CH | CH | | |
| 812 | Et | CH(cPr)CH$_2$OMe | Cl | Me | H | CH | CH | | |
| 813 | Et | CH(cBu)CH$_2$OMe | Cl | Me | H | CH | CH | | |
| 814 | Et | CH(nPr)CH$_2$OMe | Cl | Me | H | CH | CH | | |
| 815 | Et | CH(cPr)C$_2$H$_4$OMe | Cl | Me | H | CH | CH | | |
| 816 | Et | CH(cBu)C$_2$H$_4$OMe | Cl | Me | H | CH | CH | | |
| 817 | Et | CH(Et)C$_2$H$_4$OMe | Cl | Me | H | CH | CH | | |
| 818 | Et | CHEt$_2$ | Me | OMe | H | CH | CH | | |
| 819 | Et | CHPr2 | Me | OMe | H | CH | CH | | |
| 820 | Et | CH(cPr)Et | Me | OMe | H | CH | CH | | |
| 821 | Et | CH(cPr)Me | Me | OMe | H | CH | CH | | |
| 822 | Et | CH(cPr)Pr | Me | OMe | H | CH | CH | | |
| 823 | Et | CH(cBu)Me | Me | OMe | H | CH | CH | | |
| 824 | Et | CH(cBu)Et | Me | OMe | H | CH | CH | | |
| 825 | Et | CH(cBu)Pr | Me | OMe | H | CH | CH | | |
| 826 | Et | CH(Me)CH$_2$OMe | Me | OMe | H | CH | CH | | |
| 827 | Et | CH(Et)CH$_2$OMe | Me | OMe | H | CH | CH | | |
| 828 | Et | CH(cPr)CH$_2$OMe | Me | OMe | H | CH | CH | | |
| 829 | Et | CH(cBu)CH$_2$OMe | Me | OMe | H | CH | CH | | |
| 830 | Et | CH(nPr)CH$_2$OMe | Me | OMe | H | CH | CH | | |
| 831 | Et | CH(cPr)C$_2$H$_4$OMe | Me | OMe | H | CH | CH | | |
| 832 | Et | CH(cBu)C$_2$H$_4$OMe | Me | OMe | H | CH | CH | | |
| 833 | Et | CH(Et)C$_2$H$_4$OMe | Me | OMe | H | CH | CH | | |
| 834 | Et | CHEt$_2$ | Me | OMe | H | CF | CH | | |
| 835 | Et | CHPr2 | Me | OMe | H | CF | CH | | |
| 836 | Et | CH(cPr)Et | Me | OMe | H | CF | CH | | |
| 837 | Et | CH(cPr)Me | Me | OMe | H | CF | CH | | |
| 838 | Et | CH(cPr)Pr | Me | OMe | H | CF | CH | | |
| 839 | Et | CH(cBu)Me | Me | OMe | H | CF | CH | | |
| 840 | Et | CH(cBu)Et | Me | OMe | H | CF | CH | | |
| 841 | Et | CH(cBu)Pr | Me | OMe | H | CF | CH | | |
| 842 | Et | CH(Me)CH$_2$OMe | Me | OMe | H | CF | CH | | |
| 843 | Et | CH(Et)CH$_2$OMe | Me | OMe | H | CF | CH | | |
| 844 | Et | CH(cPr)CH$_2$OMe | Me | OMe | H | CF | CH | | |
| 845 | Et | CH(cBu)CH$_2$OMe | Me | OMe | H | CF | CH | | |
| 846 | Et | CH(nPr)CH$_2$OMe | Me | OMe | H | CF | CH | | |
| 847 | Et | CH(cPr)C$_2$H$_4$OMe | Me | OMe | H | CF | CH | | |
| 848 | Et | CH(cBu)C$_2$H$_4$OMe | Me | OMe | H | CF | CH | | |
| 849 | Et | CH(Et)C$_2$H$_4$OMe | Me | OMe | H | CF | CH | | |
| 850 | Et | CHEt$_2$ | Me | OMe | H | CH | N | | |
| 851 | Et | CHPr2 | Me | OMe | H | CH | N | | |
| 852 | Et | CH(cPr)Et | Me | OMe | H | CH | N | | |
| 853 | Et | CH(cPr)Me | Me | OMe | H | CH | N | | |
| 854 | Et | CH(cPr)Pr | Me | OMe | H | CH | N | | |
| 855 | Et | CH(cBu)Me | Me | OMe | H | CH | N | | |
| 856 | Et | CH(cBu)Et | Me | OMe | H | CH | N | | |
| 857 | Et | CH(cBu)Pr | Me | OMe | H | CH | N | | |
| 858 | Et | CH(Me)CH$_2$OMe | Me | OMe | H | CH | N | | |

TABLE 2-continued

| Ex. # | R¹ | R³ | R^A | R^B | R^C | Y | Z | MS (m/z) | IC₅₀ Range* |
|---|---|---|---|---|---|---|---|---|---|
| 859 | Et | CH(Et)CH₂OMe | Me | OMe | H | CH | N | | |
| 860 | Et | CH(cPr)CH₂OMe | Me | OMe | H | CH | N | | |
| 861 | Et | CH(cBu)CH₂OMe | Me | OMe | H | CH | N | | |
| 862 | Et | CH(nPr)CH₂OMe | Me | OMe | H | CH | N | | |
| 863 | Et | CH(cPr)C₂H₄OMe | Me | OMe | H | CH | N | | |
| 864 | Et | CH(cBu)C₂H₄OMe | Me | OMe | H | CH | N | | |
| 865 | Et | CH(Et)C₂H₄OMe | Me | OMe | H | CH | N | | |
| 866 | Et | CHEt₂ | Cl | OCHF₂ | H | CH | CH | | |
| 867 | Et | CHPr2 | Cl | OCHF₂ | H | CH | CH | | |
| 868 | Et | CH(cPr)Et | Cl | OCHF₂ | H | CH | CH | | |
| 869 | Et | CH(cPr)Me | Cl | OCHF₂ | H | CH | CH | | |
| 870 | Et | CH(cPr)Pr | Cl | OCHF₂ | H | CH | CH | | |
| 871 | Et | CH(cBu)Me | Cl | OCHF₂ | H | CH | CH | | |
| 872 | Et | CH(cBu)Et | Cl | OCHF₂ | H | CH | CH | | |
| 873 | Et | CH(cBu)Pr | Cl | OCHF₂ | H | CH | CH | | |
| 874 | Et | CH(Me)CH₂OMe | Cl | OCHF₂ | H | CH | CH | | |
| 875 | Et | CH(Et)CH₂OMe | Cl | OCHF₂ | H | CH | CH | | |
| 876 | Et | CH(cPr)CH₂OMe | Cl | OCHF₂ | H | CH | CH | | |
| 877 | Et | CH(cBu)CH₂OMe | Cl | OCHF₂ | H | CH | CH | | |
| 878 | Et | CH(nPr)CH₂OMe | Cl | OCHF₂ | H | CH | CH | | |
| 879 | Et | CH(cPr)C₂H₄OMe | Cl | OCHF₂ | H | CH | CH | | |
| 880 | Et | CH(cBu)C₂H₄OMe | Cl | OCHF₂ | H | CH | CH | | |
| 881 | Et | CH(Et)C₂H₄OMe | Cl | OCHF₂ | H | CH | CH | | |
| 882 | Et | CHEt₂ | Cl | CF₃ | H | CH | CH | | |
| 883 | Et | CHPr2 | Cl | CF₃ | H | CH | CH | | |
| 884 | Et | CH(cPr)Et | Cl | CF₃ | H | CH | CH | | |
| 885 | Et | CH(cPr)Me | Cl | CF₃ | H | CH | CH | | |
| 886 | Et | CH(cPr)Pr | Cl | CF₃ | H | CH | CH | | |
| 887 | Et | CH(cBu)Me | Cl | CF₃ | H | CH | CH | | |
| 888 | Et | CH(cBu)Et | Cl | CF₃ | H | CH | CH | | |
| 889 | Et | CH(cBu)Pr | Cl | CF₃ | H | CH | CH | | |
| 890 | Et | CH(Me)CH₂OMe | Cl | CF₃ | H | CH | CH | | |
| 891 | Et | CH(Et)CH₂OMe | Cl | CF₃ | H | CH | CH | | |
| 892 | Et | CH(cPr)CH₂OMe | Cl | CF₃ | H | CH | CH | | |
| 893 | Et | CH(cBu)CH₂OMe | Cl | CF₃ | H | CH | CH | | |
| 894 | Et | CH(nPr)CH₂OMe | Cl | CF₃ | H | CH | CH | | |
| 895 | Et | CH(cPr)C₂H₄OMe | Cl | CF₃ | H | CH | CH | | |
| 896 | Et | CH(cBu)C₂H₄OMe | Cl | CF₃ | H | CH | CH | | |
| 897 | Et | CH(Et)C₂H₄OMe | Cl | CF₃ | H | CH | CH | | |
| 898 | Et | CHEt₂ | Cl | OEt | H | CH | CH | | |
| 899 | Et | CHPr2 | Cl | OEt | H | CH | CH | | |
| 900 | Et | CH(cPr)Et | Cl | OEt | H | CH | CH | | |
| 901 | Et | CH(cPr)Me | Cl | OEt | H | CH | CH | | |
| 902 | Et | CH(cPr)Pr | Cl | OEt | H | CH | CH | | |
| 903 | Et | CH(cBu)Me | Cl | OEt | H | CH | CH | | |
| 904 | Et | CH(cBu)Et | Cl | OEt | H | CH | CH | | |
| 905 | Et | CH(cBu)Pr | Cl | OEt | H | CH | CH | | |
| 906 | Et | CH(Me)CH₂OMe | Cl | OEt | H | CH | CH | | |
| 907 | Et | CH(Et)CH₂OMe | Cl | OEt | H | CH | CH | | |
| 908 | Et | CH(cPr)CH₂OMe | Cl | OEt | H | CH | CH | | |
| 909 | Et | CH(cBu)CH₂OMe | Cl | OEt | H | CH | CH | | |
| 910 | Et | CH(nPr)CH₂OMe | Cl | OEt | H | CH | CH | | |
| 911 | Et | CH(cPr)C₂H₄OMe | Cl | OEt | H | CH | CH | | |
| 912 | Et | CH(cBu)C₂H₄OMe | Cl | OEt | H | CH | CH | | |
| 913 | Et | CH(Et)C₂H₄OMe | Cl | OEt | H | CH | CH | | |
| 914 | Et | CHEt₂ | Cl | OiPr | H | CH | CH | | |
| 915 | Et | CHPr2 | Cl | OiPr | H | CH | CH | | |
| 916 | Et | CH(cPr)Et | Cl | OiPr | H | CH | CH | | |
| 917 | Et | CH(cPr)Me | Cl | OiPr | H | CH | CH | | |

TABLE 2-continued

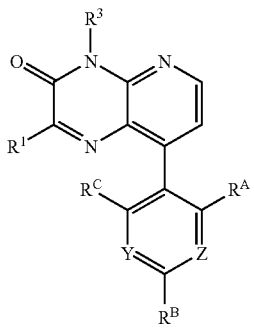

| Ex. # | R¹ | R³ | R^A | R^B | R^C | Y | Z | MS (m/z) | IC50 Range* |
|---|---|---|---|---|---|---|---|---|---|
| 918 | Et | CH(cPr)Pr | Cl | OiPr | H | CH | CH | | |
| 919 | Et | CH(cBu)Me | Cl | OiPr | H | CH | CH | | |
| 920 | Et | CH(cBu)Et | Cl | OiPr | H | CH | CH | | |
| 921 | Et | CH(cBu)Pr | Cl | OiPr | H | CH | CH | | |
| 922 | Et | CH(Me)CH₂OMe | Cl | OiPr | H | CH | CH | | |
| 923 | Et | CH(Et)CH₂OMe | C | OiPr | H | CH | CH | | |
| 924 | Et | CH(cPr)CH₂OMe | Cl | OiPr | H | CH | CH | | |
| 925 | Et | CH(cBu)CH₂OMe | Cl | OiPr | H | CH | CH | | |
| 926 | Et | CH(nPr)CH₂OMe | Cl | OiPr | H | CH | CH | | |
| 927 | Et | CH(cPr)C₂H₄OMe | Cl | OiPr | H | CH | CH | | |
| 928 | Et | CH(cBu)C₂H₄OMe | Cl | OiPr | H | CH | CH | | |
| 928 | Et | CH(Et)C₂H₄OMe | Cl | OiPr | H | CH | CH | | |
| 930 | Et | CHEt₂ | CF₃ | OMe | H | CH | CH | | |
| 931 | Et | CHPr2 | CF₃ | OMe | H | CH | CH | | |
| 932 | Et | CH(cPr)Et | CF₃ | OMe | H | CH | CH | | |
| 933 | Et | CH(cPr)Me | CF₃ | OMe | H | CH | CH | | |
| 934 | Et | CH(cPr)Pr | CF₃ | OMe | H | CH | CH | | |
| 935 | Et | CH(cBu)Me | CF₃ | OMe | H | CH | CH | | |
| 936 | Et | CH(cBu)Et | CF₃ | OMe | H | CH | CH | | |
| 937 | Et | CH(cBu)Pr | CF₃ | OMe | H | CH | CH | | |
| 938 | Et | CH(Me)CH₂OMe | CF₃ | OMe | H | CH | CH | | |
| 939 | Et | CH(Et)CH₂OMe | CF₃ | OMe | H | CH | CH | | |
| 940 | Et | CH(cPr)CH₂OMe | CF₃ | OMe | H | CH | CH | | |
| 941 | Et | CH(cBu)CH₂OMe | CF₃ | OMe | H | CH | CH | | |
| 942 | Et | CH(nIPr)CH₂OMe | CF₃ | OMe | H | CH | CH | | |
| 943 | Et | CH(cPr)C₂H₄OMe | CF₃ | OMe | H | CH | CH | | |
| 944 | Et | CH(cBu)C₂H₄OMe | CF₃ | OMe | H | CH | CH | | |
| 945 | Et | CH(Et)C₂H₄OMe | CF₃ | OMe | H | CH | CH | | |
| 946 | Et | CHEt₂ | Me | OMe | H | N | CH | | |
| 947 | Et | CHPr2 | Me | OMe | H | N | CH | | |
| 948 | Et | CH(cPr)Et | Me | OMe | H | N | CH | | |
| 949 | Et | CH(cPr)Me | Me | OMe | H | N | CH | | |
| 950 | Et | CH(cPr)Pr | Me | OMe | H | N | CH | | |
| 951 | Et | CH(cBu)Me | Me | OMe | H | N | CH | | |
| 952 | Et | CH(cBu)Et | Me | OMe | H | N | CH | | |
| 953 | Et | CH(cBu)Pr | Me | OMe | H | N | CH | | |
| 954 | Et | CH(Me)CH₂OMe | Me | OMe | H | N | CH | | |
| 955 | Et | CH(Et)CH₂OMe | Me | OMe | H | N | CH | | |
| 956 | Et | CH(cPr)CH₂OMe | Me | OMe | H | N | CH | | |
| 957 | Et | CH(cBu)CH₂OMe | Me | OMe | H | N | CH | | |
| 958 | Et | CH(nPr)CH₂OMe | Me | OMe | H | N | CH | | |
| 959 | Et | CH(cPr)C₂H₄OMe | Me | OMe | H | N | CH | | |
| 960 | Et | CH(cBu)C₂H₄OMe | Me | OMe | H | N | CH | | |
| 961 | Et | CH(EQC₂H₄OMe | Me | OMe | H | N | CH | | |
| 962 | Et | CHEt₂ | Cl | CN | H | CH | CH | | |
| 963 | Et | CHPr2 | Cl | CN | H | CH | CH | | |
| 964 | Et | CH(cPr)Et | Cl | CN | H | CH | CH | | |
| 965 | Et | CH(cPr)Me | Cl | CN | H | CH | CH | | |
| 966 | Et | CH(cPr)Pr | Cl | CN | H | CH | CH | | |
| 967 | Et | CH(cBu)Me | Cl | CN | H | CH | CH | | |
| 968 | Et | CH(cBu)Et | Cl | CN | H | CH | CH | | |
| 969 | Et | CH(cBu)Pr | Cl | CN | H | CH | CH | | |
| 970 | Et | CH(Me)CH₂OMe | Cl | CN | H | CH | CH | | |
| 971 | Et | CH(Et)CH₂OMe | Cl | CN | H | CH | CH | | |
| 972 | Et | CH(cPr)CH₂OMe | Cl | CN | H | CH | CH | | |
| 973 | Et | CH(cBu)CH₂OMe | Cl | CN | H | CH | CH | | |
| 974 | Et | CH(nPr)CH₂OMe | Cl | CN | H | CH | CH | | |
| 975 | Et | CH(cPr)C₂H₄OMe | Cl | CN | H | CH | CH | | |
| 976 | Et | CH(cBu)C₂H₄OMe | Cl | CN | H | CH | CH | | |

TABLE 2-continued

| Ex. # | R¹ | R³ | R^A | R^B | R^C | Y | Z | MS (m/z) | IC$_{50}$ Range* |
|---|---|---|---|---|---|---|---|---|---|
| 977 | Et | CH(Et)C$_2$H$_4$OMe | Cl | CN | H | CH | CH | | |
| 978 | Et | CHEt$_2$ | Cl | CN | H | CH | N | | |
| 979 | Et | CHPr2 | Cl | CN | H | CH | N | | |
| 980 | Et | CH(cPr)Et | Cl | CN | H | CH | N | | |
| 981 | Et | CH(cPr)Me | Cl | CN | H | CH | N | | |
| 982 | Et | CH(cPr)Pr | Cl | CN | H | CH | N | | |
| 983 | Et | CH(cBu)Me | Cl | CN | H | CH | N | | |
| 984 | Et | CH(cBu)Et | Cl | CN | H | CH | N | | |
| 985 | Et | CH(cBu)Pr | Cl | CN | H | CH | N | | |
| 986 | Et | CH(Me)CH$_2$OMe | Cl | CN | H | CH | N | | |
| 987 | Et | CH(Et)CH$_2$OMe | Cl | CN | H | CH | N | | |
| 988 | Et | CH(cPr)CH$_2$OMe | Cl | CN | H | CH | N | | |
| 989 | Et | CH(cBu)CH$_2$OMe | Cl | CN | H | CH | N | | |
| 990 | Et | CH(nPr)CH$_2$OMe | Cl | CN | H | CH | N | | |
| 991 | Et | CH(cPr)C$_2$H$_4$OMe | Cl | CN | H | CH | N | | |
| 992 | Et | CH(cBu)C$_2$H$_4$OMe | Cl | CN | H | CH | N | | |
| 993 | Et | CH(Et)C$_2$H$_4$OMe | Cl | CN | H | CH | N | | |
| 994 | Me | CH(cPr)2 | Cl | Cl | H | CH | CH | 401.1 | c |
| 995 | Me | CH$_2$iPr | Me | OMe | H | CCl | CH | | |
| 996 | Me | CH(Me)Pr | Me | OMe | H | CCl | CH | | |
| 997 | Me | CH(cPr)Et | Me | OMe | H | CCl | CH | | |
| 998 | Me | CH(cPr)Me | Me | OMe | H | CCl | CH | | |
| 999 | Me | CH(cPr)Pr | Me | OMe | H | CCl | CH | | |
| 1000 | Me | CH(cBu)Me | Me | OMe | H | CCl | CH | | |
| 1001 | Me | CH(cBu)Et | Me | OMe | H | CCl | CH | | |
| 1002 | Me | CH(cBu)Pr | Me | OMe | H | CCl | CH | | |
| 1003 | Me | CH(Me)CH$_2$OMe | Me | OMe | H | CCl | CH | | |
| 1004 | Me | CH(Et)CH$_2$OMe | Me | OMe | H | CCl | CH | | |
| 1005 | Me | CH(cPr)CH$_2$OMe | Me | OMe | H | CCl | CH | | |
| 1006 | Me | CH(cBu)CH$_2$OMe | Me | OMe | H | CCl | CH | | |
| 1007 | Me | CH(nPr)CH$_2$OMe | Me | OMe | H | CCl | CH | | |
| 1008 | Me | CH(cPr)C$_2$H$_4$OMe | Me | OMe | H | CCl | CH | | |
| 1009 | Me | CH(cBu)C$_2$H$_4$OMe | Me | OMe | H | CCl | CH | | |
| 1010 | Me | CH(Et)C$_2$H$_4$OMe | Me | OMe | H | CCl | CH | | |
| 1011 | Me | CH$_2$iPr | Me | OMe | H | CMe | CH | | |
| 1012 | Me | CH(Me)Pr | Me | OMe | H | CMe | CH | | |
| 1013 | Me | CH(cPr)Et | Me | OMe | H | CMe | CH | | c |
| 1014 | Me | CH(cPr)Me | Me | OMe | H | CMe | CH | | |
| 1015 | Me | CH(cPr)Pr | Me | OMe | H | CMe | CH | | |
| 1016 | Me | CH(cBu)Me | Me | OMe | H | CMe | CH | | |
| 1017 | Me | CH(cBu)Et | Me | OMe | H | CMe | CH | | |
| 1018 | Me | CH(cBu)Pr | Me | OMe | H | CMe | CH | | |
| 1019 | Me | CH(Me)CH$_2$OMe | Me | OMe | H | CMe | CH | | |
| 1020 | Me | CH(Et)CH$_2$OMe | Me | OMe | H | CMe | CH | | |
| 1021 | Me | CH(cPr)CH$_2$OMe | Me | OMe | H | CMe | CH | | |
| 1022 | Me | CH(cBu)CH$_2$OMe | Me | OMe | H | CMe | CH | | |
| 1023 | Me | CH(nPr)CH$_2$OMe | Me | OMe | H | CMe | CH | | |
| 1024 | Me | CH(cPr)C$_2$H$_4$OMe | Me | OMe | H | CMe | CH | | |
| 1025 | Me | CH(cBu)C$_2$H$_4$OMe | Me | OMe | H | CMe | CH | | |
| 1026 | Me | CH(Et)C$_2$H$_4$OMe | Me | OMe | H | CMe | CH | | |
| 1027 | Me | CH$_2$iPr | Cl | OMe | H | CMe | CH | | |
| 1028 | Me | CH(Me)Pr | Cl | OMe | H | CMe | CH | | |
| 1029 | Me | CH(cPr)Et | Cl | OMe | H | CMe | CH | | |
| 1030 | Me | CH(cPr)Me | Cl | OMe | H | CMe | CH | | |
| 1031 | Me | CH(cPr)Pr | Cl | OMe | H | CMe | CH | | |
| 1032 | Me | CH(cBu)Me | Cl | OMe | H | CMe | CH | | |
| 1033 | Me | CH(cBu)Et | Cl | OMe | H | CMe | CH | | |
| 1034 | Me | CH(cBu)Pr | Cl | OMe | H | CMe | CH | | |
| 1035 | Me | CH(Me)CH$_2$OMe | Cl | OMe | H | CMe | CH | | |

TABLE 2-continued

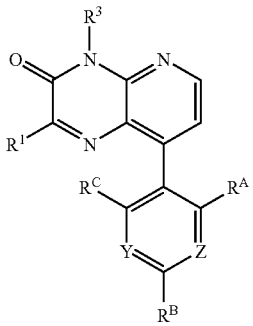

| Ex. # | R[1] | R[3] | R[A] | R[B] | R[C] | Y | Z | MS (m/z) | IC$_{50}$ Range* |
|---|---|---|---|---|---|---|---|---|---|
| 1036 | Me | CH(Et)CH$_2$OMe | Cl | OMe | H | CMe | CH | | |
| 1037 | Me | CH(cPr)CH$_2$OMe | Cl | OMe | H | CMe | CH | | |
| 1038 | Me | CH(cBu)CH$_2$OMe | Cl | OMe | H | CMe | CH | | |
| 1039 | Me | CH(nPr)CH$_2$OMe | Cl | OMe | H | CMe | CH | | |
| 1040 | Me | CH(cPr)C$_2$H$_4$OMe | Cl | OMe | H | CMe | CH | | |
| 1041 | Me | CH(cBu)C$_2$H$_4$OMe | Cl | OMe | H | CMe | CH | | |
| 1042 | Me | CH(Et)C$_2$H$_4$OMe | Cl | OMe | H | CMe | CH | | |
| 1043 | Me | CH$_2$iPr | Cl | NMe$_2$ | H | CF | CH | | |
| 1044 | Me | CH(Me)Pr | Cl | NMe$_2$ | H | CF | CH | | |
| 1045 | Me | CH(cPr)Et | Cl | NMe$_2$ | H | CF | CH | | |
| 1046 | Me | CH(cPr)Me | Cl | NMe$_2$ | H | CF | CH | | |
| 1047 | Me | CH(cPr)Pr | Cl | NMe$_2$ | H | CF | CH | | |
| 1048 | Me | CH(cBu)Me | Cl | NMe$_2$ | H | CF | CH | | |
| 1049 | Me | CH(cBu)Et | Cl | NMe$_2$ | H | CF | CH | | |
| 1050 | Me | CH(cBu)Pr | Cl | NMe$_2$ | H | CF | CH | | |
| 1051 | Me | CH(Me)CH$_2$OMe | Cl | NMe$_2$ | H | CF | CH | | |
| 1052 | Me | CH(Et)CH$_2$OMe | Cl | NMe$_2$ | H | CF | CH | | |
| 1053 | Me | CH(cPr)CH$_2$OMe | Cl | NMe$_2$ | H | CF | CH | | |
| 1054 | Me | CH(cBu)CH$_2$OMe | Cl | NMe$_2$ | H | CF | CH | | |
| 1055 | Me | CH(nPr)CH$_2$OMe | Cl | NMe$_2$ | H | CF | CH | | |
| 1056 | Me | CH(cPr)C$_2$H$_4$OMe | Cl | NMe$_2$ | H | CF | CH | | |
| 1057 | Me | CH(cBu)C$_2$H$_4$OMe | Cl | NMe$_2$ | H | CF | CH | | |
| 1058 | Me | CH(Et)C$_2$H$_4$OMe | Cl | NMe$_2$ | H | CF | CH | | |
| 1059 | Me | CH$_2$iPr | Cl | OCF$_3$ | H | CH | CH | | |
| 1060 | Me | CH(Me)Pr | Cl | OCF$_3$ | H | CH | CH | | |
| 1061 | Me | CH(cPr)Et | Cl | OCF$_3$ | H | CH | CH | | c |
| 1062 | Me | CH(cPr)Me | Cl | OCF$_3$ | H | CH | CH | 425.2 | d |
| 1063 | Me | CH(cPr)Pr | Cl | OCF$_3$ | H | CH | CH | | |
| 1064 | Me | CH(cBu)Me | Cl | OCF$_3$ | H | CH | CH | | |
| 1065 | Me | CH(cBu)Et | Cl | OCF$_3$ | H | CH | CH | | |
| 1066 | Me | CH(cBu)Pr | Cl | OCF$_3$ | H | CH | CH | | |
| 1067 | Me | CH(Me)CH$_2$OMe | Cl | OCF$_3$ | H | CH | CH | | c |
| 1068 | Me | CH(Et)CH$_2$OMe | Cl | OCF$_3$ | H | CH | CH | | |
| 1069 | Me | CH(cPr)CH$_2$OMe | Cl | OCF$_3$ | H | CH | CH | | |
| 1070 | Me | CH(cBu)CH$_2$OMe | Cl | OCF$_3$ | H | CH | CH | | |
| 1071 | Me | CH(nPr)CH$_2$OMe | Cl | OCF$_3$ | H | CH | CH | | |
| 1072 | Me | CH(cPr)C$_2$H$_4$OMe | Cl | OCF$_3$ | H | CH | CH | | |
| 1073 | Me | CH(cBu)C$_2$H$_4$OMe | Cl | OCF$_3$ | H | CH | CH | | |
| 1074 | Me | CH(Et)C$_2$H$_4$OMe | Cl | OCF$_3$ | H | CH | CH | | |
| 1075 | Me | CH$_2$iPr | OMe | OMe | H | N | N | | |
| 1076 | Me | CH(Me)Pr | OMe | OMe | H | N | N | | |
| 1077 | Me | CH(cPr)Et | OMe | OMe | H | N | N | | |
| 1078 | Me | CH(cPr)Me | OMe | OMe | H | N | N | | |
| 1079 | Me | CH(cPr)Pr | OMe | OMe | H | N | N | | |
| 1080 | Me | CH(cBu)Me | OMe | OMe | H | N | N | | |
| 1081 | Me | CH(cBu)Et | OMe | OMe | H | N | N | | |
| 1082 | Me | CH(cBu)Pr | OMe | OMe | H | N | N | | |
| 1083 | Me | CH(Me)CH$_2$OMe | OMe | OMe | H | N | N | | |
| 1084 | Me | CH(Et)CH$_2$OMe | OMe | OMe | H | N | N | | |
| 1085 | Me | CH(cPr)CH$_2$OMe | OMe | OMe | H | N | N | | |
| 1086 | Me | CH(cBu)CH$_2$OMe | OMe | OMe | H | N | N | | |
| 1087 | Me | CH(nPr)CH$_2$OMe | OMe | OMe | H | N | N | | |
| 1088 | Me | CH(cPr)C$_2$H$_4$OMe | OMe | OMe | H | N | N | | |
| 1089 | Me | CH(cBu)C$_2$H$_4$OMe | OMe | OMe | H | N | N | | |
| 1090 | Me | CH(Et)C$_2$H$_4$OMe | OMe | OMe | H | N | N | | |

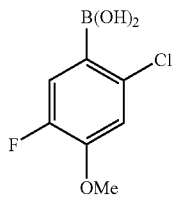

Preparation 1

2-Chloro-5-fluoro-4-methoxyphenylboronic acid

Part A

To a 1-chloro-3,4-difluorobenzene (25 g, 0.17 mol) cooled to 0° C. was added fuming nitric acid (50 mL) dropwise over 30 min. The orange solution was warmed to room temperature and stirred for 2 h. The solution was poured slowly over ice and the resultant mixture extracted with diethyl ether. The diethyl ether layers were washed with brine, dried ($Na_2SO_4$), filtered and concentrated in vacuo to give 26 g (80%) of 1-chloro-4,5-difluoro-2-nitro-benzene: Crude $^1$H NMR (400 MHz, $CDCl_3$): δ 7.88 (dd, J=9.3, 7.6 Hz, 1H), 7.43 (dd, J=9.3, 7.1 Hz, 1H). The crude material was pure enough to carry on to the next step.

Part B

To sodium methoxide (100 mL of a 0.5 M solution in methanol, 50.1 mmol) cooled to 0° C. was added a solution of 1-chloro-4,5-difluoro-2-nitro-benzene (9.7 g, 50.1 mmol) in methanol (10 mL) dropwise over 15 min. The solution was warmed to room temperature and stirred for 2 h, then poured slowly over ice. The yellow precipitate was collected by filtration and washed with cold water. The crystals were air dried to give 8.2 g (79%) of 1-chloro-4-fluoro-5-methoxy-2-nitro-benzene: Crude $^1$H NMR (400 MHz, $CDCl_3$): δ 7.85 (d, J=10.5 Hz, 1H), 7.06 (d, J=7.3 Hz, 1H), 3.98 (s, 3H). The crude material was pure enough to carry on to the next step.

Part C

1-Chloro-4-fluoro-5-methoxy-2-nitro-benzene (16.3 g, 79.3 mmol) and Sn granules (29.1 g, 246 mmol) were suspended in water (200 mL). Concentrated HCl (79 mL, 952 mmol) was added dropwise over 20 min. The resulting mixture was heated to 55° C. for 3 h. The solution was cooled to room temperature and carefully quenched with 1 N NaOH. The thick mixture was filtered through celite eluting the ethyl acetate to give a clear solution which was extracted with ethyl acetate. The ethyl acetate layers were washed with brine, dried ($Na_2SO_4$), filtered and concentrated in vacuo to give 26 g (80%) of 2-chloro-5-fluoro-4-methoxyaniline: Crude $^1$H NMR (400 MHz, $CDCl_3$): δ 6.88 (d, J=8.3 Hz, 1H), 6.57 (d, J=12.2 Hz, 1H), 3.79 (s, 3H), 3.77 (br s, 2H). The crude material was pure enough to carry on to the next step.

Part D

2-Chloro-5-fluoro-4-methoxyaniline (14.0 g, 79.7 mmol) was cooled to 0° C. and conc. HCl (40 mL) was added over 20 min. The suspension was heated to 55° C. until the aniline was completely dissolved, then cooled back to 0° C. A solution of sodium nitrite (6.1 g, 87.7 mmol) in water (15 mL) was added dropwise over 15 min. After complete addition the mixture was stirred at 0° C. for 30 min. Hexanes (24 mL) and dichloromethane (24 mL) were added followed by a solution of potassium iodide (26.5 g, 159.4 mmol) in water (25 mL) which was added dropwise over 30 min. After stirring at 0° C. for 4 h dichloromethane (50 mL) was added and the reaction quenched with sat. aq. $NaHSO_3$. The solution was extracted with dichloromethane. The organic layers were washed with brine, dried ($Na_2SO_4$), filtered and concentrated in vacuo to give 21 g (92%) of 1-chloro-4-fluoro-2-iodo-5-methoxy-benzene: Crude $^1$H NMR (400 MHz, $CDCl_3$): δ 7.48 (d, J=10.3 Hz, 1H), 7.04 (d, J=7.8 Hz, 1H), 3.86 (s, 3H). The crude material was pure enough to carry on to the next step.

Part E

To 1-chloro-4-fluoro-2-iodo-5-methoxy-benzene (10.0 g, 34.9 mmol) in THF (70 mL) was cooled to −78° C. was added triisopropylborate (8.9 mL, 38.4 mmol) followed by dropwise addition of n-butyl lithium (24 mL of a 1.6 M solution in hexanes, 38.4 mL). The solution was stirred and allowed to warm to room temperature over night by dissipation of the dry ice/acetone bath. 1N HCl (50 mL0 and water (50 mL) were added and the solution stirred at room temperature for 1 h. The solution was extracted with ethyl acetate. The organic layers were washed with brine, dried ($Na_2SO_4$), filtered and concentrated in vacuo. The residue was triturated with 1:1 hexanes/diethyl ether and the solid collected by filtration to give 3.8 g (53%) of pure 1-chloro-4-fluoro-2-iodo-5-methoxyphenyl boronic acid: $^1$H NMR (400 MHz, $CDCl_3$): δ 7.64 (d, J=11.7 Hz, 1H), 6.91 (d, J=7.3 Hz, 1H), 5.21 (br s, 2H), 3.90 (s, 3H).

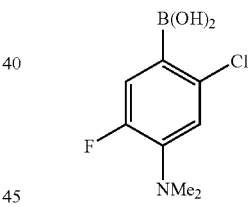

Preparation 2

2-Chloro-4-dimethylamino-5-fluorophenylboronic acid

Parts A and B

A solution of 1-chloro-4,5-difluoro-2-nitro-benzene (Preparation 1) (20.0 g, 103.3 mmol), $K_2CO_3$ (31.4 g, 227.3 mmol) and dimethyl amine. HCl (9.3 g, 113.6 mmol) in acetonitrile (200 mL) was heated to reflux for 2 h. The solution cooled to room temperature, quenched with water and extracted with ethyl acetate. The ethyl acetate layers were washed with brine, dried ($Na_2SO_4$), filtered and concentrated in vacuo to give 22.1 g (98%) of 1-chloro-5-dimethylamino-4-fluoro-2-nitro-benzene: Crude $^1$H NMR (400 MHz, $CDCl_3$): δ 7.83 (d, J=14.2 Hz, 1H), 6.72 (d, J=8.3 Hz, 1H), 3.09 (d, J=2.2 Hz, 6H), 3.77 (br s, 2H). The crude material was pure enough to carry on to the next step.

Parts C, D and E

1-Chloro-4-fluoro-2-iodo-5-methoxyphenyl boronic acid was prepared substantially as described in Preparation 1, Parts C, D and E: $^1$H NMR (400 MHz, CDCl$_3$): δ 7.52 (d, J=14.4 Hz, 1H), 6.71 (d, J=7.8 Hz, 1H), 5.18 (br s, 2H), 2.93 (d, J=1.2 Hz, 6H).

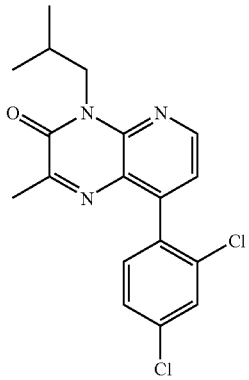

Example 1

(R,S)-8-(2,4-dichloro-phenyl)-4-isobutyl-2-methyl-4H-pyrido[2,3-b]pyrazin-3-one

Parts A, B, and C

2-Chloro-4-(2,4-dichloro-phenyl)-3-nitro-pyridine was prepared substantially as described in Example 9 and isolated as a brown viscous oil: crude $^1$H NMR (300 MHz, CDCl$_3$): δ 8.6 (d, 1H), 7.5 (s, 1H), 7.38 (s, 1H), 7.34 (d, 1H), 7.20 (d, 1H).

Part D

2-Chloro-4-(2,4-dichloro-phenyl)-3-nitro-pyridine (0.20 g, 0.66 mmol) and isobutylamine (0.096 g, 1.32 mmol) were treated substantially as described in Part D of Example 9 to yield 0.24 g (100%) of crude [4-(2.4-dichloro-phenyl)-2-nitro-pyridin-2-yl]-isobutyl-amine: MS (AP) m/z 340.2 [(M+H)$^+$, 98].

Part E

[4-(2.4-Dichloro-phenyl)-2-nitro-pyridin-2-yl]-isobutyl-amine (0.24 g, 0.71 mmol) and Na$_2$S$_2$O$_4$ (0.99 g, 5.69 mmol) were treated substantially as described in Part E of Example 9 to yield 0.22 g of 4-(2,4-dichloro-phenyl)-4-(2,4-dichloro-phenyl)-N$^2$-isobutyl-pyridine-2,3-diamine: MS (AP) m/z 310.23 [(M+H)$^+$, 78]. Taken on to Part F Part F 4-(2,4-Dichloro-phenyl)-4-(2,4-dichloro-phenyl)-N$^2$-isobutyl-pyridine-2,3-diamine (0.22 g, 0.71 mmol) was treated substantially as described in Part F of Example 9 to give 6.7 mg (2.0%) of 8-(2,4-dichloro-phenyl)-4-isobutyl-2-methyl-4H-pyrido[2,3-b]pyrazin-3-one (Example 1): $^1$H NMR (300 MHz, CD$_3$OD): □δ 8.6 (d, 1H), 7.6 (s, 1H), 7.45 (d, 1H), 7.39 (d, 1H), 7.25 (d, 1H), 4.4 (d, 2H), 2.4 (s, 2H), 2.35 (m, 1H), 1.25 (s, 1H), 0.95 (d, 6H). MS (ESI) m/z 362.3 [(M+H)$^+$, 100].

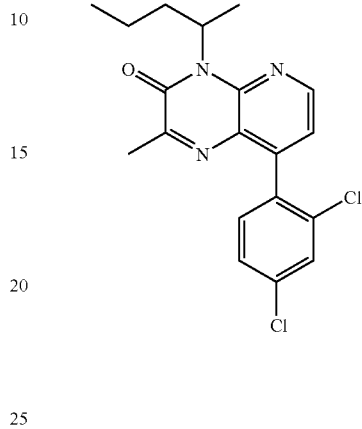

Example 2

(R,S)-8-(2,4-dichloro-phenyl)-2-methyl-4-(1-methyl-butyl)-4H-pyrido[2,3-b]pyrazin-3-one Parts A, B, and C 2-Chloro-4-(2,4-dichloro-phenyl)-3-nitro-pyridine was prepared substantially as described in Example 9.

Part D

2-Chloro-4-(2,4-dichloro-phenyl)-3-nitro-pyridine (0.20 g, 0.66 mmol) and 1-methyl-butylamine (0.11 g, 1.32 mmol) were treated substantially as described in Part D of Example 9 to produce 0.20 g (87%) of crude [4-(2,4-dichloro-phenyl)-3-nitro-pyridin-2-yl]-(1-methyl-butyl)-amine: MS (AP) m/z 354.2 [(M+H)+, 100].

Part E

[4-(2,4-Dichloro-phenyl)-3-nitro-pyridin-2-yl]-(1-methyl-butyl)-amine (0.25 g, 0.71 mmol) and Na$_2$S$_2$O$_4$ (1.00 g, 5.72 mmol) were treated substantially as described in Part E of Example 9 to yield 0.22 g (96%) of crude 4-(2,4-dichloro-phenyl)-N$^2$-(1-methyl-butyl)-pyridine-2,3-diamine: MS (AP) m/z 324.3 [(M+H)+, 76].

Part F 4-(2,4-Dichloro-phenyl)-N$^2$-(1-methyl-butyl)-pyridine-2,3-diamine (0.22 g, 0.68 mmol) was treated substantially as described in Part F of Example 9 to give 3.5 mg (1.0%) of crude 8-(2,4-dichloro-phenyl)-2-methyl-4-(1-methyl-butyl)-4H-pyrido[2,3-b]pyrazin-3-one (Example 2): $^1$H NMR (300 MHz, CD$_3$OD): δ 8.6 (d, 1H), 7.6 (s, 1H), 7.4 (d, 1H), 7.39 (d, 1H), 7.25 (d, 1H), 2.4 (s, 3H), 1.90 (m, 1H), 1.6 (s, 3H), 1.3 (s, 2H), 1.15 (m, 2H), 0.95 (t, 3H). MS (ESI) m/z 376.3 [(M+H)+, 100].

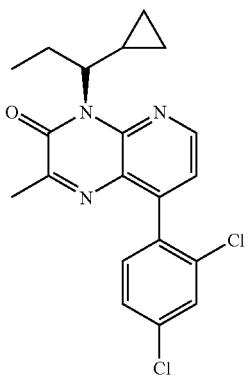

Example 3a (S)-4-(1-cyclopropyl-propyl)-8-(2,4-dichloro-phenyl)-2-methyl-4H-pyrido[2,3-b]pyrazin-3-one Parts A, B, and C 2-Chloro-4-(2,4-dichloro-phenyl)-3-nitro-pyridine was prepared substantially as described in Example 9.

Part D

2-Chloro-4-(2,4-dichloro-phenyl)-3-nitro-pyridine (0.26 g, 0.86 mmol) and 1-cyclopropyl-propylamine (0.23 g, 1.71 mmol) were substantially as described in Part D of Example 9 to produce 2.32 g (100%) of crude (1-cyclopropyl-propyl)-[4-(2,4-dichloro-phenyl)-3-nitro-pyridin-2-yl]-amine: MS (AP) m/z 366.2 [(M+H)$^+$, 96].

Part E (1-Cyclopropyl-propyl)-[4-(2,4-dichloro-phenyl)-3-nitro-pyridin-2-yl]-amine (0.26 g, 0.71 mmol) and Na$_2$S$_2$O$_4$ (1.00 g, 5.72 mmol) were treated substantially as described in Part E of Example 9 to yield 1.60 g (75%) of crude N$^2$-(1-cyclopropyl-propyl)-4-(2,4-dichloro-phenyl)-pyridine-2,3-diamine: MS (AP) m/z 336.3 [(M+H)$^+$, 98].

Part F

N$^2$-(1-cyclopropyl-propyl)-4-(2,4-dichloro-phenyl)-pyridine-2,3-diamine (0.16 g, 0.48 mmol) was treated substantially as described in Part F of Example 9 to give 8.3 mg (4.0%) of 4-(1-cyclopropyl-propyl)-8-(2,4-dichloro-phenyl)-2-methyl-4H-pyrido[2,3-b]pyrazin-3-one (Example 3a): $^1$H NMR (300 MHz, CD$_3$OD): δ 8.6 (d, 1H), 7.6 (s, 1H), 7.45 (d, 1H), 7.39 (d, 1H), 7.25 (d, 1H), 5.10 (m, 1H), 4.4 (m, 1H), 2.4 (s, 3H), 1.25 (s, 2H), 0.85 (t, 3H), 0.75 (m, 1H), 0.50–0.15 (m, 3H). MS (ESI) m/z 388.3 [(M+H)$^+$, 100].

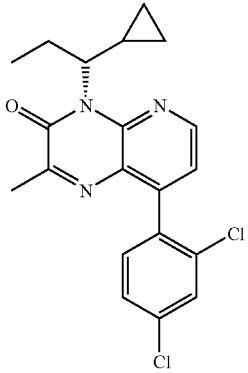

Example 3b (R)-4-(1-cyclopropyl-propyl)-8-(2,4-dichloro-phenyl)-2-methyl-4H-pyrido[2,3-b]pyrazin-3-one Parts A, B, and C 2-Chloro-4-(2,4-dichloro-phenyl)-3-nitro-pyridine was prepared substantially as described in Example 9.

Part D

2-Chloro-4-(2,4-dichloro-phenyl)-3-nitro-pyridine (0.34 g, 1.12 mmol) and 1-cyclopropyl-propylamine (0.30 g, 2.24 mmol) were treated substantially as described in Part D of Example 9 to produce 0.26 g (83%) of crude (1-cyclopropyl-propyl)-[4-(2,4-dichloro-phenyl)-3-nitro-pyridin-2-yl]-amine: MS (AP) m/z 366.3 [(M+H)$^+$, 100].

Part E (1-Cyclopropyl-propyl)-[4-(2,4-dichloro-phenyl)-3-nitro-pyridin-2-yl]-amine (0.46 g, 1.26 mmol) and Na$_2$S$_2$O$_4$ (1.76 g, 10.1 mmol) were treated substantially as described in Part E of Example 9 to yield 0.16 g (66%) of crude N$^2$-(1-cyclopropyl-propyl)-4-(2,4-dichloro-phenyl)-pyridine-2,3-diamine: MS (AP) m/z 336.3 [(M+H)$^+$, 100].

Part F

N$^2$-(1-cyclopropyl-propyl)-4-(2,4-dichloro-phenyl)-pyridine-2,3-diamine (0.25 g, 0.74 mmol) was treated substantially as described in Part F of Example 9 to give 6.1 mg (3%) of 4-(1-cyclopropyl-propyl)-8-(2,4-dichloro-phenyl)-2-methyl-4H-pyrido[2,3-b]pyrazin-3-one (Example 3b) $^1$H NMR (300 MHz, CD$_3$OD): δ 8.5 (d, 1H), 7.6 (s, 1H), 7.4 (d, 1H), 7.35 (d, 1H), 7.25 (d, 1H), 5.1 (q, 1H), 4.4 (q, 1H), 2.4 (s, 3H), 1.25 (s, 2H), 0.85 (t, 3H), 0.65 (m, 1H), 0.50–0.10 (m, 3H). MS (ESI) m/z 388.3 [(M+H)$^+$, 100].

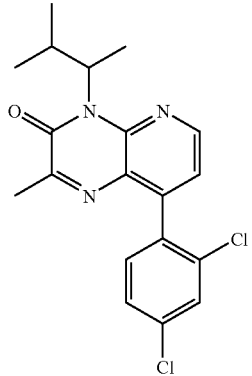

Example 4

(R,S)-8-(2,4-dichloro-phenyl)-4-(1,2-dimethyl-propyl)-2-methyl-4H-pyrido[2,3-b]pyrazin-3-one Parts A, B, and C 2-Chloro-4-(2,4-dichloro-phenyl)-3-nitro-pyridine was prepared substantially as described in Example 9.

Part D

2-Chloro-4-(2,4-dichloro-phenyl)-3-nitro-pyridine (0.20 g, 0.66 mmol) and 1,2-dimethyl-propylamine (0.11 g, 1.32 mmol) were treated substantially as described in Part D of Example 9 to produce 0.26 g (100%) of [4-(2,4-dichlorophenyl)-3-nitro-pyridin-2-yl]-(1,2-dimethyl-propyl)-amine. MS (AP) m/z 354.2 [(M+H)+, 100].

Part E

[4-(2,4-Dichloro-phenyl)-3-nitro-pyridin-2-yl]-(1,2-dimethyl-propyl)-amine (0.26 g, 0.74 mmol) and $Na_2S_2O_4$ (1.03 g, 5.94 mmol) were treated substantially as described in Part E of Example 9 to yield 0.18 g (75%) of crude 4-(2,4-dichloro-phenyl)-$N^2$-(1,2-dimethyl-propyl)-pyridine-2,3-diamine: MS (AP) m/z 324.3 [(M+H)+, 70].

Part F 4-(2,4-Dichloro-phenyl)-$N^2$-(1,2-dimethyl-propyl)-pyridine-2,3-diamine (0.18 g, 0.56 mmol) was treated substantially as described in Part F of Example 9 to give 4.0 mg (2%) of 8-(2,4-dichloro-phenyl)-4-(1,2-dimethyl-propyl)-2-methyl-4H-pyrido[2,3-b]pyrazin-3-one (Example 4): $^1$H NMR (300 MHz, $CD_3OD$): δ 8.6 (d, 1H), 7.6 (s, 1H), 7.4 (d, 1H), 7.35 (d, 1H), 7.25 (d, 1H), 2.2 (s, 3H), 1.6 (m, 2H), 1.3 (s, 2H), 1.15 (d, 3H), 0.95 (m, 1H), 0.65 (bs, 3H). MS (ESI) m/z 376.3 [(M+H)+, 100].

(2,4-dichloro-phenyl)-3-nitro-pyridin-2-yl]-amine: MS (AP) m/z 380.3 [(M+H)+, 100].

Part D (1-Cyclopropyl-butyl)-[4-(2,4-dichloro-phenyl)-3-nitro-pyridin-2-yl]-amine (0.66 g, 1.74 mmol) and $Na_2S_2O_4$ (2.45 g, 14.0 mmol) were treated substantially as described in Part E of Example 9 to yield 0.44 g (72%) of $N^2$-(1-cyclopropyl-butyl)-4-(2,4-dichloro-phenyl)-pyridine-2,3-diamine: MS (AP) m/z 350.3 [(M+H)+, 100].

Part E $N^2$-(1-Cyclopropyl-butyl)-4-(2,4-dichloro-phenyl)-pyridine-2,3-diamine (0.44 g, 1.26 mmol) was treated substantially as described in Part F of Example 9 to give 7.8 mg (2%) of 4-(1-cyclopropyl-butyl)-8-(2,4-dichloro-phenyl)-2-methyl-4H-pyrido[2,3-b]pyrazin-3-one (Example 5): $^1$H NMR (300 MHz, $CDCl_3$): δ 8.5 (d, 1H), 7.5 (s, 1H), 7.39 (d, 1H), 7.30 (s, 1H), 7.2 (d, 1H), 5.10 (q, 1H), 4.5 (q, 1H), 2.5 (s, 3H), 2.4–2.0 (m, 3H), 1.2 (m, 1H), 0.90 (t, 3H), 0.70 (m, 1H), 0.50–0.20 (m, 3H). MS (AP) m/z 402.33 [(M+H)+, 100].

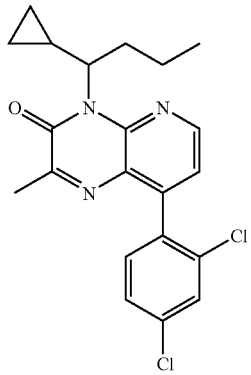

Example 5

(R,S)-4-(1-cyclopropyl-butyl)-8-(2,4-dichloro-phenyl)-2-methyl-4H-pyrido[2,3-b]pyrazin-3-one Part A 2-Benzyloxy-4-chloro-3-nitro-pyridine (Wilde, et. al. WO 99/01454, which is incorporated herein by reference in its entirety) (11 g, 41.6 mmol) and 2,4-dichlorophenylboronic acid (11.9 g, 62.3 mmol) were treated substantially as described in Part A of Example 19a to give 8.0 g (51%) of 2-benzyloxy-4-(2,4-dichloro-phenyl)-3-nitro-pyridine: MS (AP) m/z 375.2 [(M+H)+, 100].

Part B

2-Benzyloxy-4-(2,4-dichloro-phenyl)-3-nitro-pyridine (8.0 g, 21.3 mmol) was treated substantially as described in Part B of Example 19a to give 4-(2,4-dichloro-phenyl)-3-nitro-1H-pyridin-2-one (3.5 g, 58%): MS (AP) m/z 285.1 [(M+H)+, 98].

Part C

Trifluoro-methanesulfonic acid 4-(2,4-dichloro-phenyl)-3-nitro-pyridin-2-yl-ester (1.0 g, 2.40 mmol), prepared substantially as described in Part C of Example 19a, and 1-cyclopropyl-butylamine HCl (1.0 g, 4.79 mmol) were treated substantially as described in Part C of Example 19a to produce 0.66 g (72%) of crude (1-cyclopropyl-butyl)-[4-

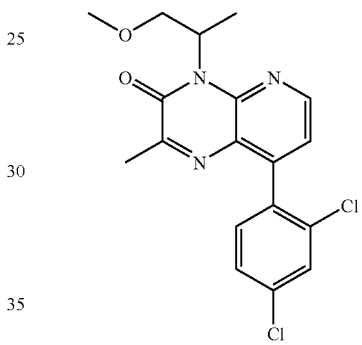

Example 9

(R,S)-8-(2,4-dichloro-phenyl)-4-(2-methoxy-1-methyl-ethyl)-2-methyl-4H-pyrido[2,3-b]pyrazin-3-one Part A To a solution of 2-benzyloxy-4-chloro-3-nitro-pyridine (Wilde, et. al. WO 99/01454, which is incorporated herein by reference)(5 g, 18.9 mmol) in $DME/H_2O$, was added 2,4-dichlorophenylboronic acid (3.60 g, 18.9 mmol), $Ba(OH)_2$ $0.8H_2O$ (5.96 g, 18.9 mmol), and $Pd(PPh_3)_2Cl_2$ (0.77 g, 1.09 mmol) and the mixture was heated at reflux for 5 h. The reaction was cooled and poured into EtOAc and $H_2O$ (500 mL). The EtOAc layer was washed with $H_2O$, brine, dried ($Na_2SO_4$), filtered and concentrated in vacuo. Purification using flash chromatography (10% EtOAc-Hexane) gave 5.79 g (82%) of 2-benzyloxy-4-(2,4-dichloro-phenyl)-3-nitro-pyridine as a viscous oil: crude MS (AP) m/z 375.2 [(M+H)+, 100].

Part B

2-Benzyloxy-4-(2,4-dichloro-phenyl)-3-nitro-pyridine (5.79 g, 15.4 mmol) was dissolved in TFA (20 mL) and stirred at room temperature for 4 h. The reaction mixture was concentrated and washed with 20% EtOAc/Hexane, and concentrated in vacuo to yield 1.0 g (23%) of 4-(2,4-dichloro-phenyl)-3-nitro-1H-pyridin-2-one as a solid: crude MS (AP) m/z 285.1 [(M+H)+, 100].

Part C

To 10 mL of POCl$_3$ was added 4-(2,4-dichloro-phenyl)-3-nitro-1H-pyridin-2-one (1.0 g, 3.51 mmol), followed by the addition of DMF (1-2 mL) and the reaction refluxed for 5 h. The reaction mixture was cooled to room temperature and poured over ice-H$_2$O (200 mL). The solution was extracted with EtOAc, washed with H$_2$O, brine, dried (MgSO$_4$), filtered, and concentrated in vacuo to give 0.20 g (19%) of 2-chloro-4-(2,4-dichloro-phenyl)-3-nitro-pyridine as a brown viscous oil: crude $^1$H NMR (300 MHz, CDCl$_3$): δ 8.6 (d, 1H), 7.5 (s, 1H), 7.38 (s, 1H), 7.34 (d, 1H), 7.20 (d, 1H).

Part D

2-Chloro-4-(2,4-dichloro-phenyl)-3-nitro-pyridine (0.20 g, 0.66 mmol) was dissolved in acetonitrile (20 mL), followed by the addition of 2-methoxy-1-methyl-ethylamine (0.12 g, 1.32 mmol) and Hunig's base (0.037 g, 0.29 mmol). The reaction was stirred at reflux for 64 h. The solution was cooled to room temperature and extracted with EtOAc/H$_2$O. The organic layer was washed with brine, dried (Na$_2$SO$_4$), filtered, and concentrated to yield 0.20 g (87%) of [4-(2,4-dichloro-phenyl)-3-nitro-pyridin-2-yl]-(2-methoxy-1-methyl-ethyl)-amine: MS (AP) m/z 356.2 [(M+H)$^+$, 86].

Part E

[4-(2,4-Dichloro-phenyl)-3-nitro-pyridin-2-yl]-(2-methoxy-1-methyl-ethyl)-amine (0.20 g, 0.56 mmol was dissolved in dioxane (8 mL) and H$_2$O (8 mL), followed by conc. NH$_4$OH (0.3 mL) and Na$_2$S$_2$O$_4$ (0.79 g, 4.53 mmol) and stirred at room temperature for 4 h. The solution was extracted with EtOAc, washed with H$_2$O, brine, dried (Na$_2$SO$_4$), filtered, and concentrated in vacuo to produce 0.13 g (72%) of 4-(2,4-dichloro-phenyl)-N$^2$-(2-methoxy-1-methyl-ethyl)-pyridine-2,3-diamine: MS (AP) m/z 326.2 [(M+H)$^+$, 90].

Part F 4-(2,4-Dichloro-phenyl)-N$^2$-(2-methoxy-1-methyl-ethyl)-pyridine-2,3-diamine (0.13 g, 0.40 mmol) was dissolved in toluene (20 mL), followed by methyl pyruvate (0.081 g, 0.80 mmol) and heated at reflux overnight. The reaction was concentrated in vacuo and purified by reverse phase prep HPLC to yield 3.2 mg (2%) of 8-(2,4-dichloro-phenyl)-4-(2-methoxy-1-methyl-ethyl)-2-methyl-4H-pyrido[2,3-b]pyrazin-3-one (Example 9): $^1$H NMR (300 MHz, CD$_3$OD): δ 8.6 (d, 1H), 7.6 (s, 1H), 7.4-7.25 (m, 3H), 4.4 (m, 1H). 3.8 (m, 1H), 3.3 (s, 3H), 2.4 (s, 3H), 1.6 (d, 2H), 1.25 (s, 2H). MS (AP) m/z 378.3 [(M+H)$^+$, 100].

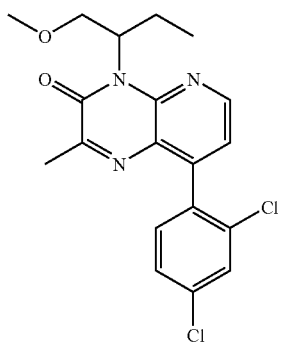

Example 10

(R,S)-8-(2,4-dichloro-phenyl)-4-(1-methoxymethyl-propyl)-2-methyl-4H-pyrido[2,3-b]pyrazin-3-one Parts A, B, and C 2-Chloro-4-(2,4-dichloro-phenyl)-3-nitro-pyridine was prepared substantially as described in Example 9.

Part D

2-Chloro-4-(2,4-dichloro-phenyl)-3-nitro-pyridine (0.20 g, 0.66 mmol) and 1-methoxymethyl-propylamine (0.14 g, 1.32 mmol) were treated as in Part D of Example 9 to yield 0.21 g (88%) of [4-(2,4-dichloro-phenyl)-3-nitro-pyridin-2-yl]-(1-methoxymethyl-propyl)-amine: MS (AP) m/z 370.2 [(M+H)$^+$, 97].

Part E 4-(2,4-Dichloro-phenyl)-3-nitro-pyridin-2-yl]-(1-methoxymethyl-propyl)-amine (0.21 g, 0.57 mmol) and Na$_2$S$_2$O$_4$ (0.80 g, 4.58 mmol) were treated as in Part E of Example 9 to give 0.13 g (68%) crude 4-(2,4-dichloro-phenyl)-N$^2$-(1-methoxymethyl-propyl)-pyridine-2,3-diamine: MS (AP) m/z 340.3 [(M+H)$^+$, 100].

Part F 4-(2,4-Dichloro-phenyl)-N$^2$-(1-methoxymethyl-propyl)-pyridine-2,3-diamine (0.13 g, 0.38 mmol) was treated as in Part F of Example 9 to yield 3.0 mg (2%) of 8-(2,4-dichloro-phenyl)-4-(1-methoxymethyl-propyl)-2-methyl-4H-pyrido[2,3-b]pyrazin-3-one (Example 10): $^1$H NMR (300 MHz, CD$_3$OD): δ 8.6 (bs, 1H), 7.6 (s, 1H), 7.45-7.25 (m, 3H), 3.3 (s, 3H), 2.43 (s, 1H), 2.40 (s, 3H), 1.9 (m, 1H), 1.5 (m, 1H), 1.3 (s, 2H), 0.85 (t, 3H). MS (ESI) m/z 392.3 [(M+H)$^+$, 100].

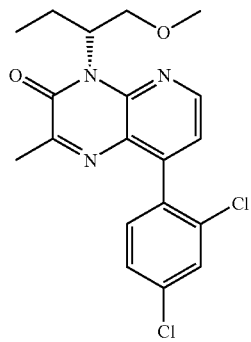

Example 10a (R)-8-(2,4-dichloro-phenyl)-4-(1-methoxymethyl-propyl)-2-methyl-4H-pyrido[2,3-b]pyrazin-3-one Parts A and B 4-(2,4-Dichloro-phenyl)-3-nitro-1H-pyridin-2-one was prepared substantially as described in Example 19a.

Part C

Trifluoro-methanesulfonic acid 4-(2,4-dichloro-phenyl)-3-nitro-pyridin-2-yl-ester (3.0 g, 7.19 mmol), prepared substantially as described in Part C of Example 19a, and 1-methoxymethyl-propylamine HCl (2.01 g, 14.4 mmol) were treated substantially as described in Part C of Example 19a to produce 2.11 g (79%) of [4-(2,4-dichloro-phenyl)-3- nitro-pyridin-2-yl]-(1-methoxymethyl-propyl)-amine: MS (AP) m/z 370.2 [(M+H)+, 100].

Part D

[4-(2,4-Dichloro-phenyl)-3-nitro-pyridin-2-yl]-(1-methoxymethyl-propyl)-amine (2.11 g, 5.72 mmol) and $Na_2S_2O_4$ (8.03 g, 46.1 mmol) were treated substantially as described in Part E of Example 9 to yield 1.14 g (59%) of 4-(2,4-dichloro-phenyl)-$N^2$-(1-methoxymethyl-propyl)-pyridine-2,3-diamine: MS (AP) m/z 340.2 [(M+H)+, 100].

Part E $N^2$-(1-cyclopropyl-butyl)-4-(2,4-dichloro-phenyl)-pyridine-2,3-diamine (1.14 g, 3.35 mmol) was treated substantially as described in Part F of Example 9 to give 6.7 mg (0.5%) of (R)-8-(2,4-dichloro-phenyl)-4-(1-methoxymethyl-propyl)-2-methyl-4H-pyrido[2,3-b]pyrazin-3-one (Example 10a): $^1$H NMR (300 MHz, CDCl$_3$): δ 8.54 (bs, 1H), 7.54 (s, 1H), 7.40 (d, 1H), 7.28 (s, 1H), 7.20 (d, 1H), 6.2 (m, 1H), 4.3 (m, 1H), 3.8 (m, 1H), 3.3 (s, 3H), 2.47 (s, 3H), 2.0 (m, 1H), 1.30 (s, 1H), 0.90 (t, 3H). MS (AP) m/z 392.3 [(M+H)+, 100].

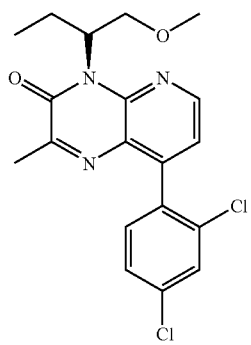

Example 10b (S)-8-(2,4-dichloro-phenyl)-2-methyl-4-(1-methoxymethyl-propyl)-2-methyl-4H-pyrido[2,3-b]pyrazin-3-one Parts A, B, and C 2-Chloro-4-(2,4-dichloro-phenyl)-3-nitro-pyridine was prepared substantially as described in Example 9.

Part D

2-Chloro-4-(2,4-dichloro-phenyl)-3-nitro-pyridine (0.25 g, 0.82 mmol) and 1-methoxymethyl-propylamine (0.23 g, 1.65 mmol) were treated substantially as described in Part D of Example 9 to produce 0.25 g (83%) of [4-(2,4-dichloro-phenyl)-3-nitro-pyridin-2-yl]-(1-methoxymethyl-propyl)-amine: MS (AP) m/z 370.2 [(M+H)+, 98].

Part E

[4-(2,4-Dichloro-phenyl)-3-nitro-pyridin-2-yl]-(1-methoxymethyl-propyl)-amine (0.25 g, 0.67 mmol) and $Na_2S_2O_4$ (0.95 g, 5.45 mmol) were treated substantially as described in Part E of Example 9 to yield 0.13 g (56%) of 4-(2,4-dichloro-phenyl)-$N^2$-(1-methoxymethyl-propyl)-pyridine-2,3-diamine: MS (AP) m/z 340.3 [(M+H)+, 100].

Part F 4-(2,4-Dichloro-phenyl)-$N^2$-(1-methoxymethyl-propyl)-pyridine-2,3-diamine (0.13 g, 0.38 mmol) was treated substantially as described in Part F of Example 9 to give 5.1 mg (3%) of (S)-8-(2,4-dichloro-phenyl)-2-methyl-4-(1-methoxymethyl-propyl)-2-methyl-4H-pyrido[2,3-b]pyrazin-3-one (Example 10b): $^1$H NMR (300 MHz, CD$_3$OD): δ 8.5 (d, 1H), 7.5 (s, 1H), 7.4 (d, 1H), 7.39 (d, 1H), 7.25 (d, 1H), 3.75 (m, 2H), 3.25 (s, 3H), 2.39 (s, 3H), 1.95 (m, 1H), 1.25 (s, 2H), 0.80 (t, 3H). MS (ESI) m/z 392.29 [(M+H)+, 100].

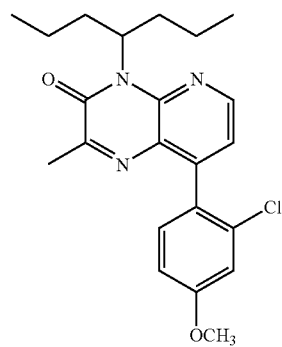

Example 18

(R,S)-8-(2-chloro-4-methoxy-phenyl)-2-methyl-4-(1-propyl-butyl)-4H-pyrido[2,3-b]pyrazin-3-one Parts A and B 4-(2,4-Dichloro-phenyl)-3-nitro-1H-pyridin-2-one was prepared substantially as described in Example 19a.

Part C

Trifluoro-methanesulfonic acid 4-(2-chloro-4-methoxy-phenyl)-3-nitro-pyridin-2-yl ester(0.50 g, 1.21 mmol), prepared substantially as described in Part C of Example 19a, and 1-propyl-butylamine (0.28 g, 2.42 mmol) were treated in the same manner as in Part C of Example 19a to produce 0.31 g (69%) of [4-(2-chloro-4-methoxy-phenyl)-3-nitro-pyridin-2-yl]-(1-propyl-butyl)-amine: MS (AP) m/z 377.9 [(M+H)+, 100].

Part D

[4-(2-Chloro-4-methoxy-phenyl)-3-nitro-pyridin-2-yl]-(1-propyl-butyl)-amine (0.31 g, 0.82 mmol) and $Na_2S_2O_4$ (1.15 g, 6.62 mmol) were treated substantially as described in Part E of Example 9 to give 0.49 g (100%) 4-(2-chloro-4-methoxy-phenyl)-$N^2$-(1-propyl-butyl)-pyridine-2,3-diamine: MS (AP) m/z 347.9 [(M+H)+, 100].

Part E 4-(2-Chloro-4-methoxy-phenyl)-$N^2$-(1-propyl-butyl)-pyridine-2,3-diamine (0.49 g, 1.41 mmol) was treated substantially as described in Part F of Example 9 to give 1.3 mg (0.23%) of 8-(2-chloro-4-methoxy-phenyl)-2-methyl-4-(1-propyl-butyl)-4H-pyrido[2,3-b]pyrazin-3-one (Example 18): $^1$H NMR (300 MHz, CDCl$_3$): δ 8.5 (d, 1H), 7.20 (d, 1H), 7.07 (s, 1H), 6.98 (d, 1H), 6.95 (d, 1H), 3.88 (s, 3H), 2.45 (s, 3H), 2.35–1.80 (m, 8H), 1.3–1.15 (m, 4H), 0.90 (t, 3H). MS (AP) m/z 399.9 [(M+H)+, 100].

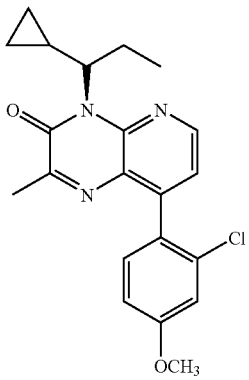

Example 19a (S)-8-(2-chloro-4-methoxy-phenyl)-4-(1-cyclopropyl-propyl)-2-methyl-4H-pyrido[2,3-b]pyrazin-3-one Part A To a solution of 2-benzyloxy-4-chloro-3-nitro-pyridine (Wilde, et al. WO 99/01454, which is incorporated herein by reference) (3.0 g, 11.3 mmol) in ethanol (10 mL) and toluene (40 mL), was added Na$_2$CO$_3$ (14.17 mL, 2 M), 2-chloro-4-methoxyphenylboronic acid (3.17 g, 17.0 mmol), and Pd(PPh$_3$)$_2$Cl$_2$ (0.48 g, 0.68 mmol) and the mixture was heated at reflux for 5 h. The reaction was cooled and poured into EtOAc and H$_2$O (500 mL). The EtOAc layer was washed with H$_2$O, brine, dried (Na$_2$SO$_4$), filtered and concentrated in vacuo. Purification using flash chromatography (10% EtOAc-Hexane) gave 1.51 g (36%) of 2-benzyloxy-4-(2-chloro-4-methoxy-phenyl)-3-nitro-pyridine as a viscous oil: MS (AP) m/z 370.8 [(M+H)+, 100].

Part B

2-Benzyloxy-4-(2-chloro-4-methoxy-phenyl)-3-nitro-pyridine (1.51 g, 4.07 mmol) was dissolved in TFA (20 mL) and stirred at room temperature for 4 h. The reaction mixture was concentrated, washed with toluene, and concentrated in vacuo to yield 1.19 g (100%) of 4-(2-chloro-4-methoxy-phenyl)-3-nitro-1H-pyridin-2-one as a solid: MS (AP) m/z 280.7 [(M+H)+, 100].

Part C

To a solution of 4-(2-chloro-4-methoxy-phenyl)-3-nitro-1H-pyridin-2-one (1.19 g, 4.24 mmol) in CH$_2$Cl$_2$ (50 mL), was added Na$_2$CO$_3$ (1.10 g, 10.4 mmol). The reaction was cooled to −78° C., and trifluoromethanesulfonic anhydride (3.55 g, 12.6 mmol) was added dropwise. After the addition, the reaction stirred for 15 min at −78° C., then warmed to 0° C. for 1 h to yield trifluoro-methanesulfonic acid 4-(2-chloro-4-methoxy-phenyl)-3-nitro-pyridin-2-yl ester. The reaction mixture was filtered and the collected solid was washed with CHCl$_3$. The filtrate was concentrated in vacuo and dissolved in toluene (20 mL), followed by Et$_3$N (0.20 mL, 1.45 mmol) and 1-cyclopropyl-propylamine HCl (0.16 g, 1.45 mmol), and heated at 130° C. overnight. The reaction was cooled and poured over an ice water bath. The mixture was extracted with CH$_2$Cl$_2$, washed with H$_2$O, brine, dried (MgSO$_4$), filtered, and concentrated in vacuo. Purification using flash chromatography (20% EtOAc/Hexane yielded 0.17 g (65%) of [4-(2-chloro-4-methoxy-phenyl)-3-nitro-pyridin-2-yl]-(1-cyclopropyl-propyl)-amine: MS (AP) m/z 361.8 [(M+H)+, 100].

Part D

[4-(2-Chloro-4-methoxy-phenyl)-3-nitro-pyridin-2-yl]-(1-cyclopropyl-propyl)-amine (0.17 g, 0.47 mmol) and Na$_2$S$_2$O$_4$ (0.66 g, 3.79 mmol) were treated substantially as described in Part E of Example 9 to give 0.14 g (88%) crude 4-(2-chloro-4-methoxy-phenyl)-N$^2$-(1-cyclopropyl-propyl)-pyridine-2,3-diamine: MS (AP) m/z 331.8 [(M+H)+, 100].

Part E 4-(2-Chloro-4-methoxy-phenyl)-N$^2$-(1-cyclopropyl-propyl)-pyridine-2,3-diamine (0.14 g, 0.42 mmol) was treated substantially as described in Part F of Example 9 to give 4.2 mg (3%) of (R)-8-(2-chloro-4-methoxy-phenyl)-4-(1-cyclopropyl-propyl)-2-methyl-4H-pyrido[2,3-b]pyrazin-3-one (Example 19a): $^1$H NMR (300 MHz, CDCl$_3$): δ □8.5 (d, 1H), 7.30 (s, 1H), 7.20 (s, 1H), 7.07 (s, 1H), 6.9 (d, 1H), 5.0 (q, 1H), 4.45 (q, 1H), 3.88 (s, 3H), 2.5 (s, 3H), 2.4–2.0 (m, 3H), 0.90 (t, 3H), 0.75 (m, 1H), 0.50–0.25 (m, 2H). MS (AP) m/z 383.9 [(M+H)+, 100].

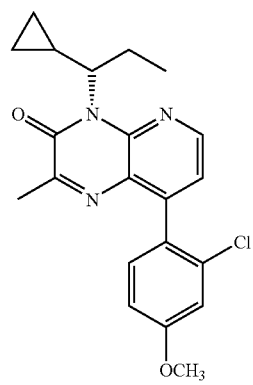

Example 19b (R)-8-(2-chloro-4-methoxy-phenyl)-4-(1-cyclopropyl-propyl)-2-methyl-4H-pyrido[2,3-b]pyrazin-3-one Parts A and B 4-(2-Chloro-4-methoxy-phenyl)-3-nitro-1H-pyridin-2-one was prepared substantially as described in Example 19a.

Part C

Trifluoro-methanesulfonic acid 4-(2-chloro-4-methoxy-phenyl)-3-nitro-pyridin-2-yl ester (0.91 g, 2.20 mmol), prepared substantially as described in Part C of Example 19a, and 1-cyclopropyl-propylamine HCl (0.56 g, 4.41 mmol) were treated substantially as described in Part C of Example 19a to produce 0.56 g (72%) of [4-(2-chloro-4-methoxy-phenyl)-3-nitro-pyridin-2-yl]-(1-cyclopropyl-propyl)-amine: MS (AP) m/z 361.8 [(M+H)+, 100].

Part D

[4-(2-Chloro-4-methoxy-phenyl)-3-nitro-pyridin-2-yl]-(1-cyclopropyl-propyl)-amine (0.56 g, 1.55 mmol) and Na$_2$S$_2$O$_4$ (2.17 g, 12.5 mmol) were treated substantially as described in Part E of Example 9 to give 0.49 g (96%) of crude 4-(2-chloro-4-methoxy-phenyl)-N$^2$-(1-cyclopropyl-propyl)-pyridine-2,3-diamine: MS (AP) m/z 331.8 [(M+H)$^+$, 100].

Part E 4-(2-Chloro-4-methoxy-phenyl)-N$^2$-(1-cyclopropyl-propyl)-pyridine-2,3-diamine (0.49 g, 1.48 mmol) was treated substantially as described in Part F of Example 9 to give 6.1 mg (1%) of 8-(2-chloro-4-methoxy-phenyl)-4-(1-cyclopropyl-propyl)-2-methyl-4H-pyrido[2,3-b]pyrazin-3-one (Example 19b). $^1$H NMR (300 MHz, CDCl$_3$): δ 8.43 (d, 1H), 7.29 (s, 1H), 7.20 (d, 1H), 7.07 (d, 1H), 6.94 (d, 1H), 5.0 (q, 1H), 4.5 (q, 2.5 (s, 3H), 2.3–2.0 (m, 3H), 0.90 (t, 3H), 0.85 (m, 1H), 0.50–0.30 (m, 2H). MS (AP) m/z 383.9 [(M+H)$^+$, 100].

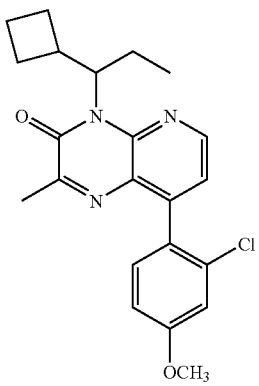

Example 23a 8-(2-chloro-4-methoxy-phenyl)-4-(1-cyclobutyl-propyl)-2-methyl-4H-pyrido[2,3-b]pyrazin-3-one
(Isomer A, R or S)

Parts A and B 4-(2-Chloro-4-methoxy-phenyl)-3-nitro-1H-pyridin-2-one was prepared substantially as described in Example 19a.

Part C

Trifluoro-methanesulfonic acid 4-(2-chloro-4-methoxy-phenyl)-3-nitro-pyridin-2-yl ester (0.50 g, 1.21 mmol), prepared substantially as described in Example 19a, and 1-cyclobutyl-propylamine HCl (0.36 g, 2.42 mmol) were treated substantially as described in Part C of Example 19a to produce 0.33 g (73%) of [4-(2-chloro-4-methoxy-phenyl)-3-nitro-pyridin-2-yl]-(1-cyclobutyl-propyl)-amine: MS (AP) m/z 375.9 [(M+H)$^+$, 100].

Part D

[4-(2-Chloro-4-methoxy-phenyl)-3-nitro-pyridin-2-yl]-(1-cyclopropyl-propyl)-amine (0.33 g, 0.88 mmol) and Na$_2$S$_2$O$_4$ (1.33 g, 7.6 mmol) were treated substantially as described in Part E of Example 9 to give 0.33 g (100%) 4-(2-chloro-4-methoxy-phenyl)-N$^2$-(1-cyclobutyl-propyl)-pyridine-2,3-diamine: MS (AP) m/z 345.9 [(M+H)$^+$, 100].

Part E 4-(2-Chloro-4-methoxy-phenyl)-N$^2$-(1-cyclobutyl-propyl)-pyridine-2,3-diamine (0.33 g, 9.53 mmol) was treated substantially as described in Part F of Example 9 to give 1.3 mg (0.34%) of 8-(2-chloro-4-methoxy-phenyl)-4-(1-cyclobutyl-propyl)-2-methyl-4H-pyrido[2,3-b]pyrazin-3-one (Example 23a): $^1$H NMR (300 MHz, CDCl$_3$): δ 8.5 (d, 1H), 7.22 (d, 1H), 7.20 (d, 1H), 7.06 (s, 1H), 6.90 (d, 1H), 5.9 (m, 1H), 3.88 (s, 3H), 2.45 (s, 3H), 2.2 (m, 1H), 1.9–1.6 (m, 8H), 0.75 (t, 3H). MS (AP) m/z 397.9 [(M+H)$^+$, 100].

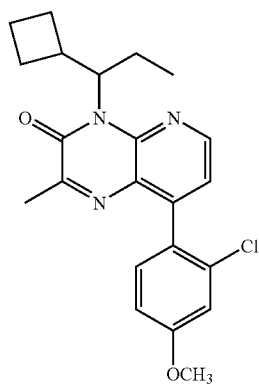

Example 23b 8-(2-chloro-4-methoxy-phenyl)-4-(1-cyclobutyl-propyl)-2-methyl-4H-pyrido[2,3-b]pyrazin-3-one
(Isomer B, R or S)

Parts A and B 4-(2-Chloro-4-methoxy-phenyl)-3-nitro-1H-pyridin-2-one was prepared substantially as described in Example 19a.

Part C

Trifluoro-methanesulfonic acid 4-(2-chloro-4-methoxy-phenyl)-3-nitro-pyridin-2-yl ester (0.50 g, 1.21 mmol), prepared substantially as described in Example 19a, and 1-cyclobutyl-propylamine HCl (0.36 g, 2.42 mmol) were treated substantially as described in Part C of Example 19a to produce 0.33 g (72%) of [4-(2-chloro-4-methoxy-phenyl)-3-nitro-pyridin-2-yl]-(1-cyclobutyl-propyl)-amine: MS (AP) m/z 375.9 [(M+H)$^+$, 25].

Part D

[4-(2-Chloro-4-methoxy-phenyl)-3-nitro-pyridin-2-yl]-(1-cyclobutyl-propyl)-amine (0.33 g, 0.88 mmol) and Na$_2$S$_2$O$_4$ (1.33 g, 7.6 mmol) were treated substantially as described in Part E of Example 9 to give 0.46 g (100%) 4-(2-chloro-4-methoxy-phenyl)-N$^2$-(1-cyclobutyl-propyl)-pyridine-2,3-diamine: MS (AP) m/z 345.9 [(M+H)$^+$, 100].

Part E 4-(2-chloro-4-methoxy-phenyl)-N²-(1-cyclobutyl-propyl)-pyridine-2,3-diamine (0.46 g, 1.33 mmol) was treated substantially as described in Part F of Example 9 to give 0.7 mg (0.13%) of 8-(2-chloro-4-methoxy-phenyl)-4-(1-cyclobutyl-propyl)-2-methyl-4H-pyrido[2,3-b]pyrazin-3-one (Example 23b): ¹H NMR (300 MHz, CDCl₃): δ 8.5 (d, 1H), 7.22 (d, 1H), 7.20 (d, 1H), 7.07 (s, 1H), 6.9 (d, 1H), 5.9 (m, 1H), 3.88 (s, 3H), 2.5 (s, 3H), 2.3–1.8 (m, 9H), 0.80 (t, 3H). MS (AP) m/z 397.9 [(M+H)⁺, 100].

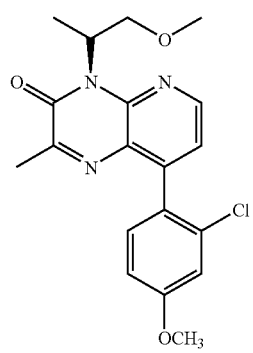

Example 25a (S)-8-(2-chloro-4-methoxy-phenyl)-4-(2-methoxy-1-methyl-ethyl)-2-methyl-4H-pyrido[2,3-b]pyrazin-3-one Parts A and B 4-(2-Chloro-4-methoxy-phenyl)-3-nitro-1H-pyridin-2-one was prepared substantially as described in Example 19a.

Part C

Trifluoro-methanesulfonic acid 4-(2-chloro-4-methoxy-phenyl)-3-nitro-pyridin-2-yl ester (0.48 g, 1.16 mmol), prepared substantially as described in Part C of Example 19a, and 2-methoxy-1-methyl-ethylamine (0.21 g, 2.32 mmol) were treated substantially as described in Part C of Example 19a to produce 0.28 g (68%) of [4-(2-chloro-4-methoxy-phenyl)-3-nitro-pyridin-2-yl]-(2-methoxy-1-methyl-ethyl)-amine: MS (AP) m/z 351.8 [(M+H)⁺, 90].

Part D

[4-(2-Chloro-4-methoxy-phenyl)-3-nitro-pyridin-2-yl]-(2-methoxy-1-methyl-ethyl)-amine (0.28 g, 0.80 mmol) and Na₂S₂O₄ (1.12 g, 6.42 mmol) were treated substantially as described in Part E of Example 9 to give 0.22 g (84%) 4-(2-chloro-4-methoxy-phenyl)-N²-(2-methoxy-1-methyl-ethyl)-pyridine-2,3-diamine: MS (AP) m/z 321.8 [(M+H)⁺, 72].

Part E 4-(2-chloro-4-methoxy-phenyl)-N²-(2-methoxy-1-methyl-ethyl)-pyridine-2,3-diamine (0.22 g, 0.68 mmol) was treated substantially as described in Part F of Example 9 to give 6.8 mg (3%) of 8-(2-chloro-4-methoxy-phenyl)-4-(2-methoxy-1-methyl-ethyl)-2-methyl-4H-pyrido[2,3-b]pyrazin-3-one (Example 25a): ¹H NMR (300 MHz, CDCl₃): δ 8.50 (d, 1H), 7.23 (d, 1H), 7.21 (d, 1H), 7.07 (s, 1H), 6.93 (d, 1H), 4.4 (t, 1H), 3.87 (s, 3H), 3.80 (q, 1H), 3.34 (s, 3H), 2.48 (s, 3H), 1.62 (d, 3H) 1.25 (s, 1H). MS (AP) m/z 373.8 [(M+H)⁺, 100].

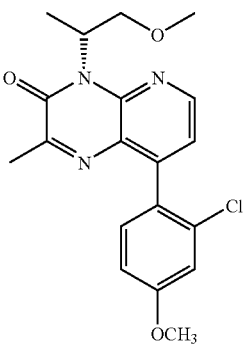

Example 25b (R)-8-(2-chloro-4-methoxy-phenyl)-4-(2-methoxy-1-methyl-ethyl)-2-methyl-4H-pyrido[2,3-b]pyrazin-3-one Parts A and B 4-(2-Chloro-4-methoxy-phenyl)-3-nitro-1H-pyridin-2-one was prepared substantially as described in Example 19a.

Part C

Trifluoro-methanesulfonic acid 4-(2-chloro-4-methoxy-phenyl)-3-nitro-pyridin-2-yl ester (1.0 g, 2.42 mmol), prepared substantially as described in Part C of Example 19a, and 2-methoxy-1-methyl-ethylamine HCl (0.61 g, 4.85 mmol) were treated substantially as described in Part C of Example 19a to produce 0.29 g (34%) of [4-(2-chloro-4-methoxy-phenyl)-3-nitro-pyridin-2-yl]-(2-methoxy-1-methyl-ethyl)-amine: MS (AP) m/z 351.8 [(M+H)⁺, 100].

Part D

[4-(2-Chloro-4-methoxy-phenyl)-3-nitro-pyridin-2-yl]-(2-methoxy-1-methyl-ethyl)-amine (0.10 g, 0.27 mmol) and Na₂S₂O₄ (0.38 g, 2.21 mmol) were treated substantially as described in Part E of Example 9 to give 0.21 g (81%) 4-(2-chloro-4-methoxy-phenyl)-N²-(2-methoxy-1-methyl-ethyl)-pyridine-2,3-diamine: MS (AP) m/z 321.8 [(M+H)⁺, 100].

Part E 4-(2-Chloro-4-methoxy-phenyl)-N²-(2-methoxy-1-methyl-ethyl)-pyridine-2,3-diamine (0.21 g, 0.65 mmol) was treated substantially as described in Part F of Example 9 to give 7.3 mg (3%) of (R)-8-(2-chloro-4-methoxy-phenyl)-4-(2-methoxy-1-methyl-ethyl)-2-methyl-4H-pyrido[2,3-b]pyrazin-3-one (Example 25b): ¹H NMR (300 MHz, CDCl₃):

δ 8.51 (d, 1H), 7.26 (d, 1H), 7.21 (s, 1H), 7.07 (s, 1H), 6.93 (d, 1H), 4.4 (t, 1H), 3.87 (s, 3H), 3.80 (m, 2H), 3.3 (s, 3H), 2.50 (s, 3H), 1.60 (d, 3H). MS (AP) m/z 373.8 [(M+H)+, 100].

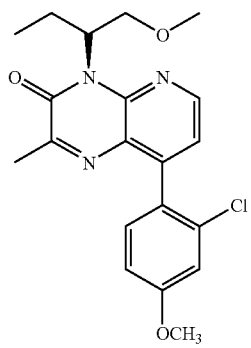

Example 26a (S)-8-(2-chloro-4-methoxy-phenyl)-4-(1-methoxymethyl-propyl)-2-methyl-4H-pyrido[2,3-b]pyrazin-3-one Parts A and B 4-(2-Chloro-4-methoxy-phenyl)-3-nitro-1H-pyridin-2-one was prepared substantially as described in Example 19a.

Part C

Trifluoro-methanesulfonic acid 4-(2-chloro-4-methoxy-phenyl)-3-nitro-pyridin-2-yl ester (0.40 g, 0.97 mmol), prepared substantially as described in Part C of Example 19a, and 1-methoxymethyl-propylamine HCl (0.27 g, 1.94 mmol) were treated substantially as described in Part C of Example 19a to produce 0.10 g (28%) of [4-(2-chloro-4-methoxy-phenyl)-3-nitro-pyridin-2-yl]-(1-methoxymethyl-propyl)-amine: MS (AP) m/z 365.8 [(M+H)+, 100].

Part D

[4-(2-Chloro-4-methoxy-phenyl)-3-nitro-pyridin-2-yl]-(1-methoxymethyl-propyl)-amine (0.10 g, 0.27 mmol) and $Na_2S_2O_4$ (0.38 g, 2.21 mmol) were treated substantially as described in Part E of Example 9 to give 0.08 g (87%) 4-(2-chloro-4-methoxy-phenyl)-$N^2$-(1-methoxymethyl-propyl)-pyridine-2,3-diamine: MS (AP) m/z 335.8 [(M+H)+, 100].

Part E 4-(2-Chloro-4-methoxy-phenyl)-$N^2$-(1-methoxymethyl-propyl)-pyridine-2,3-diamine (0.080 g, 0.24 mmol) was treated substantially as described in Part F of Example 9 to give 2.7 mg (3%) of 8-(2-chloro-4-methoxy-phenyl)-4-(1-methoxymethyl-propyl)-2-methyl-4H-pyrido[2,3-b]pyrazin-3-one (Example 26a): $^1$H NMR (300 MHz, CDCl3): δ 8.50 (bs, 1H), 7.28 (s, 1H), 7.22 (d, 1H), 7.07 (s, 1H), 6.91 (d, 1H), 3.88 (s, 3H), 3.84 (m, 1H), 3.38 (s, 3H), 2.50 (s, 3H), 1.25 (s, 1H), 0.90 (t, 3H), 0.10 (s, 3H). MS (AP) m/z 387.9 [(M+H)+, 100].

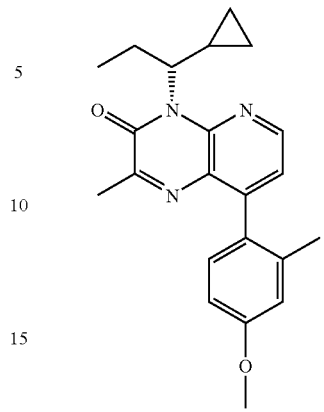

Example 67a (R)-4-(1-cylcopropropyl-propyl)-8-(4-methoxy-2-methyl-phenyl)-2-methyl-4H-pyrido[2,3-b]pyrazin-3-one Part A To a solution of 2-benzyloxy-4-chloro-3-nitro-pyridine (Wilde, et al. WO 99/01454, which is incorporated herein by reference) (0.98 g, 3.7 mmol) in ethanol (10 mL) and toluene (40 mL), was added $Na_2CO_3$ (4.6 mL, 2M), 4-methoxy-2-methylphenyl boronic acid (1.0 g, 5.6 mmol), and Pd(PPh3)2Cl2 (0.156 g, 0.22 mmol) and the mixture was heated at reflux for 5 h. The reaction was cooled and poured into EtOAc and $H_2O$ (500 mL). The EtOAc layer was washed with $H_2O$, brine, dried $Na_2SO_4$, filtered and concentrated in vacuo. Purification using flash chromatography (10% EtOAc/hexane) gave 1.01 g (78%) of 2-benzyloxy-4-(4-methoxy-2-methyl-phenyl)-3-nitro-2,3-dihydro-pyridine as a viscous oil; MS(AP) m/z 351.6 [(M+H)+, 100], 392.0 [(M+H+CH3CN)+, 35]. The purified intermediate was used in the following step.

Part B

2-Benzyloxy-4-(4-methoxy-2-methyl-phenyl)-3-nitro-2, 3-dihydro-pyridine (1.01 g, 2.9 mmol) was dissolved in TFA (25 mL) and stirred at room temperature for 4 h. The reaction mixture was concentrated in vacuo and the crude product 4-(4-methoxy-2-methyl-phenyl)-3-nitro-3H-pyridin-2-one: MS(AP) m/z 261.0 [(M+H)+, 87]. The crude intermediate was used in the next step.

Part C

To a solution of 4-(4-methoxy-2-methyl-phenyl)-3-nitro-3H-pyridin-2-one (0.321 g, 1.23 mmol) $CH_2Cl_2$ (13 mL), was added $Na_2CO_3$ (0.317 g, 3.02 mmol). The reaction was cooled to −78° C., and trifluoromethanesulfonic anhydride (617 μL, 3.65 mmol) was added dropwise. After the addition, the reaction stirred for 15 min at −78° C., then warmed to 0° C. for 1 h. The reaction mixture was filtered and the collected solid was washed with CHCl3. The filtrate was concentrated in vacuo and dissolved in toluene (20 mL) followed by Et3N (343 μL, 2.4 mmol) and 1-cyclopropyl propyl amine HCl (0.331 g, 2.4 mmol), and heated at 130° C. overnight. The reaction was cooled and poured onto ice/$H_2O$. The mixture was extracted with $CH_2Cl_2$, washed with $H_2O$, brine, dried $Na_2SO_4$, filtered, and concentrated in vacuo. Purification using flash chromatography (10% EtOAc/Hexane) gave 0.220 g (54%) of (1-cyclopropyl-propyl)-[4-(4-methoxy-2-methyl-phenyl)-3-nitro-pyridin-2-yl]-amine: MS(AP) m/z 342.1 [(M+H)+, 100]. The purified intermediate was used in the following step.

Part D (1-Cyclopropyl-propyl)-[4-(4-methoxy-2-methyl-phenyl)-3-nitro-pyridin-2-yl]-amine (0.220, 0.64 mmol) was dissolved in dioxane (10 mL) and H$_2$O (10 mL), followed by conc. NH$_4$OH (0.4 mL) and Na$_2$S$_2$O$_4$ (0.906 g, 5.2 mmol) and stirred at room temperature for 4 h. The solution was extracted with EtOAc, washed with H$_2$O, brine, dried Na$_2$SO$_4$, filtered, and concentrated in vacuo to produce the crude intermediate N$^2$-(1-cyclopropyl-propyl)-4-(4-methoxy-2-methyl-phenyl)-pyridine-2,3-diamine; MS(AP) m/z 312.2 [(M+H)+, 100]. The crude intermediate was used in the following step.

Part E

N$^2$-(1-cyclopropyl-propyl)-4-(4-methoxy-2-methyl-phenyl)-pyridine-2,3-diamine (0.183 g, 0.59 mmol) was dissolved in toluene (10 mL), followed by methyl pyruvate (106 μL, 1.2 mmol) and heated to 130° C. overnight. The reaction was concentrated in vacuo and purified by reverse phase reverse phase prep HPLC to yield 4-(1-cylcopropropyl-propyl)-8-(4-methoxy-2-methyl-phenyl)-2-methyl-4H-pyrido[2,3-b]pyrazin-3-one (Example 67a): $^1$H NMR (300 MHz, CDCl$_3$): δ 8.48–8.41 (2d, 1H, J=4.7 Hz), 7.26–7.10 (m, 2H), (m, 2H), 6.87–6.83 (m, 2H), 5.09–5.02, 4.53–4.43 (2m, 1H), 3.87 (s, 3H), 2.49 (s, 3H), 2.42–2.38 (m,1H), 2.12 (s, 3H), 2.09–2.02 (m, 1H), 0.90–0.87 (t, 3H, J=5.1 Hz), 0.80–0.77 (m, 1H), 0.59–0.55 (m, 1H), 0.41–0.29 (m, 1H), 0.26–0.22 (m, 1H). MS (AP) 364.1 [(M+H)+, 100].

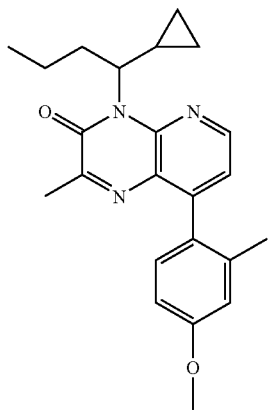

Example 69

(R,S)-4-(1-cyclopropyl-butyl)-8-(4-methoxy-2-methyl-phenyl)-2-methyl-4H-pyrido[2,3-b]pyrazin-3-one Part A-B 4-(4-Methoxy-2-methyl-phenyl)-3-nitro-3H-pyridin-2-one was prepared as substantially described in Example 67a.

Part C

Trifluoro-methanesulfonic acid 4-(4-methoxy-2-methyl-phenyl)-3-nitro-pyridin-2-yl-ester (0.764 g, 1.95 mmol), prepared substantially as described in Part C of Example 67a, and 1-cylcopropyl-butyl amine HCl (0.580 g, 3.9 mmol) were treated substantially as described in Part C of Example 67a to produce 0.230 g (50%) of (1-cyclopropyl-butyl)-[4-(4-methoxy-2-methyl-phenyl)-3-nitro-pyridin-2-yl]amine.

Part D (1-Cyclopropyl-butyl)-[4-methoxy-2-methyl-phenyl)-3-nitro-pyridin-2-yl]amine (0.230 g, 0.65 mmol), and Na$_2$SO$_4$ (0.910 g, 5.2 mmol), were treated substantially as described in Part D of Example 67a to give a crude yield of 0.226 g (107%) of N$^2$-(1-cyclopropyl-butyl)-4-(4-methoxy-2-methyl-phenyl)-pyridine-2,3-diamine: MS(AP) m/z 326.3 [(M+H)+, 94].

Part E

N$^2$-(1-cylcopropyl-butyl)-4-(4-methoxy-2-methyl-phenyl)-pyridine-2,3-diamine (0.226 g, 0.69 mmol) and methyl pyruvate (126 μL, 1.4 mmol) were treated substantially as described in Part E of Example 67a to give 4-(1-cyclopropyl-butyl)-8-(4-methoxy-2-methyl-phenyl)-2-methyl-4H-pyrido[2,3-b]pyrazin-3-one (Example 69): $^1$H NMR (300 MHz, CDCl$_3$): δ 8.47–8.39 (2d, 1H, J=4.7 Hz), 7.23–7.08 (m, 2H), 6.85–6.80 (m, 2H), 5.17–5.09, 4.57–4.49 (2m, 1H), 3.84 (s, 3H), 2.47 (s,3H), 2.4–2.2 (m, 3H), 2.16 (s, 3H), 1.98–1.94 (m, 2H), 0.89–0.84 (t, 3H, J=7.4 Hz), 0.69–0.67 (m, 1H), 0.53–0.49 (m, 1H), 0.46–0.43 (m, 1H), 0.22–0.19 (m, 1H). MS (AP) 378.1 [(M+H)+, 100].

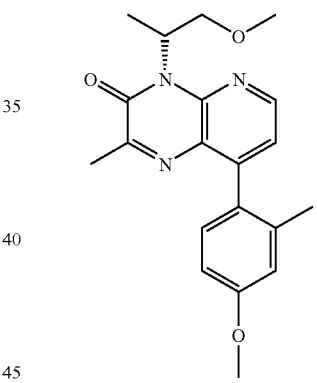

Example 73a (R)-4-(2-methoxy-1-methyl-ethyl)-8-(4-methoxy-2-methyl-phenyl)-2-methyl-4H-pyrido[2,3-b]pyrazin-3-one Part A-B 4-(4-Methoxy-2-methyl-phenyl)-3-nitro-3H-pyridin-2-one was prepared substantially as described in Example 67a.

Part C

Trifluoro-methanesulfonic acid 4-(4-methoxy-2-methyl-phenyl)-3-nitro-pyridin-2-yl-ester (0.332 g, 0.74 mmol), prepared substantially as described in Part C of Example 67a, and 2-methoxy-1-methyl-ethylamine HCl (0.263 g, 67 mmol) were treated substantially as described in Part C of Example 67a to produce 0.120 g (54%) of (2-methoxy-1-methyl-ethyl)-[4-(4-methoxy-2-methyl-phenyl)-3-nitro-pyridin-2-yl]amine; MS(AP) m/z 332.1 [(M+H)+, 94].

Part D

2-Methoxy-1-methyl-ethyl)-[4-(4-methoxy-2-methyl-phenyl)-3-nitro-pyridin-2-yl]amine (0.120 g, 0.36 mmol), and Na$_2$SO$_4$ (0.509 g, 2.9 mmol), were treated as in Part D of Example 67a to give a crude yield of 0.066 g (61%) of N$^2$-(2-methoxy-1-methyl-ethyl)-4-(4-methoxy-2-methyl-phenyl)-pyridine-2,3-diamine; MS(AP) m/z 302.2 [(M+H)$^+$, 100]. The crude product was taken on to Part E.

Part E

N$^2$-(2-Methoxy-1-methyl-ethyl)-4-(4-methoxy-2-methyl-phenyl)-pyridine-2,3-diamine (0.066 g, 0.22 mmol) and methyl pyruvate (79 μL, 0.88 mmol) were treated substantially as in Part E of Example 67a to give 4-(2-methoxy-1-methyl-ethyl)-8-(4-methoxy-2-methyl-phenyl)-2-methyl-4H-pyrido[2,3-b]pyrazin-3-one (Example 73a): $^1$H NMR (300 MHz, CDCl$_3$): δ 8.49–8.47 (d, 1H, J=4.8 Hz), 7.16–7.12 (m, 2H), 6.86–6.82 (m, 2H), 4.41–4.36 (m, 1H), 3.87 (s, 3H), 3.84–3.80 (m, 2H), 3.34 (s, 3H), 2.48 (s, 3H), 2.12 (s, 3H), 1.62–1.60 (d, 3H, J=6.9 Hz). MS (AP) 354.2 [(M+H)$^+$, 100].

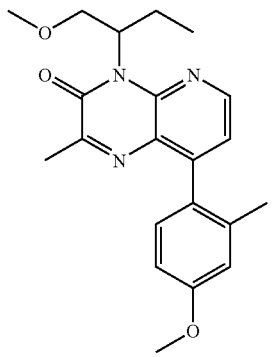

Example 74a (R,S)-8-(4-Methoxy-2-methyl-phenyl)-4-(1-methoxymethyl-propyl)-2-methyl-4H-pyrido[2,3-b]pyrazin-3-one Part A-B 4-(4-Methoxy-2-methyl-phenyl)-3-nitro-3H-pyridin-2-one was prepared substantially as described in Example 67a.

Part C

Trifluoro-methanesulfonic acid 4-(4-methoxy-2-methyl-phenyl)-3-nitro-pyridin-2-yl-ester (0.78 g, 1.98 mmol), prepared substantially as described in Part C of Example 67a, and 1-methoxymethyl-propylamine (0.45 g, 4.36 mmol) were treated substantially as described in Part C of Example 67a to produce 27 mg (40%) of [4-(4-methoxy-2-methyl-phenyl)-3-nitro-pyridin-2-yl]-(1-methoxymethyl-propyl)-amine; MS (EI) m/z 346.33 [(M+H)$^+$, 100].

Part D

[4-(4-Methoxy-2-methyl-phenyl)-3-nitro-pyridin-2-yl]-(1-methoxymethyl-propyl)-amine (0.43 g, 0.36 mmol) and SnCl$_2$ (0.2 g, 1.08 mmol) in ethanol (2 mL) were heated to 70° C. for 4 h. The solution was cooled to room temperature and quenched with saturated aqueous NaHCO$_3$ then extracted with EtOAc, washed with H$_2$O, brine, dried (Na$_2$SO$_4$), filtered, and concentrated in vacuo to give a crude yield of 0.40 g (99%) of 4-(4-methoxy-2-methyl-phenyl)-N$^2$-(1-methoxymethyl-propyl)-pyridine-2,3-diamine; MS(EI) m/z 316.28 [(M+H)$^+$, 100]. The crude product was taken on to Part E.

Part E 4-(4-Methoxy-2-methyl-phenyl)-N$^2$-(1-methoxymethyl-propyl)-pyridine-2,3-diamine (0.08 g, 0.25 mmol) and methyl pyruvate (33 μL, 0.38 mmol) were treated substantially as in Part E of Example 67a to give 3.0 mg of 8-(4-methoxy-2-methyl-phenyl)-4-(1-methoxymethyl-propyl)-2-methyl-4H-pyrido[2,3-b]pyrazin-3-one (Example 74a): $^1$H NMR (400 MHz, CDCl$_3$) δ ppm 8.46 (d, J=4.89 Hz, 1 H), 7.15 (d, J=8.31 Hz, 1 H), 7.12 (d, J=4.40 Hz, 1 H), 6.85 (d, J=6.60 Hz, 1 H), 6.83 (d, J=12.23 Hz, 1 H), 5.89 (m, 1 H), 4.38 (m, 1 H), 3.86 (s, 3 H), 3.77 (m, 1 H), 3.32 (s, 3 H), 2.46 (s, 3 H), 2.11 (s, 3 H), 1.77 (m, 2 H), 0.86 (t, J=7.34 Hz, 2 H). MS (EI) 368.30 [(M+H)$^+$, 100]

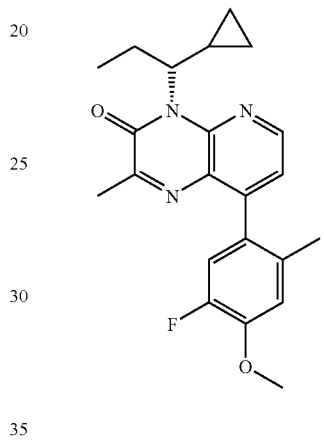

Example 83a (R)-4-(1-Cyclopropyl-propyl)-8-(5-fluoro-4-methoxy-2-methyl-phenyl)-2-methyl-4H-pyrido[2,3-b]pyrazin-3-one Part A and B 4-(5-Fluoro-4-methoxy-2-methyl-phenyl)-3-nitro-1H-pyridin-2-one was prepared substantially as described in Example 90a.

Part C

Trifluoro-methanesulfonic acid 4-(5-fluoro-4-methoxy-2-methyl-phenyl)-3-nitro-pyridin-2-yl ester (0.5 g, 1.22 mmol), prepared substantially as described in Part C of Example 19a, and (R)-1-cyclopropyl-propylamine (0.33 g, 2.44 mmol) were treated substantially as described in Part C of Example 19a to produce 0.17 g (43%) of crude (R)-(1-Cyclopropyl-propyl)-[4-(5-fluoro-4-methoxy-2-methyl-phenyl)-3-nitro-pyridin-2-yl]-amine.

Part D (R)-(1-Cyclopropyl-propyl)-[4-(5-fluoro-4-methoxy-2-methyl-phenyl)-3-nitro-pyridin-2-yl]-amine (0.17 g, 0.47 mmol) and Na$_2$S$_2$O$_4$ (1.24 g, 7.10 mmol) were treated as in Part E of Example 9 to give 0.15 g (98%) crude (R)-N$^2$-(1-Cyclopropyl-propyl)-4-(5-fluoro-4-methoxy-2-methyl-phenyl)-pyridine-2,3-diamine.

Part E (R)-N$^2$-(1-Cyclopropyl-propyl)-4-(5-fluoro-4-methoxy-2-methyl-phenyl)-pyridine-2,3-diamine (0.15 g, 0.46 mmol)

was treated substantially as described in Part F of Example 9 to give 4.5 mg (3%) of (R)-4-(1-Cyclopropyl-propyl)-8-(5-fluoro-4-methoxy-2-methyl-phenyl)-2-methyl-4H-pyrido[2,3-b]pyrazin-3-one (Example 83a). $^1$H NMR (300 MHz, CDCl$_3$) δ ppm 8.36 (d, J=4.76 Hz, 1 H), 7.03 (d, J=4.76 Hz, 1 H), 6.93 (d, J=11.72 Hz, 1 H), 6.83 (d, J=8.42 Hz, 1 H), 4.95 (m, 1 H), 3.89 (s, 3 H), 2.43 (s, 3 H), 2.20 (m, 2 H), 2.03 (s, 3 H), 0.80 (t, J=7.51 Hz, 3 H), 0.53 (m, 2 H), 0.26 (m, 2 H), 0.10 (m, 1 H). MS (EI) m/z 382.3 [(M+H)+, 100].

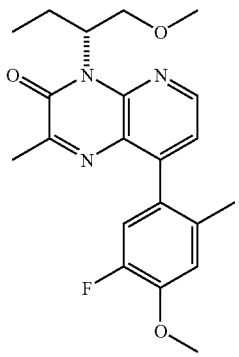

Example 90a (R)-8-(5-Fluoro-4-methoxy-2-methyl-phenyl)-4-(1-methoxymethyl-propyl)-2-methyl-4H-pyrido[2,3-b]pyrazin-3-one Part A 2-Benzyloxy-4-chloro-3-nitro-pyridine (Wilde, et. al. WO 99/01454) (1.0 g, 3.78 mmol) and 5-fluoro-4-methoxy-2-methyl-phenylboronic acid (prepared substantially as described in Speicher, A.; Kolz, J.; Sambanje, R. P. *Synthesis*, 2002, 17, 2503, which is incorporated herein by reference) (1.2 mg, 5.67 mmol) were treated substantially as described in Part A of Example 19a to give 1.15 g (83%) of 2-benzyloxy-4-(5-fluoro-4-methoxy-2-methyl-phenyl)-3-nitro-pyridine: MS (EI) m/z 369.3 [(M+H)$^+$, 100].

Part B

2-Benzyloxy-4-(5-fluoro-4-methoxy-2-methyl-phenyl)-3-nitro-pyridine (1.5 g, 4.1 mmol) was treated substantially as described in Part B of Example 19a to give 4-(2-chloro-4-methoxy-5-methyl-phenyl)-3-nitro-1H-pyridin-2-one (1.1 g, 92%): MS (EI) m/z 279.1 [(M+H)$^+$, 100].

Part C

Trifluoro-methanesulfonic acid 4-(5-fluoro-4-methoxy-2-methyl-phenyl)-3-nitro-pyridin-2-yl ester (0.5 g, 1.2 mmol), prepared substantially as described in Part C of Example 19a, and (R)-1-methoxymethyl-propylamine.HCl (0.34 g, 2.4 mmol) were treated substantially as described in Part C of Example 19a to produce 0.16 g (37%) of crude (R)-[4-(5-fluoro-4-methoxy-2-methyl-phenyl)-3-nitro-pyridin-2-yl]-(1-methoxymethyl-propyl)-amine.

Part D (R)-[4-(5-fluoro-4-methoxy-2-methyl-phenyl)-3-nitro-pyridin-2-yl]-(1-methoxymethyl-propyl)-amine (0.16 g, 0.44 mmol) and Na$_2$S$_2$O$_4$ (1.15 g, 6.6 mmol) were treated as in Part E of Example 9 to give 0.15 g (98%) crude (R)-4-(5-Fluoro-4-methoxy-2-methyl-phenyl)-N$^2$-(1-methoxymethyl-propyl)-pyridine-2,3-diamine. MS (AP) m/z 334.3 [(M+H)$^+$, 100].

Part E (R)-4-(5-Fluoro-4-methoxy-2-methyl-phenyl)-N$^2$-(1-methoxymethyl-propyl)-pyridine-2,3-diamine (0.15 g, 0.45 mmol) was treated substantially as described in Part F of Example 9 to give 4.8 mg (3%) of (R)-8-(5-Fluoro-4-methoxy-2-methyl-phenyl)-4-(1-methoxymethyl-propyl)-2-methyl-4H-pyrido[2,3-b]pyrazin-3-one (Example 90a): $^1$H NMR (300 MHz, CDCl$_3$) δ ppm 8.43 (d, J=5.13 Hz, 1 H), 7.04 (d, J=5.13 Hz, 1 H), 6.90 (d, J=11.72 Hz, 1 H), 6.82 (d, J=8.42 Hz, 1 H), 6.16 (m, 1 H), 4.30 (m, 1 H), 3.89 (s, 3 H), 3.72 (m, 1 H), 3.27 (s, 3 H), 2.41 (s, 3 H), 2.03 (m, 3 H), 1.64 (m, 2 H), 1.53 (d, J=6.96 Hz, 3 H). MS (EI) m/z 386.3 [(M+H)$^+$, 100].

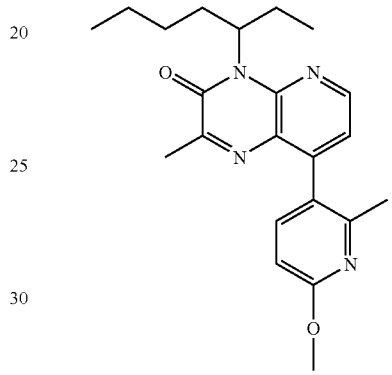

Example 97

(R,S)-4-(1-ethyl-pentyl)-8-(6-methoxy-2-methyl-pyridin-3-yl)-2-methyl-4H-pyrido[2,3-b]pyrazin-3-one Parts A and B 6-Methoxy-2-methyl-3'-nitro-3-H[3,4']bipyridinyl-2'-one was prepared substantially as described in Example 99a.

Part C

Trifluoro-methanesulfonic acid 6-methoxy-2-methyl-3'-nitro-3'H-[3,4']bipyridinyl ester (0.280 g, 0.71 mmol), prepared substantially as described in Part C of Example 99a, an 1-ethyl-pentyl amine (0.430 g, 2.8 mmol) were treated substantially as described in Part C of Example 99a to produce 0.200 g (51%) of (1-ethyl-pentyl)-6-methoxy-2-methyl-3'-nitro-[3,4']bipyridinyl-2'-yl)amine.

Part D (1-Ethyl-pentyl)-6-methoxy-2-methyl-3'-nitro-[3,4']bipyridinyl-2'-yl)amine (0.200 g, 0.56 mmol), and Na$_2$SO$_4$ (0.785 g, 4.5 mmol), were treated substantially as described in Part D of Example 99a to give a crude yield of 0.066 g (36%) of 6-methoxy-N$^2$-(1-ethyl-pentyl)-2-methyl-[3,4']bipyridinyl-2',3'-diamine; MS (AP) m/z 329.2 [(M+H)$^+$, 42].

Part E

6-Methoxy-N$^2$-(1-ethyl-pentyl)-2-methyl-[3,4']bipyridinyl-2',3'-diamine (0.066 g, 0.20 mmol) and methyl pyruvate (36 μL, 0.40 mmol) were treated substantially as described in Part E of Example 99a to give 4-(1-ethyl-pentyl)-8-(6-methoxy-2-methyl-pyridin-3-yl)-2-methyl-4H-pyrido[2,3- b]pyrazin-3-one (Example 97): $^1$H NMR (300 MHz, CDCl$_3$) δ 8.51–8.43 (m, 1H), 7.50–7.47 (d, 1H, J=8.5 Hz), 7.16–7.11 (m, 1H), 6.71–6.68 (d, 1H, J=8.1 Hz), 4.01 (s, 3H), 2.48–2.46 (m, 3H), 2.29 (s, 3H), 0.88–0.79 (m, 9H), 0.57–0.49 (m, 4H). MS (AP) 381.1 [(M+H)$^+$, 100].

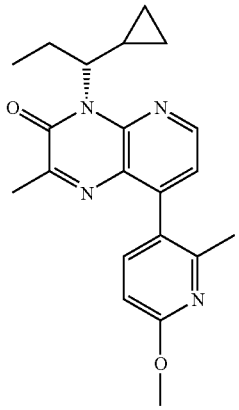

Example 99a (R)-4-(1-cyclopropyl-propyl)-8-(6-methoxy-2-methyl-pyridin-3-yl)-2-methyl-4H-pyrido[2,3-b]pyrazin-3-one Part A To a solution of 2-benzyloxy-4-chloro-3-nitro-pyridine (Wilde, et al. WO 99/01454, which is incorporated herein by reference) (1.95 g, 7.4 mmol) in ethanol (10 mL) and toluene (40 mL), was added Na$_2$CO$_3$ (9.2 mL, 2M), 2-methoxy-6-methyl pyridine boronic acid (Wilde, et al. WO99/01454) (1.85 g, 11.1 mmol), and Pd(PPh$_3$)$_2$Cl$_2$ (0.31 g, 4.44 mmol) and the mixture was heated at reflux for 5 h. The reaction was cooled and poured into EtOAc and H$_2$O (500 mL). The EtOAc layer was washed with H$_2$O, brine, dried Na$_2$SO$_4$, filtered and concentrated in vacuo. Purification using flash chromatography (10% EtOAc/hexane) gave 2.5 g (96%) of 2'-benzyl-6-methoxy-2-methyl-3'-nitro-2',3'-dihydro-[3,4']bipyridinyl as a viscous oil: MS (AP) m/z 352.5 [(M+H)$^+$, 100], 392.9 [(M+H+CH$_3$CN)$^+$, 65]. The purified intermediate was used in the following step.

Part B

2'-Benzyl-6-methoxy-2-methyl-3'-nitro-2',3'-dihydro-[3,4']bipyridinyl (2.50 g, 7.1 mmol) was dissolved in TFA (25 mL) and stirred at room temperature for 4 h. The reaction mixture was concentrated in vacuo and the crude product 6-methoxy-2-methyl-3'-nitro-3-H[3,4']bipyridinyl-2'-one; MS (AP) m/z 262.4 [(M+H)$^+$, 100], 303.0 [(M+H+CH$_3$CN)$^+$, 72]. The crude intermediate was used in the following step.

Part C

To a solution of 6-methoxy-2-methyl-3'-nitro-3-H[3,4']bipyridinyl-2'-one (0.300 g, 1.1 mmol) CH$_2$Cl$_2$ (20 mL), was added Na$_2$CO$_3$ (0.296 g, 2.7 mmol). The reaction was cooled to –78° C., and trifluoromethanesulfonic anhydride (574 µL, 3.4 mmol) was added dropwise. After the addition, the reaction stirred for 15 min at –78° C., then warmed to 0° C. for 1 h. The reaction mixture was filtered and the collected solid was washed with CHCl$_3$. The filtrate was concentrated in vacuo and dissolved in triethylamine (20 mL) followed by and 1-cyclopropyl propyl amine HCl (0.441 g, 3.3 mmol), and heated to reflux overnight. The reaction was cooled and poured onto ice/H$_2$O. The mixture was extracted with CH$_2$Cl$_2$, washed with H$_2$O, brine, dried Na$_2$SO$_4$, filtered, and concentrated in vacuo. Purification using flash chromatography (10% EtOAc/Hexane) gave 0.138 g (49%) of (1-cyclopropyl-propyl)-(6-methoxy-2-methyl-3'-nitro-[3,4']bipyridinyl-2'-yl)-amine: MS (AP) m/z 343.1 [(M+H)$^+$, 100]. The purified intermediate was used in the following step.

Part D (1-Cyclopropyl-propyl)-(6-methoxy-2-methyl-3'-nitro-[3,4']bipyridinyl-2'-yl)-amine (0.138, 0.40 mmol) was dissolved in dioxane (10 mL) and H$_2$O (10 mL), followed by conc. NH$_4$OH (0.4 mL) and Na$_2$S$_2$O$_4$ (0.57 g, 3.3 mmol) and stirred at room temperature for 4 h. The solution was extracted with EtOAc, washed with H$_2$O, brine, dried Na$_2$SO$_4$, filtered, and concentrated in vacuo to produce in crude yield 0.108 g (86%) of N$^2$-(cyclopropyl-propyl)-6-methoxy-2-methyl-[3,4']bipyridinyl-2',3'-diamine: MS (AP) m/z 313.2 [(M+H)$^+$, 47]. The crude intermediate was used in the following step.

Part E

N$^2$-(cyclopropyl-propyl)-6-methoxy-2-methyl-[3,4']bipyridinyl-2',3'-diamine (0.053 g, 0.17 mmol) was dissolved in EtOH (10 mL), followed by methyl pyruvate (31 µL, 0.34 mmol) and heated to reflux overnight. The reaction was concentrated in vacuo and purified by reverse phase prep HPLC to yield 4-(1-cyclopropyl-propyl)-8-(6-methoxy-2-methyl-pyridin-3-yl)-2-methyl-4H-pyrido[2,3-b]pyrazin-3-one (Example 99a). $^1$H NMR (300 MHz, CDCl$_3$) δ 8.48–8.46 (2d, 1H, J=4.7), 7.66–7.63 (d, 1H, J=8.8 Hz), 7.13–7.12 (d, 1H, J=4.7 Hz), 6.82–6.79 (d, 1H, J=8.4 Hz), 5.11–4.91, 4.52–4.42 (2m, 1H), 4.06 (s, 3H), 2.50 (s, 3H), 2.38 (s, 3H), 2.37–2.18 (m, 2H), 2.09–1.9 (m, 1H), 0.9–0.85 (t, 3H, J=7.4 Hz), 0.80–0.70 (m, 1H), 0.51–0.42 (m, 1H), 0.40–0.29 (m, 1H), 0.22–0.17 (m, 1H). MS (AP) m/z 365.4 [(M+H)$^+$, 100].

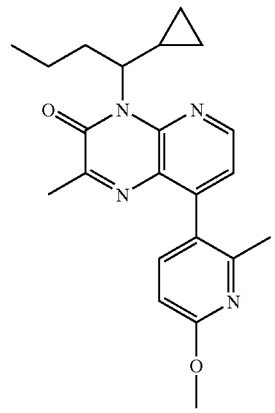

Example 101

(R,S)-4-(1-cyclopropyl-butyl)-8-(6-methoxy-2-methyl-pyridin-3-yl)-2-methyl-4H-pyrido[2,3-b]pyrazin-3-one Parts A and B 6-Methoxy-2-methyl-3'-nitro-3-H[3,4']bipyridinyl-2'-one was prepared substantially as described in Example 99a.

Part C

Trifluoro-methanesulfonic acid 6-methoxy-2-methyl-3'-nitro-3'H-[3,4']bipyridinyl ester (0.335 g, 1.3 mmol), prepared substantially as described in Part C of Example 99a, and 1-cyclopropyl-butylamine HCl (0.561 g, 5.2 mmol) were treated substantially as described in Part C of Example 99a to produce 0.075 g (15%) of (1-cyclopropyl-butyl)-6-methoxy-2-methyl-3'-nitro-[3,4']bipyridinyl-2'-yl)amine: MS (AP) m/z 357.1 [(M+H)$^+$, 100].

Part D (1-Cyclopropyl-butyl)-6-methoxy-2-methyl-3'-nitro-[3,4']bipyridinyl-2'-yl)amine (0.075 g, 0.21 mmol), and Na$_2$SO$_4$ (0.296 g, 1.7 mmol), were treated substantially as described in Part D of Example 99a to give a crude yield of 0.055 g (80%) of 6-methoxy-N$^2$-(1-cyclopropyl-butyl)-2-methyl-[3,4']bipyridinyl-2',3'-diamine.

Part E

6-Methoxy-N$^2$-(1-cyclopropyl-butyl)-2-methyl-[3,4']bipyridinyl-2',3'-diamine (0.055 g, 0.20 mmol) and methyl pyruvate (30 µL, 0.40 mmol) were treated substantially as described in Part E of Example 99a to give 4-(1-cyclopropyl-butyl)-8-(6-methoxy-2-methyl-pyridin-3-yl)-2-methyl-4H-pyrido[2,3-b]pyrazin-3-one (Example 101): $^1$H NMR (300 MHz, CDCl$_3$) δ 8.51–8.43 (2d, 1H, J=4.8 Hz), 7.48–7.46 (d, 1H, J=8.4), 7.12–7.10 (m, 1H), 6.70–6.68 (d, 1H, J=8.4 Hz), 5.17–5.09, 4.60–4.53 (2m, 1H), 4.01 (s,3H), 3.17–3.13 (m, 2H), 2.50 (s, 3H), 2.31 (s, 3H), 2.22–2.15 (m, 3H), 0.92–0.87 (t, 3H, J=7.3 Hz), 0.79–0.73 (m, 1H), 0.53–0.43 (m, 1H), 0.40–0.38 (m, 1H), 0.21–0.17 (m, 1H). MS (AP) 379.1 [(M+H)$^+$, 100].

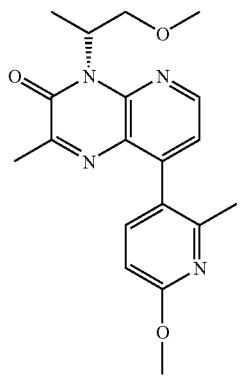

Example 105a (R)-4-(2-methoxy-1-methyl-ethyl)-8-(6-methoxy-2-methyl-pyridyl)-2-methyl-4H-pyrido[2,3-b]pyrazin-3-one Parts A and B 6-Methoxy-2-methyl-3'-nitro-3-H[3,4']bipyridinyl-2'-one was prepared substantially as described in Example 99a.

Part C

Trifluoro-methanesulfonic acid 6-methoxy-2-methyl-3'-nitro-3'H-[3,4']bipyridinyl ester (0.280 g, 0.71 mmol), prepared as substantially described in Part C of Example 99a, and 2-methoxy-1-methyl-ethylamine HCl (0.358 g, 2.8 mmol) were treated substantially as described in Part C of Example 99a to produce 0.070 g (30%) of (2-methoxy-1-methyl-ethyl)-6-methoxy-2-methyl-3'-nitro-[3,4']bipyridinyl-2'-yl)amine: MS (AP) m/z 333.4 [(M+H)$^+$, 100].

Part D (2-Methoxy-1-methyl-ethyl)-6-methoxy-2-methyl-3'-nitro-[3,4']bipyridinyl-2'-yl)amine (0.070 g, 0.21 mmol), and Na$_2$SO$_4$ (0.296 g, 1.7 mmol), were treated substantially as described in Part D of Example 99a to give a crude yield of 0.054 g (85%) of 6-methoxy-N$^2$-(2-methoxy-1-methyl-ethyl)-2-methyl-[3,4']bipyridinyl-2',3'-diamine: MS (AP) m/z 303.2 [(M+H)$^+$, 100].

Part E

6-Methoxy-N$^2$-(2-methoxy-1-methyl-ethyl)-2-methyl-[3,4']bipyridinyl-2',3'-diamine (0.054 g, 0.18 mmol) and methyl pyruvate (32 µL, 0.36 mmol) were treated substantially as described in Part E of Example 99a to give 4-(2-methoxy-1-methyl-ethyl)-8-(6-methoxy-2-methyl-pyridyl)-2-methyl-4H-pyrido[2,3-b]pyrazin-3-one (Example 105a): $^1$H NMR (300 MHz, CDCl$_3$) δ 8.57–8.56 (d, 1H, J=4.7 Hz), 7.78–7.75 (d, 1H, J=8.5 Hz), 7.16–7.14 (d, 1H, J=5.1 Hz), 6.91–6.88 (d, 1H, J=8.7 Hz), 4.44–4.38 (t, 1H, J=9.1 Hz), 4.11 (s, 3H), 3.79–3.74 (m, 2H), 3.34 (s, 3H), 2.48 (s, 3H), 2.42 (s, 3H), 1.62–1.59 (d, 3H), J=7.0 Hz). MS (AP) 355.6 [(M+H)$^+$, 100].

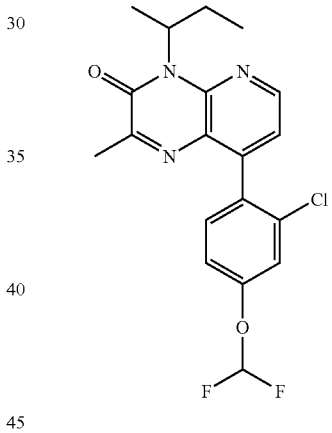

Example 113

(R,S)-4-sec-butyl-8-(2-chloro-4-difluoromethoxy-phenyl)-2-methyl-4H-pyrido[2,3-b]pyrazin-3-one Part A To a solution of 2-benzyloxy-4-chloro-3-nitro-pyridine (Wilde, et al. WO 99/01454, which is incorporated herein by reference) (6.59 g, 24.9 mmol) in DME/H$_2$O, was added 2-chloro-4-difluoromethoxy-phenylboronic acid (Wilde, et al. WO 99/01454) (5.54 g, 24.9 mmol), Ba(OH)$_2$ 8H$_2$O (7.86 g, 24.9 mmol), and Pd(PPh$_3$)$_2$Cl$_2$ (1.01 g, 1.45 mmol) and the mixture was heated at reflux for 5 h. The reaction was cooled and poured into EtOAc and H$_2$O (500 mL). The EtOAc layer was washed with H$_2$O, brine, dried Na$_2$SO$_4$, filtered and concentrated in vacuo to give 6.9 g (68%) of 2-benzyloxy-4-(2-chloro-4-difluoromethoxy-phenyl)-3-nitro-pyridine as a viscous oil; MS(AP) m/z 408.9 [(M+H)$^+$, 100].

Part B

2-Benzyloxy-4-(2-chloro-4-difluoromethoxy-phenyl)-3-nitro-pyridine(6.90 g, 17.0 mmol) was dissolved in TFA (25 mL) and stirred at room temperature for 4 h. The reaction mixture was concentrated in vacuo. Purification using flash chromatography (15% MeOH/DCM) gave 1.00 g (19%) of 4-(2-chloro-4-difluoromethoxy-phenyl)-3-nitro-3H-pyridin-2-one as an orange solid: MS(AP) m/z 316.9 [(M+H)$^+$, 98], 359.8 [(M+H+CH$_3$CN)$^+$, 100].

Part C

To 10 mL of POCl$_3$ was added 4-(2-chloro-4-difluoromethoxy-phenyl)3-nitro-3H-pyridin-2-one (0.20 g, 0.63 mmol), followed by the addition of DMF (1–2 mL) and the reaction refluxed overnight. The reaction mixture was cooled to room temperature and poured over ice/H$_2$O (200 mL). The solution was extracted with EtOAc, washed H$_2$O, brine, dried Na$_2$SO$_4$, filtered, and concentrated in vacuo to give 0.176 g (96%) of 2-chloro-4-(2-chloro-4-difluoromethoxy-phenyl)-3-nitro-2,3-dihydro-pyridine as brown viscous oil.

Part D

2-Chloro-4-(2-chloro-4-difluoromethoxy-phenyl)-3-nitro-2,3-dihydro-pyridine (0.176 g, 0.53 mmol) was dissolved in acetonitrile (20 mL), followed by the addition of sec butylamine (106 µL, 1.06 mmol) and Hunig's base (184 µL, 1.06 mmol). The reaction was stirred at reflux for 64 h. The solution was cooled to room temperature, extracted with EtOAc/H$_2$O, organic layer was then washed with 1N HCl and made basic with 1N NaOH. The organic layer was washed with brine, dried Na$_2$SO$_4$, filtered and concentrated to yield 0.163 g (83%) of sec-butyl-[4-(chloro-4-difluoromethoxy-phenyl)-3-nitro-2,3-dihydro-pyridin-2-yl]-amine as a yellow oil; MS (AP) 413.0 [(M+H+CH$_3$CN)$^+$, 50].

Part E

Sec-butyl-[4-(chloro-4-difluoromethoxy-phenyl)-3-nitro-2,3-dihydro-pyridin-2-yl]-amine (0.163, 0.44 followed by conc. NH$_4$OH (0.4 mL) and Na$_2$S$_2$O$_4$ (0.62 g, 3.55 mmol) and stirred at room temperature for 4 h. The solution was extracted with EtOAc, washed with H$_2$O, brine, dried Na$_2$SO$_4$, filtered, and concentrated in vacuo to produce 0.145 g (97%) of N$^2$-sec-butyl-4-(2-chloro-4-difluoromethoxy-phenyl)-2,3-dihydro-pyridine-2,3-diamine as a yellow oil.

Part F

Sec-butyl-[4-(chloro-4-difluoromethoxy-phenyl)-3-nitro-2,3-dihydro-pyridin-2-yl]-amine (0.145 g, 0.43 mmol) was dissolved in toluene (20 mL), followed by methyl pyruvate (77 µL, 0.86 mmol) and heated to reflux overnight. The reaction was concentrated in vacuo and purified by reverse phase prep HPLC giving 4-sec-butyl-8-(2-chloro-4-difluoromethoxy-phenyl)-2-methyl-4H-pyrido[2,3-b]pyrazin-3-one (Example 113): $^1$H NMR (300 MHz, CDCl$_3$) δ 8.53–8.52 (d, 1H, J=4.8 Hz), 7.35–7.32 (m, 2H), 7.19–7.13 (m, 2H), 6.85–6.36 (t, 1H, J=73.2 Hz), 2.47 (s, 3H), 2.40–2.20 (m, 1H), 2.10–2.07 (m,1H), 1.65–1.63 (d, 3H, J=6.9 Hz), 0.89–0.84 (t, 3H, J=3.7). MS(AP) m/z 394.2 [(M+H)$^+$, 100], 435.3 [(M+H+CH$_3$CN)$^+$, 10].

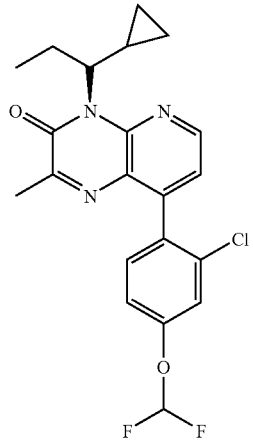

Example 115a (S)-8-(2-Chloro-4-difluoromethoxy-phenyl)-4-(1-cyclopropyl-propyl)2-methyl-4H-pyrido[2,3-b]pyrazin-3-one Parts A and B 4-(2-Chloro-4-difluoromethoxy-phenyl)-3-nitro-3H-pyridin-2-one was prepared substantially as described in Example 113.

Part C

Trifluoro-methanesulfonic acid 4-(2-chloro-4-difluoromethoxy-phenyl)-3-nitro-pyridin-2-yl ester (0.269 g, 0.60 mmol), prepared substantially as described in Part C of Example 115b, and 1-cyclopropyl-proply amine HCl (0.162 g, 1.2 mmol) were treated in the same manner as in Part C of Example 115b with the exception that the crude product was purified using flash chromatography (10% EtOAc/Hexane) to produce 0.138 g (67%) of [4-2-chloro-4-difluoromethoxy-phenyl)-3-nitro-pyridin-2-yl]-(1-cyclopropyl-propyl) amine: MS (AP) m/z 398.0 [(M+H)$^+$, 100).

Part D

[4-(2-Chloro[4[difluoromethoxy-phenyl)-3-nitro-pyridin-2-yl]-(1-cyclopropyl-propyl)-amine (0.138 g, 0.40 mmol), and Na$_2$SO$_4$ (0.567 g, 8.07 mmol), were treated as in Part E of Example 113 to give in crude yield 0.170 g (116%) of 4-(2-chloro-4-difluoromethoxy-phenyl)-N$^2$-(1-cyclopropyl-propyl)-pyridine-2,3-diamine: MS (AP) m/z 368.1 [(M+H)$^+$, 40].

Part E 4-(2-chloro-4-difluoromethoxy-phenyl)-N$^2$-(1-cyclopropyl-propyl)-pyridine-2,3-diamine (0.088 g, 0.24 mmol) and methyl pyruvate (140 µL, 1.54 mmol) were treated as in Part F of Example 113 with the exception that ethanol was used as the solvent, gave 8-(2-Chloro-4-difluoromethoxy-phenyl)-4-(1-cyclopropyl-propyl)2-methyl-4H-pyrido[2,3-b]pyrazin-3-one (Example 115a): $^1$H NMR (300 MHz, CDCl$_3$) δ 8.48–8.46 (2d, 1H, J=4.7 Hz), 7.37–7.33 (m, 2H), 7.19–7.14 (m, 2H), 6.86–6.37 (t,1H, J=73.3 Hz), 5.16–4.92, 4.90–4.41 (2m, 1H), 2.57 (s, 3H), 2.49–2.38 (m, 1H), 2.29–2.19 (m, 1H), 2.10–1.93 (m, 1H), 0.90–0.85 (t, 3H, J=7.3), 0.80–0.71 (m, 1H), 0.59–0.50 (m, 1H), 0.49–0.48 (m, 1H), 0.23–0.18 (m, 1H). MS (AP) m/z 420.1 [(M+H)$^+$, 100].

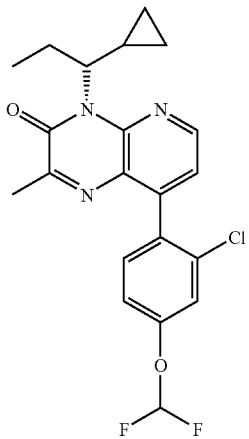

Example 115b (R)-8-(2-Chloro-4-difluoromethoxy-phenyl)-4-(1-cyclopropyl-propyl)2-methyl-4H-pyrido[2,3-b]pyrazin-3-one Part A To a solution of 2-benzyloxy-4-chloro-3-nitro-pyridine (Wilde, et al. WO 99/01454, which is incorporated herein by reference) (5.0 g, 18.9 mmol) in DME/H$_2$O, was added 2-chloro-4-difluoromethoxy-phenylboronic acid (Wilde, et al. WO 99/01454, which is incorporated by reference herein in its entirety) (4.20 g, 18.9 mmol), Ba(OH)$_2$ 8H$_2$O (5.96 g, 18.9 mmol), and Pd(PPh$_3$)$_2$Cl$_2$ (0.769 g, 1.10 mmol) were treated as in Part A of Example 113 to give 5.40 g (70%) of 2-benzyloxy-4-(2-chloro-4-difluoromethoxy-phenyl)-3-nitro-pyridine as a viscous oil. The crude intermediate was used in the following step.

Part B

2-Benzyloxy-4-(2-chloro-4-difluoromethoxy-phenyl)-3-nitro-pyridine (5.40 g, 13.3 mmol) and TFA (25 mL) were treated as in Part B of Example 113 with the exception that the crude product was isolated as 3.90 g (93%) of 4-(2-chloro-4-difluoromethoxy-phenyl)-3-nitro-3H-pyridin-2-one: MS(AP) m/z 317.0 [(M+H)$^+$, 90], 357.9 [(M+H+CH$_3$CN)$^+$, 100].

Part C

To a solution of 2-benzyloxy-4-(2-chloro-4-difluoromethoxy-phenyl)-3-nitro-pyridin-2-one (0.364 g, 1.2 mmol) CH$_2$Cl$_2$ (20 mL), was added Na$_2$CO$_3$ (0.299 g, 2.94 mmol). The reaction was cooled to −78° C., and trifluoromethanesulfonic anhydride (576 µL, 3.6 mmol) was added dropwise. After the addition, the reaction stirred for 15 min at −78° C., then warmed to 0° C. for 1 h. The reaction mixture was filtered and the collected solid was washed with CHCl$_3$. The filtrate was concentrated in vacuo and dissolved in toluene (20 mL) followed by Et$_3$N(231 µL, 1.7 mmol) and 1-cyclopropyl propyl amine HCl (0.224 g, 1.7 mmol), and heated at 130° C. overnight. The reaction was cooled and poured onto ice/H$_2$O. The mixture was extracted with CH$_2$Cl$_2$, washed with H$_2$O, brine, dried Na$_2$SO$_4$, filtered, and concentrated in vacuo to produce in crude yield 0.301 g, (91%) of [4-(2-chloro[4[difluoromethoxy-phenyl)-3-nitro-pyridin-2-yl]-(1-cyclopropyl-propyl)-amine. MS(AP) m/z 398.0 [(M+H)$^+$, 100]. The crude intermediate was used in the following step.

Part D

[4-(2-Chloro[4[difluoromethoxy-phenyl)-3-nitro-pyridin-2-yl]-(1-cyclopropyl-propyl)-amine (0.301 g, 0.76 mmol), and Na$_2$SO$_4$ (1.07 g, 6.12 mmol), were treated substantially as described in Part E of Example 113 to give 0.284 g (91%) of 4-(2-chloro-4-difluoromethoxy-phenyl)-N$^2$-(1-cyclopropyl-propyl)-pyridine-2,3-diamine. The crude intermediate was used in the following step.

Part E 4-(2-Chloro-4-difluoromethoxy-phenyl)-N$^2$-(1-cyclopropyl-propyl)-pyridine-2,3-diamine (0.284 g, 0.77 mmol) and methyl pyruvate (140 µL, 1.54 mmol) were treated substantially as described in Part F of Example 113 to give 8-(2-Chloro-4-difluoromethoxy-phenyl)-4-(1-cyclopropyl-propyl)2-methyl-4H-pyrido[2,3-b]pyrazin-3-one (Example 115b): $^1$H NMR (300 MHz, CDCl$_3$) δ 8.52–8.46 (2d, 1H, J=4.8), 7.37–7.32 (m, 2H), 7.26–7.14 (m, 2H), 6.85–6.37(t, 1H, J=73.3 Hz), 5.09–4.95, 4.75–4.2 (2m, 1H), 2.48 (s, 3H), 2.4–2.25 (m, 1H), 2.23–2.16 (m, 1H), 2.13–1.93 (m, 1H), 0.90–0.85 (t, 3H, J=7.3 Hz), 0.80–0.67 (m, 1H), 0.57–0.42 (m, 1H), 0.40–0.29 (m, 1H), 0.24–0.18 (m, 1H). MS (AP) m/z 420.2 [(M+H)$^+$, 100], 461.3 [(M+H+CH$_3$CN)$^+$, 20].

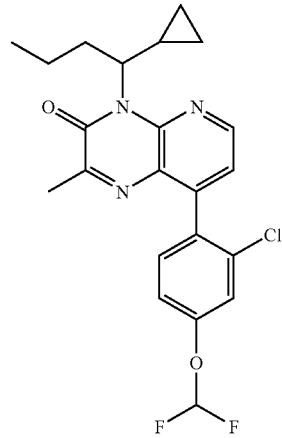

Example 117

(R,S)-8-(2-Chloro-4-difluoromethoxy-phenyl)-4-(1-cyclopropyl-butyl)-2-methyl-4H-pyrido[2,3-b]pyrazin-3-one Parts A and B 4-(2-Chloro-4-difluoromethoxy-phenyl)-3-nitro-3H-pyridin-2-one was prepared substantially as described in Example 113.

Part C

Trifluoro-methanesulfonic acid 4-(2-chloro-4-difluoromethoxy-phenyl)-3-nitro-pyridin-2-yl ester (0.369 g, 0.83 mmol), prepared substantially as described in Part C of Example 155b, and 1-cyclo-proply-butylamine HCl (0.246 g, 1.7 mmol) were treated substantially as described in Part C of Example 115b to produce in crude yield 0.380 g (111%) of [4-2-chloro-4-difluoromethoxy-phenyl)-3-nitro-pyridin-2-yl]-(1-cyclopropyl-butyl)-amine: MS (AP) m/z 412.0 [(M+H)$^+$, 100].

Part D

[4-2-Chloro-4-difluoromethoxy-phenyl)-3-nitro-pyridin-2-yl]-(1-cyclopropyl-butyl)-amine (0.380 g, 0.92 mmol), and Na$_2$SO$_4$ (1.30 g, 7.5 mmol), were treated substantially as described in Part E of Example 113 to give a crude yield of 0.300 g (86%) of 4-(2-chloro-4-difluoromethoxy-phenyl)-N$^2$-(1-cyclopropyl-butyl)-pyridine-2,3-diamine.

Part E 4-(2-Chloro-4-difluoromethoxy-phenyl)-N$^2$-(1-cyclopropyl-butyl)-pyridine-2,3-diamine (0.300 g, 0.79 mmol) and methyl pyruvate (142 µL, 1.58 mmol) were treated substantially as described in Part F of Example 113 to give 8-(2-chloro-4-difluoromethoxy-phenyl)-4-(1-cyclopropyl-butyl)-2-methyl-4H-pyrido[2,3-b]pyrazin-3-one (Example 117). $^1$H NMR (300 MHz, CDCl$_3$) δ 8.47–8.46 (2d, 1H, J=4.8 Hz), 7.37–7.28 (m, 2H), 7.20–7.10 (m, 2H), 6.85–6.37 (t, 1H, J=72.8 Hz), 5.18–5.02, 4.60–4.51 (2m, 1H), 2.49 (s, 3H), 2.40–2.32 (m, 1H), 2.29–2.17 (m, 2H), 2.10–2.00 (m, 1H), 0.92–0.88 (t, 3H, J=7.4 Hz), 0.87–0.77 (m, 1H), 0.59–0.42 (m, 2H), 0.40–0.31 (m, 2H). MS (AP) m/z 434.1 [(M+H)$^+$, 100)].

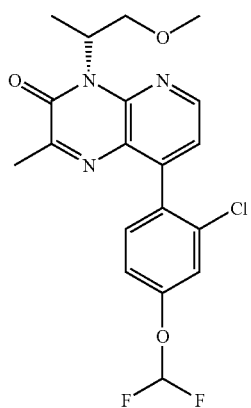

Example 121a (R)-8-(2-chloro-4-difluoromethoxy-phenyl)-4-(2-methoxy-1-methyl-ethyl)-2-methyl-4H-pyrido[2,3-b]pyrazin-3-one Parts A and B 4-(2-Chloro-4-difluoromethoxy-phenyl)-3-nitro-3H-pyridin-2-one was prepared substantially as described in Example 113.

Part C

Trifluoro-methanesulfonic acid 4-(2-chloro-4-difluromethoxy-phenyl)-3-nitro-pyridin-2-yl ester (0.332 g, 0.74 mmol), prepared substantially as described in Part C of Example 115b, and 2-methoxy-1-methyl-ethylamine HCl (0.207 g, 1.5 mmol) were treated substantially as described in Part C of Example 115b to produce 0.231 g (78%) of [4-2-chloro-4-difluoromethoxy-phenyl)-3-nitro-pyridin-2-yl]-(2-methoxy-1-methyl-ethyl)-amine: MS (AP) m/z 387.9 [(M+H)$^+$, 100].

Part D

[4-2-Chloro-4-difluoromethoxy-phenyl)-3-nitro-pyridin-2-yl]-(2-methoxy-1-methyl-ethyl)-amine (0.231 g, 0.58 mmol), and Na$_2$SO$_4$ (0.809 g, 4.7 mmol), were treated substantially as described in Part E of Example 113 to give 0.149 g (72%) of 4-(2-chloro-4-difluoromethoxy-phenyl)-N$^2$-(2-methoxy-1-methyl-ethyl)-pyridine-2,3-diamine: MS (AP) m/z 358.0 [(M+H)$^+$, 100]. Crude intermediate was taken on to Part E Part E 4-(2-Chloro-4-difluoromethoxy-phenyl)-N$^2$-(2-methoxy-1-methyl-ethyl)-pyridine-2,3-diamine (0.149 g, 0.42 mmol) and methyl pyruvate (75 µL, 0.83 mmol) were treated substantially as described in Part F of Example 113 to give 8-(2-chloro-4-difluoromethoxy-phenyl)-4-(2-methoxy-1-methyl-ethyl)-2-methyl-4H-pyrido[2,3-b]pyrazin-3-one (Example 121a): $^1$H NMR (300 MHz, CDCl$_3$): δ 8.54–8.53 (d, 1H, J=4.8 Hz), 7.34–7.32 (m, 2H), 7.21–7.13 (m, 2H), 6.85–6.36 (t, 1H, J=73.2 Hz), 4.41–4.37 (m, 1H), 3.82–3.76 (m, 2H), 3.34 (s, 3H), 2.47 (s, 3H), 1.62 (d, 3H, J=6.9 Hz). MS (AP) m/z 410.0 [(M+H)$^+$, 100].

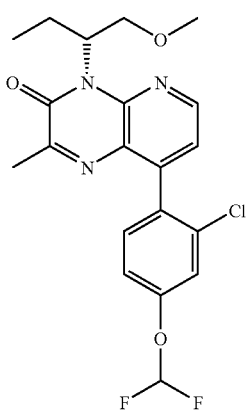

Example 122a (R)-8-(2-Chloro-4-difluoromethoxy-phenyl)-4-(1-methoxymethyl-propyl)-2-methyl-4H-pyrido[2,3-b]pyrazin-3-one Parts A and B 4-(2-Chloro-4-difluoromethoxy-phenyl)-3-nitro-3H-pyridin-2-one was prepared substantially as described in Example 113.

Part C

Trifluoro-methanesulfonic acid 4-(2-chloro-4-difluromethoxy-phenyl)-3-nitro-pyridin-2-yl ester (0.405 g, 0.9 mmol), prepared substantially as described in Part C of Example 155b, and 2-methoxymethyl-propylamine HCl (0.252 g, 1.8 mmol) were treated in the same manner as in Part C of Example 115b to produce in crude yield 0.350 g (97%) of [4-2-chloro-4-difluoromethoxy-phenyl)-3-nitro-pyridin-2-yl]-(1-methoxymethyl-propyl)amine. MS (AP) m/z 402.0 [(M+H)$^+$, 100].

Part D

[4-2-Chloro-4-difluoromethoxy-phenyl)-3-nitro-pyridin-2-yl]-(1-methoxymethyl-propyl)amine (0.350 g, 0.87 mmol), and Na$_2$SO$_4$ (1.23 g, 7.04 mmol), were treated substantially as described in Part E of Example 113 to give a crude yield of 0.268 g (83%) of 4-(2-chloro-4-difluoromethoxy-phenyl)-N$^2$-(1-methoxymethyl-propyl)-pyridine-2,3-diamine; MS (AP) m/z 372.0 [(M+H)$^+$, 100].

Part E 4-(2-Chloro-4-difluoromethoxy-phenyl)-N²-(1-methoxymethyl-propyl)-pyridine-2,3-diamine (0.268 g, 0.72 mmol) and methyl pyruvate (130 µL, 1.44 mmol) were treated substantially as described in Part F of Example 113 to give 8-(2-chloro-4-difluoromethoxy-phenyl)-4-(1-methoxymethyl-propyl)-2-methyl-4H-pyrido[2,3-b]pyrazin-3-one (Example 122a): ¹H NMR (300 MHz, CDCl₃) δ ☐8.54–8.51 (m, 1H), 7.33–7.32 (m,2H), 7.21–7.14 (m, 2H), 6.85–6.37 (t, 1H, J=72.9 Hz), 6.21–6.19, 5.64–5.58 (2m, 1H), 4.40–4.31 (m, 1H), 3.92–3.79 (m, 1H), 3.33 (s, 3H), 2.48 (s, 3H), 2.30–2.20 (m, 1H),2.13–1.96 (m, 1H), 0.90–0.85 (t, 3H, J=7.7 Hz). MS (AP) m/z 424.1 [(M+H)⁺, 100].

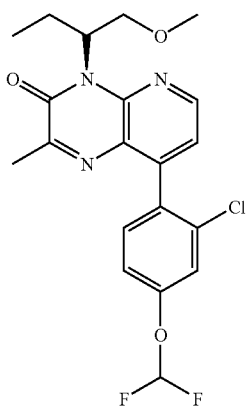

Example 122b (S)-8-(2-Chloro-4-difluoromethoxy-phenyl)-4-(1-methoxymethyl-propyl)-2-methyl-4H-pyrido[2,3-b]pyrazin-3-one Parts A and B 4-(2-Chloro-4-difluoromethoxy-phenyl)-3-nitro-3H-pyridin-2-one was prepared substantially as described in Example 113.

Part C

Trifluoro-methanesulfonic acid 4-(2-chloro-4-difluoromethoxy-phenyl)-3-nitro-pyridin-2-yl ester (0.473 g, 1.1 mmol), prepared substantially as described in Part C of Example 115b, and 2-methoxymethyl-propylamine HCl (0.295 g, 2.2 mmol) were treated in the same manner as in Part C of Example 115b to produce 0.380 g (86%) of [4-2-chloro-4-difluoromethoxy-phenyl)-3-nitro-pyridin-2-yl]-(1-methoxymethyl-propyl)amine: MS (AP) m/z 402.0 [(M+H)⁺, 100].

Part D

[4-2-Chloro-4-difluoromethoxy-phenyl)-3-nitro-pyridin-2-yl]-(1-methoxymethyl-propyl)amine (0.38 g, 0.95 mmol), and Na₂SO₄ (1.33 g, 7.6 mmol), were treated substantially as described in Part E of Example 113 to give a crude yield of 0.366 g of 4-(2-chloro-4-difluoromethoxy-phenyl)-N²-(1-methoxymethyl-propyl)-pyridine-2,3-diamine: MS (AP) m/z 372.0 [(M+H)⁺, 100].

Part E 4-(2-Chloro-4-difluoromethoxy-phenyl)-N²-(1-methoxymethyl-propyl)-pyridine-2,3-diamine (0.366 g, 0.99 mmol) and methyl pyruvate (178 µL, 1.97 mmol) were treated as in Part F of Example 133 to give 8-(2-chloro-4-difluoromethoxy-phenyl)-4-(1-methoxymethyl-propyl)-2-methyl-4H-pyrido[2,3-b]pyrazin-3-one (Example 122b): ¹H NMR (300 MHz, CDCl₃) δ 8.56–8.51 (m, 1H), 7.33–7.30 (m, 2H), 7.27–7.23 (m, 2H), 6.82–6.33 (t, 1H, J=72.9 Hz), 6.20–6.18, 5.62–5.57 (2m, 1H), 4.38–4.32 (m,1H), 3.93–3.80 (m, 1H), 3.33 (s, 3H), 2.47 (s, 3H), 2.08–2.00 (m, 2H), 0.90–0.88 (t, 3H, J=6.3 Hz). MS (AP) 424.1 [(M+H)⁺, 100].

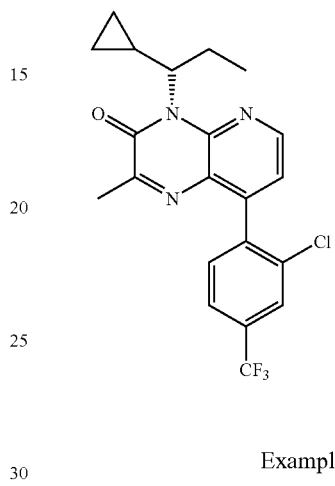

Example 131a (S)-8-(2-chloro-4-trifluoromethyl-phenyl)-4-(1-cyclopropyl-propyl)-2-methyl-4H-pyrido[2,3-b]pyrazin-3-one Part A 2-Benzyloxy-4-chloro-3-nitro-pyridine (Wilde, et al. WO 99/01454, which is incorporated herein by reference in its entirety) (2.0 g, 7.56 mmol) and 2-chloro-4-trifluoromethylphenylboronic acid (2.31 g, 11.3 mmol) were treated substantially as described in Part A of Example 19a to give 2.44 g (79%) of 2-benzyloxy-4-(2-chloro-4-trifluoromethyl-phenyl)-3-nitro-pyridine: MS (AP) m/z 408.8 [(M+H)⁺, 72].

Part B

2-Benzyloxy-4-(2-chloro-4-trifluoromethyl-phenyl)-3-nitro-pyridine (2.44 g, 5.97 mmol) was treated as in Part B of Example 19a to give 2.01 g (100%) of 4-(2-chloro-4-trifluoromethyl-phenyl)-3-nitro-1H-pyridin-2-one: MS (AP) m/e 318.6 [(2M–H)⁻, 100].

Part C

Trifluoro-methanesulfonic acid 4-(2-chloro-4-trifluoromethyl-phenyl)-3-nitro-pyridin-2-yl-ester (0.62 g, 1.38 mmol), prepared substantially as described in Part C of Example 19a, and 1-cyclopropyl-propylamine HCl (0.37 g, 2.75 mmol) were treated substantially as described in Part C of Example 19a to produce 0.55 g (100%) of [4-(2-chloro-4-trifluoromethyl-phenyl)-3-nitro-pyridin-2-yl]-(1-cyclopropyl-propyl)-amine: MS (AP) m/z 399.8 [(M+H)⁺, 25].

Part D

[4-(2-Chloro-4-trifluoromethyl-phenyl)-3-nitro-pyridin-2-yl]-(1-cyclopropyl-propyl)-amine (0.55 g, 1.38 mmol) and Na₂S₂O₄ (1.93 g, 11.1 mmol) were treated substantially as in Part E of Example 9 to yield 94% of 4-(2-chloro-4-trifluoromethyl-phenyl)-N²-(1-cyclopropyl-propyl)-pyridine-2,3-diamine: MS (AP) m/z 369.8 [(M+H)⁺, 100].

Part E 4-(2-Chloro-4-trifluoromethyl-phenyl)-N²-(1-cyclopropyl-propyl)-pyridine-2,3-diamine (0.31 g, 0.86 mmol) was treated substantially as described in Part F of Example 9 to give 8.2 mg (2%) of 8-(2-chloro-4-trifluoromethyl-phenyl)-4-(1-cyclopropyl-propyl)-2-methyl-4H-pyrido[2,3-b]pyrazin-3-one (Example 131a): ¹H NMR (300 MHz, CDCl₃): δ 8.5 (d, 1H), 7.77 (s, 1H), 7.6 (d, 1H), 7.5 (d, 1H), 7.17 (s, 1H), 5.0 (q, 1H), 4.45 (q, 1H), 2.45 (s, 2H), 2.4–2.10 (m, 1H), 1.3 (s, 3H), 0.90 (t, 3H), 0.70 (m, 1H), 0.50–0.30 (m, 2H). MS (AP) m/z 421.9 [(M+H)⁺, 100].

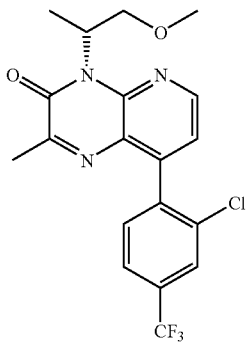

Example 137a (R)-8-(2-chloro-4-trifluoromethyl-phenyl)-4-(2-methoxy-1-methyl-ethyl)-2-methyl-4H-pyrido[2,3-b]pyrazin-3-one Part A 2-Benzyloxy-4-chloro-3-nitro-pyridine (Wilde, et al. WO 99/01454, which is incorporated herein by reference in its entirety) (2.0 g, 7.56 mmol) and 2-chloro-4-trifluoromethylphenylboronic acid (2.31 g, 11.3 mmol) were treated as in Part A of Example 19a to give 2.44 g (79%) of 2-benzyloxy-4-(2-chloro-4-trifluoromethyl-phenyl)-3-nitro-pyridine: MS (AP) m/z 408.8 [(M+H)⁺, 72].

Part B

2-Benzyloxy-4-(2-chloro-4-trifluoromethyl-phenyl)-3-nitro-pyridine (2.44 g, 5.97 mmol) was treated as in Part B of Example 19a to give 2.01 g (100%) of 4-(2-chloro-4-trifluoromethyl-phenyl)-3-nitro-1H-pyridin-2-one: MS (AP) m/e 318.6 [(2M–H)⁻, 100].

Part C

Trifluoro-methanesulfonic acid 4-(2-chloro-4-trifluoromethyl-phenyl)-3-nitro-pyridin-2-yl-ester (0.50 g, 1.11 mmol), prepared substantially as described in Part C of Example 19a, and 2-methoxy-1-methyl-ethylamine HCl (0.28 g, 2.22 mmol) were treated in the same manner as in Part C of Example 19a to produce 0.45 g (100%) of [4-(2-chloro-4-trifluoromethyl-phenyl)-3-nitro-pyridin-2-yl]-(2-methoxy-1-methyl-ethyl)-amine: MS (AP) m/z 389.8 [(M+H)⁺, 100].

Part D

[4-(2-Chloro-4-trifluoromethyl-phenyl)-3-nitro-pyridin-2-yl]-(2-methoxy-1-methyl-ethyl)-amine (0.45 g, 1.15 mmol) and Na₂S₂O₄ (1.62 g, 9.32 mmol) were treated substantially as described in Part E of Example 9 to yield 0.31 g (74%) of 4-(2-chloro-4-trifluoromethyl-phenyl)-N²-(2-methoxy-1-methyl-ethyl)-pyridine-2,3-diamine: MS (AP) m/z 359.8 [(M+H)⁺, 97].

Part E 4-(2-Chloro-4-trifluoromethyl-phenyl)-N²-(2-methoxy-1-methyl-ethyl)-pyridine-2,3-diamine (0.31 g, 0.86 mmol) was treated substantially as described in Part F of Example 9 to give 8.2 mg (2%) of 8-(2-chloro-4-trifluoromethyl-phenyl)-4-(2-methoxy-1-methyl-ethyl)-2-methyl-4H-pyrido[2,3-b]pyrazin-3-one (Example 137a): ¹H NMR (300 MHz, CDCl₃): δ 8.5 (d, 1H), 7.7 (s, 1H), 7.6 (d, 1H), 7.4 (d, 1H), 7.20 (d, 1H), 4.4 (t, 1H), 3.8 (q, 1H), 3.3 (s, 3H), 2.5 (bs, 1H), 2.4 (s, 3H), 1.6 (d, 3H). MS (AP) m/z 411.8 [(M+H)⁺, 100].

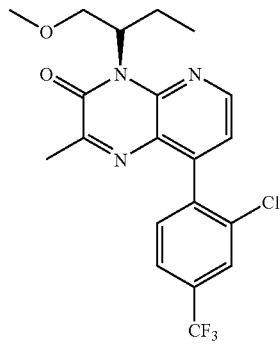

Example 138a (R)-8-(2-chloro-4-trifluoromethyl-phenyl)-4-(1-methoxymethyl-propyl)-2-methyl-4H-pyrido[2,3-b]pyrazin-3-one Parts A and B 4-(2-Chloro-4-trifluoromethyl-phenyl)-3-nitro-1H-pyridin-2-one was prepared substantially as described in Example 137a.

Part C

Trifluoro-methanesulfonic acid 4-(2-chloro-4-trifluoromethyl-phenyl)-3-nitro-pyridin-2-yl-ester (0.50 g, 1.11 mmol), prepared substantially as described in Part C of Example 19a, and 1-methoxymethyl-propylamine HCl (0.31 g, 2.22 mmol) were treated substantially as described in Part C of Example 19a to produce 0.40 g (89%) of [4-(2-chloro-4-trifluoromethyl-phenyl)-3-nitro-pyridin-2-yl]-(1-methoxymethyl-propyl)-amine: MS (AP) m/z 403.8 [(M+H)⁺, 98].

Part D

[4-(2-Chloro-4-trifluoromethyl-phenyl)-3-nitro-pyridin-2-yl]-(1-methoxymethyl-propyl)-amine (0.40 g, 1.0 mmol) and Na₂S₂O₄ (1.39 g, 8.0 mmol) were treated substantially as described in Part E of Example 9 to yield 0.29 g (78%) of 4-(2-chloro-4-trifluoromethyl-phenyl)-N²-(1-methoxymethyl-propyl)-pyridine-2,3-diamine: MS (AP) m/z 373.8 [(M+H)⁺, 100].

Part E 4-(2-Chloro-4-trifluoromethyl-phenyl)-N²-(1-methoxymethyl-propyl)-pyridine-2,3-diamine (0.29 g, 0.78 mmol) was treated substantially as described in Part F of Example 9 to give 6.5 mg (2%) of 8-(2-chloro-4-trifluoromethyl-phenyl)-4-(1-methoxymethyl-propyl)-2-methyl-4H-pyrido[2,3-b]

pyrazin-3-one (Example 138a): ¹H NMR (300 MHz, CDCl₃): δ 8.5 (bs, 1H), 7.7 (s, 1H), 7.6 (d, 1H), 7.45 (d, 1H), 7.17 (d, 1H), 6.10 (m, 1H), 4.3 (m, 1H), 3.8 (m, 1H), 3.3 (s, 3H), 2.45 (s, 3H), 2.0 (m, 1H), 1.2 (s, 1H), 0.90 (t, 3H). MS (AP) m/z 425.8 [(M+H)⁺, 100].

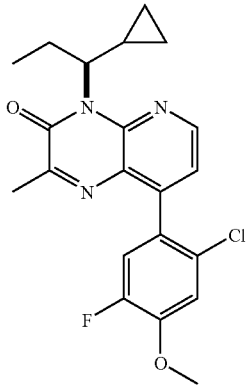

Example 243a (S)-8-(2-Chloro-5-fluoro-4-methoxy-phenyl)-4-(1-cyclopropyl-propyl)-2-methyl-4H-pyrido[2,3-b] pyrazin-3-one Part A and B 4-(2-Chloro-5-fluoro-4-methoxy-phenyl)-3-nitro-1H-pyridin-2-one was prepared substantially as described in Example 250.

Part C

Trifluoro-methanesulfonic acid 4-(2-chloro-5-fluoro-4-methoxy-phenyl)-3-nitro-pyridin-2-yl ester (0.3 g, 0.70 mmol) and (S)-1-cyclopropyl-propylamine (0.28 g, 2.09 mmol) were treated substantially as described in Part C of Example 19a to produce 30 mg (12%) of crude (S)-[4-(2-chloro-5-fluoro-4-methoxy-phenyl)-3-nitro-pyridin-2-yl]-(1-cyclopropyl-propyl)-amine.

Part D (S)-[4-(2-Chloro-5-fluoro-4-methoxy-phenyl)-3-nitro-pyridin-2-yl]-(1-cyclopropyl-propyl)-amine (30 mg, 0.08 mmol) and SnCl₂ (44 mg, 0.23 mmol) were treated substantially as described in Part D of Example 74a to yield 25 mg (92%) of (S)-4-(2-chloro-5-fluoro-4-methoxy-phenyl)-N²-(1-cyclopropyl-propyl)-pyridine-2,3-diamine.

Part E (S)-4-(2-Chloro-5-fluoro-4-methoxy-phenyl)-N²-(1-cyclopropyl-propyl)-pyridine-2,3-diamine (25 mg, 0.07 mmol) was treated substantially as described in Part F of Example 9 to give 2.5 mg (9%) of (S)-8-(2-chloro-5-fluoro-4-methoxy-phenyl)-4-(1-cyclopropyl-propyl)-2-methyl-4H-pyrido[2,3-b]pyrazin-3-one (Example 243a): ¹H NMR (400 MHz, CDCl₃) δ ppm 8.47 (d, J=4.89 Hz, 1 H), 7.18 (d, J=4.89 Hz, 1 H), 7.12 (d, J=8.07 Hz, 1 H), 7.09 (d, J=4.40 Hz, 1 H), 4.81 (m, 1 H), 3.96 (s, 3 H), 2.49 (s, 3 H), 2.21 (m, 2 H), 0.86 (t, J=7.46 Hz, 3 H), 0.83 (m, 1 H), 0.71 (m, 1 H), 0.47 (m, 1 H), 0.35 (m, 1 H), 0.15 (m, 1 H). MS (EI) m/z 402.20 [(M+H)+, 100].

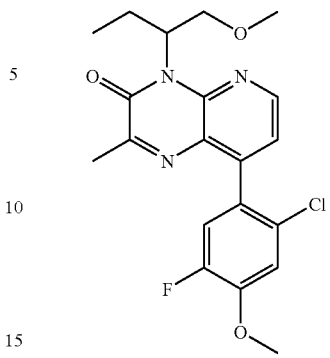

Example 250

8-(2-Chloro-5-fluoro-4-methoxy-phenyl)-4-(1-methoxymethyl-propyl)-2-methyl-4H-pyrido[2,3-b] pyrazin-3-one Part A 2-Benzyloxy-4-chloro-3-nitro-pyridine (Wilde, et. al. WO 99/01454) (3.8 g, 14.3 mmol) and 2-chloro-5-fluoro-4-methoxyphenylboronic acid (Preparation 1) (3.8 g, 18.6 mmol) were treated substantially as described in Part A of Example 19a to give 3.5 g (63%) of 2-benzyloxy-4-(2-chloro-5-fluoro-4-methoxy-phenyl)-3-nitro-pyridine: ¹H NMR (400 MHz, CDCl₃) δ ppm 8.30 (d, J=5.4 Hz, 1 H), 7.45–7.42 (m, 2H), 7.40–7.29 (m, 3H), 7.04 (d, J=7.6 Hz, 1 H), 7.00 (d, J=10.8 Hz, 1 H), 6.91 (d, J=5.4 Hz, 1 H), 5.54 (s, 2 H), 3.91 (s, 3 H).

Part B

2-Benzyloxy-4-(2-chloro-5-fluoro-4-methoxy-phenyl)-3-nitro-pyridine (3.5 g, 9.0 mmol) was treated substantially as described in Part B of Example 19a to give 4-(2-chloro-5-fluoro-4-methoxy-phenyl)-3-nitro-1H-pyridin-2-one (2.3 g, 86%): ¹H NMR (400 MHz, DMSO-d₆) δ ppm 12.97 (br s, 1H), 7.79 (d, J=6.3 Hz, 1 H), 7.44 (d, J=7.8 Hz, 1 H), 7.38 (d, J=11.3 Hz, 1 H), 6.30 (d, J=6.3 Hz, 1 H), 3.91 (s, 3 H).

Part C

Trifluoro-methanesulfonic acid 4-(2-Chloro-5-fluoro-4-methoxy-phenyl)-3-nitro-1H-pyridin-2-one (0.3 g, 0.70 mmol), prepared substantially as described in Part C of Example 19a, and 1-methoxymethyl-propylamine (0.28 g, 2.79 mmol) were treated substantially as described in Part C of Example 19a to produce 35 mg (13%) of crude [4-(2-chloro-5-fluoro-4-methoxy-phenyl)-3-nitro-pyridin-2-yl]-(1-methoxymethyl-propyl)-amine.

Part D

[4-(2-Chloro-5-fluoro-4-methoxy-phenyl)-3-nitro-pyridin-2-yl]-(1-methoxymethyl-propyl)-amine (35 mg, 0.09 mmol) and SnCl₂ (51 mg, 0.27 mmol) were treated substantially as described in Part D of Example 74a to yield 30 mg (94%) of 4-(2-Chloro-5-fluoro-4-methoxy-phenyl)-N²-(1-methoxymethyl-propyl)-pyridine-2,3-diamine: MS (EI) m/z 354.22 [(M+H)⁺, 100].

Part E 4-(2-Chloro-5-fluoro-4-methoxy-phenyl)-N²-(1-methoxymethyl-propyl)-pyridine-2,3-diamine (30 mg, 0.084 mmol) was treated substantially as described in Part F of Example 9 to give 3.3 mg (10%) of 8-(2-Chloro-5-fluoro-4-methoxy-phenyl)-4-(1-methoxymethyl-propyl)-2-methyl-4H-pyrido[2,3-b]pyrazin-3-one (Example 250): $^1$H NMR (400 MHz, CDCl$_3$) δ ppm 8.55 (d, J=4.89 Hz, 1 H), 7.21 (d, J=4.89 Hz, 1 H) 7.11 (d, J=2.94 Hz, 1 H), 7.08 (d, J=2.20 Hz, 1 H), 5.88 (m, 1 H), 4.33 (m, 1 H), 3.95 (s, 3 H), 3.81 (m, 1 H), 3.32 (s, 3 H), 2.48 (s, 3 H), 2.11 (d, J=95.37 Hz, 2 H), 0.86 (t, J=7.46 Hz, 3 H). MS (EI) m/z 406.29 [(M+H)+, 100].

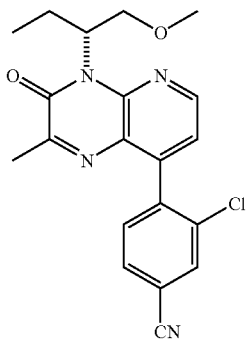

Example 449a (R)-3-Chloro-4-[4-(1-methoxymethyl-propyl)-2-methyl-3-oxo-3,4-dihydro-pyrido[2,3-b]pyrazin-8-yl-benzonitrile Part A To a solution of POCl$_3$ (100 mL) was added 2,4-hydroxy-3-nitropyridine (10.0 g, 64.1 mmol) and the reaction heated at reflux overnight. The reaction mixture was cooled and slowly added to an ice-water solution. The solution was extracted with EtOAc and the organic layer was dried (Na$_2$SO$_4$), filtered and concentrated in vacuo. The dark brown oil was purified by filtration through silica gel with 50% EtOAc/Hex to yield 4.31 g, 35% of 2,4-dichloro-3-nitropyridine as a dark yellow solid. Reaction was monitored by thin layer chromatography for completion.

Part B 2,4-Dichloro-3-nitropyridine (1.0 g, 5,18 mmol) was dissolved in EtOH (20 mL), followed by the addition of Et$_3$N (1.05 g, 10.4 mmol) and (R)-1-methoxymethyl-propylamine (0.72 g, 5.18 mmol) and the reaction was heated at 60° C. for 3 h. The reaction was concentrated in vacuo to yield 2.09 g of (R)-(4-chloro-3-nitro-pyridin-2-yl)-(1-methoxymethyl-propyl)-amine as a crude viscous oil: MS (AP) m/z 259.69 [(M+H)+, 97].

Part C (R)-(4-Chloro-3-nitropyridin-2-yl)-(1-methoxymethyl-propyl)-amine (2.09 g, 8.05 mmol) was dissolved in ether (30 mL) and cooled to 0° C. Next, SnCl$_2$.2H$_2$0 (18.1 g, 80.5 mmol) in conc. HCl (10 mL) was added, dropwise at 0° C. and stirred at room temperature for 4 h. The reaction mixture was poured over ice water containing 50% NaOH solution (20 mL) and extracted with EtOAc (2×). The aqueous layer was filtered through celite, then extracted with EtOAc (2×). The combined organic layers were dried (Na$_2$SO$_4$), filtered, and concentrated in vacuo. The crude product was purified by column chromatography (20% EtOAc/Hex) to yield 0.24 g, 13% of (R)-4-chloro-N$^2$-(1-methoxymethyl-propyl)-pyridine-2,3-diamine: MS (AP) m/z 229.71 [(M+H)+, 100].

Part D (R)-4-Chloro-N$^2$-(1-methoxymethyl-propyl)-pyridine-2,3-diamine (0.24 g, 1.04 mmol) was dissolved in n-BuOH, followed by methyl pyruvate (1.07 g, 10.4 mmol) and the reaction was heated at 60° C. for 5 h, before heating at reflux overnight. The reaction was concentrated in vacuo and purified by column chromatography (20% EtOAc/hex) to yield 0.39 g, 100% of (R)-8-chloro-4-(1-methoxymethyl-propyl)-2-methyl-4H-pyrido[2,3-b]pyrazin-3-one: MS (AP) m/z 281.74 [(M+H)+, 100].

Part E (R)-8-Chloro-4-(1-methoxymethyl-propyl)-2-methyl-4H-pyrido[2,3-b]pyrazin-3-one (0.39 g, 1.38 mmol) was dissolved in EtOH/toluene (1:4), followed by Na$_2$CO$_3$ (2M, 1.73 mL, 3.46 mmol), 2-chloro-4-cyanophenyl boronic acid (0.38 g, 2.08 mmol) and Pd$_2$(PPh$_3$)$_2$Cl$_2$ (0.048 g, 0.069 mmol) and refluxed for 5 h. The reaction was cooled to room temperature, extracted with EtOAc, washed with H$_2$O, brine, dried (MgSO$_4$), filtered and concentrated in vacuo. Purification by HPLC yielded 13.10 mg, 3% of (R)-3-chloro-4-[4-(1-methoxymethyl-propyl)-2-methyl-3-oxo-3,4-dihydro-pyrido[2,3-b]pyrazin-8-yl-benzonitrile (Ex. 449a): MS (ESI) 382.85 [(M+H)+, 100].

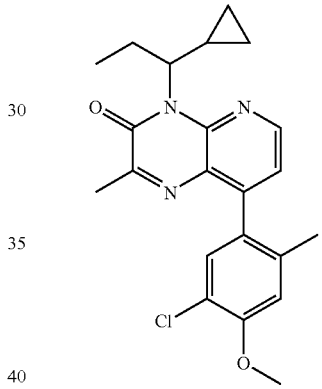

Example 452

8-(5-Chloro-4-methoxy-2-methyl-phenyl)-4-(1-cyclopropyl-propyl)-2-methyl-4H-pyrido[2,3-b]pyrazin-3-one Part A 2-Benzyloxy-4-chloro-3-nitro-pyridine (Wilde, et. al. WO 99/01454) (774 mg, 2.81 mmol) and 2-methyl-5-chloro-4-methoxyphenylboronic acid (prepared as described in Speicher, A.; Kolz, J.; Sambanje, R. P. *Synthesis*, 2002, 17, 2503) (620 mg, 3.09 mmol) were treated substantially as described in Part A of Example 19a to give 1.15 g (47%) of 2-benzyloxy-4-(5-chloro-4-methoxy-2-methyl-phenyl)-3-nitro-pyridine: $^1$H NMR (400 MHz, CDCl$_3$) δ ppm 8.26 (d, J=5.1 Hz, 1 H), 7.45–7.42 (m, 2H), 7.39–7.30 (m, 3H), 7.13 (s, 1H), 6.82 (d, J=5.1 Hz, 1 H), 6.79 (s, 1 H), 5.54 (s, 2 H), 3.90 (s, 3H), 2.14 (s, 3H).

Part B

2-Benzyloxy-4-(5-chloro-4-methoxy-2-methyl-phenyl)-3-nitro-pyridine (1.0 g, 2.6 mmol) was treated substantially as described in Part B of Example 19a to give 4-(5-chloro-4-methoxy-2-methyl-phenyl)-3-nitro-1H-pyridin-2-one (0.75 g, 98%): MS (EI) m/z 295.14 [(M+H)$^+$, 100].

Part C

Trifluoro-methanesulfonic acid 4-(5-chloro-4-methoxy-2-methyl-phenyl)-3-nitro-pyridin-2-yl ester (0.33 g, 0.76 mmol), prepared substantially as described in Part C of Example 19a, and 1-cyclopropyl-propylamine (0.25 g, 1.92 mmol) were treated substantially as described in Part C of Example 19a to produce 0.13 g (45%) of crude (1-cyclopropyl-propyl)-[4-(5-fluoro-4-methoxy-2-methyl-phenyl)-3-nitro-pyridin-2-yl]-amine: MS (EI) m/z 376.2 [(M+H)$^+$, 100].

Part D (1-Cyclopropyl-propyl)-[4-(5-fluoro-4-methoxy-2-methyl-phenyl)-3-nitro-pyridin-2-yl]-amine (0.13 g, 0.34 mmol) and SnCl$_2$ (0.19 g, 1.0 mmol) were treated substantially as described in Part D of Example 74a to yield 0.12 g (96%) of 4-(5-chloro-4-methoxy-2-methyl-phenyl)-N$^2$-(1-cyclopropyl-propyl)-pyridine-2,3-diamine.

Part E 4-(5-Chloro-4-methoxy-2-methyl-phenyl)-N$^2$-(1-cyclopropyl-propyl)-pyridine-2,3-diamine (0.12 g, 0.33 mmol) was treated substantially as described in Part F of Example 9 to give 30 mg (23%) of 8-(5-chloro-4-methoxy-2-methyl-phenyl)-4-(1-cyclopropyl-propyl)-2-methyl-4H-pyrido[2,3-b]pyrazin-3-one (Example 452): $^1$H NMR (400 MHz, CDCl$_3$) δ ppm 8.48 (d, J=4.89 Hz, 1 H), 7.24 (s, 1 H), 7.12 (d, J=4.89 Hz, 1 H), 6.87 (s, 1 H), 4.79 (m, 1 H), 3.96 (s, 3 H), 2.51 (s, 3 H), 2.26 (m, 2 H), 2.10 (s, 3 H), 0.88 (m, 1 H), 0.87 (t, J=6.72 Hz, 3 H), 0.70 (m, 1 H), 0.49 (m, 1 H), 0.34 (m, 1 H), 0.17 (m, 1 H). MS (EI) m/z 400.21 [(M+H)+, 100].

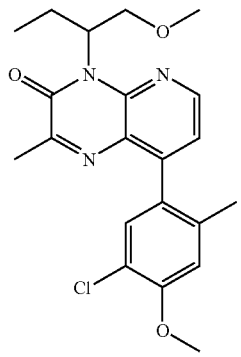

Example 459

8-(5-Chloro-4-methoxy-2-methyl-phenyl)-4-(1-methoxymethyl-propyl)-2-methyl-4H-pyrido[2,3-b]pyrazin-3-one Part A and B 4-(5-Chloro-4-methoxy-2-methyl-phenyl)-3-nitro-1H-pyridin-2-one was prepared substantially as described in Example 452.

Part C

Trifluoro-methanesulfonic acid 4-(5-chloro-4-methoxy-2-methyl-phenyl)-3-nitro-pyridin-2-yl ester (0.38 g, 0.89 mmol) and 1-methoxymethyl-propylamine (0.23 g, 2.23 mmol) were treated substantially as described in Part C of Example 19a to produce 0.13 g (40%) of crude [4-(5-chloro-4-methoxy-2-methyl-phenyl)-3-nitro-pyridin-2-yl]-(1-methoxymethyl-propyl)-amine: MS (EI) m/z 380.19 [(M+H)$^+$, 100].

Part D

[4-(5-Chloro-4-methoxy-2-methyl-phenyl)-3-nitro-pyridin-2-yl]-(1-methoxymethyl-propyl)-amine (0.13 g, 0.34 mmol) and SnCl$_2$ (0.19 g, 1.03 mmol) were treated substantially as described in Part D of Example 74a to yield 0.12 g (99%) of (S)-4-(2-chloro-5-fluoro-4-methoxy-phenyl)-N$^2$-(1-cyclopropyl-propyl)-pyridine-2,3-diamine: MS (EI) m/z 350.25 [(M+H)$^+$, 100].

Part E 4-(5-Chloro-4-methoxy-2-methyl-phenyl)-N$^2$-(1-methoxymethyl-propyl)-pyridine-2,3-diamine (0.11 g, 0.32 mmol) was treated substantially as described in Part F of Example 9 to give 48 mg (38%) of 8-(5-chloro-4-methoxy-2-methyl-phenyl)-4-(1-methoxymethyl-propyl)-2-methyl-4H-pyrido[2,3-b]pyrazin-3-one (Example 459): $^1$H NMR (400 MHz, CDCl$_3$) δ ppm 8.50 (d, J=4.89 Hz, 1 H), 7.24 (s, 1 H), 7.12 (d, J=4.89 Hz, 1 H), 6.86 (s, 1 H), 5.89 (m, 1 H), 4.38 (m, 1 H), 3.96 (s, 3 H), 3.81 (m, 1 H), 3.32 (s, 3 H), 2.47 (s, 3 H), 2.29 (m, 1 H), 2.09 (s, 3 H), 1.98 (m, 1 H), 0.85 (t, J=7.46 Hz, 3 H). MS (EI) m/z 402.20 [(M+H)+, 100].

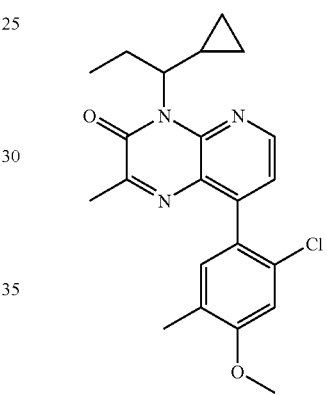

Example 484

8-(2-Chloro-4-methoxy-5-methyl-phenyl)-4-(1-cyclopropyl-propyl)-2-methyl-4H-pyrido[2,3-b]pyrazin-3-one Part A 2-Benzyloxy-4-chloro-3-nitro-pyridine (Wilde, et. al. WO 99/01454) (924 mg, 3.49 mmol) and 2-chloro-5-methyl-4-methoxyphenylboronic acid (prepared substantially as described in Speicher, A.; Kolz, J.; Sambanje, R. P. *Synthesis*, 2002, 17, 2503) (770 mg, 3.84 mmol) were treated substantially as described in Part A of Example 19a to give 514 mg (39%) of 2-benzyloxy-4-(2-chloro-4-methoxy-5-methyl-phenyl)-3-nitro-pyridine: $^1$H NMR (400 MHz, CDCl$_3$) δ ppm 8.27 (d, J=5.4 Hz, 1 H), 7.47–7.44 (m, 2H), 7.40–7.30 (m, 3H), 7.00 (s, 1H), 6.94 (d, J=5.4 Hz, 1 H), 6.90 (s, 1 H), 5.55 (s, 2 H), 3.84 (s, 3 H), 2.17 (s, 3 H).

Part B

2-Benzyloxy-4-(2-chloro-4-methoxy-5-methyl-phenyl)-3-nitro-pyridine (0.5 g, 1.30 mmol) was treated substantially as described in Part B of Example 19a to give 4-(2-chloro-4-methoxy-5-methyl-phenyl)-3-nitro-1H-pyridin-2-one (0.38 g, 100%): MS (EI) m/z 295.11 [(M+H)$^+$, 100].

Part C

Trifluoro-methanesulfonic acid 4-(2-chloro-4-methoxy-5-methyl-phenyl)-3-nitro-pyridin-2-yl ester (0.22 g, 0.51 mmol), prepared substantially as described in Part C of Example 19a, and 1-cyclopropyl-propylamine (0.17 g, 1.29 mmol) were treated substantially as described in Part C of Example 19a to produce 90 mg (47%) of crude [4-(2-chloro-4-methoxy-5-methyl-phenyl)-3-nitro-pyridin-2-yl]-(1-cyclopropyl-propyl)-amine: MS (EI) m/z 376.18 [(M+H)+, 100].

Part D

[4-(2-Chloro-4-methoxy-5-methyl-phenyl)-3-nitro-pyridin-2-yl]-(1-cyclopropyl-propyl)-amine (90 mg, 0.24 mmol) and SnCl$_2$ (0.13 g, 0.72 mmol) were treated substantially as described in Part D of Example 74a to yield 80 mg (98%) of 4-(2-chloro-4-methoxy-5-methyl-phenyl)-$N^2$-(1-cyclopropyl-propyl)-pyridine-2,3-diamine: MS (EI) m/z 346.22 [(M+H)+, 100].

Part E 4-(2-Chloro-4-methoxy-5-methyl-phenyl)-$N^2$-(1-cyclopropyl-propyl)-pyridine-2,3-diamine (80 mg, 0.23 mmol) was treated substantially as described in Part F of Example 9 to give 7.4 mg (8%) of 8-(2-Chloro-4-methoxy-5-methyl-phenyl)-4-(1-cyclopropyl-propyl)-2-methyl-4H-pyrido[2,3-b]pyrazin-3-one (Example 484): $^1$H NMR (400 MHz, CDCl$_3$) δ ppm 8.42 (d, J=4.89 Hz, 1 H), 7.17 (d, J=4.89 Hz, 1 H), 7.11 (s, 1 H), 6.95 (s, 1 H), 4.74 (m, 1 H), 3.91 (m, 3 H), 2.51 (m, 3 H), 2.34 (m, 1 H), 2.22 (m, 3 H), 2.08 (m, 1 H), 0.89 (m, 1 H), 0.86 (s, 3 H), 0.70 (m, 1 H), 0.46 (m, 1 H), 0.32 (m, 1 H), 0.17 (m, 1 H), MS (EI) m/z 398.23 [(M+H)+, 100].

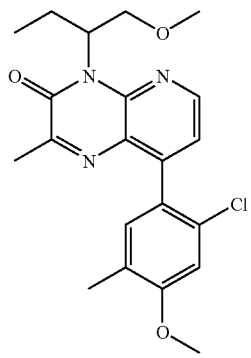

Example 491

8-(2-Chloro-4-methoxy-5-methyl-phenyl)-4-(1-methoxymethyl-propyl)-2-methyl-4H-pyrido[2,3-b]pyrazin-3-one Part A and B 4-(2-Chloro-4-methoxy-5-methyl-phenyl)-3-nitro-1H-pyridin-2-one was prepared substantially as described in Example 484.

Part C

Trifluoro-methanesulfonic acid 4-(2-chloro-4-methoxy-5-methyl-phenyl)-3-nitro-pyridin-2-yl ester (0.22 g, 0.51 mmol) and 1-methoxymethyl-propylamine (0.13 g, 1.29 mmol) were treated substantially as described in Part C of Example 19a to produce 92 mg (47%) of crude [4-(5-chloro-4-methoxy-2-methyl-phenyl)-3-nitro-pyridin-2-yl]-(1-methoxymethyl-propyl)-amine: MS (EI) m/z 380.24 [(M+H)+, 100].

Part D

[4-(5-Chloro-4-methoxy-2-methyl-phenyl)-3-nitro-pyridin-2-yl]-(1-methoxymethyl-propyl)-amine (90 mg, 0.24 mmol) and SnCl$_2$ (0.13 g, 0.71 mmol) were treated substantially as described in Part D of Example 74a to yield 82 mg (99%) of 4-(2-Chloro-4-methoxy-5-methyl-phenyl)-$N^2$-(1-methoxymethyl-propyl)-pyridine-2,3-diamine: MS (EI) m/z 350.23 [(M+H)+, 100].

Part E 4-(2-Chloro-4-methoxy-5-methyl-phenyl)-$N^2$-(1-methoxymethyl-propyl)-pyridine-2,3-diamine (82 mg, 0.22 mmol) was treated substantially as described in Part F of Example 9 to give 17.5 mg (19%) of 8-(2-chloro-4-methoxy-5-methyl-phenyl)-4-(1-methoxymethyl-propyl)-2-methyl-4H-pyrido[2,3-b]pyrazin-3-one (Example 491): $^1$H NMR (400 MHz, CDCl$_3$) δ ppm 8.51 (d, J=4.89 Hz, 1 H), 7.20 (d, J=4.89 Hz, 1 H), 7.09 (s, 1 H), 6.95 (s, 1 H), 5.89 (m, 1 H), 4.38 (m, 2 H), 3.88 (s, 3 H), 3.33 (m, 3 H), 2.48 (s, 3 H), 2.21 (s, 3 H), 2.09 (m, 2 H), 0.86 (t, J=7.46 Hz, 3 H). MS (EI) m/z 402.20 [(M+H)+, 100].

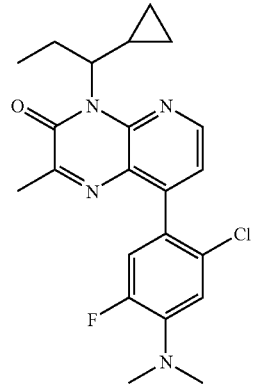

Example 500

8-(2-Chloro-4-dimethylamino-5-fluoro-phenyl)-4-(1-cyclopropyl-propyl)-2-methyl-4H-pyrido[2,3-b]pyrazin-3-one Part A and B 4-(2-Chloro-4-dimethylamino-5-fluoro-phenyl)-3-nitro-1H-pyridin-2-one was prepared substantially as described in Example 507.

Part C

Trifluoro-methanesulfonic acid 4-(2-chloro-4-dimethylamino-5-fluoro-phenyl)-3-nitro-pyridin-2-yl ester (548 mg, 1.76 mmol) and 1-cyclopropyl-propylamine HCl (479 mg, 3.5 mmol) were treated substantially as described in Part C of Example 19a to produce 300 mg (43%) of crude [4-(2-chloro-4-dimethylamino-5-fluoro-phenyl)-3-nitro-pyridin-2-yl]-(1-cyclopropyl-propyl)-amine: MS (EI) m/z 393.22 [(M+H)+, 100].

Part D

[4-(2-Chloro-4-dimethylamino-5-fluoro-phenyl)-3-nitro-pyridin-2-yl]-(1-cyclopropyl-propyl)-amine (300 mg, 0.76 mmol) and SnCl₂.H₂O (1.2 g, 6.1 mmol) were treated substantially as described in Part D of Example 74a to yield 276 mg of crude 4-(2-chloro-4-dimethylamino-5-fluoro-phenyl)-N²-(1-cyclopropyl-propyl)-pyridine-2,3-diamine: MS (EI) m/z 363.24 [(M+H)⁺, 100].

Part E 4-(2-Chloro-4-dimethylamino-5-fluoro-phenyl)-N²-(1-cyclopropyl-propyl)-pyridine-2,3-diamine (299 mg, 0.76 mmol) was treated substantially as described in Part F of Example 9 to give 20 mg (6% for 4 steps) of 8-(2-chloro-4-dimethylamino-5-fluoro-phenyl)-4-(1-cyclopropyl-propyl)-2-methyl-4H-pyrido[2,3-b]pyrazin-3-one (Example 500): ¹H NMR (400 MHz, CDCl₃) δ ppm 8.52 (d, J=4.65 Hz, 1 H), 7.60 (d, J=7.09 Hz, 1 H), 7.27 (m, 1 H), 7.19 (d, J=4.65 Hz, 1 H), 5.01 (m, 1 H), 3.26 (s, 6 H), 2.51 (s, 3 H), 2.25 (m, 2 H), 0.86 (t, J=7.34 Hz, 3 H), 0.73 (m, 1 H), 0.48 (m, 1 H), 0.34 (m, 1 H), 0.21 (m, 1 H), 0.13 (m, 1 H). MS (EI) m/z 415.26 [(M+H)+, 100].

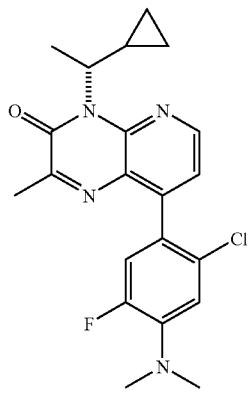

Example 501a (R)-8-(2-Chloro-4-dimethylamino-5-fluoro-phenyl)-4-(1-cyclopropyl-ethyl)-2-methyl-4H-pyrido[2,3-b]pyrazin-3-one Part A and B 4-(2-Chloro-4-dimethylamino-5-fluoro-phenyl)-3-nitro-1H-pyridin-2-one was prepared substantially as described in Example 507.

Part C

Trifluoro-methanesulfonic acid 4-(2-chloro-4-dimethylamino-5-fluoro-phenyl)-3-nitro-pyridin-2-yl ester TFA (1.06 g, 2.49 mmol) and (R)-1-cyclopropyl-ethylamine HCl (202 mg, 1.7 mmol) were treated substantially as described in Part C of Example 19a to produce 314 mg of crude (R)-[4-(2-chloro-4-dimethylamino-5-fluoro-phenyl)-3-nitro-pyridin-2-yl]-(1-cyclopropyl-ethyl)-amine.

Part D (R)-[4-(2-Chloro-4-dimethylamino-5-fluoro-phenyl)-3-nitro-pyridin-2-yl]-(1-cyclopropyl-ethyl)-amine (314 mg, 0.83 mmol) and SnCl₂.H₂O (472 mg, 2.5 mmol) were treated substantially as described in Part D of Example 74a to yield 276 mg of crude (R)-4-(2-chloro-4-dimethylamino-5-fluoro-phenyl)-N²-(1-cyclopropyl-ethyl)-pyridine-2,3-diamine: MS (EI) m/z 349.24 [(M+H)⁺, 100].

Part E (R)-4-(2-Chloro-4-dimethylamino-5-fluoro-phenyl)-N²-(1-cyclopropyl-ethyl)-pyridine-2,3-diamine (290 mg, 0.83 mmol) was treated substantially as described in Part F of Example 9 to give 22.5 mg (8% for 4 steps) of (R)-8-(2-chloro-4-dimethylamino-5-fluoro-phenyl)-4-(1-cyclopropyl-ethyl)-2-methyl-4H-pyrido[2,3-b]pyrazin-3-one (Example 501a): ¹H NMR (400 MHz, CDCl₃) δ ppm 8.47 (d, J=4.65 Hz, 1 H), 7.20 (d, J=4.65 Hz, 1 H), 7.14 (d, J=8.07 Hz, 1 H), 7.08 (d, J=12.96 Hz, 1 H), 4.85 (m, 1 H), 3.02 (s, 6 H), 2.50 (s, 3 H), 1.25 (s, 3 H), 0.87 (m, 1 H), 0.67 (m, 1 H), 0.42 (m, 2 H), 0.22 (m, 1 H). MS (EI) m/z 401.20 [(M+H)+, 100].

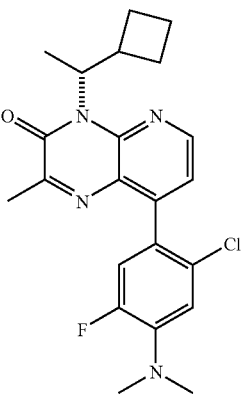

Example 503a (R)-8-(2-Chloro-4-dimethylamino-5-fluoro-phenyl)-4-(1-cyclobutyl-ethyl)-2-methyl-4H-pyrido[2,3-b]pyrazin-3-one Part A and B 4-(2-Chloro-4-dimethylamino-5-fluoro-phenyl)-3-nitro-1H-pyridin-2-one was prepared substantially as described in Example 507.

Part C

Trifluoro-methanesulfonic acid 4-(2-chloro-4-dimethylamino-5-fluoro-phenyl)-3-nitro-pyridin-2-yl ester TFA (1.1 g, 2.49 mmol) and (R)-1-cyclobutyl-ethylamine HCl (225 mg, 1.7 mmol) were treated substantially as described in Part C of Example 19a to produce 326 mg of crude (R)-[4-(2-Chloro-4-dimethylamino-5-fluoro-phenyl)-3-nitro-pyridin-2-yl]-(1-cyclobutyl-ethyl)-amine.

Part D (R)-[4-(2-Chloro-4-dimethylamino-5-fluoro-phenyl)-3-nitro-pyridin-2-yl]-(1-cyclobutyl-ethyl)-amine (326 mg, 0.83 mmol) and SnCl₂.H₂O (472 mg, 2.5 mmol) were treated substantially as described in Part D of Example 74a to yield 301 mg of crude (R)-4-(2-Chloro-4-dimethylamino-5-fluoro-phenyl)-N²-(1-cyclobutyl-ethyl)-pyridine-2,3-diamine: MS (EI) m/z 363.24 [(M+H)⁺, 100].

Part E (R)-4-(2-Chloro-4-dimethylamino-5-fluoro-phenyl)-N²-(1-cyclobutyl-ethyl)-pyridine-2,3-diamine (301 mg, 0.83 mmol) was treated substantially as described in Part F of Example 9 to give 8.5 mg (3% for 4 steps) of (R)-8-(2-Chloro-4-dimethylamino-5-fluoro-phenyl)-4-(1-cyclobutylethyl)-2-methyl-4H-pyrido[2,3-b]pyrazin-3-one (Example 503a): ¹H NMR (400 MHz, CDCl₃) δ ppm 8.52 (br s, 1 H), 7.17 (br s, 1 H), 7.04 (d, J=13.20 Hz, 1 H), 6.99 (d, J=8.07 Hz, 1 H), 5.70 (d, 1 H), 2.96 (s, 6 H), 2.49 (m, 3 H), 1.79 (m, 4 H), 1.51 (m, 2 H), H), 1.28 (m, 1 H), 1.25 (s, 3 H). MS (EI) m/z 415.24 [(M+H)+, 100].

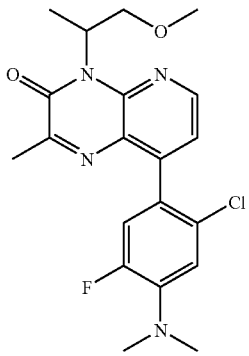

Example 506

8-(2-Chloro-4-dimethylamino-5-fluoro-phenyl)-4-(2-methoxy-1-methyl-ethyl)-2-methyl-4H-pyrido[2,3-b]pyrazin-3-one Part A and B 4-(2-Chloro-4-dimethylamino-5-fluoro-phenyl)-3-nitro-1H-pyridin-2-one was prepared substantially as described in Example 507.

Part C

Trifluoro-methanesulfonic acid 4-(2-chloro-4-dimethylamino-5-fluoro-phenyl)-3-nitro-pyridin-2-yl ester TFA (1.1 g, 2.49 mmol) and 2-methoxy-1-methyl-ethylamine HCl (208 mg, 1.7 mmol) were treated substantially as described in Part C of Example 19a to produce 318 mg of crude [4-(2-chloro-4-dimethylamino-5-fluoro-phenyl)-3-nitro-pyridin-2-yl]-(2-methoxy-1-methyl-ethyl)-amine.

Part D

[4-(2-Chloro-4-dimethylamino-5-fluoro-phenyl)-3-nitro-pyridin-2-yl]-(2-methoxy-1-methyl-ethyl)-amine (318 mg, 0.83 mmol) and SnCl₂.H₂O (472 mg, 2.5 mmol) were treated substantially as described in Part D of Example 74a to yield 290 mg of crude 4-(2-chloro-4-dimethylamino-5-fluoro-phenyl)-N²-(2-methoxy-1-methyl-ethyl)-pyridine-2,3-diamine: MS (EI) m/z 353.23 [(M+H)⁺, 100].

Part E 4-(2-Chloro-4-dimethylamino-5-fluoro-phenyl)-N²-(2-methoxy-1-methyl-ethyl)-pyridine-2,3-diamine (290 mg, 0.83 mmol) was treated substantially as described in Part F of Example 9 to give 22.5 mg (8% for 4 steps) of 8-(2-chloro-4-dimethylamino-5-fluoro-phenyl)-4-(2-methoxy-1-methyl-ethyl)-2-methyl-4H-pyrido[2,3-b]pyrazin-3-one (Example 506): ¹H NMR (400 MHz, CDCl₃) δ ppm 8.53 (d, J=4.65 Hz, 1 H), 7.26 (d, J=7.58 Hz, 1 H), 7.20 (d, J=4.65 Hz, 1 H), 7.11 (d, J=12.72 Hz, 1 H), 5.88 (m, 1 H), 4.39 (m, 1 H), 3.79 (m, 1 H), 3.34 (s, 3 H), 3.08 (s, 6 H), 2.49 (s, 3 H), 1.60 (d, J=6.85 Hz, 3 H). MS (EI) m/z 405.23 [(M+H)+, 100].

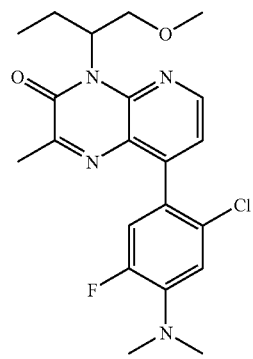

Example 507

8-(2-Chloro-4-dimethylamino-5-fluoro-phenyl)-4-(1-methoxymethyl-propyl)-2-methyl-4H-pyrido[2,3-b]pyrazin-3-one Part A 2-Benzyloxy-4-chloro-3-nitro-pyridine (Wilde, et. al. WO 99/01454) (800 mg, 3.02 mmol) and 2-chloro-4-dimethylamino-5-fluorophenylboronic acid (Example B) (854 mg, 3.93 mmol) were treated substantially as described in Part A of Example 19a to give 715 mg (59%) of 2-benzyloxy-4-(2-chloro-4-dimethylamino-5-fluoro-phenyl)-3-nitro-pyridine: ¹H NMR (400 MHz, CDCl₃) δ ppm 8.27 (d, J=5.4 Hz, 1 H), 7.45–7.43 (m, 2H), 7.40–7.29 (m, 3H), 6.93 (d, J=5.4 Hz, 1 H), 6.89 (d, J=13.2 Hz, 1 H), 6.85 (d, J=8.0 Hz, 1 H), 5.53 (s, 2 H), 2.91 (d, J=1.2 Hz, 6 H).

Part B

2-Benzyloxy-4-(2-chloro-4-dimethylamino-5-fluoro-phenyl)-3-nitro-pyridine (2.8 g, 7.0 mmol) was treated substantially as described in Part B of Example 19a to give 4-(2-chloro-4-dimethylamino-5-fluoro-phenyl)-3-nitro-1H-pyridin-2-one TFA (3.0 g, 100%): ¹H NMR (400 MHz, CDCl₃) δ ppm 7.59 (d, J=6.7 Hz, 1 H), 6.99 (d, J=7.8 Hz, 1 H), 6.96 (d, J=12.7 Hz, 1 H), 6.54 (d, J=6.7 Hz, 1 H), 2.99 (d, J=1.2 Hz, 6 H).

Part C

Trifluoro-methanesulfonic acid 4-(2-chloro-4-dimethylamino-5-fluoro-phenyl)-3-nitro-pyridin-2-yl ester TFA (39.6 mg, 0.093 mmol), prepared substantially as described in Part C of Example 19a, and 1-methoxymethyl-propylamine (191.0 mg, 1.85 mmol) were treated substantially as described in Part C of Example 19a to produce 30 mg (81%) of crude [4-(2-chloro-4-dimethylamino-5-fluoro-phenyl)-3-nitro-pyridin-2-yl]-(1-methoxymethyl-propyl)-amine: MS (EI) m/z 397.19 [(M+H)⁺, 100].

Part D

[4-(2-Chloro-4-dimethylamino-5-fluoro-phenyl)-3-nitro-pyridin-2-yl]-(1-methoxymethyl-propyl)-amine (30.0 mg, 0.076 mmol) and SnCl₂.H₂O (43.2 mg, 0.23 mmol) were treated substantially as described in Part D of Example 74a to yield 30 mg (100% crude) of 4-(2-Chloro-4-dimethylamino-5-fluoro-phenyl)-N²-(1-methoxymethyl-propyl)-pyridine-2,3-diamine: MS (EI) m/z 367.23 [(M+H)⁺, 100].

Part E 4-(2-Chloro-4-dimethylamino-5-fluoro-phenyl)-N²-(1-methoxymethyl-propyl)-pyridine-2,3-diamine (27.9 mg, 0.076 mmol) was treated substantially as described in Part F of Example 9 to give 4 mg of 8-(2-Chloro-4-dimethylamino-5-fluoro-phenyl)-4-(1-methoxymethyl-propyl)-2-methyl-4H-pyrido[2,3-b]pyrazin-3-one (Example 507): ¹H NMR (400 MHz, CDCl₃) δ ppm 8.55 (d, J=4.16 Hz, 1 H), 7.20 (d, J=4.16 Hz, 1 H), 7.10 (d, J=6.11 Hz, 1 H), 7.07 (d, J=11.49 Hz, 1 H), 6.15 (m, 1 H), 4.38 (m, 1 H), 3.81 (m, 1 H), 3.32 (m, 3 H), 3.01 (m, 6 H), 2.49 (s, 3 H), 2.11 (m, 2 H), 0.86 (t, J=7.46 Hz, 3 H). MS (EI) m/z 419.25 [(M+H)+, 100].

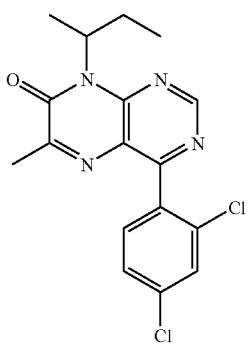

Example 546

(R,S)-8-sec-Butyl-4-(2,4-dichloro-phenyl)-6-methyl-8H-pteridin-7-one

Part A 4,6-Dichloro-5-nitropyrimidine (2.0 g, 0.012 mol) was diluted in EtOH (10 ml) and toluene (40 ml). A 2M Na₂CO₃ (15.0 ml) was added followed by Pd(PPh₃)₂Cl₂ (0.51 g, 0.0007 mol), and 2,4-dichlorophenylboronic acid (0.018 mol). The reaction was warmed to reflux under an inert atmosphere for 5 hours. The reaction was then allowed to cool to room temperature and poured over EtOAc/H₂O. The organic layer was separated and washed with sat'd sodium chloride, dried (MgSO₄), filtered and concentrated. The material was flushed through a plug of silica using 50% EtOAc/hexane as an eluting solvent. The crude material (2.9 g) was concentrated in vacuo and diluted in 20 ml butanol. Sec-butylamine was added to the solution and the mixture warmed to reflux for 18 hours. After concentrating the solution in vacuo and purification on silica gel using 80% EtOAc/hexane as the eluting solvent the desired intermediate N⁴-sec-butyl-6-(2,4-dichloro-phenyl)-pyrimidine-4,5-diamine was isolated (1.49 g, 40%). MS (AP) m/z 311.1 [(M+H)⁺, 100].

Part B

N⁴-sec-butyl-6-(2,4-dichloro-phenyl)-pyrimidine-4,5-diamine (0.10 g, 0.00032 mol) was diluted in ethanol (20 ml) and ethyl pyruvate was added (0.68 ml, 0.006 mol). The mixture was stirred for 18 hours at which time 10 ml of the solution was removed and concentrated. The residue was diluted in glacial acetic acid (10 ml) and warmed to 100 C for 1 hour. After concentrating the solution the product was purified by reverse phase HPLC to yield 9.8 mg of (R,S)-8-sec-butyl-4-(2,4-dichloro-phenyl)-6-methyl-8H-pteridin-7-one (Example 546). ¹H NMR (300 MHz, CD₃OD) δ 9.02 (s, 1H), 7.66–7.64 (d, 1H), 7.49–7.48 (m, 2H), 5.68 (m, 1H), 2.42 (s, 3H), 2.39–2.25 (m, 1H), 2.01–2.15 (m, 1H), 1.64–1.62 (d, 3H), 0.89–0.84 (t, 3H). MS (AP) 363.1 [(M+H)+, 100], 404.1 [(M+H+ACN)+, 20].

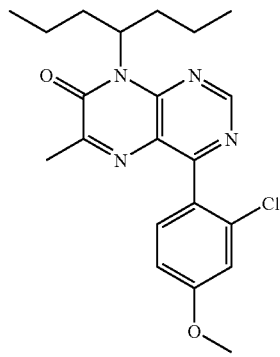

Example 563

4-(2-Chloro-4-methoxy-phenyl)-6-methyl-8-(1-propyl-butyl)-8H-pteridin-7-one

Part A 4,6-Dichloro-5-aminopyrimidine (5.8 g, 0.036 mol) was diluted in EtOH (25 ml) and toluene (100 ml). A 2M Na₂CO₃ (45.0 ml) was added followed by Pd(PPh₃)₂Cl₂ (1.5 g, 0.0021 mol), and 2-chloro-4-methoxyphenylboronic acid (0.035 mol). The reaction was warmed to reflux under an inert atmosphere for 5 hours. The reaction was then allowed to cool to room temperature and poured over EtOAc/H₂O. The organic layer was separated and washed with sat'd sodium chloride, dried (MgSO₄), filtered and concentrated. The material was flushed through a plug of silica using 50% EtOAc/hexane as an eluting solvent. The crude material was concentrated in vacuo and diluted in 5 ml butanol. 4-Heptyamine was added to the solution and the mixture warmed to reflux for 18 hours. After concentrating the solution in vacuo and purification on silica gel using 80% EtOAc/hexane as the eluting solvent the desired intermediate 6-(2-chloro-4-methoxy-phenyl)-N4-(1-propyl-butyl)-pyrimidine-4,5-diamine was isolated (0.29 g, 73%). MS (AP) 349.3 [(M+H)+, 100].

Part B 6-(2-Chloro-4-methoxy-phenyl)-N4-(1-propyl-butyl)-pyrimidine-4,5-diamine (0.29 g, 0.83 mmol) was diluted in ethanol (8 ml) and ethyl pyruvate was added (0.92 ml, 8.3 mmol). The mixture was stirred for 18 hours at which time the solution was concentrated. The residue was diluted in glacial acetic acid (10 ml) and warmed to 100° C. for 1 hour. After concentrating the solution the product was purified by reverse phase HPLC to yield 13.5 mg of 4-(2-chloro-4-methoxy-phenyl)-6-methyl-8-(1-propyl-butyl)-8H-pteridin-7-one (Example 563). ¹H NMR (300 MHz, CDCl₃) δ ppm 9.02 (s, 1 H), 7.41 (d, J=8.42 Hz, 1 H), 7.05 (d, J=2.56 Hz, 1 H), 6.93 (dd, J=8.42, 2.56 Hz, 1 H), 3.86 (s, 3 H), 4.40 (m, 1H), 2.48 (m, 2 H), 2.31 (m, 2 H), 1.89 (m, 2 H), 1.19 (m, 5 H), 0.88 (t, J=7.32 Hz, 6 H). MS (AP) 321.2 [(M+H)+, 100]. MS (AP) 401.3 [(M+H)+, 100].

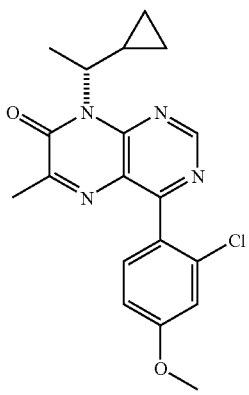

Example 565a (R)-4-(2-Chloro-4-methoxy-phenyl)-8-(1-cyclopropyl-ethyl)-6-methyl-8H-pteridin-7-one Part A 4-Chloro-6-(2-chloro-4-methoxy-phenyl)-pyrimidin-5-ylamine (prepared substantially as described in Example 466) (0.25 g, 0.93 mmol) was diluted in butanol (9 mL). (R)-1-Cyclopropyl-ethylamine (0.25 g, 2.05 mmol) and triethylamine (0.52 mL, 3.6 mmol) were added to the solution and the mixture warmed to reflux for 18 hours. After concentrating the solution in vacuo and purification on silica gel using 100% EtOAc/hexane as the eluting solvent the desired intermediate (R)-6-(2-chloro-4-methoxy-phenyl)-N4-(1-cyclopropyl-ethyl)-pyrimidine-4,5-diamine was isolated (0.17 g, 57%).

Part B (R)-6-(2-Chloro-4-methoxy-phenyl)-N4-(1-cyclopropyl-ethyl)-pyrimidine-4,5-diamine (0.20 g, 0.52 mmol) was diluted in ethanol (5 ml) and ethyl pyruvate was added (0.58 ml, 5.2 mmol). The mixture was stirred for 18 hours at which time the solution was concentrated. The residue was diluted in glacial acetic acid (10 ml) and warmed to 100° C. for 1 hour. After concentrating the solution the product was purified by reverse phase HPLC to yield 2.0 mg of (R)-4-(2-chloro-4-methoxy-phenyl)-8-(1-cyclopropyl-ethyl)-6-methyl-8H-pteridin-7-one (Example 565a). $^1$H NMR (300 MHz, CDCl$_3$) δ ppm 9.04 (s, 1 H), 7.45 (d, J=8.42 Hz, 1 H), 7.09 (d, J=2.56 Hz, 1 H), 6.98 (dd, J=8.42, 2.56 Hz, 1 H), 4.26 (m, 1 H), 3.91 (s, 3 H), 2.54 (d, J=7.32, 3 H), 2.18 (m, 3 H), 0.87 (m, 2 H), 0.45 (m, 2 H), 0.26 (m, 1 H). MS (AP) 371.3 [(M+H)+, 100].

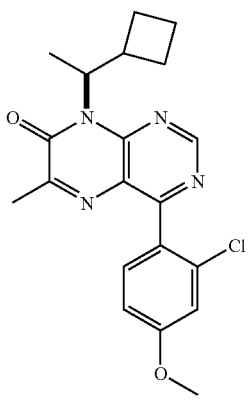

Example 567a (S)-4-(2-Chloro-4-methoxy-phenyl)-8-(1-cyclobutyl-ethyl)-6-methyl-8H-pteridin-7-one Part A 4-Chloro-6-(2-chloro-4-methoxy-phenyl)-pyrimidin-5-ylamine (prepared substantially as described in Example 466) (0.23 g, 0.86 mmol) was diluted in butanol (9 mL). (S)-1-Cyclobutyl-ethylamine (0.25 g, 1.9 mmol) and triethylamine (0.48 mL, 3.4 mmol) were added to the solution and the mixture warmed to reflux for 18 hours. After concentrating the solution in vacuo and purification on silica gel using 100% EtOAc/hexane as the eluting solvent the desired intermediate (S)-6-(2-chloro-4-methoxy-phenyl)-N4-(1-cyclobutyl-ethyl)-pyrimidine-4,5-diamine was isolated (0.23 g, 81%). MS (AP) 333.3 [(M+H)+, 100].

Part B (S)-6-(2-Chloro-4-methoxy-phenyl)-N4-(1-cyclobutyl-ethyl)-pyrimidine-4,5-diamine (0.23 g, 0.69 mmol) was diluted in ethanol (7 ml) and ethyl pyruvate was added (0.78 ml, 6.9 mmol). The mixture was stirred for 18 hours at which time the solution was concentrated. The residue was diluted in glacial acetic acid (10 ml) and warmed to 100° C. for 1 hour. After concentrating the solution the product was purified by reverse phase HPLC to yield 2.0 mg of (S)-4-(2-chloro-4-methoxy-phenyl)-8-(1-cyclobutyl-ethyl)-6-methyl-8H-pteridin-7-one (Example 567a). $^1$H NMR (300 MHz, CDCl$_3$) δ ppm 9.06 (s, 1 H), 7.46 (d, J=8.79 Hz, 1 H), 7.09 (d, J=2.56 Hz, 1 H), 6.97 (dd, J=8.79, 2.56 Hz, 1 H), 5.82 (m, 1 H), 3.91 (s, 3 H), 2.51 (s, 3 H), 2.22 (m, 2 H), 1.87 (m, 4 H), 1.74 (s, 3 H), 1.55 (m, 1 H). MS (AP) 385.3 [(M+H)+, 100].

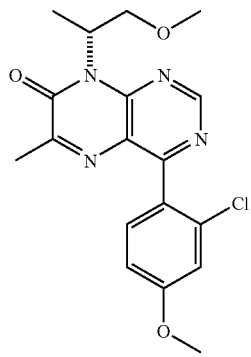

Example 570a (R)-4-(2-Chloro-4-methoxy-phenyl)-8-(2-methoxy-1-methyl-ethyl)-6-methyl-8H-pteridin-7-one Part A 4-Chloro-6-(2-chloro-4-methoxy-phenyl)-pyrimidin-5-ylamine (prepared substantially as described in Example 466) (0.28 g, 1.0 mmol) was diluted in butanol (10 mL). (R)-2-Methoxy-1-methyl-ethylamine (0.29 g, 3.3 mmol) and triethylamine (0.59 mL, 4.0 mmol) were added to the solution and the mixture warmed to reflux for 18 hours. After concentrating the solution in vacuo and purification on silica gel using 100% EtOAc/hexane as the eluting solvent the desired intermediate (R)-6-(2-chloro-4-methoxy-phenyl)-N4-(2-methoxy-1-methyl-ethyl)-pyrimidine-4,5-diamine (0.26 g, 85%). MS (AP) 321.2 [(M+H)+, 100].

Part B (R)-6-(2-Chloro-4-methoxy-phenyl)-N4-(2-methoxy-1-methyl-ethyl)-pyrimidine-4,5-diamine (0.26 g, 0.82 mmol) was diluted in ethanol (8 ml) and ethyl pyruvate was added (0.92 ml, 8.2 mmol). The mixture was stirred for 18 hours at which time the solution was concentrated. The residue was diluted in glacial acetic acid (10 ml) and warmed to 100° C. for 1 hour. After concentrating the solution the product was purified by reverse phase HPLC to yield 6.0 mg of (R)-4-(2-chloro-4-methoxy-phenyl)-8-(2-methoxy-1-methyl-ethyl)-6-methyl-8H-pteridin-7-one (Example 570a). $^1$H NMR (300 MHz, CDCl$_3$) δ ppm 9.09 (s, 1 H), 7.43 (d, J=8.79 Hz, 1 H), 7.09 (d, J=2.56 Hz, 1 H), 6.97 (dd, J=8.79, 2.56 Hz, 1 H), 4.39 (m, 3H), 3.91 (s, 3 H), 3.73 (dd, J=10.07, 5.31 Hz, 2 H), 3.35 (s, 3H), 2.53 (s, 3 H), 1.62 (6, J=6.96 Hz, 3 H). MS (AP) 375.2 [(M+H)+, 100].

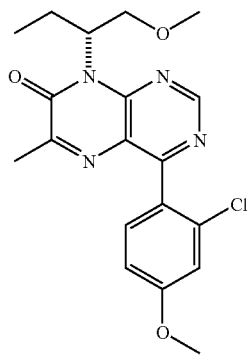

Example 571a (R)-4-(2-Chloro-4-methoxy-phenyl)-8-(1-methoxymethyl-propyl)-6-methyl-8H-pteridin-7-one Part A 4-Chloro-6-(2-chloro-4-methoxy-phenyl)-pyrimidin-5-ylamine (prepared substantially as described in Example 466) (0.22 g, 0.81 mmol) was diluted in butanol (8 mL). (R)-2-Ethoxy-1-methyl-ethylamine (0.25 g, 1.8 mmol) and triethylamine (0.45 mL, 3.0 mmol) were added to the solution and the mixture warmed to reflux for 18 hours. After concentrating the solution in vacuo and purification on silica gel using 100% EtOAc/hexane as the eluting solvent the desired intermediate (R)-6-(2-chloro-4-methoxy-phenyl)-N4-(1-methoxymethyl-propyl)-pyrimidine-4,5-diamine (0.20 g, 74%). MS (AP) 337.2 [(M+H)+, 100].

Part B (R)-6-(2-Chloro-4-methoxy-phenyl)-N4-(1-methoxymethyl-propyl)-pyrimidine-4,5-diamine (0.20 g, 0.60 mmol) was diluted in ethanol (6 ml) and ethyl pyruvate was added (0.68 ml, 6.0 mmol). The mixture was stirred for 18 hours at which time the solution was concentrated. The residue was diluted in glacial acetic acid (10 ml) and warmed to 100° C. for 1 hour. After concentrating the solution the product was purified by reverse phase HPLC to yield 5.0 mg of (R)-4-(2-chloro-4-methoxy-phenyl)-8-(1-methoxymethyl-ethyl-propyl)-6-methyl-8H-pteridin-7-one (Example 571a). $^1$H NMR (300 MHz, CDCl$_3$) δ ppm 9.02 (s, 1 H), 7.41 (d, J=8.79 Hz, 1 H), 7.05 (d, J=2.56 Hz, 1 H), 6.93 (dd, J=8.79, 2.56 Hz, 1 H), 3.87 (s, 3 H), 3.73 (m, 2 H), 3.29 (s, 3 H), 2.63 (m, 2H), 2.49 (s, 3 H), 2.10 (m, 2 H), 0.87 (t, J=7.51 Hz, 3 H). MS (AP) 389.3 [(M+H)+, 100].

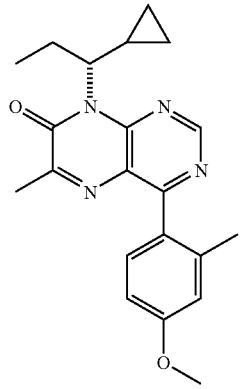

Example 612a (R)-8-(1-Cyclopropyl-propyl)-4-(4-methoxy-2-methyl-phenyl)-6-methyl-8H-pteridin-7-one Part A 4,6-Dichloro-5-aminopyrimidine (2.0 g, 12.0 mmol) was diluted in EtOH (10 ml) and toluene (40 ml). A 2M Na$_2$CO$_3$ (15.0 ml) was added followed by Pd(PPh$_3$)$_2$Cl$_2$ (0.51 g, 0.72 mmol), and 4-methoxy-2-methylphenylboronic acid (2.0 g, 12.0 mmol). The reaction was warmed to reflux under an inert atmosphere for 5 hours. The reaction was then allowed to cool to room temperature and poured over EtOAc/H$_2$O. The organic layer was separated and washed with sat'd sodium chloride, dried (MgSO$_4$), filtered and concentrated. The material was flushed through a plug of silica using 50% EtOAc/hexane as an eluting solvent. The crude material was concentrated in vacuo and diluted in 10 mL butanol. (R)-1-Cyclopropyl-propylamine (0.29 g, 2.11 mmol) and triethylamine (0.45 mL, 3.0 mmol) was added to the solution and the mixture warmed to reflux for 18 hours. After concentrating the solution in vacuo and purification on silica gel using 80% EtOAc/hexane as the eluting solvent the desired intermediate (R)-N4-(1-Cyclopropyl-propyl)-6-(4-methoxy-2-methyl-phenyl)-pyrimidine-4,5-diamine was isolated (0.20 g, 68%).

Part B (R)-N4-(1-Cyclopropyl-propyl)-6-(4-methoxy-2-methyl-phenyl)-pyrimidine-4,5-diamine (0.21 g, 0.67 mmol) was diluted in ethanol (7 ml) and ethyl pyruvate was added (0.75 ml, 6.7 mmol). The mixture was stirred for 18 hours at which time the solution was concentrated. After concentrating the solution the product was purified by reverse phase HPLC to yield 2.0 mg of (R)-8-(1-Cyclopropyl-propyl)-4-(4-methoxy-2-methyl-phenyl)-6-methyl-8H-pteridin-7-one (Example 612a). $^1$H NMR (300 MHz, CDCl$_3$) δ ppm 8.86 (s, 1 H), 7.33 (d, J=9.15 Hz, 1 H), 6.80 (d, J=2.20 Hz, 1 H), 6.78 (d, J=2.20 Hz, 1 H), 4.56 (m, 1 H), 3.80 (s, 3 H), 2.45 (s, 3

H), 2.30 (m, 1 H), 2.20 (s, 3 H), 2.12 (m, 1 H), 0.81 (t, J=7.51 Hz, 3 H), 0.76 (m, 1 H), 0.68 (m, 1 H), 0.42 (m, 1 H), 0.29 (m, 1 H), 0.12 (m, 1 H). MS (EI) 377.3 [(M+H)+, 100].

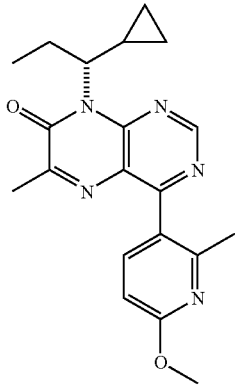

Example 644a (R)-8-(1-Cyclopropyl-propyl)-4-(6-methoxy-2-methyl-pyridin-3-yl)-6-methyl-8H-pteridin-7-one Part A 4,6-Dichloro-5-aminopyrimidine (2.5 g, 15.0 mmol) was diluted in EtOH (10 ml) and toluene (40 ml). A 2M Na₂CO₃ (18.8 ml) was added followed by Pd(PPh₃)₂Cl₂ (0.63 g, 0.90 mmol), and 2-methoxy-6-methyl pyridine boronic acid (Wilde, et al. WO99/01454) (2.5 g, 15.0 mmol). The reaction was warmed to reflux under an inert atmosphere for 5 hours. The reaction was then allowed to cool to room temperature and poured over EtOAc/H₂O. The organic layer was separated and washed with sat'd sodium chloride, dried (MgSO₄), filtered and concentrated. The material was flushed through a plug of silica using 50% EtOAc/hexane as an eluting solvent. The crude material was concentrated in vacuo and diluted in 10 mL butanol. (R)-1-Cyclopropyl-propylamine (0.29 g, 2.11 mmol) and triethylamine (0.45 mL, 3.0 mmol) was added to the solution and the mixture warmed to reflux for 18 hours. After concentrating the solution in vacuo and purification on silica gel using 80% EtOAc/hexane as the eluting solvent the desired intermediate (R)-N4-(1-cyclopropyl-propyl)-6-(6-methoxy-2-methyl-pyridin-3-yl)-pyrimidine-4,5-diamine was isolated (0.20 g, 68%). MS (AP) 314.3 [(M+H)+, 100].

Part B (R)-N4-(1-Cyclopropyl-propyl)-6-(6-methoxy-2-methyl-pyridin-3-yl)-pyrimidine-4,5-diamine (0.20 g, 0.64 mmol) was diluted in ethanol (7 ml) and ethyl pyruvate was added (0.73 ml, 6.4 mmol). The mixture was stirred for 18 hours at which time the solution was concentrated. After concentrating the solution the product was purified by reverse phase HPLC to yield 2.0 mg of (R)-8-(1-cyclopropyl-propyl)-4-(6-methoxy-2-methyl-pyridin-3-yl)-6-methyl-8H-pteridin-7-one (Example 644a). ¹H NMR (300 MHz, CDCl₃) δ ppm 8.92 (s, 1 H), 7.68 (d, J=8.05 Hz, 1 H), 6.68 (d, J=9.15 Hz, 1 H), 4.84 (m, 1 H), 3.99 (s, 3 H),), 2.51 (s, 3 H), 2.39 (s, 3 H), 1.20 (m, 2 H), 0.86 (m, 8 H). MS (EI) 366.3 [(M+H)+, 100].

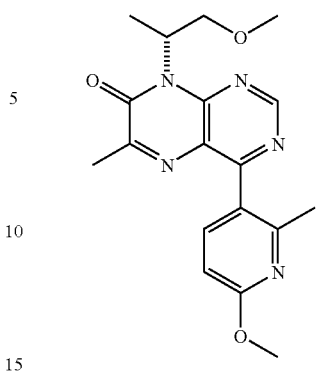

Example 650a (R)-8-(2-Methoxy-1-methyl-ethyl)-4-(6-methoxy-2-methyl-pyridin-3-yl)-6-methyl-8H-pteridin-7-one Part A 6-(6-Methoxy-2-methyl-pyridin-3-yl)-pyrimidine-4,5-diamine (prepared substantially as described in Example 644a) (0.25 g, 1.0 mmol) was diluted in 10 mL butanol. (R)-2-Methoxy-1-methyl-ethylamine (0.28 g, 2.2 mmol) and triethylamine (0.56 mL, 4.0 mmol) was added to the solution and the mixture warmed to reflux for 18 hours. After concentrating the solution in vacuo and purification on silica gel using 100% EtOAc/hexane as the eluting solvent the desired intermediate (R)-N4-(2-methoxy-1-methyl-ethyl)-6-(6-methoxy-2-methyl-pyridin-3-yl)-pyrimidine-4,5-diamine was isolated (0.22 g, 74%).

Part B (R)-N4-(2-Methoxy-1-methyl-ethyl)-6-(6-methoxy-2-methyl-pyridin-3-yl)-pyrimidine-4,5-diamine (0.22 g, 0.74 mmol) was diluted in ethanol (8 ml) and ethyl pyruvate was added (0.82 ml, 7.4 mmol). The mixture was stirred for 18 hours at which time the solution was concentrated. After concentrating the solution the product was purified by preparative TLC eluting with 35% ethyl acetate in hexanes to yield 5.0 mg of (R)-8-(2-methoxy-1-methyl-ethyl)-4-(6-methoxy-2-methyl-pyridin-3-yl)-6-methyl-8H-pteridin-7-one (Example 650a). ¹H NMR (300 MHz, CDCl₃) δ ppm 8.99 (s, 1 H), 7.65 (d, J=8.42 Hz, 1 H), 6.68 (d, J=8.42 Hz, 1 H), 5.71 (m, 1H), 3.99 (s, 3 H), 3.59 (m, 2 H), 3.31 (s, 3 H), 2.50 (s, 3H), 2.50 (s, 3H), 2.50 (s, 3H), 0.85 (d, J=7.69 Hz, 3 H). MS (EI) 356.3 [(M+H)+, 100].

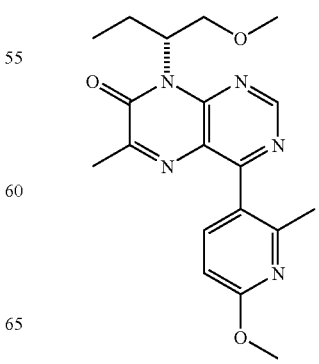

Example 651a (R)-8-(1-Methoxymethyl-propyl)-4-(6-methoxy-2-methyl-pyridin-3-yl)-6-methyl-8H-pteridin-7-one Part A 6-(6-Methoxy-2-methyl-pyridin-3-yl)-pyrimidine-4,5-diamine (prepared substantially as described in Example 644a) (0.21 g, 0.84 mmol) was diluted in 10 mL butanol. (R)-2-Methoxy-1-methyl-ethylamine (0.26 g, 1.8 mmol) and triethylamine (0.47 mL, 3.4 mmol) was added to the solution and the mixture warmed to reflux for 18 hours. After concentrating the solution in vacuo and purification on silica gel using 100% EtOAc/hexane as the eluting solvent the desired intermediate (R)-N4-(1-methoxymethyl-propyl)-6-(6-methoxy-2-methyl-pyridin-3-yl)-pyrimidine-4,5-diamine was isolated (0.20 g, 75%). MS (AP) 318.3 [(M+H)+, 100].

Part B (R)-N4-(1-Methoxymethyl-propyl)-6-(6-methoxy-2-methyl-pyridin-3-yl)-pyrimidine-4,5-diamine (0.2 g, 0.63 mmol) was diluted in ethanol (7 ml) and ethyl pyruvate was added (0.70 ml, 6.3 mmol). The mixture was stirred for 18 hours at which time the solution was concentrated. After concentrating the solution the product was purified by reverse phase HPLC to yield 4.0 mg of (R)-8-(1-methoxymethyl-propyl)-4-(6-methoxy-2-methyl-pyridin-3-yl)-6-methyl-8H-pteridin-7-one (Example 651a). $^1$H NMR (300 MHz, CDCl$_3$) δ ppm 8.93 (s, 1 H), 7.62 (d, J=8.42 Hz, 1 H), 6.64 (d, J=8.42 Hz, 1 H), 4.23 (m, 1H), 3.94 (s, 3 H), 3.68 (m, 2 H), 3.25 (s, 3 H), 2.45 (s, 3H), 2.34 (s, 3 H), 1.22 (m, 2H), 0.82 (t, J=7.51 Hz, 3 H). MS (EI) 370.3 [(M+H)+, 100].

(MgSO$_4$), filtered and concentrated. The material was flushed through a plug of silica using 100% EtOAc/hexane as an eluting solvent. The crude material was concentrated in vacuo and diluted in 10 mL butanol. (R)-1-Cyclopropyl-propylamine (0.21 g, 0.82 mmol) and triethylamine (0.46 mL, 3.3 mmol) was added to the solution and the mixture warmed to reflux for 18 hours. After concentrating the solution in vacuo and purification on silica gel using 100% EtOAc/hexane as the eluting solvent the desired intermediate (R)-6-(4-methoxy-2,5-dimethyl-phenyl)-N4-(1-methoxymethyl-propyl)-pyrimidine-4,5-diamine was isolated (0.22 g, 82%).

Part B (R)-6-(4-Methoxy-2,5-dimethyl-phenyl)-N4-(1-methoxymethyl-propyl)-pyrimidine-4,5-diamine (0.22 g, 0.68 mmol) was diluted in ethanol (7 ml) and ethyl pyruvate was added (0.76 ml, 6.8 mmol). The mixture was stirred for 18 hours at which time the solution was concentrated. After concentrating the solution the product was purified by reverse phase HPLC to yield 8.0 mg of (R)-4-(4-methoxy-2,5-dimethyl-phenyl)-8-(1-methoxymethyl-propyl)-6-methyl-8H-pteridin-7-one (Example 1013a). $^1$H NMR (300 MHz, CDCl$_3$) δ ppm 9.05 (s, 1 H), 7.21 (s, 1 H), 6.79 (s, 1 H), 4.86 (m, 1 H), 3.91 (s, 3 H), 2.55 (m, 3 H), 2.38 (m, 1 H), 2.22 (s, 3 H),), 2.22 (s, 3 H), 2.04 (m, 1 H), 1.25 (m, 1 H), 0.89 (t, J=7.51 Hz, 3 H), 0.77 (m, 1 H), 0.50 (m, 1 H), 0.39 (m, 1 H), 0.18 (m, 1 H). MS (EI) 379.3 [(M+H)+, 100].

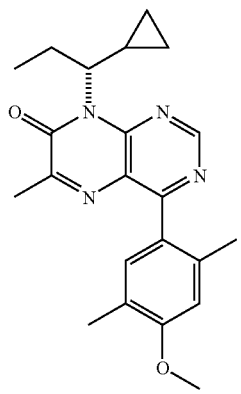

Example 1013a (R)-4-(4-Methoxy-2,5-dimethyl-phenyl)-8-(1-methoxymethyl-propyl)-6-methyl-8H-pteridin-7-one Part A 4,6-Dichloro-5-aminopyrimidine (0.91 g, 5.6 mmol) was diluted in EtOH (5 ml) and toluene (20 ml). A 2M Na$_2$CO$_3$ (6.9 ml) was added followed by Pd(PPh$_3$)$_2$Cl$_2$ (0.23 g, 0.34 mmol), and 4-methoxy-2,5-dimethylphenylboronic acid (Wilde, et al. WO99/01454)(1.0 g, 5.6 mmol). The reaction was warmed to reflux under an inert atmosphere for 5 hours. The reaction was then allowed to cool to room temperature and poured over EtOAc/H$_2$O. The organic layer was separated and washed with sat'd sodium chloride, dried

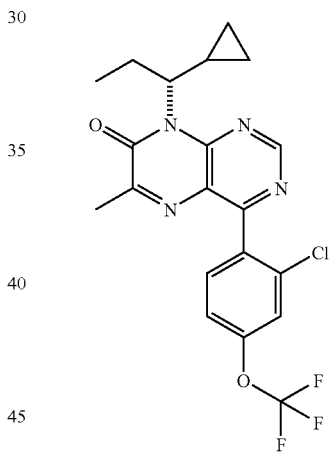

Example 1061a (R)-4-(2-Chloro-4-trifluoromethoxy-phenyl)-8-(1-cyclopropyl-propyl)-6-methyl-8H-pteridin-7-one Part A 4,6-Dichloro-5-aminopyrimidine (1.0 g, 6.3 mmol) was diluted in EtOH (10 ml) and toluene (40 ml). A 2M Na$_2$CO$_3$ (7.9 ml) was added followed by Pd(PPh$_3$)$_2$Cl$_2$ (0.26 g, 0.38 mmol), and 2-chloro-4-trimfluoromethoxyphenyl boronic acid ((prepared as described in Arvanitis, A. G.; Rescinito, J. T.; Arnold, C. R.; Wilde, R. G.; Cain, G. A.; Sun, J. H.; Yan, J.-S., Teleha, C. A.; Fitzgerald, L. W.; McElroy, J.; Zaczek, R. Bioorg. Med. Chem. Lett., 2003, 13, 129) (1.5 g, 6.3 mmol). The reaction was warmed to reflux under an inert atmosphere for 5 hours. The reaction was then allowed to cool to room temperature and poured over EtOAc/H$_2$O. The organic layer was separated and washed with sat'd sodium chloride, dried (MgSO₄), filtered and concentrated. The material was flushed through a plug of silica using 100% EtOAc/hexane as an eluting solvent. The crude material was concentrated in vacuo. A portion of 6-(2-Methyl-4-trifluoromethoxy-phenyl)-pyrimidine-4,5-diamine (0.33 g, 1.0 mmol) was diluted in 10 mL butanol. (R)-1-Cyclopropyl-propylamine (0.33 g, 2.2 mmol) and triethylamine (0.57 mL, 4.0 mmol) was added to the solution and the mixture warmed to reflux for 18 hours. After concentrating the solution in vacuo and purification on silica gel using 100% EtOAc/hexane as the eluting solvent the desired intermediate (R)-N4-(1-cyclopropyl-propyl)-6-(2-methyl-4-trifluoromethoxy-phenyl)-pyrimidine-4,5-diamine was isolated (0.31 g, 79%). MS (AP) 387.3 [(M+H)+, 100].

Part B (R)-N4-(1-Cyclopropyl-propyl)-6-(2-methyl-4-trifluoromethoxy-phenyl)-pyrimidine-4,5-diamine (0.31 g, 0.80 mmol) was diluted in ethanol (8 ml) and ethyl pyruvate was added (0.89 ml, 8.0 mmol). The mixture was stirred for 18 hours at which time the solution was concentrated. After concentrating the solution the product was purified by reverse phase HPLC to yield 6.0 mg of (R)-4-(2-Chloro-4-trifluoromethoxy-phenyl)-8-(1-cyclopropyl-propyl)-6-methyl-8H-pteridin-7-one (Example 1061a). ¹H NMR (300 MHz, CDCl₃) δ ppm 8.91 (s, 1 H), 7.47 (d, J=8.42 Hz, 1 H), 7.35 (d, J=1.10 Hz, 1 H), 7.22 (ddd, J=8.42, 2.29, 1.10 Hz, 1 H), 4.54 (m, 1 H), 2.45 (s, 3 H), 2.18 (m, 2 H), 1.32 (m, 1 H), 0.84 (m, 3 H), 0.68 (m, 1 H), 0.44 (m, 1 H), 0.30 (m, 1 H), 0.13 (m, 1 H).

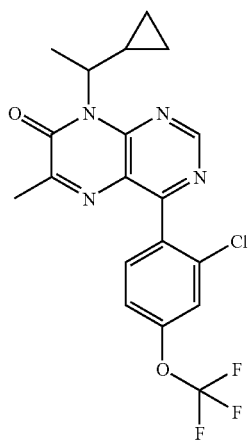

Example 1062

4-(2-Chloro-4-trifluoromethoxy-phenyl)-8-(1-cyclopropyl-ethyl)-6-methyl-8H-pteridin-7-one Part A 6-(6-Methoxy-2-methyl-pyridin-3-yl)-pyrimidine-4,5-diamine (prepared substantially as described in Example 1061a) (0.23 g, 0.71 mmol) was diluted in 10 mL butanol. 1-Cyclopropyl-ethylamine (0.21 g, 1.6 mmol) and triethylamine (0.40 mL, 4.0 mmol) was added to the solution and the mixture warmed to reflux for 18 hours. After concentrating the solution in vacuo and purification on silica gel using 100% EtOAc/hexane as the eluting solvent the desired intermediate 6-(2-chloro-4-trifluoromethoxy-phenyl)-N4-(1-cyclopropyl-ethyl)-pyrimidine-4,5-diamine was isolated (0.20 g, 80%).

Part B 6-(2-Chloro-4-trifluoromethoxy-phenyl)-N4-(1-cyclopropyl-ethyl)-pyrimidine-4,5-diamine (0.20 g, 0.52 mmol) was diluted in ethanol (6 ml) and ethyl pyruvate was added (0.58 ml, 5.2 mmol). The mixture was stirred for 18 hours at which time the solution was concentrated. After concentrating the solution the product was purified by reverse phase HPLC to yield 4.5 mg of 4-(2-chloro-4-trifluoromethoxy-phenyl)-8-(1-cyclopropyl-ethyl)-6-methyl-8H-pteridin-7-one (Example 1062). ¹H NMR (300 MHz, CDCl₃) δ ppm 8.99 (s, 1 H), 7.50 (d, J=8.79 Hz, 1 H), 7.39 (d, J=1.10 Hz, 1 H), 7.26 (dd, J=8.79, 1.10 Hz, 1 H), 4.91 (m, 1 H), 2.49 (s, 3 H), 1.71 (d, J=7.32, 3 H), 0.69 (m, 2 H), 0.41 (m, 2 H), 0.22 (m, 1 H). MS (EI) 425.2 [(M+H)+, 100].

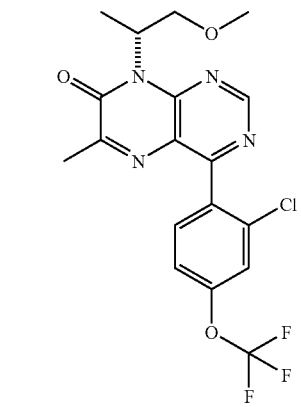

Example 1067a (R)-4-(2-Chloro-4-trifluoromethoxy-phenyl)-8-(2-methoxy-1-methyl-ethyl)-6-methyl-8H-pteridin-7-one Part A 6-(6-Methoxy-2-methyl-pyridin-3-yl)-pyrimidine-4,5-diamineylamine (prepared substantially as described in Example 1061a) (0.25 g, 0.77 mmol) was diluted in 10 mL butanol. (R)-1-cyclopropyl-ethylamine (0.25 g, 1.7 mmol) and triethylamine (0.43 mL, 3.1 mmol) was added to the solution and the mixture warmed to reflux for 18 hours. After concentrating the solution in vacuo and purification on silica gel using 100% EtOAc/hexane as the eluting solvent the desired intermediate (R)-6-(2-chloro-4-trifluoromethoxy-phenyl)-N4-(2-methoxy-1-methyl-ethyl)-pyrimidine-4,5-diamine was isolated (0.20 g, 73%).

Part B (R)-6-(2-Chloro-4-trifluoromethoxy-phenyl)-N4-(2-methoxy-1-methyl-ethyl)-pyrimidine-4,5-diamine (0.20 g, 0.53 mmol) was diluted in ethanol (6 ml) and ethyl pyruvate was added (0.59 ml, 5.3 mmol). The mixture was stirred for 18 hours at which time the solution was concentrated. After concentrating the solution the product was purified by reverse phase HPLC to yield 4.0 mg of (R)-4-(2-chloro-4-trifluoromethoxy-phenyl)-8-(2-methoxy-1-methyl-ethyl)-6-methyl-8H-pteridin-7-one (Example 1067a). ¹H NMR (300 MHz, CDCl₃) δ ppm 9.02 (s, 1 H), 7.49 (d, J=8.42 Hz, 1 H), 7.39 (d, J=1.10 Hz, 1 H), 7.26 (dd, J=8.42, 1.10 Hz, 1 H), 5.95 (s, 1 H), 4.36 (t, J=9.52 Hz, 1 H), 3.68 (dd, J=10.07, 5.31 Hz, 1 H), 3.30 (s, 3 H), 2.48 (s, 3 H), 1.58 (d, J=6.96 Hz, 3 H).

Example A

Biological Assay

The compounds of the present invention can have CRF receptor antagonist activity. A compound can be considered active if it has a $K_i$ value of less than about 10,000 nM for the inhibition of CRF. $K_i$ values can be determined by any suitable biological assay, such as, for example, the assay described below.

Provided herein is an example of a $CRF_1$ receptor binding assay that can be used for the evaluation of biological activity of compounds of the present invention. The example also includes isolation of cell membranes containing cloned human $CRF_1$ receptors for use in the binding assay.

Messenger RNA is isolated from human hippocampus by standard techniques. The mRNA is reverse transcribed using oligo (dt) 12–18 and the coding region is amplified by PCR from start to stop codons The resulting PCR fragment is cloned into the EcoRV site of pGEMV, from whence the insert is reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR is transfected in 293EBNA cells, and cells retaining the episome are selected in the presence of 400 µM hygromycin. Cells surviving 4 weeks of selection in hygromycin are pooled, adapted to growth in suspension, and used to generate membranes for the binding assay described below. Individual aliquots containing approximately $1 \times 10^8$ of the suspended cells are then centrifuged to form a pellet and frozen.

For the binding assay, a frozen pellet described above containing 293EBNA cells transfected with hCRFR1 receptors is homogenized in 10 mL of ice cold tissue buffer (50 mM HEPES buffer pH 7.0, containing 10 mM $MgCl_2$, 2 mM EGTA, 1 µg/l aprotinin, 1 µg/ml leupeptin and 1 µg/ml pepstatin). The homogenate is centrifuged at 40,000×g for 12 min and the resulting pellet rehomogenized in 10 mL of tissue buffer. After another centrifugation at 40,000×g for 12 min, the pellet is resuspended to a protein concentration of 360 µg/ml to be used in the assay.

Binding assays are performed in 96 well plates; each well having a 300 µL capacity. To each well is added 50 µL of test drug dilutions (final concentration of drugs range from $10^{-10}$ to $10^{-5}$ M), 100 µL of $^{125}$I-ovine-CRF ($^{125}$I-o-CRF) (final concentration 150 pM) and 150 µL of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND Munson, et al., *Anal. Biochem.*, 1980, 107, 220, which is incorporate herein by reference in its entirety, which provides $K_i$ values for inhibition which are then used to assess biological activity.

Other in vitro assays for the determination of $CRF_1$ receptor antagonist activity of the present compounds are described, for example, in *Endocrinology*, 1985, 116, 1653 and in *Peptides*, 1985, 10, 179, each of which is incorporated by reference in its entirety. Receptor binding activity of compounds can also be evaluated according to the methods described in Grigoriadis, et al., *Biochemical, Pharmacological, and Autoradiographic Methods to Study Corticotropin-Releasing Factor Receptors. Methods in Neurosciences*, Vol. 5, 1991, which is incorporated herein by reference in its entirety.

Example B

Inhibition of CRF-Stimulated Adenylate Cyclase Activity

Activity of the present compounds can be studied by the inhibition of CRF-stimulated adenylate cyclase activity which can be performed as described by Battaglia, et al., *Synapse*, 1987, 1, 572, which is incorporated herein by reference in its entirety. Assays are carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6}$ M) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 mL of 50 mM Tris-HCL, 45 mM ATP and 2% sodium dodecyl sulfate. In order to monitor the recovery of cAMP, 1 µL of [$^3$H]cAMP (approximately 40,000 dpm) is added to each tube prior to separation. The separation of [$^{32}$P]cAMP from [$^{32}$P]ATP is performed by sequential elution over Dowex and alumina columns.

Example C

In vivo Biological Assay

The in vivo activity of the compounds of the present invention can be assessed using any one of the biological assays available and accepted within the art. Examples of in vivo biological assays for testing axiolytic activity of compounds include the "punished drinking test" (Vogel, et al., *Psychopharmcologia*, 1971, 21, 1, which is incorporated herein by reference in its entirety); "elevated plus-maze test" (Pellow, et al., *J. Neurosci. Methods*, 1985, 14, 149, which is incorporated herein by reference in its entirety); "stress-induced coritcal norepinephrine release" (Funk, et al., *Brain Res.*, 1996, 741, 220, which is incorporated herein by referenc ein its entirety); "light-dark test" (Misslin, et al., *Behav. Process*, 1989, 8, 119, which is incorporated herein by reference in its entirety); "four-plate test" (Boissier, et al., *Eur. J. Pharmacol.*, 1968, 4, 145, which is incorporated herein by reference in its entirety); and "mouse defense test battery" (Griebel, et al., *Aggress. Behav.*, 1997, 23, 19, which is incorporated herein by reference in its entirety). Compounds may be tested in any species of rodent or small mammal.

Examples of in vivo biological assays for testing antidepressant-like activity of compounds include the "forced swimming test" (Porsolt, et al., *Nature*, 1977, 266, 730, which is incorporated herein by reference in its entirety) and "CMS test" (Willner, et al., *Clin. Neuropharmacol.*, 1992, 15 (supp. 1), 550A, which is incorporated herein by reference in its entirety).

Other models useful for the testing of compounds for their anxiolytic or antidepressant activity are outlined in Berridge, et al., *Brain Research Reviews*, 1990, 15, 71, which is incorporated herein by reference in its entirety. Models for testing activity of compounds for other indications are well known in the art.

As those skilled in the art will appreciate, numerous changes and modifications can be made to the preferred embodiments of the invention without departing from the spirit of the invention. It is intended that all such variations fall within the scope of the invention. Throughout this specification, various groupings are employed to conveniently describe constituent variables of compounds and groups of various related moieties. It is specifically intended that each occurrence of such groups throughout this specification include every possible subcombination of the members of the groups, including the individual members thereof.

It is intended that each of the patents, applications, and printed publications mentioned in this patent document be hereby incorporated by reference in its entirety.

What is claimed is:

1. A compound of Formula (I):

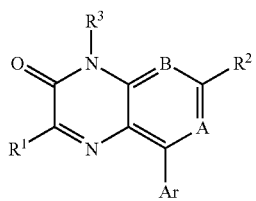

(I)

or a pharmaceutically acceptable salt form thereof, wherein:
A and B are independently $CR^4$ or N, with the proviso that at least one of A and B is N;
Ar is aryl or heteroaryl, wherein said aryl or heteroaryl is optionally substituted by one or more substituents independently selected from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $SR^5$;
$R^1$ is H, CN, $C_1$–$C_4$ haloalkyl, $NR^{1c}R^{1d}$, $NR^{1c}COR^{1b}$, $COR^{1b}$, $CONR^{1c}R^{1d}$, $OR^{1c}$, $SR^{1c}$, $C_1$–$C_4$ alkyl substituted with 0 to 3 $R^{1a}$, $C_2$–$C_4$ alkenyl substituted with 0 to 3 $R^{1a}$, $C_2$–$C_4$ alkynyl substituted with 0 to 3 $R^{1a}$, $C_3$–$C_6$ cycloalkyl substituted with 0 to 3 $R^{1a}$, or $C_4$–$C_8$ cycloalkylalkyl substituted with 0 to 3 $R^{1a}$, with the proviso that $R^1$ is not $CH_2X$, wherein X is halogen;
each $R^{1a}$ is, independently at each occurrence, halogen, CN, $N_3$, $NO_2$, $C_1$–$C_2$ haloalkyl, $NR^{1c}R^{1d}$, $NR^{1c}COR^{1b}$, $COR^{1b}$, $OR^{1c}$, $SR^{1c}$, $S(O)R^8$, or $S(O)_2R^8$;
each $R^{1b}$ is, independently at each occurrence, $C_1$–$C_4$ alkyl, $C_1$–$C_4$ haloalkyl, $C_3$–$C_6$ cycloalkyl, $C_2$–$C_4$ alkenyl, or $C_2$–$C_4$ alkynyl;
each $R^{1c}$ is, independently at each occurrence, selected from H, $C_1$–$C_4$ alkyl, $C_1$–$C_4$ haloalkyl, $C_3$–$C_6$ cycloalkyl, $C_2$–$C_4$ alkenyl, or $C_2$–$C_4$ alkynyl;
each $R^{1d}$ is, independently at each occurrence, selected from H, $C_1$–$C_4$ alkyl, $C_1$–$C_4$ haloalkyl, $C_3$–$C_6$ cycloalkyl, $C_2$–$C_4$ alkenyl, or $C_2$–$C_4$ alkynyl;
$R^2$ is H, $C_1$–$C_3$ haloalkyl, CN, OH, $COR^{2b}$, SH, $SR^{2b}$, $SO_2NHR^{2c}$, $SO_2NR^{2c}R^{2d}$, $CONHR^{2c}$, $CONR^{2c}R^{2d}$, $OCOR^{2b}$, $OR^{2b}$, $NR^{2c}R^{2d}$, $CO_2R^{2b}$, $C_1$–$C_4$ alkyl substituted with 0 to 3 $R^{2a}$, $C_2$–$C_4$ alkenyl substituted with 0 to 3 $R^{2a}$, $C_2$–$C_4$ alkynyl substituted with 0 to 3 $R^{2a}$, or $C_3$–$C_6$ cycloalkyl substituted with 0 to 3 $R^{2a}$; with the proviso that $R^2$ is not $CH_2X$, wherein X is halogen;
each $R^{2a}$ is, independently at each occurrence, halogen, CN, $N_3$, $NO_2$, $CF_3$, $OR^{2c}$, $NR^{2c}$, $NR^{2c}R^{2d}$, $NR^{2c}CO_2R^{2b}$, $SR^{2c}$, $SOR^8$, $SO_2R^8$, $CO_2R^{2b}$, $CONR^{2c}R^{2d}$, $COR^{2b}$, $OCOR^{2b}$, $NR^{2c}CONR^{2c}R^{2d}$, $NR^{2c}CO_2R^{2b}$, $OCONR^{2c}R^{2d}$, piperidinyl, pyrrolidinyl, piperazinyl, N-methylpiperazinyl, morpholinyl, or thiomorpholinyl;
each $R^{2b}$ is, independently at each occurrence, $C_1$–$C_4$ alkyl, $C_1$–$C_4$ haloalkyl, $C_3$–$C_6$ cycloalkyl, $C_4$–$C_{12}$ cycloalkylalkyl, aryl, heteroaryl, aryl-$C_1$–$C_4$ alkyl, or heteroaryl-$C_1$–$C_4$ alkyl;
each $R^{2c}$ is, independently at each occurrence, H, $C_1$–$C_4$ alkyl, $C_1$–$C_4$ haloalkyl, $C_3$–$C_6$ cycloalkyl, $C_4$–$C_{12}$ cycloalkylalkyl aryl, heteroaryl, aryl-$C_1$–$C_4$ alkyl, or heteroaryl-$C_1$–$C_4$ alkyl;
each $R^{2d}$ is, independently at each occurrence, H, $C_1$–$C_4$ alkyl, $C_1$–$C_4$ haloalkyl, $C_3$–$C_6$ cycloalkyl, $C_4$–$C_{12}$ cycloalkylalkyl aryl, heteroaryl, aryl-$C_1$–$C_4$ alkyl, or heteroaryl-$C_1$–$C_4$ alkyl;
$R^3$ is $OR^{3c}$, $NR^{3c}R^{3d}$, $NHR^{3c}$, $SR^{3c}$, $SOR^8$, $SO_2R^8$, $SO_2NHR^{3c}$, $SO_2NR^{3c}R^{3d}$, $COR^{3c}$, $CONHR^{3c}$, $CONR^{3c}R^{3d}$, aryl substituted with 0 to 3 $R^{3a}$, heteroaryl substituted with 0 to 3 $R^{3a}$, heterocyclyl substituted with 0 to 3 $R^{3f}$, $C_1$–$C_{10}$ alkyl substituted with 0 to 3 $R^{3a}$, $C_3$–$C_{10}$ alkenyl substituted with 0 to 3 $R^{3a}$, $C_3$–$C_{10}$ alkynyl substituted with 0 to 3 $R^{3a}$, $C_3$–$C_8$ cycloalkyl substituted with 0 to 3 $R^{3a}$, $C_4$–$C_{12}$ cycloalkylalkyl substituted with 0 to 3 $R^{3a}$, $C_2$–$C_{10}$ alkoxyalkyl substituted with 0 to 3 $R^{3a}$, $C_2$–$C_{10}$ thioalkoxyalkyl substituted with 0 to 3 $R^{3a}$, $C_5$–$C_{10}$ cycloalkenyl substituted with 0 to 3 $R^{3a}$, or $C_6$–$C_{10}$ cycloalkenylalkyl substituted with 0 to 3 $R^{3a}$, wherein one carbon in any cycloalkyl moiety is optionally replaced with O, S or $NR^5$;
each $R^{3a}$ is, independently at each occurrence, $C_1$–$C_{10}$ alkyl, $C_2$–$C_{10}$ alkenyl, $C_2$–$C_{10}$ alkynyl, $C_3$–$C_6$ cycloalkyl, halogen, $C_1$–$C_4$ haloalkyl, CN, $OR^{3c}$, $SR^{3c}$, $S(O)R^8$, $S(O)_2R^8$, $COR^{3b}$, $NHR^{3c}SO_2R^{3b}$, $OC(O)NR^{3c}R^{3d}$, $N_3$, $OC(O)OR^{3b}$, $CO_2R^{3c}$, $OC(O)R^{3b}$, $NR^{3c}COR^{3b}$, $N(COR^{3b})_2$, $NR^{3c}CONR^{3c}R^{3d}$, $NR^{3c}CO_2R^{3b}$, $NR^{3c}R^{3d}$, $CONR^{3c}R^{3d}$, aryl, heteroaryl, or heterocyclyl;
each $R^{3b}$ is, independently at each occurrence, $C_1$–$C_{10}$ alkyl substituted with 0 to 3 $R^{3e}$, $C_2$–$C_{10}$ alkenyl substituted with 0 to 3 $R^{3e}$, $C_2$–$C_{10}$ alkynyl substituted with 0 to 3 $R^{3e}$, $C_3$–$C_8$ cycloalkyl substituted with 0 to 3 $R^{3e}$, $C_4$–$C_{12}$ cycloalkylalkyl substituted with 0 to 3 $R^{3e}$, $C_2$–$C_{10}$ alkoxyalkyl substituted with 0 to 3 $R^{3e}$, $C_5$–$C_{10}$ cycloalkenyl substituted with 0 to 3 $R^{3e}$, or $C_6$–$C_{10}$ cycloalkenylalkyl substituted with 0 to 3 $R^{3e}$, wherein one carbon in any cycloalkyl moiety is optionally replaced with O, S or $NR^5$;
each $R^{3c}$ is, independently at each occurrence, H, $C_1$–$C_{10}$ alkyl substituted with 0 to 3 $R^{3e}$, $C_2$–$C_{10}$ alkenyl substituted with 0 to 3 $R^{3e}$, $C_2$–$C_{10}$ alkynyl substituted with 0 to 3 $R^{3e}$, $C_3$–$C_8$ cycloalkyl substituted with 0 to 3 $R^{3e}$, $C_4$–$C_{12}$ cycloalkylalkyl substituted with 0 to 3 $R^{3e}$, $C_2$–$C_{10}$ alkoxyalkyl substituted with 0 to 3 $R^{3e}$, $C_5$–$C_{10}$ cycloalkenyl substituted with 0 to 3 $R^{3e}$, or $C_6$–$C_{10}$ cycloalkenylalkyl substituted with 0 to 3 $R^{3e}$, wherein one carbon in any cycloalkyl moiety is optionally replaced with O, S or $NR^5$;
each $R^{3d}$ is, independently at each occurrence, H, $C_1$–$C_{10}$ alkyl substituted with 0 to 3 $R^{3e}$, $C_2$–$C_{10}$ alkenyl substituted with 0 to 3 $R^{3e}$, $C_2$–$C_{10}$ alkynyl substituted with 0 to 3 $R^{3e}$, $C_3$–$C_8$ cycloalkyl substituted with 0 to 3 $R^{3e}$, $C_4$–$C_{12}$ cycloalkylalkyl substituted with 0 to 3 $R^{3e}$, $C_2$–$C_{10}$ alkoxyalkyl substituted with 0 to 3 $R^{3e}$, $C_5$–$C_{10}$ cycloalkenyl substituted with 0 to 3 $R^{3e}$, or $C_6$–$C_{10}$ cycloalkenylalkyl substituted with 0 to 3 $R^{3e}$, wherein one carbon in any cycloalkyl moiety is optionally replaced with O, S or NR$^5$;

each R$^{3e}$ is, independently at each occurrence, C$_1$–C$_6$ alkyl, C$_2$–C$_6$ alkenyl, C$_2$–C$_{10}$ alkynyl, C$_3$–C$_6$ cycloalkyl, halogen, C$_1$–C$_4$ haloalkyl, CN, OR$^{7a}$, SR$^{7a}$, S(O)$_n$R$^8$, COR$^6$, CO$_2$R$^{7a}$, OC(O)R$^6$, NR$^{7a}$COR$^6$, N(COR$^6$)$_2$, NR$^{7a}$CONR$^{7a}$R$^{7b}$, NR$^{7a}$CO$_2$R$^6$, NR$^{7a}$R$^{7b}$, NHR$^{7a}$SO$_2$R$^6$, OC(O)NR$^{7a}$R$^{7b}$, N$_3$, OC(O)OR$^6$, CONR$^{7a}$R$^{7b}$, aryl, heteroaryl, or heterocyclyl;

each R$^{3f}$ is, independently at each occurrence, oxo, sulfido, or R$^{3a}$;

R$^4$ is H, halogen, CN, C$_1$–C$_3$ haloalkyl, COR$^{4b}$, OR$^{4c}$, SR$^{4c}$, SO$_2$NHR$^{4c}$, SO$_2$NR$^{4c}$R$^{4d}$, CONHR$^{4c}$, CONR$^{4c}$R$^{4d}$, OCOR$^{4b}$, NR$^{4c}$CONHR$^{4c}$, NR$^{4c}$CONR$^{4c}$R$^{4d}$, NR$^{4c}$CO$_2$R$^{4b}$, OCONR$^{4c}$R$^{4d}$, NR$^{4c}$R$^{4d}$, CO$_2$R$^{4b}$, C$_1$–C$_4$ alkyl substituted with 0 to 1 R$^{4a}$, C$_2$–C$_4$ alkenyl substituted with 0 to 1 R$^{4a}$, C$_2$–C$_4$ alkynyl substituted with 0 to 1 R$^{4a}$, C$_3$–C$_6$ cycloalkyl substituted with 0 to 1 R$^{4a}$, piperidinyl, pyrrolidinyl, piperazinyl, N-methylpiperazinyl, morpholinyl, or thiomorpholinyl;

each R$^{4a}$ is, independently at each occurrence, halogen, CN, CF$_3$, OR$^{4c}$, NHR$^{4c}$, NR$^{4c}$R$^{4d}$, NR$^{4c}$CO$_2$R$^{4b}$, SR$^{4c}$, SOR$^8$, SO$_2$R$^8$, CO$_2$R$^{4b}$, CONHR$^{4c}$, CONR$^{4c}$R$^{4d}$, COR$^{4b}$, OCOR$^{4b}$, NR$^{4c}$CONR$^{4c}$R$^{4d}$, NR$^{4c}$CO$_2$R$^{4b}$, OCONR$^{4c}$R$^{4d}$, piperidinyl, pyrrolidinyl, piperazinyl, N-methylpiperazinyl, morpholinyl, or thiomorpholinyl;

each R$^{4b}$ is, independently at each occurrence, C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl;

each R$^{4c}$ is, independently at each occurrence, H, C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl;

each R$^{4d}$ is, independently at each occurrence, H, C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl;

R$^5$ is H, C$_1$–C$_4$ alkyl, C$_1$–C$_4$ haloalkyl, C$_2$–C$_6$ alkenyl, C$_2$–C$_6$ alkynyl, C$_3$–C$_6$ cycloalkyl, C$_4$–C$_7$ cycloalkylalkyl, or C$_2$–C$_6$ alkoxyalkyl;

R$^6$ is, independently at each occurrence, C$_1$–C$_6$ alkyl, C$_1$–C$_6$ haloalkyl, C$_2$–C$_6$ alkenyl, C$_2$–C$_6$ alkynyl, C$_3$–C$_6$ cycloalkyl, C$_4$–C$_{12}$ cycloalkylalkyl, C$_2$–C$_8$ alkoxyalkyl, C$_5$–C$_{12}$ bis(alkoxy)alkyl, aryl, aryl-C$_1$–C$_4$ alkyl, heteroaryl, or heteroaryl-C$_1$–C$_4$ alkyl;

each R$^{7a}$ is, independently at each occurrence, H, C$_1$–C$_6$ alkyl, C$_1$–C$_6$ haloalkyl, C$_2$–C$_6$ alkenyl, C$_2$–C$_6$ alkynyl, C$_3$–C$_6$ cycloalkyl, C$_4$–C$_{12}$ cycloalkylalkyl, C$_2$–C$_8$ alkoxyalkyl, C$_5$–C$_{12}$ bis(alkoxy)alkyl, aryl, aryl-C$_1$–C$_4$ alkyl, heteroaryl, or heteroaryl-C$_1$–C$_4$ alkyl;

each R$^{7b}$ is, independently at each occurrence, H, C$_1$–C$_6$ alkyl, C$_1$–C$_6$ haloalkyl, C$_2$–C$_6$ alkenyl, C$_2$–C$_6$ alkynyl, C$_3$–C$_6$ cycloalkyl, C$_4$–C$_{12}$ cycloalkylalkyl, C$_2$–C$_8$ alkoxyalkyl, C$_5$–C$_{12}$ bis(alkoxy)alkyl, aryl, aryl-C$_1$–C$_4$ alkyl, heteroaryl, or heteroaryl-C$_1$–C$_4$ alkyl; and R$^8$ is C$_1$–C$_4$ alkyl, C$_1$–C$_4$ haloalkyl, C$_3$–C$_6$ cycloalkyl, C$_4$–C$_{12}$ cycloalkylalkyl, aryl, heteroaryl, aryl-C$_1$–C$_4$ alkyl, or heteroaryl-C$_1$–C$_4$ alkyl, or NR$^{7a}$R$^{7b}$.

2. The compound of claim 1, of Formula (Ia):

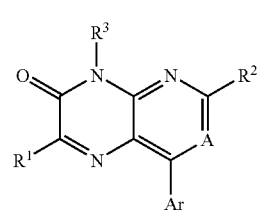

(Ia)

3. The compound of claim 2 wherein A is N.

4. The compound of claim 2 wherein A is CR$^4$.

5. The compound of claim 2 wherein Ar is aryl.

6. The compound of claim 5 wherein said aryl is phenyl substituted with 0 to 5 substituents or naphthyl substituted with 0 to 7 substituents, wherein each of said substituents is independently selected from, at each occurrence, C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, C$_1$–C$_4$ haloalkyl, C$_1$–C$_4$ haloalkoxy, halogen, CN, NO$_2$, OR$^5$, and SR$^5$.

7. The compound of claim 2 wherein Ar is heteroaryl.

8. The compound of claim 7 wherein said heteroaryl comprises a six-membered ring.

9. The compound of claim 8 wherein said heteroaryl is pyridyl or pyrimidinyl, wherein said heteroaryl is substituted with 0 to 4 substituents, wherein each of said substituents is independently selected from, at each occurrence, C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, C$_1$–C$_4$ haloalkyl, C$_1$–C$_4$ haloalkoxy, halogen, CN, NO$_2$, OR$^5$, and SR$^5$.

10. The compound of claim 7 wherein said heteroaryl comprises a five-membered ring.

11. The compound of claim 10 wherein said heteroaryl is oxazolyl, isoxazolyl, or thienyl, wherein said heteroaryl is substituted with 0 to 4 substituents, wherein each of said substituents is independently selected from, at each occurrence, C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, C$_1$–C$_4$ haloalkyl, C$_1$–C$_4$ haloalkoxy, halogen, CN, NO$_2$, OR$^5$, and SR$^5$.

12. The compound of claim 2 wherein R$^1$ is H, CN, OH, C$_1$–C$_4$ alkyl, or C$_1$–C$_2$ haloalkyl.

13. The compound of claim 2 wherein R$^1$ is C$_1$–C$_4$ alkyl.

14. The compound of claim 2 wherein R$^2$ is H, CN, OH, SH, OR$^{2b}$, SR$^{2b}$, C$_1$–C$_3$ haloalkyl, or C$_1$–C$_4$ alkyl substituted with 0 to 3 R$^{2a}$.

15. The compound of claim 2 wherein R$^2$ is H.

16. The compound of claim 2 wherein R$^3$ is S(O)R$^8$, S(O)$_2$R$^8$, COR$^{3c}$, CONHR$^{3c}$, CONR$^{3c}$R$^{3d}$, C$_1$–C$_8$ alkyl substituted with 0 to 3 R$^{3a}$, C$_3$–C$_8$ alkenyl substituted with 0 to 3 R$^{3a}$, C$_3$–C$_8$ alkynyl substituted with 0 to 3 R$^{3a}$, C$_3$–C$_6$ cycloalkyl substituted with 0 to 3 R$^{3a}$, or C$_4$–C$_{10}$ cycloalkylalkyl substituted with 0 to 3 R$^{3a}$, wherein one carbon in any cycloalkyl moiety is optionally replaced with O, S or NR$^5$.

17. The compound of claim 2 wherein R$^3$ is C$_1$–C$_6$ alkyl substituted with 0 to 2 R$^{3a}$.

18. The compound of claim 2 wherein each R$^{3a}$ is, independently at each occurrence, methyl, ethyl, propyl, cyclopropyl, cyclobutyl, F, Cl, Br, CF$_3$, CN, C$_1$–C$_{10}$ alkyl, C$_2$–C$_{10}$ alkenyl, OR$^{3c}$, SR$^{3c}$, COR$^{3b}$, NHR$^{3c}$SO$_2$R$^{3b}$, OC(O)NR$^{3c}$R$^{3d}$, N$_3$, OC(O)OR$^{3b}$, CO$_2$R$^{3c}$, OC(O)R$^{3b}$, NR$^{3c}$COR$^{3b}$, N(COR$^{3b}$)$_2$, NR$^{3c}$CONR$^{3c}$R$^{3d}$, NR$^{3c}$CO$_2$R$^{3b}$, NR$^{3c}$R$^{3d}$, or CONR$^{3c}$R$^{3d}$.

19. The compound of claim 2 wherein R$^4$ is H, CN, OH, C$_1$–C$_4$ alkyl, C$_1$–C$_3$ haloalkyl, SR$^{4c}$, or OR$^{4c}$.

20. The compound of claim 2 wherein $R^4$ is H.

21. A compound of claim 2 wherein:

$R^1$ is H, CN, OH, SH, $C_1$–$C_4$ haloalkyl, methoxy, ethoxy, cyclopropyl, cyclobutyl, cyclopropylmethyl, cyclopropylethyl, cyclobutylmethyl, cyclobutylethyl, $C_1$–$C_4$ alkyl substituted with 0 to 3 $R^{1a}$, $C_2$–$C_4$ alkenyl substituted with 0 to 3 $R^{1a}$, or $C_2$–$C_4$ alkynyl substituted with 0 to 3 $R^{1a}$;

$R^{1a}$ is F, Cl, Br, CN, $NO_2$, OH, $OCH_3$, $CF_3$, $CHF_2$, or $OCF_3$;

$R^2$ is H, CN, OH, $NR^{2c}R^{2d}$, $C_1$–$C_3$ alkyl substituted with 0 to 3 $R^{2a}$, $C_1$–$C_3$ alkoxy, $C_1$–$C_2$ haloalkyl, or $C_1$–$C_2$ haloalkoxy;

$R^3$ is $SOR^8$, $SO_2R^8$, $SO_2NR^{3c}R^{3d}$, $COR^{3c}$, $CONHR^{3c}$, $CONR^{3c}R^{3d}$, aryl substituted with 0 to 3 $R^{3a}$, heteroaryl substituted with 0 to 3 $R^{3a}$, heterocyclyl substituted with 0 to 3 $R^{3f}$, $C_1$–$C_{10}$ alkyl substituted with 0 to 3 $R^{3a}$, $C_3$–$C_{10}$ alkenyl substituted with 0 to 3 $R^{3a}$, $C_3$–$C_{10}$ alkynyl substituted with 0 to 3 $R^{3a}$, $C_3$–$C_8$ cycloalkyl substituted with 0 to 3 $R^{3a}$, $C_4$–$C_{12}$ cycloalkylalkyl substituted with 0 to 3 $R^{3a}$, $C_2$–$C_{10}$ alkoxyalkyl substituted with 0 to 3 $R^{3a}$, $C_2$–$C_{10}$ thioalkoxyalkyl substituted with 0 to 3 $R^{3a}$, $C_5$–$C_{10}$ cycloalkenyl substituted with 0 to 3 $R^{3a}$, or $C_6$–$C_{10}$ cycloalkenylalkyl substituted with 0 to 3 $R^{3a}$, wherein one carbon in any cycloalkyl moiety is optionally replaced with O, S or $NR^5$;

$R^4$ is H, halogen, CN, $C_1$–$C_3$ haloalkyl, $OR^{4c}$, $SR^{4c}$, $NR^{4c}R^{4d}$, $CO_2R^{4b}$, $C_1$–$C_4$ alkyl substituted with 0 to 1 $R^{4a}$, or $C_3$–$C_6$ cycloalkyl substituted with 0 to 1 $R^{4a}$;

each $R^{4a}$ is, independently at each occurrence, halogen, CN, $CF_3$, $OR^{4c}$, $NHR^{4c}$, $NR^{4c}R^{4d}$, $NR^{4c}CO_2R^{4b}$, $SR^{4c}$, $SOR^8$, $SO_2R^8$, $CO_2R^{4b}$, $CONHR^{4c}$, $CONR^{4c}R^{4d}$, $COR^{4b}$, $OCOR^{4b}$, $NR^{4c}CONR^{4c}R^{4d}$, $NR^{4c}CO_2R^{4b}$, $OCONR^{4c}R^{4d}$;

$R^5$ is H, $C_1$–$C_4$ alkyl, $C_1$–$C_4$ haloalkyl, $C_3$–$C_6$ cycloalkyl, $C_4$–$C_7$ cycloalkylalkyl, or $C_2$–$C_6$ alkoxyalkyl;

each $R^{7a}$ is, independently at each occurrence, H, $C_1$–$C_6$ alkyl, $C_1$–$C_6$ haloalkyl, $C_3$–$C_6$ cycloalkyl, $C_4$–$C_{12}$ cycloalkylalkyl, or $C_2$–$C_8$ alkoxyalkyl; and each $R^{7b}$ is, independently at each occurrence, H, $C_1$–$C_6$ alkyl, $C_1$–$C_6$ haloalkyl, $C_3$–$C_6$ cycloalkyl, $C_4$–$C_{12}$ cycloalkylalkyl, or $C_2$–$C_8$ alkoxyalkyl.

22. The compound of claim 21 wherein A is N.

23. The compound of claim 21 wherein A is $CR^4$.

24. The compound of claim 21 wherein $R^1$ is H, CN, OH, $C_1$–$C_4$ alkyl, or $C_1$–$C_2$ haloalkyl.

25. The compound of claim 21 wherein $R^2$ is H, CN, OH, methyl, ethyl, methoxy, $OCF_3$, $CF_3$, $CHF_2$, $CH_2CF_3$, or $CF_2CH_3$.

26. The compound of claim 21 wherein $R^2$ is H.

27. The compound of claim 21 wherein $R^3$ is $C_1$–$C_6$ alkyl substituted with 0 to 2 $R^{3a}$.

28. The compound of claim 21 wherein $R^4$ is H, CN, OH, $C_1$–$C_4$ alkyl, $C_1$–$C_3$ haloalkyl, $SR^{4c}$, or $OR^{4c}$.

29. The compound of claim 21 wherein $R^4$ is H.

30. The compound of claim 21 wherein Ar is aryl.

31. The compound of 30 wherein said aryl is phenyl substituted with 0 to 5 substituents or naphthyl substituted with 0 to 7 substituents, wherein each of said substituents is independently selected from, at each occurrence, $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $SR^5$.

32. The compound of claim 21 wherein Ar is heteroaryl.

33. The compound of claim 32 wherein said heteroaryl comprises a six-membered ring.

34. The compound of claim 33 wherein said heteroaryl is pyridyl or pyrimidinyl, wherein said heteroaryl is substituted with 0 to 4 substituents, wherein each of said substituents is independently selected from, at each occurrence, $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $SR^5$.

35. The compound of claim 32 wherein said heteroaryl comprises a five-membered ring.

36. The compound of claim 35 wherein said heteroaryl is oxazolyl, isoxazolyl, or thienyl, wherein said heteroaryl is substituted with 0 to 4 substituents, wherein each of said substituents is independently selected from, at each occurrence, $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, $C_1$–$C_4$ haloalkyl, $C_1$–$C_4$ haloalkoxy, halogen, CN, $NO_2$, $OR^5$, and $SR^5$.

37. A compound of claim 21 wherein:

Ar is phenyl, pyridyl, pyrimidinyl, oxazolyl, isoxazolyl, or thienyl, wherein said phenyl is substituted with 0 to 5 $R^{9a}$ and said pyridyl, pyrimidinyl, oxazolyl, isoxazolyl, or thienyl is substituted with 0 to 4 $R^{9b}$;

$R^1$ is H, CN, methyl, ethyl, methoxy, OH, or $C_1$–$C_2$ haloalkyl;

$R^2$ is H, CN, OH, $CH_3$, $OCH_3$, $CF_3$, $CHF_2$, or $OCF_3$;

$R^3$ is $S(O)R^8$, $S(O)_2R^8$, $COR^{3c}$, $CONHR^{3c}$, $CONR^{3c}R^{3d}$, $C_1$–$C_8$ alkyl substituted with 0 to 3 $R^{3a}$, $C_3$–$C_8$ alkenyl substituted with 0 to 3 $R^{3a}$, $C_3$–$C_8$ alkynyl substituted with 0 to 3 $R^{3a}$, $C_3$–$C_6$ cycloalkyl substituted with 0 to 3 $R^{3a}$, or $C_4$–$C_{10}$ cycloalkylalkyl substituted with 0 to 3 $R^{3a}$, wherein one carbon in any cycloalkyl moiety is optionally replaced with O, S or $NR^5$;

each $R^{3a}$ is, independently at each occurrence, methyl, ethyl, methoxy, ethoxy, thiomethoxy, thioethoxy, cyclopropyl, cyclobutyl, F, Cl, $CF_3$ $CHF_2$, $CH_3$, or $OCF_3$;

$R^4$ is H, $CHF_2$, $CF_3$, methyl, ethyl, Cl, F, OH, SH, methoxy, thiomethoxy, $CH_2CF_3$, $CF_2CH_3$; and each $R^{9a}$ and $R^{9b}$ is, independently at each occurrence, F, Cl, Br, CN, methyl, ethyl, propyl, methoxy, ethoxy, propoxy, isopropoxy, $C_1$–$C_2$ haloalkyl, or $C_1$–$C_2$ haloalkoxy.

38. The compound of claim 37 wherein A is N.

39. The compound of claim 37 wherein A is $CR^4$.

40. The compound of claim 37 wherein $R^2$ is H.

41. The compound of claim 37 wherein $R^3$ is butyl, pentyl, hexyl, heptyl, methoxyethyl, methoxypropyl, methoxybutyl, methoxypentyl, methoxyhexyl, thiomethoxyethyl, thiomethoxypropyl, thiomethoxybutyl, thiomethoxypentyl, thiomethoxyhexyl, 1-cyclopropylpropyl, 1-cyclopropylbutyl, 1-cyclopropylpentyl, 1-cyclobutylpropyl, 1-cyclobutylbutyl, 1-cyclobutylpentyl, 1-cyclopropyl-1-($CF_3$)-methyl, 1-cyclopropyl-1-($CF_3$)-ethyl, 1-cyclopropyl-1-($CF_3$)-propyl, 1-cyclobutyl-1-($CF_3$)-methyl, 1-cyclobutyl-2-($CF_3$)-ethyl, 1-cyclobutyl-3-($CF_3$)-propyl, or (cyclopropyl)$_2$CH.

42. The compound of claim 37 wherein $R^4$ is H.

43. The compound of claim 37 wherein Ar is phenyl substituted with 0 to 5 $R^{9a}$.

44. The compound of claim 37 wherein Ar is pyridyl substituted with 0 to 4 $R^{9b}$ or pyrimidinyl substituted with 0 to 4 $R^{9b}$.

45. A compound of claim 37 wherein:

Ar is phenyl substituted with 0 to 3 substituents each independently selected from F, Cl, Br, CN, methyl, ethyl, propyl, methoxy, ethoxy, propoxy, isopropoxy, $CF_3$, $CHF_2$, and $OCF_3$; or Ar is pyridyl or pyrimidinyl substituted with 0 to 2 substituents each independently selected from F, Cl, Br, CN, methyl, ethyl, propyl, methoxy, ethoxy, propoxy, isopropoxy, $CF_3$, $CHF_2$, and $OCF_3$;

$R^1$ is H, CN, OH, methyl, ethyl, methoxy, or $C_1$–$C_2$ haloalkyl;

$R^2$ is H;

$R^3$ is $C_1$–$C_6$ alkyl substituted with 0 to 2 $R^{3a}$; and $R^4$ is H.

46. The compound of claim 45 wherein Ar is phenyl substituted with 0 to 3 substituents each independently selected from F, Cl, Br, CN, methyl, ethyl, propyl, methoxy, ethoxy, propoxy, isopropoxy, $CF_3$, $CHF_2$, and $OCF_3$.

47. The compound of claim 45 wherein Ar is pyridyl or pyrimidinyl substituted with 0 to 2 substituents each independently selected from F, Cl, Br, CN, methyl, ethyl, propyl, methoxy, ethoxy, propoxy, isopropoxy, $CF_3$, $CHF_2$, and $OCF_3$.

48. The compound of claim 47 wherein said pyridyl is pyrid-3-yl.

49. The compound of claim 45 wherein A is N.

50. The compound of claim 45 wherein A is $CR^4$.

51. The compound of claim 45 wherein $R^3$ is butyl, pentyl, hexyl, heptyl, methoxyethyl, methoxypropyl, methoxybutyl, methoxypentyl, methoxyhexyl, thiomethoxyethyl, thiomethoxypropyl, thiomethoxybutyl, thiomethoxypentyl, thiomethoxyhexyl, 1-cyclopropylpropyl, 1-cyclopropylbutyl, 1-cyclopropylpentyl, 1-cyclobutylpropyl, 1-cyclobutylbutyl, 1-cyclobutylpentyl, 1-cyclopropyl-1-($CF_3$)-methyl, 1-cyclopropyl-1-($CF_3$)-ethyl, 1-cyclopropyl-1-($CF_3$)-propyl, 1-cyclobutyl-1-($CF_3$)-methyl, 1-cyclobutyl-2-($CF_3$)-ethyl, 1-cyclobutyl-3-($CF_3$)-propyl, or (cyclopropyl)$_2$CH.

52. A compound of claim 2 selected from:

(R)-8-(2,4-dichloro-phenyl)-4-isobutyl-2-methyl-4H-pyrido[2,3-b]pyrazin-3-one;

(S)-8-(2,4-dichloro-phenyl)-4-isobutyl-2-methyl-4H-pyrido[2,3-b]pyrazin-3-one;

(R)-8-(2,4-dichloro-phenyl)-2-methyl-4-(1-methyl-butyl)-4H-pyrido[2,3-b]pyrazin-3-one;

(S)-8-(2,4-dichloro-phenyl)-2-methyl-4-(1-methyl-butyl)-4H-pyrido[2,3-b]pyrazin-3-one;

(S)-4-(1-cyclopropyl-propyl)-8-(2,4-dichloro-phenyl)-2-methyl-4H-pyrido[2,3-b]pyrazin-3-one;

(R)-4-(1-cyclopropyl-propyl)-8-(2,4-dichloro-phenyl)-2-methyl-4H-pyrido[2,3-b]pyrazin-3-one;

(R)-8-(2,4-dichloro-phenyl)-4-(1,2-dimethyl-propyl)-2-methyl-4H-pyrido[2,3-b]pyrazin-3-one;

(S)-8-(2,4-dichloro-phenyl)-4-(1,2-dimethyl-propyl)-2-methyl-4H-pyrido[2,3-b]pyrazin-3-one;

(R)-4-(1-cyclopropyl-butyl)-8-(2,4-dichloro-phenyl)-2-methyl-4H-pyrido[2,3-b]pyrazin-3-one;

(S)-4-(1-cyclopropyl-butyl)-8-(2,4-dichloro-phenyl)-2-methyl-4H-pyrido[2,3-b]pyrazin-3-one;

(R)-8-(2,4-dichloro-phenyl)-4-(2-methoxy-1-methyl-ethyl)-2-methyl-4H-pyrido[2,3-b]pyrazin-3-one;

(S)-8-(2,4-dichloro-phenyl)-4-(2-methoxy-1-methyl-ethyl)-2-methyl-4H-pyrido[2,3-b]pyrazin-3-one;

(S)-8-(2,4-dichloro-phenyl)-4-(1-methoxymethyl-propyl)-2-methyl-4H-pyrido[2,3-b]pyrazin-3-one;

(R)-8-(2,4-dichloro-phenyl)-4-(1-methoxymethyl-propyl)-2-methyl-4H-pyrido[2,3-b]pyrazin-3-one;

(R,S)-8-(2-chloro-4-methoxy-phenyl)-2-methyl-4-(1-propyl-butyl)-4H-pyrido[2,3-b]pyrazin-3-one;

(S)-8-(2-chloro-4-methoxy-phenyl)-4-(1-cyclopropyl-propyl)-2-methyl-4H-pyrido[2,3-b]pyrazin-3-one;

(R)-8-(2-chloro-4-methoxy-phenyl)-4-(1-cyclopropyl-propyl)-2-methyl-4H-pyrido[2,3-b]pyrazin-3-one;

(R)-8-(2-chloro-4-methoxy-phenyl)-4-(1-cyclobutyl-propyl)-2-methyl-4H-pyrido[2,3-b]pyrazin-3-one;

(S)-8-(2-chloro-4-methoxy-phenyl)-4-(1-cyclobutyl-propyl)-2-methyl-4H-pyrido[2,3-b]pyrazin-3-one;

(S)-8-(2-chloro-4-methoxy-phenyl)-4-(2-methoxy-1-methyl-ethyl)-2-methyl-4H-pyrido[2,3-b]pyrazin-3-one;

(R)-8-(2-chloro-4-methoxy-phenyl)-4-(2-methoxy-1-methyl-ethyl)-2-methyl-4H-pyrido[2,3-b]pyrazin-3-one;

(S)-8-(2-chloro-4-methoxy-phenyl)-4-(1-methoxymethyl-propyl)-2-methyl-4H-pyrido[2,3-b]pyrazin-3-one;

(R)-4-(1-cylcopropropyl-propyl)-8-(4-methoxy-2-methyl-phenyl)-2-methyl-4H-pyrido[2,3-b]pyrazin-3-one;

(R)-4-(1-cyclopropyl-butyl)-8-(4-methoxy-2-methyl-phenyl)-2-methyl-4H-pyrido[2,3-b]pyrazin-3-one;

(S)-4-(1-cyclopropyl-butyl)-8-(4-methoxy-2-methyl-phenyl)-2-methyl-4H-pyrido[2,3-b]pyrazin-3-one;

(R)-4-(2-methoxy-1-methyl-ethyl)-8-(4-methoxy-2-methyl-phenyl)-2-methyl-4H-pyrido[2,3-b]pyrazin-3-one;

(R)-4-(1-ethyl-pentyl)-8-(6-methoxy-2-methyl-pyridin-3-yl)-2-methyl-4H-pyrido[2,3-b]pyrazin-3-one;

(S)-4-(1-ethyl-pentyl)-8-(6-methoxy-2-methyl-pyridin-3-yl)-2-methyl-4H-pyrido[2,3-b]pyrazin-3-one;

(R)-4-(1-cyclopropyl-propyl)-8-(6-methoxy-2-methyl-pyridin-3-yl)-2-methyl-4H-pyrido[2,3-b]pyrazin-3-one;

(R)-4-(1-cyclopropyl-butyl)-8-(6-methoxy-2-methyl-pyridin-3-yl)-2-methyl-4H-pyrido[2,3-b]pyrazin-3-one;

(S)-4-(1-cyclopropyl-butyl)-8-(6-methoxy-2-methyl-pyridin-3-yl)-2-methyl-4H-pyrido[2,3-b]pyrazin-3-one;

(R)-4-(2-methoxy-1-methyl-ethyl)-8-(6-methoxy-2-methyl-pyridyl)-2-methyl-4H-pyrido[2,3-b]pyrazin-3-one;

(R)-4-sec-butyl-8-(2-chloro-4-difluoromethoxy-phenyl)-2-methyl-4H-pyrido[2,3-b]pyrazin-3-one;

(S)-4-(1-cyclopropyl-butyl)-8-(6-methoxy-2-methyl-pyridin-3-yl)-2-methyl-4H-pyrido[2,3-b]pyrazin-3-one;

(S)-8-(2-chloro-4-difluoromethoxy-phenyl)-4-(1-cyclopropyl-propyl)2-methyl-4H-pyrido[2,3-b]pyrazin-3-one;

(R)-8-(2-chloro-4-difluoromethoxy-phenyl)-4-(1-cyclopropyl-propyl)2-methyl-4H-pyrido[2,3-b]pyrazin-3-one;

(R)-8-(2-chloro-4-difluoromethoxy-phenyl)-4-(1-cyclopropyl-butyl)-2-methyl-4H-pyrido[2,3-b]pyrazin-3-one;

(S)-8-(2-chloro-4-difluoromethoxy-phenyl)-4-(1-cyclopropyl-butyl)-2-methyl-4H-pyrido[2,3-b]pyrazin-3-one;

(R)-8-(2-chloro-4-difluoromethoxy-phenyl)-4-(2-methoxy-1-methyl-ethyl)-2-methyl-4H-pyrido[2,3-b]pyrazin-3-one;

(R)-8-(2-chloro-4-difluoromethoxy-phenyl)-4-(1-methoxymethyl-propyl)-2-methyl-4H-pyrido[2,3-b]pyrazin-3-one;

(S)-8-(2-chloro-4-difluoromethoxy-phenyl)-4-(1-methoxymethyl-propyl)-2-methyl-4H-pyrido[2,3-b]pyrazin-3-one;

(S)-8-(2-chloro-4-trifluoromethyl-phenyl)-4-(1-cyclopropyl-propyl)-2-methyl-4H-pyrido[2,3-b]pyrazin-3-one;

(R)-8-(2-chloro-4-trifluoromethyl-phenyl)-4-(2-methoxy-1-methyl-ethyl)-2-methyl-4H-pyrido[2,3-b]pyrazin-3-one;

(R)-8-(2-chloro-4-trifluoromethyl-phenyl)-4-(1-methoxymethyl-propyl)-2-methyl-4H-pyrido[2,3-b]pyrazin-3-one;

(R)-3-chloro-4-(4-(1-methoxymethylpropyl)-2-methyl-3-oxo-3,4-dihydro-pyrido[2,3-b]pyrazin-8-yl]-benzonitrile;

(R)-8-sec-butyl-4-(2,4-dichloro-phenyl)-6-methyl-8H-pteridin-7-one; and (S)-8-sec-butyl-4-(2,4-dichloro-phenyl)-6-methyl-8H-pteridin-7-one.

53. A compound of claim 2 selected from:

(R,S)-8-(4-Methoxy-2-methyl-phenyl)-4-(1-methoxymethyl-propyl)-2-methyl-4H-pyrido[2,3-b]pyrazin-3-one;

(R)-4-(1-Cyclopropyl-propyl)-8-(5-fluoro-4-methoxy-2-methyl-phenyl)-2-methyl-4H-pyrido[2,3-b]pyrazin-3-one;
(R)-8-(5-Fluoro-4-methoxy-2-methyl-phenyl)-4-(1-methoxymethyl-propyl)-2-methyl-4H-pyrido[2,3-b]pyrazin-3-one;
(S)-8-(2-Chloro-5-fluoro-4-methoxy-phenyl)-4-(1-cyclopropyl-propyl)-2-methyl-4H-pyrido[2,3-b]pyrazin-3-one;
8-(2-Chloro-5-fluoro-4-methoxy-phenyl)-4-(1-methoxymethyl-propyl)-2-methyl-4H-pyrido[2,3-b]pyrazin-3-one;
8-(5-Chloro-4-methoxy-2-methyl-phenyl)-4-(1-cyclopropyl-propyl)-2-methyl-4H-pyrido[2,3-b]pyrazin-3-one;
8-(5-Chloro-4-methoxy-2-methyl-phenyl)-4-(1-methoxymethyl-propyl)-2-methyl-4H-pyrido[2,3-b]pyrazin-3-one;
8-(2-Chloro-4-methoxy-5-methyl-phenyl)-4-(1-cyclopropyl-propyl)-2-methyl-4H-pyrido[2,3-b]pyrazin-3-one;
8-(2-Chloro-4-methoxy-5-methyl-phenyl)-4-(1-methoxymethyl-propyl)-2-methyl-4H-pyrido[2,3-b]pyrazin-3-one;
8-(2-Chloro-4-dimethylamino-5-fluoro-phenyl)-4-(1-cyclopropyl-propyl)-2-methyl-4H-pyrido[2,3-b]pyrazin-3-one;
(R)-8-(2-Chloro-4-dimethylamino-5-fluoro-phenyl)-4-(1-cyclopropyl-ethyl)-2-methyl-4H-pyrido[2,3-b]pyrazin-3-one;
(R)-8-(2-Chloro-4-dimethylamino-5-fluoro-phenyl)-4-(1-cyclobutyl-ethyl)-2-methyl-4H-pyrido[2,3-b]pyrazin-3-one;
8-(2-Chloro-4-dimethylamino-5-fluoro-phenyl)-4-(2-methoxy-1-methyl-ethyl)-2-methyl-4H-pyrido[2,3-b]pyrazin-3-one;
8-(2-Chloro-4-dimethylamino-5-fluoro-phenyl)-4-(1-methoxymethyl-propyl)-2-methyl-4H-pyrido[2,3-b]pyrazin-3-one;
4-(2-Chloro-4-methoxy-phenyl)-6-methyl-8-(1-propyl-butyl)-8H-pteridin-7-one;
(R)-4-(2-Chloro-4-methoxy-phenyl)-8-(1-cyclopropyl-ethyl)-6-methyl-8H-pteridin-7-one;
(S)-4-(2-Chloro-4-methoxy-phenyl)-8-(1-cyclobutyl-ethyl)-6-methyl-8H-pteridin-7-one;
(R)-4-(2-Chloro-4-methoxy-phenyl)-8-(2-methoxy-1-methyl-ethyl)-6-methyl-8H-pteridin-7-one;
(R)-4-(2-Chloro-4-methoxy-phenyl)-8-(1-methoxymethyl-propyl)-6-methyl-8H-pteridin-7-one;
(R)-8-(1-Cyclopropyl-propyl)-4-(4-methoxy-2-methyl-phenyl)-6-methyl-8H-pteridin-7-one;
(R)-8-(1-Cyclopropyl-propyl)-4-(6-methoxy-2-methyl-pyridin-3-yl)-6-methyl-8H-pteridin-7-one;
(R)-8-(2-Methoxy-1-methyl-ethyl)-4-(6-methoxy-2-methyl-pyridin-3-yl)-6-methyl-8H-pteridin-7-one;
(R)-8-(1-Methoxymethyl-propyl)-4-(6-methoxy-2-methyl-pyridin-3-yl)-6-methyl-8H-pteridin-7-one;
(R)-4-(4-Methoxy-2,5-dimethyl-phenyl)-8-(1-methoxymethyl-propyl)-6-methyl-8H-pteridin-7-one;
(R)-4-(2-Chloro-4-trifluoromethoxy-phenyl)-8-(1-cyclopropyl-propyl)-6-methyl-8H-pteridin-7-one;
4-(2-Chloro-4-trifluoromethoxy-phenyl)-8-(1-cyclopropyl-ethyl)-6-methyl-8H-pteridin-7-one; and
(R)-4-(2-Chloro-4-trifluoromethoxy-phenyl)-8-(2-methoxy-1-methyl-ethyl)-6-methyl-8H-pteridin-7-one.

54. A compound of claim 1 selected from the group consisting of:
(R)-5-(2,4-Dichloro-phenyl)-1-isobutyl-3-methyl-1H-pyrido[3,4-b]pyrazin-2-one;
(S)-5-(2,4-Dichloro-phenyl)-1-isobutyl-3-methyl-1H-pyrido[3,4-b]pyrazin-2-one;
(R)-1-(1-Cyclopropyl-propyl)-5-(2,4-dichloro-phenyl)-3-methyl-1H-pyrido[3,4-b]pyrazin-2-one;
(S)-1-(1-Cyclopropyl-propyl)-5-(2,4-dichloro-phenyl)-3-methyl-1H-pyrido[3,4-b]pyrazin-2-one;
(R)-5-(2,4-Dichloro-phenyl)-1-(1-methoxymethyl-propyl)-3-methyl-1H-pyrido[3,4-b]pyrazin-2-one;
(S)-5-(2,4-Dichloro-phenyl)-1-(1-methoxymethyl-propyl)-3-methyl-1H-pyrido[3,4-b]pyrazin-2-one;
(R)-5-(2,4-Dichloro-phenyl)-1-(2-methoxy-1-methyl-ethyl)-3-methyl-1H-pyrido[3,4-b]pyrazin-2-one;
(S)-5-(2,4-Dichloro-phenyl)-1-(2-methoxy-1-methyl-ethyl)-3-methyl-1H-pyrido[3,4-b]pyrazin-2-one;
(R)-1-(1-Cyclopropyl-2-methoxy-ethyl)-5-(2,4-dichloro-phenyl)-3-methyl-1H-pyrido[3,4-b]pyrazin-2-one;
(S)-1-(1-Cyclopropyl-2-methoxy-ethyl)-5-(2,4-dichloro-phenyl)-3-methyl-1H-pyrido[3,4-b]pyrazin-2-one;
(R)-1-(1-Cyclobutyl-ethyl)-5-(2,4-dichloro-phenyl)-3-methyl-1H-pyrido[3,4-b]pyrazin-2-one;
(S)-1-(1-Cyclobutyl-ethyl)-5-(2,4-dichloro-phenyl)-3-methyl-1H-pyrido[3,4-b]pyrazin-2-one;
(R)-1-(1-Cyclobutyl-propyl)-5-(2,4-dichloro-phenyl)-3-methyl-1H-pyrido[3,4-b]pyrazin-2-one;
(S)-1-(1-Cyclobutyl-propyl)-5-(2,4-dichloro-phenyl)-3-methyl-1H-pyrido[3,4-b]pyrazin-2-one;
(R)-5-(2-Chloro-5-fluoro-4-methoxy-phenyl)-1-(1-cyclopropyl-ethyl)-3-methyl-1H-pyrido[3,4-b]pyrazin-2-one;
(S)-5-(2-Chloro-5-fluoro-4-methoxy-phenyl)-1-(1-cyclopropyl-ethyl)-3-methyl-1H-pyrido[3,4-b]pyrazin-2-one;
(R)-5-(2-Chloro-5-fluoro-4-methoxy-phenyl)-1-(1-cyclopropyl-propyl)-3-methyl-1H-pyrido[3,4-b]pyrazin-2-one;
(S)-5-(2-Chloro-5-fluoro-4-methoxy-phenyl)-1-(1-cyclopropyl-propyl)-3-methyl-1H-pyrido[3,4-b]pyrazin-2-one;
(R)-5-(2-Chloro-5-fluoro-4-methoxy-phenyl)-1-(2-methoxy-1-methyl-ethyl)-3-methyl-1H-pyrido[3,4-b]pyrazin-2-one;
(S)-5-(2-Chloro-5-fluoro-4-methoxy-phenyl)-1-(2-methoxy-1-methyl-ethyl)-3-methyl-1H-pyrido[3,4-b]pyrazin-2-one;
(R)-5-(2-Chloro-5-fluoro-4-methoxy-phenyl)-1-(1-methoxymethyl-propyl)-3-methyl-1H-pyrido[3,4-b]pyrazin-2-one;
(S)-5-(2-Chloro-5-fluoro-4-methoxy-phenyl)-1-(1-methoxymethyl-propyl)-3-methyl-1H-pyrido[3,4-b]pyrazin-2-one;
(R)-5-(2-Chloro-5-fluoro-4-methoxy-phenyl)-1-(1-cyclopropyl-2-methoxy-ethyl)-3-methyl-1H-pyrido[3,4-b]pyrazin-2-one;
(S)-5-(2-Chloro-5-fluoro-4-methoxy-phenyl)-1-(1-cyclopropyl-2-methoxy-ethyl)-3-methyl-1H-pyrido[3,4-b]pyrazin-2-one;
(R)-5-(2-Chloro-5-fluoro-4-methoxy-phenyl)-1-(1-cyclobutyl-ethyl)-3-methyl-1H-pyrido[3,4-b]pyrazin-2-one;
(S)-5-(2-Chloro-5-fluoro-4-methoxy-phenyl)-1-(1-cyclobutyl-ethyl)-3-methyl-1H-pyrido[3,4-b]pyrazin-2-one;
(R)-5-(2-Chloro-5-fluoro-4-methoxy-phenyl)-1-(1-cyclobutyl-propyl)-3-methyl-1H-pyrido[3,4-b]pyrazin-2-one;
(S)-5-(2-Chloro-5-fluoro-4-methoxy-phenyl)-1-(1-cyclobutyl-propyl)-3-methyl-1H-pyrido[3,4-b]pyrazin-2-one;
(R)-1-(1-Cyclopropyl-ethyl)-5-(6-methoxy-2-methyl-pyridin-3-yl)-3-methyl-1H-pyrido[3,4-b]pyrazin-2-one;
(S)-1-(1-Cyclopropyl-ethyl)-5-(6-methoxy-2-methyl-pyridin-3-yl)-3-methyl-1H-pyrido[3,4-b]pyrazin-2-one;
(R)-1-(1-Cyclopropyl-propyl)-5-(6-methoxy-2-methyl-pyridin-3-yl)-3-methyl-1H-pyrido[3,4-b]pyrazin-2-one;

(S)-1-(1-Cyclopropyl-propyl)-5-(6-methoxy-2-methyl-pyridin-3-yl)-3-methyl-1H-pyrido[3,4-b]pyrazin-2-one;

(R)-1-(2-Methoxy-1-methyl-ethyl)-5-(6-methoxy-2-methyl-pyridin-3-yl)-3-methyl-1H-pyrido[3,4-b]pyrazin-2-one;

(S)-1-(2-Methoxy-1-methyl-ethyl)-5-(6-methoxy-2-methyl-pyridin-3-yl)-3-methyl-1H-pyrido[3,4-b]pyrazin-2-one;

(R)-1-(1-Methoxymethyl-propyl)-5-(6-methoxy-2-methyl-pyridin-3-yl)-3-methyl-1H-pyrido[3,4-b]pyrazin-2-one;

(S)-1-(1-Methoxymethyl-propyl)-5-(6-methoxy-2-methyl-pyridin-3-yl)-3-methyl-1H-pyrido[3,4-b]pyrazin-2-one;

(R)-1-(1-Cyclopropyl-2-methoxy-ethyl)-5-(6-methoxy-2-methyl-pyridin-3-yl)-3-methyl-1H-pyrido[3,4-b]pyrazin-2-one;

(S)-1-(1-Cyclopropyl-2-methoxy-ethyl)-5-(6-methoxy-2-methyl-pyridin-3-yl)-3-methyl-1H-pyrido[3,4-b]pyrazin-2-one;

(R)-1-(1-Cyclobutyl-ethyl)-5-(6-methoxy-2-methyl-pyridin-3-yl)-3-methyl-1H-pyrido[3,4-b]pyrazin-2-one;

(S)-1-(1-Cyclobutyl-ethyl)-5-(6-methoxy-2-methyl-pyridin-3-yl)-3-methyl-1H-pyrido[3,4-b]pyrazin-2-one;

(R)-1-(1-Cyclobutyl-propyl)-5-(6-methoxy-2-methyl-pyridin-3-yl)-3-methyl-1H-pyrido[3,4-b]pyrazin-2-one;

(S)-1-(1-Cyclobutyl-propyl)-5-(6-methoxy-2-methyl-pyridin-3-yl)-3-methyl-1H-pyrido[3,4-b]pyrazin-2-one;

(R)-1-(1-Cyclopropyl-ethyl)-5-(6-methoxy-2,5-dimethyl-pyridin-3-yl)-3-methyl-1H-pyrido[3,4-b]pyrazin-2-one;

(S)-1-(1-Cyclopropyl-ethyl)-5-(6-methoxy-2,5-dimethyl-pyridin-3-yl)-3-methyl-1H-pyrido[3,4-b]pyrazin-2-one;

(R)-1-(1-Cyclopropyl-propyl)-5-(6-methoxy-2,5-dimethyl-pyridin-3-yl)-3-methyl-1H-pyrido[3,4-b]pyrazin-2-one;

(S)-1-(1-Cyclopropyl-propyl)-5-(6-methoxy-2,5-dimethyl-pyridin-3-yl)-3-methyl-1H-pyrido[3,4-b]pyrazin-2-one;

(R)-5-(6-Methoxy-2,5-dimethyl-pyridin-3-yl)-1-(2-methoxy-1-methyl-ethyl)-3-methyl-1H-pyrido[3,4-b]pyrazin-2-one;

(S)-5-(6-Methoxy-2,5-dimethyl-pyridin-3-yl)-1-(2-methoxy-1-methyl-ethyl)-3-methyl-1H-pyrido[3,4-b]pyrazin-2-one;

(R)-5-(6-Methoxy-2,5-dimethyl-pyridin-3-yl)-1-(1-methoxymethyl-propyl)-3-methyl-1H-pyrido[3,4-b]pyrazin-2-one;

(S)-5-(6-Methoxy-2,5-dimethyl-pyridin-3-yl)-1-(1-methoxymethyl-propyl)-3-methyl-1H-pyrido[3,4-b]pyrazin-2-one;

(R)-1-(1-Cyclopropyl-2-methoxy-ethyl)-5-(6-methoxy-2,5-dimethyl-pyridin-3-yl)-3-methyl-1H-pyrido[3,4-b]pyrazin-2-one;

(S)-1-(1-Cyclopropyl-2-methoxy-ethyl)-5-(6-methoxy-2,5-dimethyl-pyridin-3-yl)-3-methyl-1H-pyrido[3,4-b]pyrazin-2-one;

(R)-1-(1-Cyclobutyl-ethyl)-5-(6-methoxy-2,5-dimethyl-pyridin-3-yl)-3-methyl-1H-pyrido[3,4-b]pyrazin-2-one;

(S)-1-(1-Cyclobutyl-ethyl)-5-(6-methoxy-2,5-dimethyl-pyridin-3-yl)-3-methyl-1H-pyrido[3,4-b]pyrazin-2-one;

(R)-1-(1-Cyclobutyl-propyl)-5-(6-methoxy-2,5-dimethyl-pyridin-3-yl)-3-methyl-1H-pyrido[3,4-b]pyrazin-2-one;

(S)-1-(1-Cyclobutyl-propyl)-5-(6-methoxy-2,5-dimethyl-pyridin-3-yl)-3-methyl-1H-pyrido[3,4-b]pyrazin-2-one;

(R)-1-(1-Cyclopropyl-ethyl)-5-(4-methoxy-2,5-dimethyl-phenyl)-3-methyl-1H-pyrido[3,4-b]pyrazin-2-one;

(S)-1-(1-Cyclopropyl-ethyl)-5-(4-methoxy-2,5-dimethyl-phenyl)-3-methyl-1H-pyrido[3,4-b]pyrazin-2-one;

(R)-1-(1-Cyclopropyl-propyl)-5-(4-methoxy-2,5-dimethyl-phenyl)-3-methyl-1H-pyrido[3,4-b]pyrazin-2-one;

(S)-1-(1-Cyclopropyl-propyl)-5-(4-methoxy-2,5-dimethyl-phenyl)-3-methyl-1H-pyrido[3,4-b]pyrazin-2-one;

(R)-5-(4-Methoxy-2,5-dimethyl-phenyl)-1-(2-methoxy-1-methyl-ethyl)-3-methyl-1H-pyrido[3,4-b]pyrazin-2-one;

(S)-5-(4-Methoxy-2,5-dimethyl-phenyl)-1-(2-methoxy-1-methyl-ethyl)-3-methyl-1H-pyrido[3,4-b]pyrazin-2-one;

(R)-5-(4-Methoxy-2,5-dimethyl-phenyl)-1-(1-methoxymethyl-propyl)-3-methyl-1H-pyrido[3,4-b]pyrazin-2-one;

(S)-5-(4-Methoxy-2,5-dimethyl-phenyl)-1-(1-methoxymethyl-propyl)-3-methyl-1H-pyrido[3,4-b]pyrazin-2-one;

(R)-1-(1-Cyclopropyl-2-methoxy-ethyl)-5-(4-methoxy-2,5-dimethyl-phenyl)-3-methyl-1H-pyrido[3,4-b]pyrazin-2-one;

(S)-1-(1-Cyclopropyl-2-methoxy-ethyl)-5-(4-methoxy-2,5-dimethyl-phenyl)-3-methyl-1H-pyrido[3,4-b]pyrazin-2-one;

(R)-1-(1-Cyclobutyl-ethyl)-5-(4-methoxy-2,5-dimethyl-phenyl)-3-methyl-1H-pyrido[3,4-b]pyrazin-2-one;

(S)-1-(1-Cyclobutyl-ethyl)-5-(4-methoxy-2,5-dimethyl-phenyl)-3-methyl-1H-pyrido[3,4-b]pyrazin-2-one;

(R)-1-(1-Cyclobutyl-propyl)-5-(4-methoxy-2,5-dimethyl-phenyl)-3-methyl-1H-pyrido[3,4-b]pyrazin-2-one;

(S)-1-(1-Cyclobutyl-propyl)-5-(4-methoxy-2,5-dimethyl-phenyl)-3-methyl-1H-pyrido[3,4-b]pyrazin-2-one;

(R)-1-(1-Cyclopropyl-ethyl)-5-(2,4-dimethoxy-pyrimidin-5-yl)-3-methyl-1H-pyrido[3,4-b]pyrazin-2-one;

(S)-1-(1-Cyclopropyl-ethyl)-5-(2,4-dimethoxy-pyrimidin-5-yl)-3-methyl-1H-pyrido[3,4-b]pyrazin-2-one;

(R)-1-(1-Cyclopropyl-propyl)-5-(2,4-dimethoxy-pyrimidin-5-yl)-3-methyl-1H-pyrido[3,4-b]pyrazin-2-one;

(S)-1-(1-Cyclopropyl-propyl)-5-(2,4-dimethoxy-pyrimidin-5-yl)-3-methyl-1H-pyrido[3,4-b]pyrazin-2-one;

(R)-5-(2,4-Dimethoxy-pyrimidin-5-yl)-1-(2-methoxy-1-methyl-ethyl)-3-methyl-1H-pyrido[3,4-b]pyrazin-2-one;

(S)-5-(2,4-Dimethoxy-pyrimidin-5-yl)-1-(2-methoxy-1-methyl-ethyl)-3-methyl-1H-pyrido[3,4-b]pyrazin-2-one;

(R)-5-(2,4-Dimethoxy-pyrimidin-5-yl)-1-(1-methoxymethyl-propyl)-3-methyl-1H-pyrido[3,4-b]pyrazin-2-one;

(S)-5-(2,4-Dimethoxy-pyrimidin-5-yl)-1-(1-methoxymethyl-propyl)-3-methyl-1H-pyrido[3,4-b]pyrazin-2-one;

(R)-1-(1-Cyclopropyl-2-methoxy-ethyl)-5-(2,4-dimethoxy-pyrimidin-5-yl)-3-methyl-1H-pyrido[3,4-b]pyrazin-2-one;

(S)-1-(1-Cyclopropyl-2-methoxy-ethyl)-5-(2,4-dimethoxy-pyrimidin-5-yl)-3-methyl-1H-pyrido[3,4-b]pyrazin-2-one;

(R)-1-(1-Cyclobutyl-ethyl)-5-(2,4-dimethoxy-pyrimidin-5-yl)-3-methyl-1H-pyrido[3,4-b]pyrazin-2-one;

(S)-1-(1-Cyclobutyl-ethyl)-5-(2,4-dimethoxy-pyrimidin-5-yl)-3-methyl-1H-pyrido[3,4-b]pyrazin-2-one;

(R)-1-(1-Cyclobutyl-propyl)-5-(2,4-dimethoxy-pyrimidin-5-yl)-3-methyl-1H-pyrido[3,4-b]pyrazin-2-one;

(S)-1-(1-Cyclobutyl-propyl)-5-(2,4-dimethoxy-pyrimidin-5-yl)-3-methyl-1H-pyrido[3,4-b]pyrazin-2-one.

55. A composition comprising a compound of claim 1 and a pharmaceutically acceptable carrier.

56. A composition comprising a compound of claim 2 and a pharmaceutically acceptable carrier.

57. A method of treating anxiety or depression in a mammal comprising administering to said mammal a therapeutically effective amount of a compound of claim 1.

58. A method of treating anxiety or depression in a mammal comprising administering to said mammal a therapeutically effective amount of a compound of claim 2.

59. A method of treating irritable bowel syndrome in a mammal comprising administering to said mammal a therapeutically effective amount of a compound of claim 1.

60. A method of treating irritable bowel syndrome in a mammal comprising administering to said mammal a therapeutically effective amount of a compound of claim 2.

* * * * *